US009597326B2

(12) United States Patent
Otten et al.

(10) Patent No.: US 9,597,326 B2
(45) Date of Patent: Mar. 21, 2017

(54) BENZONAPTHYRIDINE COMPOSITIONS AND USES THEREOF

(75) Inventors: Gillis Otten, Rowley, MA (US); Tom Yao-Hsiang Wu, San Diego, CA (US); Travis K. Warren, Middleton, MD (US); Sina Bavari, Fredrick, MD (US)

(73) Assignees: GlaxoSmithKline Biologicals SA, Rixensart (BE); U.S. Army Medical Research and Materiel Command, Fort Detrick, MD (US)

(*) Notice: Subject to any disclaimer, the term of this patent is extended or adjusted under 35 U.S.C. 154(b) by 880 days.

(21) Appl. No.: 13/640,832

(22) PCT Filed: Apr. 13, 2011

(86) PCT No.: PCT/US2011/032274
§ 371 (c)(1),
(2), (4) Date: Jan. 23, 2013

(87) PCT Pub. No.: WO2011/130379
PCT Pub. Date: Oct. 20, 2011

(65) Prior Publication Data

US 2013/0122042 A1 May 16, 2013

Related U.S. Application Data

(60) Provisional application No. 61/323,725, filed on Apr. 13, 2010, provisional application No. 61/413,658, filed on Nov. 15, 2010.

(51) Int. Cl.
*A61K 31/4745* (2006.01)
*A61K 31/4375* (2006.01)
*A61K 33/06* (2006.01)
*A61K 38/16* (2006.01)

(52) U.S. Cl.
CPC ...... *A61K 31/4745* (2013.01); *A61K 31/4375* (2013.01); *A61K 33/06* (2013.01); *A61K 38/162* (2013.01)

(58) Field of Classification Search
CPC .................................................. A61K 31/4745
See application file for complete search history.

(56) References Cited

U.S. PATENT DOCUMENTS 9,458,184 B2 * 10/2016 Vernejoul ........ A61K 47/48046

FOREIGN PATENT DOCUMENTS

| | | |
|---|---|---|
| WO | WO99/32147 | 7/1999 |
| WO | WO2008/109083 | 9/2008 |
| WO | WO2009/026292 | 2/2009 |
| WO | WO2009/111337 | 9/2009 |
| WO | WO2010/009277 | 1/2010 |
| WO | WO2010/017330 | 2/2010 |

OTHER PUBLICATIONS

International Search Report from corresponding PCT Application No. PCT/US2011/032274 dated Aug. 2, 2011.

* cited by examiner

*Primary Examiner* — Benjamin Packard
(74) *Attorney, Agent, or Firm* — Morrison & Foerster LLP

(57) ABSTRACT

The present invention generally relates to compositions comprising benzonapthyridine small molecule immune potentiators (SMIPs) that are capable of stimulating or modulating an immune response in a subject that has had pre- or post-exposure to a pathogen such as hemorrhagic fever virus. Also provided are methods of preparing and using the SMIP compositions of the invention.

15 Claims, 9 Drawing Sheets

BENZONAPTHYRIDINE COMPOSITIONS AND USES THEREOF

RELATED APPLICATIONS

This application is the U.S. National Stage of International application No. PCT/US2011/032274,filled Apr.13, 2011,published in English, and claims the benefit of U.S. Patent Application Nos. 61/323,725 filed on Apr. 13, 2010 and 61/413,658 filed on Nov. 15, 2010, the entire teachings of which are incorporated herein by reference.

STATEMENT OF GOVERNMENT SUPPORT

This invention was made in part with Government support under Defense Threat Reduction Agency Contract No. HDTRA1-07-9-0001; and 4.10022-08-RD-B and TMTI0039-09-RD-T, and the U.S. Army Medical Research and Material Command Grant No. W81XWH-09-0176. The Government has certain rights in the invention.

BACKGROUND OF THE INVENTION

Recently developed attenuated pathogen or subunit protein vaccines, while offering significant advantages over the traditional whole pathogen vaccines in terms of safety and cost of production, generally have limited immunogenicity as compared to whole pathogens. As a result, these vaccines typically require adjuvants with significant immunostimulatory capability to reach their full potential in preventing diseases.

Efforts have been made to identify new immune-modulators for use as adjuvants for vaccines and immunotherapies. In particular, an adjuvant formulation that elicits potent cell-mediated and humoral immune responses to a wide range of antigens in humans and domestic animals, but lacking the side effects of conventional adjuvants and other immune modulators, would be highly desirable. This need could be met by small molecule immune potentiators ("SMIPs") because the small molecule platform provides diverse compounds for the selective manipulation of the immune response, necessary for increasing the therapeutic index immune modulators.

Toll-like receptors (TLRs) are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Thirteen TLRs (named TLR1 to TLR13) have been identified in humans and mice together, and equivalent forms of many of these have been found in other mammalian species. In particular, TLR7 mediates recognition of microbial nucleic acids such as single stranded RNA. TLR7 comprises a subfamily of TLRs which is located in endosomal or lysosomal compartments of immune cells such as dendritic cells and monocytes. Specifically, TLR7 is expressed by plasmacytoid dendritic cells and to a lesser extent by monocytes. Agonists of TLR7 stimulate the production of various inflammatory cytokines including interleukin-6, interleukin-12, tumor necrosis factor-alpha, and interferon-gamma. Such agonists also promote the increased expression of co-stimulatory molecules such as CD40, CD80, and CD86, major histocompatibility complex molecules, and chemokine receptors. The type I interferons, IFN-α and IFN-β, are also produced by cells upon activation with TLR7 agonists.

Certain benzonapthyridine compounds that bind to TLRs, including TLR7 and TLR8, have an immunostimulating effect.

Viral hemorrhagic fevers refer to a group of illnesses that are caused by four distinct families of RNA viruses: arenaviruses, filoviruses, bunyaviruses, and flaviviruses. These four families of viruses cause different types of viral hemorrhagic fever: Lassa (arenavirus), Marburg (filovirus), Ebola (filovirus), Crimean-Congo (bunyavirus).

Filoviruses are enveloped, non-segmented viruses with a negative-sense, single-stranded RNA genome of approximately 19 kb. Filoviral infections continue to present an unresolved obstacle in the epidemiology of infectious agents. Moreover, their acuteness is associated with consequent economic and social disruption, severely impacting the areas where the outbreak was epidemic. Ebola and Marburg viruses are members of the Filoviridae family of the order Mononegavirales. Ebola and Marburg viruses cause acute, lethal hemorrhagic fevers for which no vaccines or established treatment currently exist. However, antiviral drugs (ribavirin) as well as generally supportive therapy that replenishes intravenous fluids, maintains blood pressure, and other bodily functions are administered to mammals (e.g. human beings) infected with hemorrhagic fevers. Ebola viruses cause hemorrhagic fever with mortality rates up to 88%. Together with Marburg virus, the five species of Ebola virus (Zaire, Sudan, Reston, Ivory Coast, and Bundibugyo) comprise the family Filoviridae. Whereas Marburg, Ebola Zaire and Ebola Sudan viruses are pathogenic in humans, apes, and monkeys, Ebola Reston is pathogenic only in monkeys. Early immunosuppression may contribute to pathogenesis by facilitating viral replication. Lymphocyte depletion, intravascular apoptosis and cytokine dysregulation are prominent in fatal cases.

A need exists for compositions that can be used to generate, modulate, or potentiate an immune response in a subject exposed to or infected with a hemorrhagic fever virus, such as Marburg virus or Ebola virus.

SUMMARY OF THE INVENTION

As described and exemplified herein, the inventors have found that compositions comprising benzonapthyridine SMIPs are effective hemorrhagic fever virus therapies (e.g., Ebola virus therapies).

The present invention relates to methods for treating a subject who has been exposed to a hemorrhagic fever virus such as a Filoviridae virus (e.g., Ebola virus). The present invention also relates to compositions for the treatment of exposure to a hemorrhagic fever virus such as a Filoviridae virus (e.g., Ebola virus). Additionally, the invention provides methods for inducing or potentiating an immune response to a hemorrhagic fever virus. The invention also provides compositions for inducing or potentiating an immune response to a hemorrhagic fever virus.

Also provided is an immunogenic or pharmaceutical composition comprising one or more benzonapthyridine small molecule immune potentiators (SMIPs) that are agonists of Toll-like receptor 7 (TLR7). Also provided is a composition comprising a benzonapthyridine TLR7 agonist or salt, solvate, or derivative thereof for use as a medicament.

One aspect of the invention provides a method of potentiating an immune response in a subject who has been exposed to a hemorrhagic fever virus, comprising administering to said subject a pharmaceutically effective amount of a composition comprising a benzonapthyridine TLR7 agonist of Formula (I) described herein, or salt, solvate, or derivative thereof. One aspect of the invention provides a method of potentiating an immune response in a subject who has been exposed to a hemorrhagic fever virus, comprising administering to said subject a pharmaceutically effective amount of a composition comprising a benzonapthyridine TLR7 agonist of Formula (II) described herein, or salt, solvate, or derivative thereof. One aspect of the invention provides a method of potentiating an immune response in a subject who has been exposed to a hemorrhagic fever virus, comprising administering to said subject a pharmaceutically effective amount of a composition comprising a benzonapthyridine TLR7 agonist of Formula (VIII) described herein, or salt, solvate, or derivative thereof.

One aspect of the invention provides a method of treating a subject who has been exposed to a hemorrhagic fever virus, comprising administering to said subject a pharmaceutically effective amount of a composition comprising a benzonapthyridine TLR7 agonist of Formula (I) described herein, or salt, solvate, or derivative thereof. One aspect of the invention provides a method of treating a subject who has been exposed to a hemorrhagic fever virus, comprising administering to said subject a pharmaceutically effective amount of a composition comprising a benzonapthyridine TLR7 agonist of Formula (II) described herein, or salt, solvate, or derivative thereof. One aspect of the invention provides a method of treating a subject who has been exposed to a hemorrhagic fever virus, comprising administering to said subject a pharmaceutically effective amount of a composition comprising a benzonapthyridine TLR7 agonist of Formula (VIII) described herein, or salt, solvate, or derivative thereof.

Another aspect of the invention provides a method for inducing an immune response to a hemorrhagic fever virus, comprising administering to a subject an immunogenic composition comprising: (a) a benzonapthyridine TLR7 agonist of Formula (I) described herein, or salt, solvate, or derivative thereof, and (b) an antigen from a hemorrhagic fever virus. Another aspect of the invention provides a method for inducing an immune response to a hemorrhagic fever virus, comprising administering to a subject an immunogenic composition comprising: (a) a benzonapthyridine TLR7 agonist of Formula (I) described herein, or salt, solvate, or derivative thereof; (b) an antigen from a hemorrhagic fever virus; and (c) an adjuvant.

Another aspect of the invention provides a method for inducing an immune response to a hemorrhagic fever virus, comprising administering to a subject an immunogenic composition comprising: (a) a benzonapthyridine TLR7 agonist of Formula (II) described herein, or salt, solvate, or derivative thereof, and (b) an antigen from a hemorrhagic fever virus. Another aspect of the invention provides a method for inducing an immune response to a hemorrhagic fever virus, comprising administering to a subject an immunogenic composition comprising: (a) a benzonapthyridine TLR7 agonist of Formula (II) described herein, or salt, solvate, or derivative thereof; (b) an antigen from a hemorrhagic fever virus; and (c) an adjuvant.

Another aspect of the invention provides a method for inducing an immune response to a hemorrhagic fever virus, comprising administering to a subject an immunogenic composition comprising: (a) a benzonapthyridine TLR7 agonist of Formula (VIII) described herein, or salt, solvate, or derivative thereof, and (b) an antigen from a hemorrhagic fever virus. Another aspect of the invention provides a method for inducing an immune response to a hemorrhagic fever virus, comprising administering to a subject an immunogenic composition comprising: (a) a benzonapthyridine TLR7 agonist of Formula (VIII) described herein or salt, solvate, or derivative thereof; (b) an antigen from a hemorrhagic fever virus; and (c) an adjuvant. In another aspect, the adjuvant is an aluminum-containing adjuvant or MF59.

Another aspect of the invention provides a method for inducing an immune response to a hemorrhagic fever virus, comprising administering to a subject an immunogenic composition comprising a benzonapthyridine TLR7 agonist of Formula (I) described herein or salt, solvate, or derivative thereof. Another aspect of the invention provides a method for inducing an immune response to a hemorrhagic fever virus, comprising administering to a subject an immunogenic composition comprising a benzonapthyridine TLR7 agonist of Formula (II) described herein or salt, solvate, or derivative thereof. Another aspect of the invention provides a method for inducing an immune response to a hemorrhagic fever virus, comprising administering to a subject an immunogenic composition comprising a benzonapthyridine TLR7 agonist of Formula (VIII) described herein or salt, solvate, or derivative thereof. The induced immune response can be characterized by a cytokine profile. For example, the cytokine profile can include one or more cytokines selected from the group consisting of IFN-γ, IL-12 p40, IL-1β, IL-6, MCP-1, mKC, TNF-α, and combinations thereof. In one aspect, the cytokine profile comprises IFN-γ, IL-12 p40, IL-1β, IL-6, MCP-1, mKC, and TNF-α.

Another aspect of the invention provides a method of treating a subject who has been exposed to a hemorrhagic fever virus, comprising administering to the subject a pharmaceutically effective amount of a composition comprising: (a) a benzonapthyridine TLR7 agonist of Formula (I), Formula (II), or Formula (VIII) described herein, or salt, solvate, or derivative thereof, and (b) an antiviral agent. In some aspects, the antiviral agent is ribavirin.

Another aspect of the invention provides an immunogenic composition comprising: (a) a benzonapthyridine TLR7 agonist of Formula (I) described herein, or salt, solvate, or derivative thereof, and (b) an antigen from a hemorrhagic fever virus. Another aspect of the invention provides an immunogenic composition comprising: (a) a benzonapthyridine TLR7 agonist of Formula (I) described herein, or salt, solvate, or derivative thereof, (b) an antigen from a hemorrhagic fever virus; and (c) an adjuvant.

Another aspect of the invention provides an immunogenic composition comprising: (a) a benzonapthyridine TLR7 agonist of Formula (II) described herein, or salt, solvate, or derivative thereof, and (b) an antigen from a hemorrhagic fever virus. Another aspect of the invention provides an immunogenic composition comprising: (a) a benzonapthyridine TLR7 agonist of Formula (II) described herein, or salt, solvate, or derivative thereof, (b) an antigen from a hemorrhagic fever virus; and (c) an adjuvant.

Another aspect of the invention provides an immunogenic composition comprising: (a) a benzonapthyridine TLR7 agonist of Formula (VIII) described herein, or salt, solvate, or derivative thereof, and (b) an antigen from a hemorrhagic fever virus. Another aspect of the invention provides an immunogenic composition comprising: (a) a benzonapthyridine TLR7 agonist of Formula (VIII) described herein, or salt, solvate, or derivative thereof, (b) an antigen from a hemorrhagic fever virus; and (c) an adjuvant.

In some aspects, the hemorrhagic fever virus is a Filoviridae virus. In some aspects, the Filoviridae virus is Ebola virus. In another aspect, the adjuvant is an aluminum-containing adjuvant or MF59.

In another aspect of the invention, the benzonapthyridine TLR7 agonist is a benzonapthyridine of Formula (I) having the structure:

Formula (I)

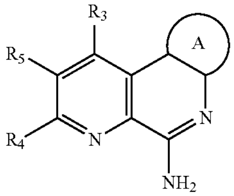

wherein:

$R^3$ is H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$C(O)N(R^9)_2$, —$S(O)_2R^8$, —$S(O)_2N(R^9)_2$ and —$NR^9S(O)_2R^8$;

$R^4$ and $R^5$ are each independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -L=NOH, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

Ring A is phenyl optionally substituted with 1 to 3 $R^A$ groups, wherein each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)CO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH{=}CHCO_2R^8$, —$C({=}NH)$—$N(R^9)_2$, and —$(CH_2)_n NHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In another aspect of the invention, the benzonapthyridine TLR7 agonist is a benzonapthyridine of Formula (II) having the structure:

Formula (II)

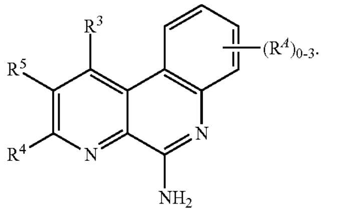

wherein:

$R^3$ is H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$C(O)N(R^9)_2$, —$S(O)_2R^8$, —$S(O)_2N(R^9)_2$ and —$NR^9S(O)_2R^8$;

$R^4$ and $R^5$ are each independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)OR^7$, —$(CH_2)R^7$, -$LR^8$, -$LR^{10}$, —$OLR^8$, —$OLR^{10}$, $C_1$-$C_6$ alkyl, $C_1$-$C_6$hetero alkyl, $C_1$-$C_6$halo alkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, $C(O)NR^{11}R^{12}$, —$C(O)NR^{11}OH$, —$S(O)_2$ $R^{11}$, —$S(O)R^{11}$, —$S(O)_2NR^{11}R^{12}$, —$NR^{11}S(O)_2$ $R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$C(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)CO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH{=}CHCO_2R^8$, —$C(=NH)$—$N(R^9)_2$, and —$(CH_2)_n$$NHC(O)R^8$; or two adjacent $R^A$ substituents form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In another aspect of the invention the benzonapthyridine TLR7 agonist is a benzonapthyridine of Formula (VIII) having the structure:

Formula (VIII)

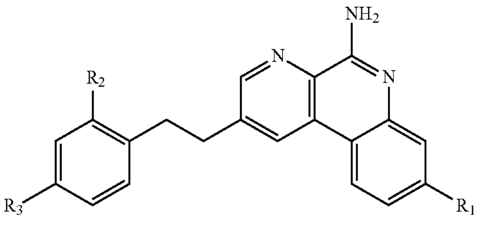

wherein:

$R^1$ is H, $C_1$-$C_6$alkyl, —$C(R^5)_2OH$, -$L^1R^5$, -$L^1R^6$, -$L^2R^5$, -$L^2R^6$, -$OL^2R^5$, or —$OL^2R^6$;

$L^1$ is —C(O)— or —O—;

$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;

each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;

$L^4$ is arylene or heteroarylene;

$R^2$ is H or $C_1$-$C_6$alkyl;

$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, -$OL^3R^7$, -$OL^3L^4R^7$, -$OL^3L^4L^3R^7$, —$OR^8$, -$OL^3L^4R^5$, -$OL^3L^4L^3R^5$ and —$C(R^5)_2OH$;

each $R^4$ is independently selected from H and fluoro;

$R^5$ is —$P(O)(OR^9)_2$, $R^6$ is —$CF_2P(O)(OR^9)_2$ or —$C(O)OR^{10}$;

$R^7$ is —$CF_2P(O)(OR^9)_2$ or —$C(O)OR^{10}$;

$R^8$ is H or $C_1$-$C_4$alkyl;

each $R^9$ is independently selected from H and $C_1$-$C_6$alkyl;

$R^{10}$ is H or $C_1$-$C_4$alkyl;

each p is independently selected from 1, 2, 3, 4, 5 and 6, and q is 1, 2, 3 or 4;

with the proviso that when $R^3$ is $C_1$-$C_4$ alkyl or —$OR^8$, $R^1$ is —$C(R^5)_2OH$, -$L^1R^5$, -$L^1R^6$, -$L^2R^5$, -$L^2R^6$, -$OL^2R^5$, or —$OL^2R^6$, wherein $R^6$ is —$CF_2P(O)(OR^9)_2$ and $R^7$ is —$CF_2P(O)(OR^9)_2$.

In another aspect of the invention, the benzonapthyridine TLR7 agonist is 2-(4-methoxy-2-methylphenethyl)-8-methylbenzo[f][1,7]naphthyridin-5-amine having the structure:

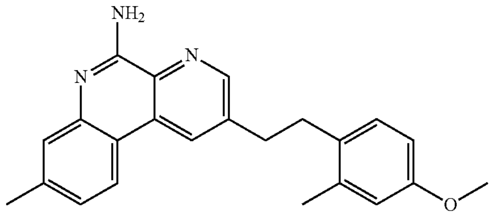

.

In another aspect of the invention, the benzonapthyridine TLR7 agonist is 2-(4-(2-(5-amino-8-methylbenzo[f][1,7]naphthyridin-2-yl)ethyl)-3-methylphenyl)propan-2-ol having the structure:

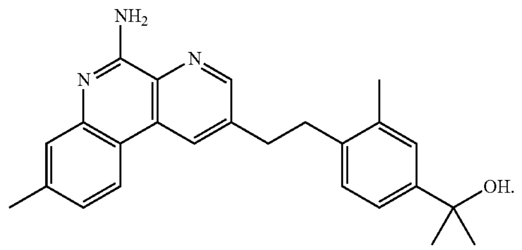 [SMILES: Cc1ccc2c(c1)nc(N)c1ncc(CCc3ccc(C(C)(C)O)cc3C)cc12]

In another aspect of the invention, the benzonapthyridine TLR7 agonist is 2-(2-(4-(2-(5-amino-8-methylbenzo[f][1,7]naphthyridin-2-yl)ethyl)-3-methylphenoxy)ethoxy)ethanol having the structure:

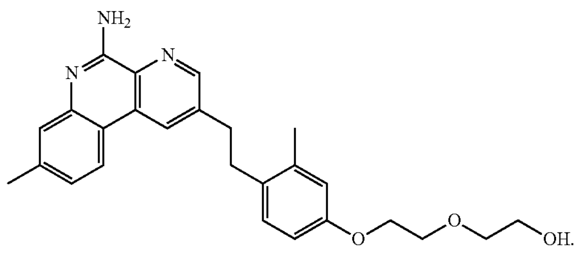 [SMILES: Cc1ccc2c(c1)nc(N)c1ncc(CCc3ccc(OCCOCCO)cc3C)cc12]

BRIEF DESCRIPTION OF THE DRAWINGS

FIG. 5 shows that compositions comprising benzonapthyridine SMIPs protected guinea pigs that had been challenged intraperitoneally or subcutaneously with a guinea pig-adapted strain of the Zaire strain of Ebola virus.

FIG. 6 shows the peak cytokine concentration measured over 24 hours in mice following administration of the composition comprising SMIP 28. The composition induced expression of specific cytokines in the mice. FIG. 6 also shows the serum level (serum pK) of SMIP 28 over the 24 hour time period.

DETAILED DESCRIPTION OF THE INVENTION

1. Overview

Figure 1:
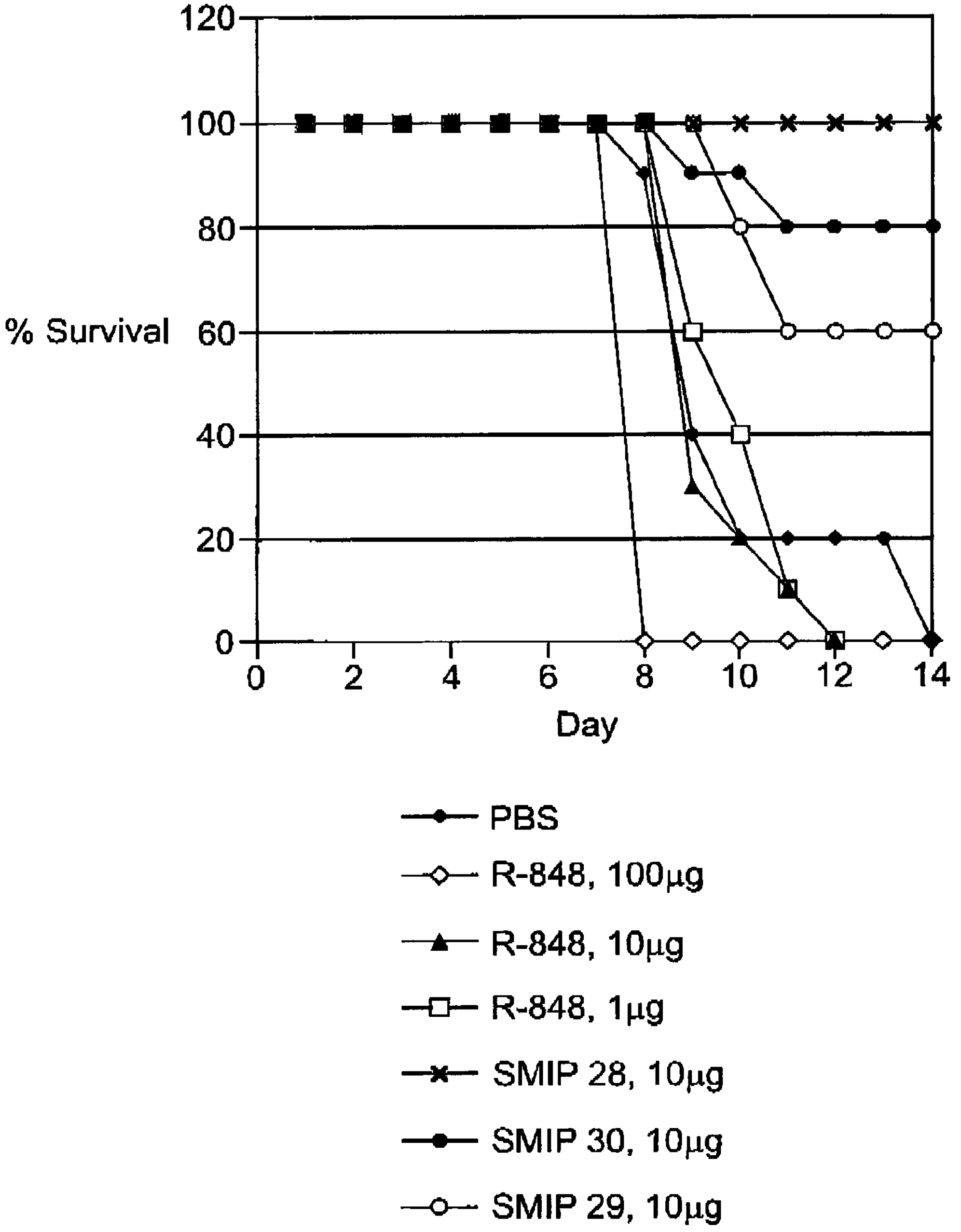
FIG. 1 shows that compositions comprising benzonapthyridine SMIPs protected mice that had been challenged with a mouse-adapted strain of the Zaire strain of Ebola virus. Mice were administered phosphate buffered saline (PBS) or 1 μg, 10 μg, or 100 μg of R-848, or 10 μg of SMIP 28 (2-(4-methoxy-2-methylphenethyl)-8-methylbenzo[f][1,7]naphthyridin-5-amine), 10 μg of SMIP 29 (2-(2-(4-(2-(5-amino-8-methylbenzo[f][1,7]naphthyridin-2-yl)ethyl)-3-methylphenoxy)ethoxy)ethanol), or 10 μg of SMIP 30 (2-(4-(2-(5-amino-8-methylbenzo[f][1,7]naphthyridin-2-yl)ethyl)-3-methylphenyl)propan-2-ol). Following administration, the animals were monitored for survival.

This invention generally relates to compositions comprising benzonapthyridine SMIPs (e.g., 2-(4-methoxy-2-methylphenethyl)-8-methylbenzo[f][1,7]naphthyridin-5-amine; 2-(4-(2-(5-amino-8-methylbenzo[f][1,7]naphthyridin-2-yl)ethyl)-3-methylphenyl)propan-2-ol; or 2-(2-(4-(2-(5-amino-8-methylbenzo[f][1,7]naphthyridin-2-yl)ethyl)-3-methylphenoxy)ethoxy)ethanol) that are Toll-like receptor 7 (TLR7) agonists. The benzonapthyridine compositions can be used to generate or potentiate an immune response against a hemorrhagic fever virus, such as a Filoviridae virus (e.g., Ebola virus). The benzonapthyridine compositions can be used to protect or to treat a subject against a hemorrhagic fever virus, such as a Filoviridae virus.

As described and exemplified herein, the inventors have found that compositions comprising benzonapthyridine SMIPs are effective Ebola virus therapies.

2. Definitions

As used herein, the singular forms "a," "an" and "the" include plural references unless the content clearly dictates otherwise.

The term "about", as used here, refers to +/−10% of a value.

As used herein, an "immunological response" or "immune response" is the development in a subject of a humoral and/or a cellular immune response to the immunogenic species.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Reported TLRs (along with examples of some reported ligands, which may be included in various aspects of the invention) include the following: TLR1 (bacterial lipoproteins from *Mycobacteria, Neisseria*), TLR2 (zymosan yeast particles, peptidoglycan, lipoproteins, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from mycoplasma), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others.

Dendritic cells are recognized as some of the most important cell types for initiating the priming of naive $CD4^+$ helper T ($T_H$) cells and for inducing $CD8^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, *Nature Medicine,* 11, S63-S68 (2005), K. S. Rosenthal and D. H. Zimmerman, *Clinical and Vaccine Immunology,* 13(8), 821-829 (2006), and the references cited therein.

For purposes of the present invention, a humoral immune response refers to an immune response mediated by antibody molecules, while a cellular immune response is one mediated by T-lymphocytes and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from $CD4^+$ and $CD8^+$ T-cells.

A composition such as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) *J. Immunol.* 151:4189-4199; Doe et al. (1994) *Eur. J. Immunol.* 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve, for example, to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "antigen" refers to a molecule containing one or more epitopes (either linear, conformational or both) that elicit an immunological response. The term may be used interchangeably with the term "immunogen." An "epitope" is that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids. The term "antigen" denotes both subunit antigens, i.e., antigens which are separate and discrete from a whole organism or cell with which the antigen is associated in nature, as well as killed, attenuated or inactivated bacteria, viruses, fungi, parasites or other microbes or tumor cells. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An immunogenic composition which contains an antigen in accordance with the present invention displays "enhanced immunogenicity" when it possesses a greater capacity to elicit an immune response than the immune response elicited by an equivalent amount of the antigen administered using a different delivery system, e.g., wherein the antigen is administered as a soluble protein. Thus, an immunogenic or vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the antigen composition and antigen controls to animals and comparing antibody titers and/or cellular-mediated immunity against the two using standard assays described herein.

The term "adjuvant" or "immunological adjuvant" refers to any substance that assists or modifies the action of an antigen in the immune system. Adjuvants can potentiate humoral and/or cellular immunity.

The term "excipient" refers to any essentially accessory substance that may be present in the finished dosage form. For example, the term "excipient" includes vehicles, binders, disintegrants, fillers (diluents), suspending/dispersing agents, and so forth.

The term "carrier" as used herein refers to chemical compounds or agents that facilitate the incorporation of a compound described herein into cells or tissues.

The term "diluent," as used herein, refers to chemical compounds that are used to dilute a compound described herein prior to delivery. Diluents can also be used to stabilize compounds described herein.

The term "modulator," as used herein, refers to a molecule that interacts with a target either directly or indirectly. The interactions include, but are not limited to, the interactions of an agonist or an antagonist.

As used herein, "treating" or "treatment" refers to any of (i) the prevention of a condition (e.g., a disease or disorder) in question (e.g. cancer or a pathogenic infection, as in a traditional vaccine), (ii) the reduction or elimination of symptoms associated with the condition in question, and (iii) the substantial or complete elimination of the condition in question. Treatment may be effected prophylactically (prior to arrival of the condition in question) or therapeutically (following arrival of the same).

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

The terms "effective amount" or "pharmaceutically effective amount" of a homogenous suspension of the present invention refers to an amount sufficient to potentiate an immune response, for example by at least about 10%, as described herein. The terms "effective amount" or "pharmaceutically effective amount" of an immunogenic composition of the present invention refer herein to a sufficient amount of the immunogenic composition for the treatment or diagnosis of a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "pharmaceutically acceptable" or "pharmacologically acceptable" is meant a material which is not biologically or otherwise undesirable, e.g., the material may be administered to an individual without causing any unduly undesirable biological effects or interacting in an unduly deleterious manner with any of the components of the composition in which it is contained.

By "physiological pH" or a "pH in the physiological range" is meant a pH in the range of approximately 6.5 to 8.0 inclusive, more typically in the range of approximately 7.2 to 7.6 inclusive.

As used here, the term "injectable composition", or variants thereof, refers to pharmaceutically acceptable compositions suitable for injection into a vertebrate subject, which compositions are typically sterile, pyrogen-free, and possess specific pH and isotonicity values suitable for injection.

The term "alkenyl," as used herein, refers to a partially unsaturated branched or straight chain hydrocarbon having at least one carbon-carbon double bond. Atoms oriented about the double bond are in either the cis (Z) or trans (E) conformation. An alkenyl group can be optionally substituted. As used herein, the terms "C2-C3alkenyl", "C2-C4alkenyl", "C2-C5alkenyl", "C2-C6alkenyl", "C2-C7alkenyl", and "C2-C8alkenyl" refer to an alkenyl group containing at least 2, and at most 3, 4, 5, 6, 7 or 8 carbon atoms, respectively. If not otherwise specified, an alkenyl group generally is a C2-C6 alkenyl. Non-limiting examples of alkenyl groups, as used herein, include ethenyl, propenyl, butenyl, pentenyl, hexenyl, heptenyl, octenyl, nonenyl, decenyl and the like.

The term "alkenylene," as used herein, refers to a partially unsaturated branched or straight chain divalent hydrocarbon radical derived from an alkenyl group. An alkenylene group can be optionally substituted. As used herein, the terms "C2-C3alkenylene", "C2-C4alkenylene", "C2-C5alkenylene", "C2-C6alkenylene", "C2-C7alkenylene", and "C2-C8alkenylene" refer to an alkenylene group containing at least 2, and at most 3, 4, 5, 6, 7 or 8 carbon atoms respectively. If not otherwise specified, an alkenylene group generally is a C1-C6 alkenylene. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. An alkyl group can be optionally substituted. As used herein, the terms "C1-C3alkyl", "C1-C4alkyl", "C1-C5alkyl", "C1-C6alkyl", "C1-C7alkyl" and "C1-C8alkyl" refer to an alkyl group containing at least 1, and at most 3, 4, 5, 6, 7 or 8 carbon atoms, respectively. If not otherwise specified, an alkyl group generally is a C1-C6 alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. An alkylene group can be optionally substituted. As used herein, the terms "C1-C3alkylene", "C1-C4alkylene", "C1-C5alkylene", "C1-C6alkylene", "C1-C7alkylene" and "C1-C8alkylene" refer to an alkylene group containing at least 1, and at most 3, 4, 5, 6, 7 or 8 carbon atoms respectively. If not otherwise specified, an alkylene group generally is a C1-C6 alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl," as used herein, refers to a partially unsaturated branched or straight chain hydrocarbon having at least one carbon-carbon triple bond. An alkynyl group can be optionally substituted. As used herein, the terms "C2-

C3alkynyl", "C2-C4alkynyl", "C2-C5alkynyl", "C2-C6alkynyl", "C2-C7alkynyl", and "C2-C8alkynyl" refer to an alkynyl group containing at least 2, and at most 3, 4, 5, 6, 7 or 8 carbon atoms, respectively. If not otherwise specified, an alkynyl group generally is a C2-C6 alkynyl. Non-limiting examples of alkynyl groups, as used herein, include ethynyl, propynyl, butynyl, pentynyl, hexynyl, heptynyl, octynyl, nonynyl, decynyl and the like.

The term "alkynylene," as used herein, refers to a partially unsaturated branched or straight chain divalent hydrocarbon radical derived from an alkynyl group. An alkynylene group can be optionally substituted. As used herein, the terms "C2-C3alkynylene", "C2-C4alkynylene", "C2-C5alkynylene", "C2-C6alkynylene", "C2-C7alkynylene", and "C2-C8alkynylene" refer to an alkynylene group containing at least 2, and at most 3, 4, 5, 6, 7 or 8 carbon atoms respectively. If not otherwise specified, an alkynylene group generally is a C2-C6 alkynylene. Non-limiting examples of alkynylene groups as used herein include, ethynylene, propynylene, butynylene, pentynylene, hexynylene, heptynylene, octynylene, nonynylene, decynylene and the like.

The term "alkoxy," as used herein, refers to the group —ORa, where Ra is an alkyl group as defined herein. An alkoxy group can be optionally substituted. As used herein, the terms "C1-C3 alkoxy", "C1-C4alkoxy", "C1-C5alkoxy", "C1-C6alkoxy", "C1-C7alkoxy" and "C1-C8alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. An aryl group can be optionally substituted. Non-limiting examples of aryl groups, as used herein, include phenyl, naphthyl, fluorenyl, indenyl, azulenyl, anthracenyl and the like.

The term "arylene," as used means a divalent radical derived from an aryl group. An arylene group can be optionally substituted.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "C3-C5 cycloalkyl", "C3-C6 cycloalkyl", "C3-C7 cycloalkyl", "C3-C8 cycloalkyl", "C3-C9 cycloalkyl" and "C3-C10 cycloalkyl" refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. A cycloalkyl group can be optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. A haloalkenyl group can be optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The terms "haloalkynyl" or "halo-substituted alkynyl," as used herein, refers to an alkynyl group as defined above, substituted with one or more halogen groups, wherein the halogen groups are the same or different. A haloalkynyl group can be optionally substituted. Non-limiting examples of such branched or straight chained haloalkynyl groups, as used herein, include ethynyl, propynyl, butynyl, pentynyl, hexynyl, heptynyl, octynyl, nonynyl, decynyl, and the like substituted with one or more halogen groups, wherein the halogen groups are the same or different.

The term "haloalkoxy," as used herein, refers to an alkoxy group as defined herein, substituted with one or more halogen groups, wherein the halogen groups are the same or different. A haloalkoxy group can be optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. A heteroaryl group may contain one or more substituents. A heteroaryl group can be optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heterocycloalkyl," as used herein, refers to a cycloalkyl, as defined herein, wherein one or more of the ring carbons are replaced by a moiety selected from —O—, —N═, —NR—, —C(O)—, —S—, —S(O)— or —S(O)2-, wherein R is hydrogen, $C_1$-$C_4$alkyl or a nitrogen protecting group, with the proviso that the ring of said group does not contain two adjacent O or S atoms. A heterocycloalkyl group can be optionally substituted. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

As used here, the term "injectable composition", or variants thereof, refers to pharmaceutically acceptable compositions suitable for injection into a vertebrate subject, which compositions are typically sterile, pyrogen-free, and possess specific pH and isotonicity values suitable for injection.

The term "isocyanato," as used herein, refers to a —N═C═O group.

The term "isothiocyanato," as used herein, refers to a —N═C═S group

The term "mercaptyl," as used herein, refers to an (alkyl) S— group.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, ═O, ═N—OH, ═N—OR, ═N—R, OR, —C(O)R, —C(O)OR, —OC(O)R, —OC(O)OR, —C(O)NHR, —C(O)$NR_2$, —OC(O)NHR, —OC(O)$NR_2$, —SR—, —S(O)R, —$S(O)_2R$, —NHR, —$N(R)_2$, —NHC(O)R, NRC(O)R, —NHC(O)OR, —NRC(O)OR, $S(O)_2NHR$, $S(O)_2N(R)_2$, —$NHS(O)_2NR_2$, —$NRS(O)_2NR_2$, —$NHS(O)_2R$, —$NRS(O)_2R$, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substituent groups is done in accordance with the well-understood valence limitations of each group, for example ═O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

3. Immunogenic Compositions and Pharmaceutical Compositions

Immunogenic Compositions

The invention provides immunogenic compositions that comprise a benzonapthyridine compound that is an agonist of TLR-7, and a hemorrhagic fever virus antigen. Optionally, the immunogenic compositions further comprises an immunoregulatory agent which includes one or more adjuvants. The immunogenic composition can be used to produce an immune response against the hemorrhagic fever virus, which preferably results in protective immunity.

In some aspects, the benzonapthyridine compound is a compound of Formula (I), disclosed herein or salt, solvate, or derivative thereof. For example, the immunogenic composition can comprise: (a) a benzonapthyridine TLR7 agonist of Formula (I) described herein, or salt, solvate, or derivative thereof, and (b) an antigen from a hemorrhagic fever virus, such as a Filoviridae virus described herein. In another aspect, an immunogenic composition of the invention can comprise: (a) a benzonapthyridine TLR7 agonist of Formula (I) described herein, or salt, solvate, or derivative thereof; (b) an antigen from a hemorrhagic fever virus, such as a Filoviridae virus; and (c) an immunoregulatory agent. An immunoregulatory agent includes one or more adjuvants described herein.

In some aspects, the benzonapthyridine compound is a compound of Formula (VIII), disclosed herein or salt, solvate, or derivative thereof. For example, the immunogenic composition can comprise: (a) a benzonapthyridine TLR7 agonist of Formula (VIII), or salt, solvate, or derivative thereof, and (b) an antigen from a hemorrhagic fever virus, such as a Filoviridae virus described herein. In another aspect, an immunogenic composition of the invention can comprise: (a) a benzonapthyridine TLR7 agonist of Formula (VIII), or salt, solvate, or derivative thereof; (b) an antigen from a hemorrhagic fever virus, such as a Filoviridae virus; and (c) an immunoregulatory agent. An immunoregulatory agent includes one or more adjuvants.

An immunogenic composition of the invention can further comprise a pharmaceutically acceptable carrier. Such carriers include, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances.

Pharmaceutical Compositions

The invention provides pharmaceutical compositions that comprise a benzonapthyridine compound that is an agonist of TLR7. The pharmaceutical composition can be used to treat hemorrhagic fever virus. In some aspects, the pharmaceutical composition can comprise a benzonapthyridine SMIP that is a TLR7 agonist of Formula (I) described herein, or salt, solvate, or derivative thereof, and may further comprise one or more pharmaceutically acceptable carriers, diluents, or excipients as disclosed herein. In other aspects, the pharmaceutical composition can comprise a benzonapthyridine SMIP that is a TLR7 agonist of Formula (VIII) described herein, or salt, solvate, or derivative thereof, and may further comprise one or more pharmaceutically acceptable carriers, diluents, or excipients.

Benzonapthyridines

The compositions described herein comprise benzonapthyridine compounds that are agonists of TLR7.

In some aspects, TLR7 agonists are benzonapthyridine compounds of Formula (I), (II), (III), (IV), (V), (VI), (VII) and/or (VIII) disclosed herein.

In some aspects, the TLR7 agonists bind an aluminum-containing adjuvant. Examples of an aluminum-containing adjuvant include, but are not limited to, aluminum hydroxide, aluminum oxyhydroxide and aluminum hydroxyphosphate. For example, the TLR7 agonists of the invention that bind an aluminum-containing adjuvant can be a benzonapthyridine compound of Formula (VIII) disclosed herein.

In some aspects, the TLR7 agonists are benzonapthyridine compounds having the structure of Formula (I), Formula (I)

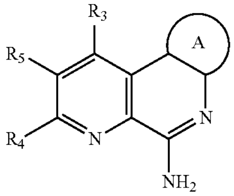

wherein:

$R^3$ is H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$C(O)N(R^9)_2$, —$S(O)_2R^8$, —$S(O)_2N(R^9)_2$ and —$NR^9S(O)_2R^8$;

$R^4$ and $R^5$ are each independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)OR^7$, —$(CH_2)R^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$C(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, $-LR^9$, $-LOR^9$, $—OLR^9$, $-LR^{10}$, $-LOR^{10}$, $—OLR^{10}$, $-LR^8$, $-LOR^8$, $—OLR^8$, $-LSR^8$, $-LSR^{10}$, $-LC(O)R^8$, $—OLC(O)R^8$, $-LC(O)OR^8$, $-LC(O)R^{10}$, $-LOC(O)OR^8$, $-LC(O)NR^9R^{11}$, $-LC(O)NR^9R^8$, $-LN(R^9)_2$, $-LNR^9R^8$, $-LNR^9R^{10}$, -L=NOH, $-LC(O)N(R^9)_2$, $-LS(O)_2R^8$, $-LS(O)R^8$, $-LC(O)NR^8OH$, $-LNR^9C(O)R^8$, $-LNR^9C(O)OR^8$, $-LS(O)_2N(R^9)_2$, $—OLS(O)_2N(R^9)_2$, $-LNR^9S(O)_2R^8$, $-LC(O)NR^9LN(R^9)_2$, $-LP(O)(OR^8)_2$, $-LOP(O)(OR^8)_2$, $-LP(O)(OR^{10})_2$ and $—OLP(O)(OR^{10})_2$;

Ring A is phenyl optionally substituted with 1 to 3 $R^A$ groups, wherein each $R^A$ is independently selected from halogen, $—R^8$, $—R^7$, $—OR^7$, $—OR^8$, $—R^{10}$, $—OR^{10}$, $—SR^8$, $—NO_2$, —CN, $—N(R^9)_2$, $—NR^9C(O)R^8$, $—NR^9C(S)R^8$, $—NR^9C(O)N(R^9)_2$, $—NR^9C(S)N(R^9)_2$, $—NR^9CO_2R^8$, $—NR^9NR^9C(O)R^8$, $—NR^9NR^9C(O)N(R^9)_2$, $—NR^9NR^9CO_2R^8$, $—C(O)C(O)R^8$, $—C(O)CH_2C(O)R^8$, $—CO_2R^8$, $—(CH_2)CO_2R^8$, $—C(O)R^8$, $—C(S)R^8$, $—C(O)N(R^9)_2$, $—C(S)N(R^9)_2$, $—OC(O)N(R^9)_2$, $—OC(O)R^8$, $—C(O)N(OR^8)R^8$, $—C(NOR^8)R^8$, $—S(O)_2R^8$, $—S(O)_3R^8$, $—SO_2N(R^9)_2$, $—S(O)R^8$, $—NR^9SO_2N(R^9)_2$, $—NR^9SO_2R^8$, $—P(O)(OR^8)_2$, $—OP(O)(OR^8)_2$, $—P(O)(OR^{10})_2$, $—OP(O)(OR^{10})_2$, $—N(OR^8)R^8$, $—CH{=}CHCO_2R^8$, $—C(=NH)—N(R^9)_2$, and $—(CH_2)_nNHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain aspects of compounds of Formulas (I), ring A is phenyl which is optionally substituted with 1 to 3 $R^A$ groups, wherein each $R^A$ is independently selected from halogen, $—R^8$, $—R^7$, $—OR^8$, $—OR^8$, $—R^{10}$, $—OR^{10}$, $—SR^8$, $—NO_2$, —CN, $—N(R^9)_2$, $—NR^9C(O)R^8$, $—NR^9C(S)R^8$, $—NR^9C(O)N(R^9)_2$, $—NR^9C(S)N(R^9)_2$, $—NR^9CO_2R^8$, $—NR^9NR^9C(O)R^8$, $—NR^9NR^9C(O)N(R^9)_2$, $—NR^9NR^9CO_2R^8$, $—C(O)C(O)R^8$, $—C(O)CH_2C(O)R^8$, $—CO_2R^8$, $—(CH_2)CO_2R^8$, $—C(O)R^8$, $—C(S)R^8$, $—C(O)N(R^9)_2$, $—C(S)N(R^9)_2$, $—OC(O)N(R^9)_2$, $—OC(O)R^8$, $—C(O)N(OR^8)R^8$, $—C(NOR^8)R^8$, $—S(O)_2R^8$, $—S(O)_3R^8$, $—SO_2N(R^9)_2$, $—S(O)R^8$, $—NR^9SO_2N(R^9)_2$, $—NR^9SO_2R^8$, $—P(O)(OR^8)_2$, $—OP(O)(OR^8)_2$, $—P(O)(OR^{10})_2$, $—OP(O)(OR^{10})_2$, $—N(OR^8)R^8$, $—CH{=}CHCO_2R^8$, $—C(=NH)—N(R^9)_2$, and $—(CH_2)_nNHC(O)R^8$.

In certain aspects compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (II), Formula (II)

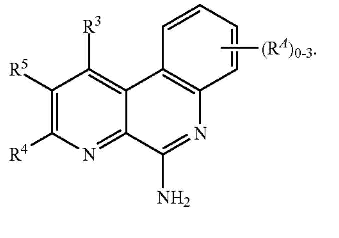

wherein:

$R^3$ is H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, $—R^7$, $—OR^8$, $—C(O)R^8$, $—OC(O)R^8$, $—C(O)OR^8$, $—N(R^9)_2$, $—C(O)N(R^9)_2$, $—S(O)_2R^8$, $—S(O)_2N(R^9)_2$ and $—NR^9S(O)_2R^8$;

$R^4$ and $R^5$ are each independently selected from H, halogen, $—C(O)OR^7$, $—C(O)R^7$, $—C(O)N(R^{11}R^{12})$, $—N(R^{11}R^{12})$, $—N(R^9)_2$, $—NHN(R^9)_2$, $—SR^7$, $—(CH_2)OR^7$, $—(CH_2)R^7$, $-LR^8$, $-LR^{10}$, $—OLR^8$, $—OLR^{10}$, $C_1$-$C_6$alkyl, $C_1$-$C_6$hetero alkyl, $C_1$-$C_6$halo alkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, $—NO_2$, $—R^7$, $—OR^8$, $—C(O)R^8$, $—OC(O)R^8$, $—C(O)OR^8$, $—N(R^9)_2$, $—P(O)(OR^8)_2$, $—OP(O)(OR^{10})_2$, $—P(O)(OR^{10})_2$, $—OP(O)(OR^{10})_2$, $—C(O)N(R^9)_2$, $—S(O)_2R^8$, $—S(O)R^8$, $—S(O)_2N(R^9)_2$, and $—NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, $—(O(CH_2)_m)_t—$, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, $—R^8$, $—OR^8$, $—N(R^9)_2$, $—P(O)(OR^8)_2$, $—OP(O)(OR^8)_2$, $—P(O)(OR^{10})_2$, and $—OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, $-LR^9$, $-LOR^9$, $—OLR^9$, $-LR^{10}$, $-LOR^{10}$, $—OLR^{10}$, $-LR^8$, $-LOR^8$, $—OLR^8$, $-LSR^8$, $-LSR^{10}$, $-LC(O)R^8$, $—OLC(O)R^8$, $-LC(O)OR^8$, $-LC(O)R^{10}$, $-LOC(O)OR^8$, $-LC(O)NR^9R^{11}$, $-LC(O)NR^9R^8$, $-LN(R^9)_2$, $-LNR^9R^8$, $-LNR^9R^{10}$, $-LC(O)N(R^9)_2$, $-LS(O)_2R^8$, $-LS(O)R^8$, $-LC(O)NR^8OH$, $-LNR^9C(O)R^8$, $-LNR^9C(O)OR^8$, $-LS(O)_2N(R^9)_2$, $—OLS(O)_2N(R^9)_2$, $-LNR^9S(O)_2R^8$, $-LC(O)NR^9LN(R^9)_2$, $-LP(O)(OR^8)_2$, $-LOP(O)(OR^8)_2$, $-LP(O)(OR^{10})_2$ and $—OLP(O)(OR^{10})_2$;

each $R^8$ is independently selected from H, $—CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$C(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)CO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH{=}CHCO_2R^8$, —$C({=}NH)$—$N(R^9)_2$, and —$(CH_2)_n NHC(O)R^8$; or two adjacent $R^A$ substituents form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain aspects compounds of Formula (I) or Formula (II), or pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (III), Formula (III)

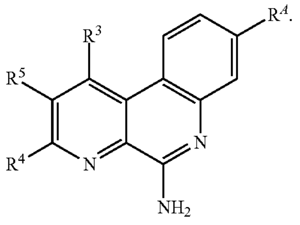

In certain aspects compounds of Formula (I)-(III), or pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (IV), Formula (IV)

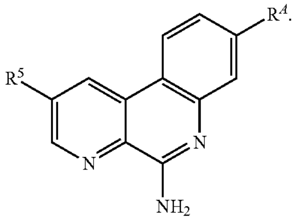

In certain aspects of compounds of Formulas (I)-(IV), $R^4$ and $R^5$, when present, are independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)OR^7$, —$(CH_2)R^7$, -$LR^8$, -$LR^{10}$, —$OLR^8$, —$OLR^{10}$, $C_1$-$C_6$ alkyl, $C_1$-$C_6$hetero alkyl, $C_1$-$C_6$halo alkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ and $R^5$ are each optionally substituted with 1 to 3 substituents independently selected from halogen, —CN, ═O, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$, and wherein the aryl and heteroaryl groups of $R^4$ and $R^5$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$.

In certain aspects compounds of Formula (I) or Formula (II), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (V), Formula (V)

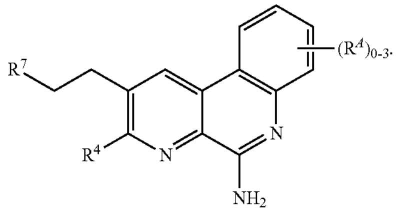

In certain aspects of compounds of Formulas (V), $R^4$ is selected from H, halogen, —C(O)$OR^7$, —C(O)$R^7$, —C(O)N($R^{11}R^{12}$), —N($R^{11}R^{12}$), —N$(R^9)_2$, —NHN$(R^9)_2$, —$SR^7$, —$(CH_2)OR^7$, —$(CH_2)R^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$hetero alkyl, $C_1$-$C_6$halo alkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ are each optionally substituted with 1 to 3 substituents independently selected from halogen, —CN, =O, —$NO_2$, —$R^7$, —$OR^8$, —C(O)$R^8$, —OC(O)$R^8$, —C(O)$OR^8$, —N$(R^9)_2$, —P(O)$(OR^8)_2$, —OP(O)$(OR^8)_2$, —P(O)$(OR^{10})_2$, —OP(O)$(OR^{10})_2$, —C(O)N$(R^9)_2$, —Si$(R^8)_3$, —$S(O)_2R^8$, —S(O)$R^8$, —$S(O)_2N(R^9)_2$, and —$NR^9S(O)_2R^8$, and wherein the aryl and heteroaryl groups of $R^4$ are each optionally substituted with 1 to 3 substituents independently selected from halogen, —CN, —$R^7$, —$OR^8$, —C(O)$R^8$, —OC(O)$R^8$, —C(O)$OR^8$, —N$(R^9)_2$, —P(O)$(OR^8)_2$, —OP(O)$(OR^8)_2$, —P(O)$(OR^{10})_2$, —OP(O)$(OR^{10})_2$, —C(O)N$(R^9)_2$, —Si$(R^8)_3$, —$S(O)_2R^8$, —S(O)$R^8$, —$S(O)_2N(R^9)_2$, and —$NR^9S(O)_2R^8$.

In certain aspects of compounds of Formulas (I)-(V), $R^7$ is selected from H, $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups and each $R^{13}$ is independently selected from halogen —CN, =O, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -LC(O)$R^8$, —OLC(O)$R^8$, -LC(O)$OR^8$, -LC(O)$R^{10}$, -LOC(O)$OR^8$, -LC(O)$NR^9R^{11}$, -LC(O)$NR^9R^8$, -LN$(R^9)_2$, -$LNR^9R^8$, -$LNR^9R^{10}$, -LC(O)N$(R^9)_2$, -$LS(O)_2R^8$, -LS(O)$R^8$, -LC(O)$NR^8$OH, -$LNR^9$C(O)$R^8$, -$LNR^9$C(O)$OR^8$, -LC(=N—$OR^8$)$R^8$, -LC(=NH)—$NHOR^8$, —NHC(=NH)$NH_2$, -$LS(O)_2N(R^9)_2$, —$OLS(O)_2N(R^9)_2$, -$LNR^9S(O)_2R^8$, -LC(O)$NR^9$LN$(R^9)_2$, -LP(O)$(OR^8)_2$, -LOP(O)$(OR^8)_2$, -LP(O)$(OR^{10})_2$ and —OLP(O)$(OR^{10})_2$.

In certain aspects of compounds of Formulas (I)-(V), $R^7$ is an aryl or heteroaryl group optionally substituted with 1 to 3 $R^{13}$ groups and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -LC(O)$R^8$, —OLC(O)$R^8$, -LC(O)$OR^8$, -LC(O)$R^{10}$, -LOC(O)$OR^8$, -LC(O)$NR^9R^{11}$, -LC(O)$NR^9R^8$, -LN$(R^9)_2$, -$LNR^9R^8$, -$LNR^9R^{10}$, -LC(O)N$(R^9)_2$, -$LS(O)_2R^8$, -LS(O)$R^8$, -LC(O)$NR^8$OH, -$LNR^9$C(O)$R^8$, -$LNR^9$C(O)$OR^8$, -LC(=N—$OR^8$)$R^8$, -LC(=NH)—$NHOR^8$, —NHC(=NH)$NH_2$, -$LS(O)_2N(R^9)_2$, —$OLS(O)_2N(R^9)_2$, -$LNR^9S(O)_2R^8$, -LC(O)$NR^9$LN$(R^9)_2$, -LP(O)$(OR^8)_2$, -LOP(O)$(OR^8)_2$, -LP(O)$(OR^{10})_2$ and —OLP(O)$(OR^{10})_2$.

In certain aspects of compounds of Formulas (I)-(V), $R^7$ is selected from H, $C_1$-$C_6$alkyl, $C_3$-$C_8$cycloalkyl, and $C_3$-$C_8$heterocycloalkyl, and the $C_1$-$C_6$alkyl, $C_3$-$C_8$cycloalkyl, and $C_3$-$C_8$heterocycloalkyl groups are each optionally substituted with 1-3 $R^{13}$ groups and each $R^{13}$ is independently selected from halogen, $C_1$-$C_6$haloalkyl, =O, $LR^8$, $LR^9$, $OLR^8$ and -$LOR^8$.

In certain aspects of compounds of Formulas (I)-(V), $R^7$ is an aryl or heteroaryl group optionally substituted with 1-3 $R^{13}$ groups.

In certain aspects of compounds of Formulas (I)-(V), each $R^{13}$ is independently selected from halogen, $C_1$-$C_6$haloalkyl, $LR^8$, $OLR^8$, $LR^9$, $OLR^9$, $LR^{10}$, $OLR^{10}$ and -$LOR^8$.

In certain aspects compounds of Formula (I), Formula (II) or Formula (V) have a structure of Formula (VI), Formula (VI)

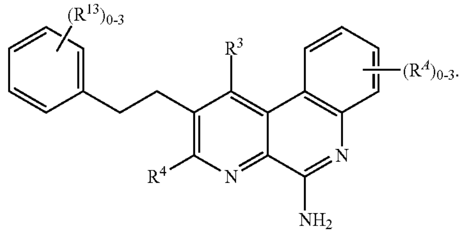

or pharmaceutically acceptable salts, pharmaceutically acceptable solvates (e.g. hydrates), the N-oxide derivatives, prodrug derivatives, protected derivatives, individual isomers and mixture of isomers thereof.

In certain aspects compounds of Formulas (I)-(VI) have a structure of Formula (VII), Formula (VII)

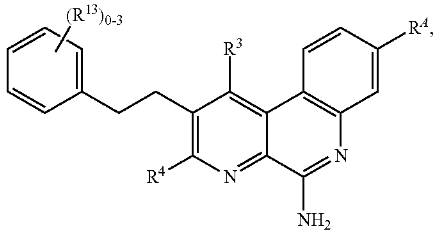

or pharmaceutically acceptable salts, pharmaceutically acceptable solvates (e.g. hydrates), the N-oxide derivatives, prodrug derivatives, protected derivatives, individual isomers and mixture of isomers thereof.

In certain aspects of compounds of Formulas (I)-(VII), $R^3$ is H.

In certain aspects of compounds of Formula (VI) and Formula (VII), $R^3$ is H and $R^4$ is selected from H, halogen, —C(O)$OR^7$, —C(O)$R^7$, —C(O)N($R^{11}R^{12}$), —N($R^{11}R^{12}$), —N$(R^9)_2$, —NHN$(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ are each optionally substituted with 1 to 3 substituents independently selected from halogen, —CN, =O, —$NO_2$, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —Si($R^8$)$_3$, —S(O)$_2R^8$, —S(O)$R^8$, —S(O)$_2$N($R^9$)$_2$, and —$NR^9$S(O)$_2R^8$, and wherein the aryl and heteroaryl groups of $R^4$ are each optionally substituted with 1 to 3 substituents independently selected from halogen, —CN, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^{10}$)$_2$, —P(O)($OR^{10}$)$_2$, —OP(O)($OR^{10}$)$_2$, —C(O)N($R^9$)$_2$, —Si($R^8$)$_3$, —S(O)$_2R^8$, —S(O)$R^8$, —S(O)$_2$N($R^9$)$_2$, and —$NR^9$S(O)$_2R^8$.

In certain aspects of compounds of Formulas (I)-(VII), $R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups.

In certain aspects of compounds of Formulas (I)-(VII), each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -LC(O)$R^8$, —OLC(O)$R^8$, -LC(O)$OR^8$, -LC(O)$R^{10}$, -LOC(O)$OR^8$, -LC(O)$NR^9R^{11}$, -LC(O)$NR^9R^8$, -LN($R^9$)$_2$, -$LNR^9R^8$, -$LNR^9R^{10}$, -LC(O)N($R^9$)$_2$, -LS(O)$_2R^8$, -LS(O)$R^8$, -LC(O)$NR^8$OH, -$LNR^9$C(O)$R^8$, -$LNR^9$C(O)$OR^8$, -LS(O)$_2$N($R^9$)$_2$, —OLS(O)$_2$N($R^9$)$_2$, -$LNR^9$S(O)$_2R^8$, -LP(O)($OR^8$)$_2$, -LC(O)$NR^9$LN($R^9$)$_2$, -LOP(O)($OR^8$)$_2$, -LP(O)($OR^{10}$)$_2$ and —OLP(O)($OR^{10}$)$_2$; and each L is independently selected from a bond, —(O($CH_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —N($R^9$)$_2$, —P(O)($OR^8$)$_2$, —OP(O)($OR^8$)$_2$, —P(O)($OR^{10}$)$_2$, and —OP(O)($OR^{10}$)$_2$.

In certain aspects of compounds of Formulas (I)-(VII), each $R^{13}$ is independently selected from halogen, $C_1$-$C_6$haloalkyl, $LR^8$, $LOR^{10}$, $LR^8$, -$LOR^8$, $LR^9$, $OLR^9$, -$LSR^8$, $LSR^{10}$, -LC(O)$OR^8$, -LN($R^9$)$_2$, -LC(O)N($R^9$)$_2$, -LS(O)$_2R^8$, -LS(O)$R^8$, -LP(O)($OR^8$)$_2$, —OLP(O)($OR^8$)$_2$, -LP(O)(O)($OR^{10}$)$_2$ and —OLP(O)($OR^{10}$)$_2$.

In certain aspects of compounds of Formulas (I)-(VII), each $R^{13}$ is independently selected from halogen, $C_1$-$C_6$haloalkyl, $LR^8$, $OLR^8$, $LR^9$, $OLR^9$, $LR^{10}$, $OLR^{10}$ and -$LOR^8$.

In certain aspects of compounds of Formulas (I)-(VII), each L is independently selected from a bond, —(O($CH_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —N($R^9$)$_2$, —P(O)($OR^8$)$_2$, —OP(O)($OR^8$)$_2$, —P(O)($OR^{10}$)$_2$, and —OP(O)($OR^{10}$)$_2$.

In certain aspects of compounds of Formulas (I)-(VII), each L is independently selected from a bond, —(O($CH_2$)$_m$)$_t$— and $C_1$-$C_6$alkyl, wherein the $C_1$-$C_6$alkyl of L is optionally substituted with 1 to 4 substituents independently selected from halogen, —$R^8$, —$OR^8$, —N($R^9$)$_2$, —P(O)($OR^8$)$_2$, —OP(O)($OR^8$)$_2$, —P(O)($OR^{10}$)$_2$, and —OP(O)($OR^{10}$)$_2$.

In certain aspects of compounds of Formulas (I)-(VII), $R^4$ is selected from H, halogen and $C_1$-$C_6$alkyl, wherein the $C_1$-$C_6$alkyl of $R^4$ are each optionally substituted with 1 to 3 substituents independently selected from halogen, —CN, —$NO_2$, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —S(O)$_2R^8$, —S(O)$R^8$, —S(O)$_2$N($R^9$)$_2$, and —$NR^9$S(O)$_2R^8$.

In certain aspects of compounds of Formulas (I)-(VII), each $R^8$ is independently selected from H, —CH($R^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —C(O)$R^{11}$, —OC(O)$R^{11}$, —C(O)N($R^9$)$_2$, —C(O)$OR^{11}$, —$NR^9$C(O)$R^{11}$, —$NR^9R^{10}$, —$NR^{11}R^{12}$, —N($R^9$)$_2$, —$OR^9$, —$OR^{10}$, —C(O)$NR^{11}R^{12}$, —C(O)$NR^{11}$OH, —S(O)$_2R^{11}$, —S(O)$_2NR^{11}R^{12}$, —$NR^{11}$S(O)$_2R^{11}$, —P(O)($OR^{11}$)$_2$, and —OP(O)($OR^{11}$)$_2$.

In certain aspects of compounds of Formulas (I)-(VII), each $R^9$ is independently selected from H, —C(O)$R^8$, —C(O)$OR^8$, —C(O)$R^{10}$, —C(O)$OR^{10}$, —S(O)$_2R^{10}$, $C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —C(O)$R^{11}$, —OC(O)$R^{11}$, —C(O)$OR^{11}$, —$NR^{11}R^{12}$, —C(O)$NR^{11}R^{12}$, —C(O)$NR^{11}$OH, —S(O)$_2R^{11}$, —S(O)$R^{11}$, —S(O)$_2NR^{11}R^{12}$, —$NR^{11}$S(O)$_2R^{11}$, —P(O)($OR^{11}$)$_2$, and —OP(O)($OR^{11}$)$_2$.

In certain aspects of compounds of Formulas (I)-(VII), each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —N($R^9$)$_2$, —$NR^9$C(O)$R^8$, —$NR^9CO_2R^8$, —$CO_2R^8$, —C(O)$R^8$ and —C(O)N($R^9$)$_2$.

In certain aspects of compounds of Formulas (I)-(VII), $R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —C(O)$R^8$, —C(O)$R^8$, —C(O)$OR^8$, —N($R^9$)$_2$, —$NR^8$C(O)$R^8$, —$NR^8$C(O)$OR^8$, —C(O)N($R^9$)$_2$, $C_3$-$C_8$heterocycloalkyl, —S(O)$_2R^8$, —S(O)$_2$N($R^9$)$_2$, —$NR^9$S(O)$_2R^8$, $C_1$-$C_6$haloalkyl and $C_1$-$C_6$haloalkoxy, or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S.

In certain aspects of compounds of Formulas (I)-(VII), each $R^A$ is independently selected from —$R^8$, —$R^7$, —$OR^7$, —$OR^8$, —$R^{10}$, —$OR^{10}$, —$SR^8$, —$NO_2$, —CN, —N($R^9$)$_2$, —$NR^9$C(O)$R^8$, —$NR^9$C(S)$R^8$, —$NR^9$C(O)N($R^9$)$_2$, —$NR^9$C(S)N($R^9$)$_2$, —$NR^9CO_2R^8$, —$NR^9NR^9$C(O)$R^8$, —$NR^9NR^9$C(O)N($R^9$)$_2$, —$NR^9NR^9CO_2R^8$, —C(O)C(O)$R^8$, —C(O)$CH_2$C(O)$R^8$, —$CO_2R^8$, —($CH_2$)$CO_2R^8$, —C(O)$R^8$, —C(S)$R^8$, —C(O)N($R^9$)$_2$, —C(S)N($R^9$)$_2$, —OC(O)N $(R^9)_2$, —OC(O)$R^8$, —C(O)N(O$R^8$)$R^8$, —C(NO$R^8$)$R^8$, —S(O)$_2R^8$, —S(O)$_3R^8$, —SO$_2$N($R^9$)$_2$, —S(O)$R^8$, —N$R^9$SO$_2$N($R^9$)$_2$, —N$R^9$SO$_2R^8$, —P(O)(O$R^8$)$_2$, —OP(O)(O$R^8$)$_2$, —P(O)(O$R^{10}$)$_2$, —OP(O)(O$R^{10}$)$_2$, —N(O$R^8$)$R^8$, —CH═CHCO$_2R^8$, —C(═NH)—N($R^9$)$_2$, and —(CH$_2$)$_n$NHC(O)$R^8$.

In certain aspects of compounds of Formulas (I)-(VII), each $R^{13}$ is selected from -L$R^9$, -LO$R^9$, —OL$R^9$, -L$R^{10}$, -LO$R^{10}$, —OL$R^{10}$, -L$R^8$, -LO$R^8$, —OL$R^8$, -LS$R^8$, -LS$R^{10}$, -LC(O)$R^8$, —OLC(O)$R^8$, -LC(O)O$R^8$, -LC(O)$R^{10}$, -LOC(O)O$R^8$, -LC(O)N$R^9R^{11}$, -LC(O)N$R^9R^8$, -LN($R^9$)$_2$, -LN$R^9R^8$, -LN$R^9R^{10}$, -LC(O)N($R^9$)$_2$, -LS(O)$_2R^8$, -LS(O)$R^8$, -LC(O)N$R^8$OH, -LN$R^9$C(O)$R^8$, -LN$R^9$C(O)O$R^8$, -LS(O)$_2$N($R^9$)$_2$, —OLS(O)$_2$N($R^9$)$_2$, -LN$R^9$S(O)$_2R^8$, -LC(O)N$R^9$LN($R^9$)$_2$, -LP(O)(O$R^8$)$_2$, -LOP(O)(O$R^8$)$_2$, -LP(O)(O$R^{10}$)$_2$ and —OLP(O)(O$R^{10}$)$_2$; and each $R^A$ is independently selected from —$R^7$, —O$R^7$, —$R^8$, —O$R^8$, —$R^{10}$, —O$R^{10}$, —S$R^8$, —N($R^9$)$_2$, —S(O)$_2R^8$, —S(O)$_3R^8$, —SO$_2$N($R^9$)$_2$, —S(O)$R^8$, —N$R^9$SO$_2$N(R)$_2$, —CH═CHCO$_2R^8$, (CH$_2$)$_n$CO$_2R^8$, —N$R^9$SO$_2R^8$, —P(O)(O$R^8$)$_2$, —OP(O)(O$R^8$)$_2$, —P(O)(O$R^{10}$)$_2$, and —OP(O)(O$R^{10}$)$_2$.

In certain aspects of compounds of Formulas (I)-(VII), each L is independently selected from a —(O(CH$_2$)$_m$)$_t$—, and $C_1$-$C_6$alkyl, wherein the $C_1$-$C_6$alkyl of L is optionally substituted with 1 to 4 substituents independently selected from halogen, —$R^8$, —O$R^8$, —N($R^9$)$_2$, —P(O)(O$R^8$)$_2$, —OP(O)(O$R^8$)$_2$, —P(O)(O$R^{10}$)$_2$, and —OP(O)(O$R^{10}$)$_2$.

In certain aspects of compounds of Formulas (I)-(VII), $R^A$ is H or $C_1$-$C_6$alkyl.

In certain aspects of compounds of Formulas (I)-(VII), $R^A$ is H, —CH$_3$ or —CH$_2$CH$_3$; and each $R^{13}$ is independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$ and $C_2$-$C_6$ alkyl substituted with 1-3 substituents selected from —OH, —CH$_3$, —COOH, —COOCH$_3$, cyclopropyl, —O(CH$_2$)$_{2-4}$—COOH, —O(CH$_2$)$_{2-4}$(PO$_3$H$_2$), and —COOCH$_2$CH$_3$.

In certain aspects of compounds of Formulas (I)-(VII), each $R^8$ is independently selected from H, —CH($R^{10}$)$_2$, $C_1$-$C_8$alkyl, $C_2$-$C_8$ alkene, $C_2$-$C_8$ alkyne, $C_1$-$C_6$haloalkyl, $C_1$-$C_6$alkoxy, $C_1$-$C_6$heteroalkyl, $C_3$-$C_8$ cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$ alkyne, $C_1$-$C_6$hetero alkyl, $C_1$-$C_6$halo alkyl, $C_1$-$C_6$ alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —O$R^{11}$, —S$R^{11}$, —C(O)$R^{11}$, —C(O)$R^{11}$, —C(O)N($R^9$)$_2$, —C(O)O$R^{11}$, —N$R^9$C(O)$R^{11}$, —N$R^9R^{10}$, —N$R^{11}R^{12}$, —N($R^9$)$_2$, —O$R^9$, —O$R^{10}$, —O$R^{10}$, —C(O)N$R^{11}R^{12}$, —C(O)N$R^{11}$OH, —S(O)$_2R^{11}$, —S(O)$R^{11}$, —S(O)$_2$N$R^{11}R^{12}$, —N$R^{11}$S(O)$_2R^{11}$, —P(O)(O$R^{11}$)$_2$, and —OP(O)(O$R^{11}$)$_2$.

In certain aspects of compounds of Formulas (I)-(VII), each $R^8$ is independently selected from H, —CH($R^{10}$)$_2$ or $C_1$-$C_8$alkyl, wherein the $C_1$-$C_8$alkyl of $R^8$ is optionally substituted with 1 to 3 substituents independently selected from —CN, $R^{11}$, —O$R^{11}$, —S$R^{11}$, —C(O)$R^{11}$, —OC(O)$R^{11}$, —C(O)N($R^9$)$_2$, —C(O)O$R^{11}$, —N$R^9$C(O)$R^{11}$, —N$R^9R^{10}$, —N$R^{11}R^{12}$, —N($R^9$)$_2$, —O$R^9$, —O$R^{10}$, —C(O)N$R^{11}R^{12}$, —C(O)N$R^{11}$OH, —S(O)$_2R^{11}$, S(O)$R^{11}$, —S(O)$_2$N$R^{11}R^{12}$, —N$R^{11}$S(O)$_2R^{11}$, —P(O)(O$R^{11}$)$_2$, and —OP(O)(O$R^{11}$)$_2$.

In certain aspects of compounds of Formulas (I)-(VII), $R^8$ is H, $C_1$-$C_6$alkyl or $C_1$-$C_6$haloalkyl. In certain aspects of compounds of Formulas (I)-(VII), $R^9$ is H or $C_1$-$C_6$alkyl. In certain aspects of compounds of Formulas (I)-(VII), $R^A$ is H or —CH$_3$.

In certain aspects of compounds of Formulas (I)-(VII), $R^4$ is H.

In certain aspects of compounds of Formulas (I)-(VII), n is, independently at each occurrence, 0, 1, 2 or 3. In certain aspects of compounds of Formulas (I)-(VII), each m is independently selected from 1, 2 or 3 and in certain aspects of compounds of Formulas (I)-(VII), t is 1, 2, 3, 4 or 5.

In certain aspects of compounds of Formulas (I)-(VII), $R^4$, $R^A$ and $R^{13}$ are independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$, $C_2$-$C_6$ alkyl substituted with 1-3 substituents selected from —OH, —CH$_3$, cyclopropyl, —O(CH$_2$)$_{2-4}$—COOH, —O(CH$_2$)$_{2-4}$(PO$_3$H$_2$), —COOH, COOCH$_3$, and —COOCH$_2$CH$_3$.

In certain embodiments of compounds of Formula (I)-Formula (VII), $R^7$ is a phenyl ring substituted with one to three $R^{13}$ groups. In other embodiments of compounds of Formulas (I)-(VII), $R^7$ is a phenyl ring substituted with two $R^{13}$ groups, and the $R^{13}$ groups are selected from the group consisting of —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, —CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$, $C_2$-$C_6$ alkyl substituted with 1-3 substituents selected from —OH, —CH$_3$, cyclopropyl, —O(CH$_2$)$_{2-4}$—COOH, —O(CH$_2$)$_{2-4}$(PO$_3$H$_2$), —COOH, —COOCH$_3$, and —COOCH$_2$CH$_3$.

In certain aspects of the compounds of Formula (I)-(VII), the compound is selected from: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; 2-(2,4-dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine, and 2-(4-methoxyphenethyl)-8-methylbenzo[f][1,7]naphthyridin-5-amine.

In certain aspects the compound of Formulas (I) is 3-chloro-2-methylbenzo[f][1,7]naphthyridin-5-amine; 2-methylbenzo[f][1,7]naphthyridin-5-amine; 2-(ethoxymethyl)benzo[f][1,7]naphthyridin-5-amine; (E)-2-(2-cyclopropylvinyl)benzo[f][1,7]naphthyridin-5-amine; (E)-2-(pent-1-enyl)benzo[f][1,7]naphthyridin-5-amine; 4-(5-aminobenzo[f][1,7]naphthyridin-2-yl)-2-methylbut-3-yn-2-ol; 2-pentylbenzo[f][1,7]naphthyridin-5-amine; (E)-2-(prop-1-enyl)benzo[f][1,7]naphthyridin-5-amine; (E)-2-(3-phenylprop-1-enyl)benzo[f][1,7]naphthyridin-5-amine; 2-(2-cyclopropylethyl)benzo[f][1,7]naphthyridin-5-amine; 4-(5-aminobenzo[f][1,7]naphthyridin-2-yl)-2-methylbutan-2-ol; 2-propylbenzo[f][1,7]naphthyridin-5-amine; 2-(3-phenylpropyl)benzo[f][1,7]naphthyridin-5-amine; 2-ethylbenzo[f][1,7]naphthyridin-5-amine; 2-(2-methylprop-1-enyl)benzo[f][1,7]naphthyridin-5-amine; 2-isobutylbenzo[f][1,7]naphthyridin-5-amine; (E)-2-(2,4-difluorostyryl)benzo[f][1,7]naphthyridin-5-amine; (E)-2-(hex-1-enyl)benzo[f][1,7]naphthyridin-5-amine; (E)-2-(2-cyclohexylvinyl)benzo[f][1,7]naphthyridin-5-amine; E)-2-(3-(trifluoromethyl)styryl)benzo[f][1,7]naphthyridin-5-amine; (E)-2-(3- methoxystyryl)benzo[f][1,7]naphthyridin-5-amine; 8-methyl-2-vinylbenzo[f][1,7]naphthyridin-5-amine; (E)-8-methyl-2-styrylbenzo[f][1,7]naphthyridin-5-amine; 2-(2-cyclohexylethyl)benzo[f][1,7]naphthyridin-5-amine; 2-fluorobenzo[f][1,7]naphthyridin-5-amine; 2-(3-(trifluoromethyl)phenethyl)benzo[f][1,7]naphthyridin-5-amine; 2-(2,4-difluorophenethyl)benzo[f][1,7]naphthyridin-5-amine; 2-(3-methoxyphenethyl)benzo[f][1,7]naphthyridin-5-amine; 2-hexylbenzo[f][1,7]naphthyridin-5-amine; 2-ethyl-8-methylbenzo[f][1,7]naphthyridin-5-amine; 8-methylbenzo[f][1,7]naphthyridin-5-amine; 8-methyl-2-phenethylbenzo[f][1,7]naphthyridin-5-amine; methyl 5-aminobenzo[f][1,7]naphthyridine-3-carboxylate; 5-amino-N-methylbenzo[f][1,7]naphthyridine-3-carboxamide; (5-aminobenzo[f][1,7]naphthyridin-3-yl)methanol; 8-phenylbenzo[f][1,7]naphthyridin-5-amine; 3-(ethoxymethyl)benzo[f][1,7]naphthyridin-5-amine; benzo[f][1,7]naphthyridine-3,5-diamine; benzo[f][1,7]naphthyridin-5-amine; methyl 5-aminobenzo[f][1,7]naphthyridine-8-carboxylate; 5-aminobenzo[f][1,7]naphthyridine-8-carboxylic acid; ethyl 5-aminobenzo[f][1,7]naphthyridine-8-carboxylate; (5-aminobenzo[f][1,7]naphthyridin-8-yl)methanol; 5-aminobenzo[f][1,7]naphthyridine-3-carboxylic acid; 5-aminobenzo[f][1,7]naphthyridine-3-carbaldehyde; 2-(o-tolylethynyl)benzo[f][1,7]naphthyridin-5-amine; 2-(m-tolylethynyl)benzo[f][1,7]naphthyridin-5-amine; 2-(p-tolylethynyl)benzo[f][1,7]naphthyridin-5-amine; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine; 3-chloro-2-(ethoxymethyl)benzo[f][1,7]naphthyridin-5-amine; 9-chlorobenzo[f][1,7]naphthyridin-5-amine; 8-chlorobenzo[f][1,7]naphthyridin-5-amine; 9-methylbenzo[f][1,7]naphthyridin-5-amine; 10-methylbenzo[f][1,7]naphthyridin-5-amine; ethyl 5-aminobenzo[f][1,7]naphthyridine-9-carboxylate; 5-aminobenzo[f][1,7]naphthyridine-9-carboxylic acid; 8-methoxybenzo[f][1,7]naphthyridin-5-amine; 7-fluorobenzo[f][1,7]naphthyridin-5-amine; 8-(methylsulfonyl)benzo[f][1,7]naphthyridin-5-amine; 8-(trifluoromethyl)benzo[f][1,7]naphthyridin-5-amine; 8-fluorobenzo[f][1,7]naphthyridin-5-amine; 3-methoxybenzo[f][1,7]naphthyridin-5-amine; 3-butoxybenzo[f][1,7]naphthyridin-5-amine; 3-(benzyloxy)benzo[f][1,7]naphthyridin-5-amine; 3-methylbenzo[f][1,7]naphthyridin-5-amine; 3-chlorobenzo[f][1,7]naphthyridin-5-amine; $N^3$,$N^3$-dimethylbenzo[f][1,7]naphthyridine-3,5-diamine; $N^3$-butylbenzo[f][1,7]naphthyridine-3,5-diamine; 3-vinylbenzo[f][1,7]naphthyridin-5-amine; 3-ethylbenzo[f][1,7]naphthyridin-5-amine; 3-fluorobenzo[f][1,7]naphthyridin-5-amine; 2-(trifluoromethyl)benzo[f][1,7]naphthyridin-5-amine; 2-methoxybenzo[f][1,7]naphthyridin-5-amine; 2-(benzyloxy)benzo[f][1,7]naphthyridin-5-amine; 2-vinylbenzo[f][1,7]naphthyridin-5-amine; 2-phenylbenzo[f][1,7]naphthyridin-5-amine; (E)-2-styrylbenzo[f][1,7]naphthyridin-5-amine; 2-phenethylbenzo[f][1,7]naphthyridin-5-amine; (E)-2-(3-methoxyprop-1-enyl)benzo[f][1,7]naphthyridin-5-amine; 2-(3-methoxypropyl)benzo[f][1,7]naphthyridin-5-amine; 2-(prop-1-en-2-yl)benzo[f][1,7]naphthyridin-5-amine; 2-isopropylbenzo[f][1,7]naphthyridin-5-amine; 1-methylbenzo[f][1,7]naphthyridin-5-amine; pyrido[3,2-f][1,7]naphthyridin-6-amine; 8-methyl-2-(naphthalen-2-ylethynyl)benzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 8-methyl-2-(naphthalen-1-ylethynyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(trifluoromethyl)benzo[f][1,7]naphthyridin-5-amine; 2-tert-butoxybenzo[f][1,7]naphthyridin-5-amine; 5-aminobenzo[f][1,7]naphthyridin-2-ol; 2-((4-butylphenyl)ethynyl)benzo[f][1,7]naphthyridin-5-amine; 2-(4-butylphenethyl)benzo[f][1,7]naphthyridin-5-amine; 2-(2-(6-methoxynaphthalen-2-yl)ethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; (Z)-2-(2-(biphenyl-4-yl)vinyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 2-(4-(2-(tert-butyldimethylsilyloxy)ethoxy)phenethyl)-8-methylbenzo[f][1,7]naphthyridin-5-amine; 2-(4-butoxy-2-methylphenethyl)-N-butyl-8-methylbenzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 2-(4-(2-(tert-butyldimethylsilyloxy)ethoxy)-2-methylphenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; diethyl 3-(2-(4-(2-(2-hydroxyethoxy)ethoxy)-2-methylphenethyl)-8-methylbenzo[f][1,7]naphthyridin-5-ylamino)propylphosphonate; (E)-N-(4-(2-(5-aminobenzo[f][1,7]naphthyridin-2-yl)vinyl)phenyl)acetamide; N-(4-(2-(5-amino-8-methylbenzo[f][1,7]naphthyridin-2-yl)ethyl)phenyl)acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 2-(4-(2-(5-amino-3-chloro-8-methylbenzo[f][1,7]naphthyridin-2-yl)ethyl)-3-methylbenzamido)acetic acid; (S)-2-(4-(2-(5-amino-3-chloro-8-methylbenzo[f][1,7]naphthyridin-2-yl)ethyl)-3-methylbenzamido)-4-methylpentanoic acid; 4-(2-(5-amino- 3-chloro-8-methylbenzo[f][1,7]naphthyridin-2-yl)ethyl)-N-(2-(dimethylamino)ethyl)-N,3-dimethylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; 2-phenethylbenzo[f][1,7]naphthyridin-5-amine; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 2-(4-cyclobutoxyphenethyl)-8-methylbenzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 8-bromo-3-methoxybenzo[f][1,7]naphthyridin-5-amine; 2-((tert-butyldimethylsilyl)ethynyl)benzo[f][1,7]naphthyridin-5-amine; 2-((2-fluorophenyl)ethynyl)benzo[f][1,7]naphthyridin-5-amine; 2-((3-fluorophenyl)ethynyl)benzo[f][1,7]naphthyridin-5-amine; 2-((4-fluorophenyl)ethynyl)benzo[f][1,7]naphthyridin-5-amine; 2-(thiophen-3-ylethynyl)benzo[f][1,7]naphthyridin-5-amine; 2-ethynylbenzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; ethyl 5-aminobenzo[f][1,7]naphthyridine-2-carboxylate; ethyl 5-amino-8-methylbenzo[f][1,7]naphthyridine-2-carboxylate; (5-aminobenzo[f][1,7]naphthyridin-2-yl)methanol; 2-(3,4-dimethylphenethyl)benzo[f][1,7]naphthyridin-5-amine; 1-chloro-8-methylbenzo[f][1,7]naphthyridin-5-amine; 8-methyl-1-(3-phenylpropyl)benzo[f][1,7]naphthyridin-5-amine; (Z)-2-(2-(benzo[d][1,3]dioxol-5-yl)vinyl)-8-methylbenzo[f][1,7]naphthyridin-5-amine; (Z)-2-(4-methoxy-2-methylstyryl)-8-methylbenzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 8-methyl-2-(1-phenylvinyl)benzo[f][1,7]naphthyridin-5-amine; 8-methyl-2-(4-phenylbutyl)benzo[f][1,7]naphthyridin-5-amine; 8-methyl-2-(1-phenylethyl)benzo[f][1,7]naphthyridin-5-amine; 2-(2-(benzofuran-5-yl)ethyl)-8-methylbenzo[f][1,7]naphthyridin-5-amine; (Z)-2-(2-ethoxyvinyl)-8-methylbenzo[f][1,7]naphthyridin-5-amine; 2-(2-ethoxyethyl)-8-methylbenzo[f][1,7]naphthyridin-5-amine; 2-(chloromethyl)-8-methylbenzo[f][1,7]naphthyridin-5-amine; 8-methyl-2-(2-nitroethyl)benzo[f][1,7]naphthyridin-5-amine; diethyl 2-((5-amino-8-methylbenzo[f][1,7]naphthyridin-2-yl)methyl)malonate; 2-(isopropylsulfonyl)-8-methylbenzo[f][1,7]naphthyridin-5-amine; 2-((methoxymethoxy)methyl)-8-methylbenzo[f][1,7]naphthyridin-5-amine; 8-methyl-2-((methylamino)methyl)benzo[f][1,7]naphthyridin-5-amine; tert-butyl 5-amino-8-methylbenzo[f][1,7]naphthyridin-2-ylcarbamate; 8-methyl-2-((phenylamino)methyl)benzo[f][1,7]naphthyridin-5-amine; 2-(aminomethyl)-8-methylbenzo[f][1,7]naphthyridin-5-amine; 8-methyl-2-(pyrrolidin-1-ylmethyl)benzo[f][1,7]naphthyridin-5-amine; $N^2$-(2,4-dimethoxybenzyl)-8-methylbenzo[f][1,7]naphthyridine-2,5-diamine; $N^2$,$N^2$, 8-trimethylbenzo[f][1,7]naphthyridine-2,5-diamine; $N^2$, 8-dimethylbenzo[f][1,7]naphthyridine-2,5-diamine; 8-methyl-2-(pyrrolidin-1-yl)benzo[f][1,7]naphthyridin-5-amine; 2-(5-amino-8-methylbenzo[f][1,7]naphthyridin-2-yl)-1-phenylethanol; 2-(2-aminoethyl)-8-methylbenzo[f][1,7]naphthyridin-5-amine; 2-hydrazinyl-8-methylbenzo[f][1,7]naphthyridin-5-amine; 1-(5-amino-8-methylbenzo[f][1,7]naphthyridin-2-yl)-2-methylpropan-2-ol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 3-methyldibenzo[b,f][1,7]naphthyridin-6-amine; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; $N^3$,$N^5$-dibutylbenzo[f][1,7]naphthyridine-3,5-diamine; 8-(prop-1-en-2-yl)benzo[f][1,7]naphthyridin-5-amine; 5-aminobenzo[f][1,7]naphthyridine-8-carbonitrile; (E)-8-(3-methylbut-1-enyl)benzo[f][1,7]naphthyridin-5-amine; 8-(2-methylprop-1-enyl)benzo[f][1,7]naphthyridin-5-amine; (E)-8-(pent-1-enyl)benzo[f][1,7]naphthyridin-5-amine; (E)-8-styrylbenzo[f][1,7]naphthyridin-5-amine; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; methyl 5-amino-2-(4-methoxyphenethyl)benzo[f][1,7]naphthyridine-8-carboxylate; 8-nitrobenzo[f][1,7]naphthyridin-5-amine; 3-chloro-8-methylbenzo[f][1,7]naphthyridin-5-amine; methyl 5-amino-3-chlorobenzo[f][1,7]naphthyridine-8-carboxylate; methyl 5-amino-3-fluorobenzo[f][1,7]naphthyridine-8-carboxylate; 3-chloro-8-nitrobenzo[f][1,7]naphthyridin-5-amine; (5-amino-3-chlorobenzo[f][1,7]naphthyridin-8-yl)methanol; (5-amino-2-phenethylbenzo[f][1,7]naphthyridin-8-yl)methanol; 4-(2-(5-amino-8-fluorobenzo[f][1,7]naphthyridin-2-yl)ethyl)benzaldehyde; 2-(4-(2-(5-amino-8-fluorobenzo[f][1,7]naphthyridin-2-yl)ethyl)benzylamino)ethanol; 3-(4-(2-(5-amino-8-fluorobenzo[f][1,7]naphthyridin-2-yl)ethyl)$_b$enzylamino)propan-1-ol; 8-fluoro-2-(4-((2-methoxyethylamino)methyl)phenethyl)benzo[f][1,7]naphthyridin-5-amine; 8-((tert-butyldimethylsilyloxy)methyl)-2-(4-methoxy-2-methylphenethyl)benzo[f][1,7]naphthyridin-5-amine; (5-amino-2-(4-methoxy-2-methylphenethyl)benzo[f][1,7]naphthyridin-8-yl)methanol; 3-(2-(5-aminobenzo[f]

[1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 8-methyl-2-(2-(1-methyl-1H-imidazol-5-yl)ethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholino ethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-ethyl 3-(5-amino-2-(4-methoxy-2-methylphenethyl)benzo[f][1,7]naphthyridin-8-yl)acrylate; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; (5-aminobenzo[f][1,7]naphthyridin-8-yl)methanol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-phenethylbenzo[f][1,7]naphthyridin-8-yl)methanol; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; N-(4-(2-(5-amino-8-methylbenzo[f][1,7]naphthyridin-2-yl)ethyl)phenyl)acetamide; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5- amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-amino-8-methylbenzo[f][1,7]naphthyridin-2-yl)ethyl)-N-(2-aminoethyl)-3-methylbenzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(4-(2-(5-aminobenzo[f][1,7]naphthyridin-2-yl)ethyl)-3-methylphenoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; $N^1$-(1-(4-(2-(5-amino-8-methylbenzo[f][1,7]naphthyridin-2-yl)ethyl)phenyl)ethyl)-$N^2$,$N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2$,$N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-(2-(5-amino-8-methylbenzo[f][1,7]naphthyridin-2 yl)ethyl)phenyl)ethyl)pyrrolidin-3-ol; and 2-(4-(2-aminopropan-2-yl)phenethyl)-8-methylbenzo[f][1,7]naphthyridin-5-amine.

In certain aspects the compound of Formula (I) is 2-methylbenzo[f][1,7]naphthyridin-5-amine; 2-propylbenzo[f][1,7]naphthyridin-5-amine; 2-ethylbenzo[f][1,7]naphthyridin-5-amine; 2-(3-methoxyphenethyl)benzo[f][1,7]naphthyridin-5-amine; 8-methylbenzo[f][1,7]naphthyridin-5-amine, 8-methyl-2-phenethylbenzo[f][1,7]naphthyridin-5-amine; methyl-5-aminobenzo[f][1,7]naphthyridine-3-carboxylate; (5-aminobenzo[f][1,7]naphthyridin-3-yl)methanol; benzo[f][1,7]naphthyridin-5-amine; (5-aminobenzo[f][1,7]naphthyridin-8-yl)methanol; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine, 8-chlorobenzo[f][1,7]naphthyridin-5-amine; ethyl 5-aminobenzo[f][1,7]naphthyridine-9-carboxylate; 8-methoxybenzo[f][1,7]naphthyridin-5-amine; 8-(trifluoromethyl)benzo[f][1,7]naphthyridin-5-amine; 8-fluorobenzo[f][1,7]naphthyridin-5-amine; 3-methylbenzo[f][1,7]naphthyridin-5-amine; 3-fluorobenzo[f][1,7]naphthyridin-5-amine; 2-phenethylbenzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-(2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; N-(4-(2-(5-amino-8-methylbenzo[f][1,7]naphthyridin-2-yl)ethyl)phenyl)acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; (E)-8-(2-cyclopropylvinyl)-2-phenethylbenzo[f][1,7]naphthyridin-5- amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; (5-amino-2-phenethylbenzo[f][1,7]naphthyridin-8-yl)methanol; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4- methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(2-(4-(2-(5-aminobenzo[f][1,7]naphthyridin-2-yl)ethyl)-3-methylphenoxy)ethoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; $N^1$-(1-(4-(2-(5-amino-8-methylbenzo[f][1,7]naphthyridin-2-yl)ethyl)phenyl)ethyl)-$N^2$,$N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2$,$N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-(2-(5-amino-8-methylbenzo[f][1,7]naphthyridin-2 yl)ethyl)phenyl)ethyl)pyrrolidin-3-ol, and 2-(4-(2-aminopropan-2-yl)phenethyl)-8-methylbenzo[f][1,7]naphthyridin-5-amine.

The compounds of Formula (I), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^{2}H$, $^{3}H$, $^{11}C$, $^{14}C$, $^{15}N$, $^{17}O$, $^{18}O$, $^{35}S$, $^{18}F$, $^{36}Cl$ and $^{123}I$. Certain isotopic variations of the compounds provided herein and pharmaceutically acceptable salts thereof, for example, those in which a radioactive isotope such as $^{3}H$ or $^{14}C$ is incorporated, are useful in drug and/or substrate tissue distribution studies. In particular examples, $^{3}H$ and $^{14}C$ isotopes may be used for their ease of preparation and detectability. In other examples, substitution with isotopes such as $^{2}H$ may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

In some aspects, TLR7 agonists provided herein are compounds having the structure of Formula (VIII), and pharmaceutically acceptable salts, pharmaceutically acceptable solvates (e.g. hydrates), the N-oxide derivatives, prodrug derivatives, protected derivatives, individual isomers and mixture of isomers thereof:

Formula (VIII)

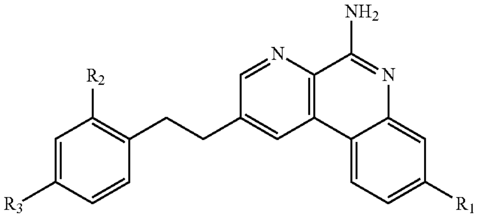

wherein:

$R^1$ is H, $C_1$-$C_6$alkyl, —$C(R^5)_2OH$, -$L^1R^5$, -$L^1R^6$, -$L^2R^5$, -$L^2R^6$, -$OL^2R^5$, or —$OL^2R^6$;

$L^1$ is —C(O)— or —O—;

$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;

each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;

$L^4$ is arylene or heteroarylene;

$R^2$ is H or $C_1$-$C_6$alkyl;

$R^3$ is selected from $C_1$-$C_4$alkyl, $L^3R^5$, $L^1R^5$, -$L^3R^7$, -$L^3L^4L^3R^7$, -$L^3L^4R^5$, -$L^3L^4L^3R^5$, —$OL^3R^5$, -$OL^3R^7$, -$OL^3L^4R^7$, -$OL^3L^4L^3R^7$, —$OR^8$, -$OL^3L^4R^5$, —$OL^3L^4L^3R^5$ and —$C(R^5)_2OH$;

each $R^4$ is independently selected from H and fluoro;

$R^5$ is —$P(O)(OR^9)_2$, $R^6$ is —$CF_2P(O)(OR^9)_2$ or —$C(O)OR^{10}$;

$R^7$ is —$CF_2P(O)(OR^9)_2$ or —$C(O)OR^{10}$;

$R^8$ is H or $C_1$-$C_4$alkyl;

each $R^9$ is independently selected from H and $C_1$-$C_6$alkyl;

$R^{10}$ is H or $C_1$-$C_4$alkyl;

each p is independently selected from 1, 2, 3, 4, 5 and 6, and q is 1, 2, 3 or 4;

with the proviso that when $R^3$ is $C_1$-$C_4$ alkyl or $OR^8$, $R^1$ is —$C(R^5)_2OH$, -$L^1R^5$, -$L^1R^6$, -$L^2R^5$, -$L^2R^6$, —$OL^2R^5$, or —$OL^2R^6$, wherein $R^6$ is —$CF_2P(O)(OR^9)_2$ and $R^7$ is —$CF_2P(O)(OR^9)_2$.

In certain aspects of the compounds of Formula (VIII), $R^1$ is $C_1$-$C_6$ alkyl, in other aspects $R^1$ is a methyl. In certain aspects, $R^1$ is H. In other aspects, $R^1$ is —$C(R^5)_2OH$, -$L^1R^5$, -$L^1R^6$, -$L^2R^5$, -$L^2R^6$, —$OL^2R^5$, or —$OL^2R^6$.

In certain aspects of the compounds of Formula (VIII), when $R^1$—$C(R^5)_2OH$, -$L^1R^5$, -$L^1R^6$, -$L^2R^5$, -$L^2R^6$, —$OL^2R^5$, or —$OL^2R^6$, then $R^3$ is —$OR^8$ or $C_1$-$C_6$ alkyl. In certain aspects, $R^1$ is —$C(R^5)_2OH$, -$L^1R^5$, -$L^1R^6$, -$L^2R^5$, -$L^2R^6$, —$OL^2R^5$, or —$OL^2R^6$, and $R^3$ is —OMe.

In some aspects of the compounds of Formula (VIII), $R^2$ is $C_1$-$C_6$alkyl. In certain aspects, $R^2$ is methyl.

In some aspects of the compounds of Formula (VIII), $R^3$ is selected from $C_1$-$C_4$ alkyl, -$L^3R^5$, -$L^1R^5$, -$L^3R^7$, -$L^3L^4L^3R^7$, -$L^3L^4R^5$, and -$L^3L^4L^3R^5$. In alternative aspects, $R^3$ is selected from —$OL^3R^5$, -$OL^3R^7$, -$OL^3L^4R^7$, -$OL^3L^4L^3R^7$, —$OR^8$, —$OL^3L^4R^5$, -$OL^3L^4L^3R^5$ and —$C(R^5)_2OH$. In certain aspects, $R^3$ is —$OL^3R^5$, wherein —$OL^3R^5$ is a group of the formula —$O(CH_2)_{1-5}P(O)(OR)_2$. In other aspects, $R^3$ is —$OL^3R^5$, wherein —$OL^3R^5$ is a group of the formula —$O(CH_2)_{1-5}CF_2P(O)(OR)_2$.

Where more than one $R^9$ is present, as in compounds comprising a —$P(O)(OR^9)_2$, moiety, the $R^9$ groups are the same or are different. In certain aspects of such compounds of Formula (VIII), $R^9$ is H at each occurrence. In other aspects, at least one $R^9$ is H and the other $R^9$ is $C_1$-$C_6$alkyl. In other aspects, at least one $R^9$ is H and the other $R^9$ is methyl. In other aspects, at least one $R^9$ is H and the other $R^9$ is ethyl. In other aspects of such compounds of Formula (VIII), each $R^9$ is $C_1$-$C_6$alkyl and in certain aspects, $R^9$ is methyl or ethyl, or a combination thereof In certain aspects of the compounds of Formula (VIII), $L^2$ and/or $L^3$ is a group of the formula —$((CR^4R^4)_pO)_q(CH_2)_p$—, and in certain aspects, this group is of the formula —$(CH_2CH_2O)_{1-3}(CH_2)_{1-3}$—.

In certain aspects of the compounds of Formula (VIII), $L^2$ is $C_1$-$C_6$ alkylene, while in other aspects $L^2$ is $C_1$-$C_6$ alkylene substituted with one to four fluoro groups. In certain aspects of such compounds of Formula (VIII), $L^2$ is of the formula $(CH_2)_{0-5}CF_2$, wherein the fluoro-substituted carbon is not directly attached to the phenyl ring of Formula (VIII). In certain aspects of the compounds of Formula (VIII), $L^2$ is $C_2$-$C_6$ alkenylene, while in other aspects $L^2$ is $C_2$-$C_6$ alkenylene substituted with one to four fluoro groups.

In certain aspects of the compounds of Formula (VIII), $L^3$ is $C_1$-$C_6$ alkylene while in other aspects $L^3$ is $C_1$-$C_6$ alkylene substituted with one to four fluoro groups. In certain aspects of such compounds of Formula (VIII), $L^3$ is of the formula $(CH_2)_{0-5}CF_2$, wherein the fluoro-substituted carbon is not directly attached to the phenyl ring of Formula (VIII).

In certain aspects of the compounds of Formula (VIII), $L^2$ is arylene or heteroarylene. In some of these aspects, $L^2$ is phenylene, such as 1,3-disubstituted phenylene or 1,4-disubstituted phenylene.

In certain aspects of such compounds of Formula (VIII), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OR^9)_2$; $R^7$ is —$CF_2P(O)(OR^9)_2$, and $L^3$ is $C_1$-$C_6$alkylene.

In certain aspects of such compounds of Formula (VIII), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OR^9)_2$; $R^7$ is —$CF_2P(O)(OR^9)_2$; $L^3$ is —$((CR^4R^4)_pO)_q(CH_2)_p$—; $R^4$ is H; q is 1 or 2, and p is 2.

In certain aspects of such compounds of Formula (VIII), $R^1$ is $L^2R^6$; $R^2$ is $C_1$-$C_6$alkyl; $R^3$ is —$OL^3R^5$ or —$OL^3R^7$; $R^5$ is —$P(O)(OR^9)_2$; $R^6$ is —$C(O)OR^{10}$; $R^7$ is —$CF_2P(O)(OR^9)_2$; $L^2$ is $C_1$-$C_6$alkylene, and $L^3$ is $C_1$-$C_6$alkylene.

In certain aspects of such compounds of Formula (VIII), $R^1$ is $L^2R^6$; $R^2$ is $C_1$-$C_6$alkyl; $R^3$ is —$OL^3R^5$ or —$OL^3R^7$; $R^5$ is —$P(O)(OR^9)_2$; $R^6$ is —$C(O)OR^{10}$; $R^7$ is $CF_2P(O)(OR^9)_2$; $L^2$ is $C_1$-$C_6$alkylene; $L^3$ is —$((CR^4R^4)_pO)_q(CH_2)_p$—; $R^4$ is H; q is 1 or 2, and p is 2.

In certain aspects of such compounds of Formula (VIII), $R^1$ is —$C(R^5)_2OH$, -$L^1R^5$, -$L^2R^5$ or -$L^1R^6$; $R^2$ is $C_1$-$C_6$alkyl; $R^3$ is —$OR^8$; $R^8$ is $C_1$-$C_6$alkyl; $R^5$ is —$P(O)(OR^9)_2$; $R^6$ is —$CF_2P(O)(OR^9)_2$; $L^1$ is —C(O)—, and $L^2$ is $C_1$-$C_6$alkylene or $C_2$-$C_6$alkenylene, each optionally substituted with 1 to 4 fluoro groups.

In certain aspects of such compounds of Formula (VIII), $R^1$ is $C_1$-$C_6$alkyl; $R^2$ is $C_1$-$C_6$alkyl; $R^3$ is —$OL^3L^4R^5$ —$OL^3L^4L^3R^5$, or —$OL^3L^4L^3R^7$; $R^5$ is —$P(O)(OR^9)_2$; $R^7$ is —$CF_2P(O)(OR^9)_2$; each $L^3$ is independently a $C_1$-$C_6$alkylene, and $L^4$ is phenylene.

In certain aspects of such compounds of Formula (VIII), $R^1$ is $C_1$-$C_6$alkyl; $R^2$ is $C_1$-$C_6$alkyl; $R^3$ is —$C(R^5)_2OH$ or -$L^1R^5$; $R^5$ is —$P(O)(OR^9)_2$, and $L^1$ is —C(O)— or —O—.

In certain aspects, of such compounds of Formula (VIII), and pharmaceutically acceptable salts, pharmaceutically acceptable solvates (e.g. hydrates), the N-oxide derivatives, prodrug derivatives, protected derivatives, individual isomers and mixture of isomers thereof:

Formula (VIII)

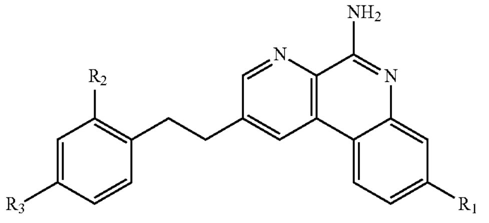

$R^1$ is $C_1$-$C_4$alkyl, —$C(R^5)_2OH$, -$L^1R^5$, -$L^2R^5$, -$L^2R^6$, —$OL^2R^5$, or —$OL^2R^6$;

$L^1$ is —C(O)— or —O—;

$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;

each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;

$L^4$ is arylene or heteroarylene;

$R^2$ is H or $C_1$-$C_4$alkyl;

$R^3$ is selected from -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2OH$;

each $R^4$ is independently selected from H and fluoro;

$R^5$ is —$P(O)(OH)_2$, $R^6$ is —$CF_2P(O)(OH)_2$ or —C(O)OH;

$R^7$ is —$CF_2P(O)(OH)_2$ or —C(O)OH;

$R^8$ is H or $C_1$-$C_4$alkyl;

each p is independently selected from 1, 2, 3, 4, 5 and 6, and q is 1, 2, 3 or 4, with the proviso that when $R^3$ is —$OR^8$, $R^1$ is —$C(R^5)_2$ OH, -$L^1R^5$, -$L^1R^6$, -$L^2R^5$, -$L^2R^6$, —$OL^2R^5$, or —$OL^2R^6$, wherein $R^6$ is —$CF_2P(O)(OH)_2$ and $R^7$ is —$CF_2P(O)(OH)_2$.

In certain aspects of such compounds of Formula (VIII), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OH)_2$; $R^7$ is —$CF_2P(O)(OH)_2$, and $L^3$ is $C_1$-$C_6$alkylene.

In certain aspects of such compounds of Formula (VIII), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OH)_2$; $R^7$ is —$CF_2P(O)(OH)_2$; $L^3$ is —$((CR^4R^4)_pO)_q(CH_2)_p$—; $R^4$ is H; q is 1 or 2, and p is 2.

In certain aspects of such compounds of Formula (VIII), $R^1$ is $L^2R^6$; $R^2$ is $C_1$-$C_6$alkyl; $R^3$ is —$OL^3R^5$ or —$OL^3R^7$; $R^5$ is —$P(O)(OH)_2$; $R^6$ is —C(O)OH; $R^7$ is —$CF_2P(O)(OH)_2$; $L^2$ is $C_1$-$C_6$alkylene, and $L^3$ is $C_1$-$C_6$alkylene.

In certain aspects of such compounds of Formula (VIII), $R^1$ is $L^2R^6$; $R^2$ is $C_1$-$C_6$alkyl; $R^3$ is —$OL^3R^5$ or —$OL^3R^7$; $R^5$ is —$P(O)(OH)_2$; $R^6$ is —C(O)OH; $R^7$ is —$CF_2P(O)(OH)_2$; $L^2$ is $C_1$-$C_6$alkylene; $L^3$ is —$((CR^4R^4)_pO)_q(CH_2)_p$—; $R^4$ is H; q is 1 or 2, and p is 2.

In certain aspects of such compounds of Formula (VIII), $R^1$ is —$C(R^5)_2OH$, -$L^1R^5$, -$L^2R^5$ or -$L^1R^6$; $R^2$ is $C_1$-$C_6$alkyl; $R^3$ is —$OR^8$; $R^8$ is $C_1$-$C_6$alkyl; $R^5$ is —$P(O)(OH)_2$; $R^6$ is —$CF_2P(O)(OH)_2$; $L^1$ is —C(O)—, and $L^2$ is $C_1$-$C_6$alkylene or $C_2$-$C_6$alkenylene, each optionally substituted with 1 to 4 fluoro groups.

In certain aspects of such compounds of Formula (VIII), $R^1$ is $C_1$-$C_6$alkyl; $R^2$ is $C_1$-$C_6$alkyl; $R^3$ is —$OL^3L^4R^5$ —$OL^3L^4L^3R^5$, or —$OL^3L^4L^3R^7$; $R^5$ is —$P(O)(OH)_2$; $R^7$ is —$CF_2P(O)(OH)_2$; each $L^3$ is independently a $C_1$-$C_6$alkylene, and $L^4$ is phenylene.

In certain aspects of such compounds of Formula (VIII), $R^1$ is $C_1$-$C_6$alkyl; $R^2$ is $C_1$-$C_6$alkyl; $R^3$ is —$C(R^5)_2OH$ or -$L^1R^5$; $R^5$ is —$P(O)(OH)_2$, and $L^1$ is —C(O)— or —O—.

In certain aspects of the aforementioned compounds of Formula (VIII), $R^8$ is methyl. In certain aspects of the aforementioned compounds of Formula (VIII), $R^1$ is methyl. In certain aspects of the aforementioned compounds of Formula (VIII), $R^2$ is methyl.

In other aspects of compounds of Formula (VIII), $R^5$ is —$P(O)(O^-X^+)_2$ or —$P(O)(O^-)_2X^{2+}$;

$R^6$ is —$CF_2P(O)(O^-X^+)_2$, —$CF_2P(O)(O^-)_2X^{2+}$ or —C(O)$O^-X^+$, and $R^7$ is —$CF_2P(O)(O^-X^+)_2$, —$CF_2P(O)(O^-)_2X^{2+}$ or —C(O)$O^-X^+$, wherein $X^+$ and $X^{2+}$ are pharmaceutically acceptable cations. In certain aspects, such pharmaceutically acceptable cations are selected from sodium, potassium, calcium, zinc, and magnesium.

In certain aspects of compounds of Formula (VIII), $R^5$ is —$PO_3^-X^{3+}$;

$R^6$ is —$CF_2PO_3^-X^{3+}$, and $R^7$ is —$CF_2PO_3^-X^{3+}$, wherein $X^{3+}$ is $Al^{3+}$.

Aluminum-containing adjuvants, such as aluminum hydroxide, aluminum oxyhydroxide and aluminum hydroxyphosphate, are used in vaccines to bind antigens. A discussion of aluminum-containing adjuvants and their uses in vaccines is given in *Expert Rev. Vaccines,* 46(5), 2007, 685-698 and *Vaccines,* 25, 2007, 6618-6624, the disclosures of which are herein incorporated by references in their entirety.

Compounds of Formula (VIII) provided herein are TLR7 agonists that can bind aluminum-containing adjuvants, such as, by way of example only, aluminum hydroxide, aluminum oxyhydroxide and aluminum hydroxyphosphate. In certain aspects, such compounds of Formula (VIII) have a phosphate, a phosphonic acid, a phosphonate, a fluorinated phosphonic acid or a fluorinated phosphonate group. While in other aspects, such compounds of Formula (VIII) have a phosphate, a phosphonic acid, a phosphonate, a fluorinated phosphonic acid or fluorinated phosphonate group, and one or more additional ionizable groups selected from a carboxylic acid and sulphate.

WO 2009/111337 and U.S. Provisional Patent Application Nos. 61/185,954 filed Jun. 10, 2009, 61/239,156 filed Sep. 2, 2009, and 61/239,217 filed Sep. 2, 2009, which are incorporated herein by reference, disclose benzonapthyridines compounds that have been found to be useful as immunopotentiators.

Antigen

The immunogenic composition as described herein comprises at least one hemorrhagic fever virus antigen. The immunogenic composition can contain other antigens, such as a bacterial antigen or other viral antigens, if desired.

Antigens for use with the immunogenic compositions provided herein include, but are not limited to, hemorrhagic fever virus antigens. For example, the immunogenic compositions can include, one or more of the following antigens set forth below, or antigens from one or more of the hemorrhagic fever viral pathogens set forth below.

Hemorrhagic fever viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, and Virus Like Particles (VLPs). In certain aspects, the hemorrhagic fever viral antigens are derived from viruses propagated on cell culture or other substrate. In other aspects, hemorrhagic fever viral antigens are expressed recombinantly. In certain aspects, hemorrhagic fever viral antigens preferably include epitopes which are exposed on the surface of the virus during at least one stage of its life cycle. Hemorrhagic fever viral antigens are preferably conserved across multiple serotypes or isolates. Hemorrhagic fever viral antigens suitable for use in the immunogenic compositions provided herein include, but are not limited to, antigens derived from one or more of the viruses set forth below as well as the specific antigens examples identified below.

Filoviridae: Viral antigens include, but are not limited to, those derived from Marburg virus and Ebola virus.

Ebolavirus: Viral antigens include, but are not limited to, those derived from Zaire Ebola virus, Sudan Ebola virus, Reston Ebola virus, Cote d'Ivoire Ebola virus, and Bundibugyo Ebola virus. In certain aspects, Ebola virus antigens are selected from one or more of the following proteins: glycoprotein (GP), nucleoprotein (NP), minor nucleoprotein (VP30), matrix proteins (VP40, VP24), RNA-dependent RNA polymerase (L), and VP35.

Arenaviridae: Viral antigens include, but are not limited to, those derived from Arenavirus.

Arenavirus: Viral antigens include, but are not limited to, those derived from Lassa virus, Junin virus, and Whitewater Arroyo virus.

Bunyaviridae: Viral antigens include, but are not limited to, those derived from Nairovirus.

Nairovirus: Viral antigens include, but are not limited to, those derived from Crimean-Congo hemorrhagic fever virus.

Flavaviridae: Viral antigens include, but are not limited to, those derived from Flavavirus.

Flavavirus: Viral antigens include, but are not limited to, those derived from Dengue virus.

Adjuvant

In certain aspects, the immunogenic compositions provided herein include or optionally include one or more immunoregulatory agents such as adjuvants. Exemplary adjuvants include, but are not limited to, a TH1 adjuvant and/or a TH2 adjuvant, further discussed below. In certain aspects, the adjuvants used in the immunogenic compositions provide herein include, but are not limited to:

1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles.

Mineral Containing Compositions

Mineral containing compositions suitable for use as adjuvants include mineral salts, such as aluminum salts and calcium salts. The invention includes mineral salts such as hydroxides (e.g., oxyhydroxides), phosphates (e.g., hydroxyphosphates, orthophosphates), sulfates, etc. (see, e.g., Vaccine Design: The Subunit and Adjuvant Approach (Powell, M. F. and Newman, M. J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In one aspect, the aluminum based adjuvant for use in the present invention is alum (aluminum potassium sulfate ($AlK(SO_4)_2$), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. In another aspect, the aluminum based adjuvant is aluminum phosphate adjuvant ($AlPO_4$) or aluminum hydroxyphosphate, which contains phosphate groups in place of some or all of the hydroxyl groups of aluminum hydroxide adjuvant. Aluminum phosphate adjuvants provided herein are amorphous and soluble in acidic, basic and neutral media.

In another aspect, the adjuvant comprises both aluminum phosphate and aluminum hydroxide. In a more particular aspect thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another aspect, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep=4). Alternatively, pretreatment of aluminum hydroxide with phosphate lowers its isoelectric point, making it a preferred adjuvant for more basic antigens.

Oil-Emulsions

Oil-emulsion compositions and formulations suitable for use as adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) Vaccine 19: 2673-2680; Frey et al. (2003) Vaccine 21:4234-4237. MF59 is used as the adjuvant in the FLUAD™ influenza virus trivalent subunit vaccine.

Particularly preferred oil-emulsion adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-SM-glycero-3-huydroxyphosphosphoryloxy)-ethylamine (MTP-PE), for example, the submicron oil-in-water emulsion known as "MF59" (WO 90/14837; U.S. Pat. Nos. 6,299,884; 6,451,325; and Ott et al., "MF59—Design and Evaluation of a Safe and Potent Adjuvant for Human Vaccines" in Vaccine Design: The Subunit and Adjuvant Approach (Powell, M. F. and Newman, M. J. eds.) (New York: Plenum Press) 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 11OY microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO 90/14837; U.S. Pat. Nos. 6,299,884; and 6,451,325.

Complete Freund's adjuvant (CFA) and incomplete Freund's adjuvant (IFA) may also be used as adjuvants in the invention.

Other Immunological Adjuvants

Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Saponin formulations may include sterols, cholesterols and lipid formulations. Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) Adv. Drug Del. Rev. 32:247-271. See also Sjolander et al. (1998) Adv. Drug Del. Rev. 32:321-338.

Virosomes and Virus Like Particles (VLPs) generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein pi). VLPs are discussed further in WO 03/024480; WO 03/024481; Niikura et al. (2002) Virology 293:273-280; Lenz et al. (2001) J. Immunol. 166(9):5346-5355' Pinto et al. (2003) J. Infect. Dis. 188:327-338; and Gerber et al. (2001) J. Virol. 75(10):4752-4760. Virosomes are discussed further in, for example, Gluck et al. (2002) Vaccine 20:B10-B16. Immunopotentiating reconstituted influenza virosomes (IRIV) are used as the subunit antigen delivery system in the intranasal trivalent INFLEXAL™ product (Mischler and Metcalfe (2002) VACCINE 20 Suppl 5:B17-B23) and the INFLUVAC PLUS™ product.

Bacterial or microbial derivatives suitable for use as adjuvants include, but are not limited to:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) Bioorg. Med. Chem. Lett. 9:2273-2278.

(2) Lipid A Derivatives: Lipid A derivatives include derivatives of lipid A from *Escherichia coli* such as OM-174. OM-174 is described for example in Meraldi et al. (2003) Vaccine 21:2485-2491; and Pajak et al. (2003) Vaccine 21: 836-842. Another exemplary adjuvant is the synthetic phospholipid dimer, E6020 (Eisai Co. Ltd., Tokyo, Japan), which mimics the physicochemical and biological properties of many of the natural lipid A's derived from Gram-negative bacteria.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) Nucl. Acids Res. 31(9): 2393-2400; WO 02/26757; and WO 99/62923 for examples of possible analog substitutions. The adjuvant effect of CpG oligonucleotides is further discussed in Krieg (2003) Nat. Med. 9(7):831-835; McCluskie et al. (2002) FEMS Immunol. Med. Microbiol. 32: 179-185; WO 98/40100; U.S. Pat. Nos. 6,207,646; 6,239,116; and 6,429,199.

The CpG sequence may be directed to TLR9, such as the motif GTCGTT or TTCGTT. See Kandimalla et al. (2003) Biochem. Soc. Trans. 31 (part 3):654-658. The CpG sequence may be specific for inducing a ThI immune response, such as a CpG-A ODN, or it may be more specific for inducing a B cell response, such a CpG-B ODN. CpG-A and CpG-B ODNs are discussed in Blackwell et al. (2003) J. Immunol. 170(8):4061-4068; Krieg (2002) TRENDS Immunol. 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) BBRC 306:948-953; Kandimalla et al. (2003) Biochem. Soc. Trans. 31 (part 3):664-658' Bhagat et al. (2003) BBRC 300:853-861; and WO03/035836.

Immunostimulatory oligonucleotides and polymeric molecules also include alternative polymer backbone structures such as, but not limited to, polyvinyl backbones (Pitha et al. (1970) Biochem. Biophys. Acta 204(1):39-48; Pitha et al. (1970) Biopolymers 9(8):965-977), and morpholino backbones (U.S. Pat. Nos. 5,142,047; 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

Adjuvant IC31, Intercell AG, Vienna, Austria, is a synthetic formulation that contains an antimicrobial peptide, KLK, and an immunostimulatory oligonucleotide, ODNIa. The two component solution may be simply mixed with antigens (e.g., particles in accordance with the invention with an associated antigen), with no conjugation required.

(4) ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) Infect. Immun. 70(6):3012-3019; Pizza et al. (2001) Vaccine 19:2534-2541; Pizza et al. (2000) J. Med. Microbiol. 290(4-5):455-461; Scharton-Kersten et al. (2000) Infect. Immun. 68(9):5306-5313' Ryan et al. (1999) Infect. Immun. 67(12):6270-6280; Partidos et al. (1999) Immunol. Lett. 67(3):209-216; Peppoloni et al. (2003) Vaccines 2(2): 285-293; and Pine et al. (2002) J. Control Release 85(1-3): 263-270. Numerical reference for amino acid substitutions is preferably based on the alignments of the A and B subunits of ADP-ribosylating toxins set forth in Domenighini et al. (1995) MoI. Microbiol. 15(6): 1165-1167.

Bioadhesives and mucoadhesives may also be used as adjuvants. Suitable bioadhesives include esterified hyaluronic acid microspheres (Singh et al. (2001) J. Cont. Release 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

Examples of liposome formulations suitable for use as adjuvants are described in U.S. Pat. Nos. 6,090,406; 5,916,588; and EP Patent Publication No. EP 0 626 169.

Adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

PCPP formulations suitable for use as adjuvants are described, for example, in Andrianov et al. (1998) Biomaterials 19(1-3): 109-115; and Payne et al. (1998) Adv. Drug Del. Rev. 31(3): 185-196.

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

Examples of imidazoquinoline compounds suitable for use as adjuvants include Imiquimod and its analogues, which are described further in Stanley (2002) Clin. Exp. Dermatol. 27(7):571-577; Jones (2003) Curr. Opin. Investig. Drugs 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

Examples of thiosemicarbazone compounds suitable for use as adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

Examples of tryptanthrin compounds suitable for use as adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α.

Examples of benzonaphthyridine compounds suitable for use as adjuvants, as well as methods of formulating and manufacturing, include those described in WO 2009/111337.

Lipopeptides suitable for use as adjuvants are described above. Other exemplary lipopeptides include, e.g., LP 40, which is an agonist of TLR2. See, e.g., Akdis, et al, Eur. J. Immunology, 33: 2717-26 (2003). Murein lipopeptides are lipopeptides derived from *E. coli*. See, Hantke, et al., Eur. J. Biochem., 34: 284-296 (1973). Murein lipopeptides comprise a peptide linked to N-acetyl muramic acid, and are thus related to Muramyl peptides, which are described in Baschang, et al., Tetrahedron, 45(20): 6331-6360 (1989).

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-), macrophage colony stimulating factor, and tumor necrosis factor.

Microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain aspects, such microparticles are treated to have a negatively-charged surface (e.g. with SDS) or a positively-charged surface (e.g. with a cationic detergent, such as CTAB). The microparticles suitable for use as adjuvants have a particle diameter of about 100 nm to about 150 μm in diameter. In certain aspects, the particle diameter is about 200 nm to about 30 μm, and in other aspects the particle diameter is about 500 nm to 10 μm.

4. Methods of Using the Immunogenic or Pharmaceutical Composition

In some aspects, the pharmaceutical compositions provided herein are used in the treatment of a viral infection, or a symptom or a viral infection caused by a hemorrhagic fever virus. In some aspects, the pharmaceutical composition is used to treat, for example, a hemorrhagic fever caused by a hemorrhagic fever virus. In some aspects, the hemorrhagic fever virus is a Filoviridae virus, an Arenaviridae virus, a Bunyaviridae virus, or a Flavaviridae virus. In some aspects, the hemorrhagic fever virus is Ebola virus. In other aspects, the hemorrhagic fever virus can be, but is not limited to, Lassa virus, Junin virus, Whitewater Arroyo virus, Crimean-Congo hemorrhagic fever virus, or Dengue virus.

The invention also provides a method of generating an immune response in a subject in need thereof, such as a mammal, comprising administering an effective amount of an immunogenic composition as disclosed herein. The invention also provides a method of inducing an immune response in a subject in need thereof, such as a mammal, comprising administering an effective amount of an immunogenic composition as disclosed herein. The immune response is preferably protective and preferably involves antibodies and/or cell-mediated immunity. The method may raise a booster response.

In another aspect, the generated or induced immune response of the invention includes induction of a cytokine profile. A "cytokine profile" refers to expression of one or more cytokines. An induced cytokine profile comprises increased expression of one or more cytokines. Exemplary cytokines in a cytokine profile include, but are not limited to, IFN-γ, IL-12 p40, IL-1β, IL-6, MCP-1, mKC, and TNF-α. The cytokine profile may include about 5, 10, 15, 20, 25, or 30 cytokines. The above numbers are merely exemplary. A person of ordinary skill in the art would understand that the invention includes a cytokine profile having any integer of cytokines between 1 and 30 or any percent integer of the cytokines. For example, a cytokine profile of an induced or generated immune response of the invention includes various numbers of cytokines inclusive of each and every integer from about 1 through about 30, inclusive. The person of ordinary skill in the art also would understand that the cytokine profiles contemplated include, for example, a cytokine profile having induction of 7 cytokines or 10 cytokines Additionally, the invention provides a method of potentiating an immune response in a subject who has been exposed to a hemorrhagic fever virus, comprising administering to the subject a pharmaceutically effective amount of a composition comprising a benzonapthyridine TLR7 agonist or salt, solvate, or derivative thereof. In some aspects, the invention provides a method of potentiating an immune response in a subject who has been exposed to a hemorrhagic fever virus, comprising administering to the subject a pharmaceutically effective amount of a composition comprising a benzonapthyridine TLR7 agonist of Formula (I) described herein, or salt, solvate, or derivative thereof the invention provides a method of potentiating an immune response in a subject who has been exposed to a hemorrhagic fever virus, comprising administering to the subject a pharmaceutically effective amount of a composition comprising a benzonapthyridine TLR7 agonist of Formula (VIII) described herein, or salt, solvate, or derivative thereof.

In some aspects, the invention relates to an immunogenic or pharmaceutical composition comprising one or more benzonapthyridine TLR7 agonists that can be administered to a subject pre- or post-exposure to a hemorrhagic fever virus such as Filaviridae virus (e.g., Ebola virus). In some aspects, the benzonapthyridine TLR7 agonist is a compound of Formula (I) described herein. In some aspects, the benzonapthyridine TLR7 agonist is a compound of Formula (VIII) described herein. In some aspects, the invention is a method to reduce or prevent hemorrhagic fever virus infection, such as Filoviridae virus infection, comprising the step of administering to a subject in need thereof a pharmaceutically effective amount of a composition comprising a benzonapthyridine TLR7 agonist. In another aspect, the invention is a method to protect against hemorrhagic fever virus infection, such as Filiviridae virus infection, comprising the step of administering to a subject in need thereof a pharmaceutically effective amount of a composition comprising a benzonapthyridine TLR7 agonist.

The invention also provides a method of treating a subject prior to or pre-exposure to a hemorrhagic fever virus, such as Filaviridae virus (e.g., Ebola virus), comprising administering to said subject an immunogenic composition comprising: (a) a benzonapthyridine TLR7 agonist of Formula (I), or salt, solvate, or derivative thereof, and (b) an antigen from a hemorrhagic fever virus. The invention also provides a method of treating a subject prior to or pre-exposure to a hemorrhagic fever virus, such as Filaviridae virus (e.g., Ebola virus), comprising administering to said subject an immunogenic composition comprising: (a) a benzonapthyridine TLR7 agonist of Formula (VIII), or salt, solvate, or derivative thereof, and (b) an antigen from a hemorrhagic fever virus.

In another aspect, the invention provides a method of treating a subject pre-exposure to a hemorrhagic fever virus, such as a Filaviridae virus (e.g., Ebola virus), comprising administering to said subject an immunogenic composition comprising: (a) a benzonapthyridine TLR7 agonist of Formula (I) disclosed herein, or salt, solvate, or derivative thereof, (b) an antigen from a hemorrhagic fever virus; and (c) an adjuvant. In another aspect, the invention provides a method of treating a subject pre-exposure to a hemorrhagic fever virus, such as a Filaviridae virus (e.g., Ebola virus), comprising administering to said subject an immunogenic composition comprising: (a) a benzonapthyridine TLR7 agonist of Formula (VIII) disclosed herein, or salt, solvate, or derivative thereof, (b) an antigen from a hemorrhagic fever virus; and (c) an adjuvant.

In another aspect, the invention provides a method of treating a subject that has been exposed to a hemorrhagic fever virus, comprising administering to said subject a pharmaceutically effective amount of a composition comprising a benzonapthyridine TLR7 agonist of Formula (I) disclosed herein, or salt, solvate, or derivative thereof. In another aspect, the invention provides a method of treating a subject that has been exposed to a hemorrhagic fever virus, comprising administering to said subject a pharmaceutically effective amount of a composition comprising a benzonapthyridine TLR7 agonist of Formula (VIII) disclosed herein, or salt, solvate, or derivative thereof.

The immunogenic compositions disclosed herein may be used as a medicament, e.g., for use in raising or enhancing an immune response in a subject, such as a mammal, pre- or post-exposure to a hemorrhagic fever virus, such as a Filaviridae virus (e.g., Ebola virus).

The immunogenic compositions disclosed herein may be used in the manufacture of a medicament for raising an immune response in a subject, such as a mammal, pre- or post-exposure to a hemorrhagic fever virus, such as a Filaviridae virus (e.g., Ebola virus).

The immunogenic or pharmaceutical composition provided herein may be used in the treatment of an infectious or pathogenic disease and/or disorder caused by a hemorrhagic fever virus. In some aspects, the disease and/or disorder is associated with TLR7. In some aspects, the disease is caused by Ebola virus or Marburg virus. In one aspect, the disease is a viral hemorrhagic fever. In another aspect, the disease is Ebola Hemorrhagic Fever. In another aspect, the disease is Marburg Hemorrhagic Fever.

In some aspects, the disease can be Lassa fever or Lassa hemorrhagic fever that is caused by Lassa virus. In some aspects, the disease can be Whitewater Arroyo hemorrhagic fever that is caused by Whitewater Arroyo virus. In some aspects, the disease can be Argentine hemorrhagic fever caused by Junin virus. In some aspects, the disease can be Bolivian hemorrhagic fever caused by Manchupo virus. In some aspects, the disease can be Dengue hemorrhagic fever caused by Dengue virus. In some aspects, the disease can be Crimean-Congo hemorrhagic fever caused by Crimean-Congo hemorrhagic fever virus.

In certain aspects, the pharmaceutical compositions provided herein are used in the treatment of viral infections. In another aspect, the infection is a strain of Ebola virus. In another aspect, the strain of Ebola virus includes, but is not limited to, Zaire Ebola virus, Sudan Ebola virus, Reston Ebola virus, Cote d'Ivoire Ebola virus, and Bundibugyo Ebola virus.

5. Administration of Compositions of the Invention

The immunogenic or pharmaceutical composition provided herein is administered singly or in combination with one or more additional therapeutic agents. Suitable modes of administration include, but are not limited to, oral administration, rectal administration, parenteral, intravenous administration, intraperitoneal administration, intravitreal administration, intramuscular administration, inhalation, intranasal administration, topical administration, ophthalmic administration or otic administration, or any combination thereof.

The therapeutically effective amount of a benzonapthyridine SMIP of the invention will vary depending on, among others, the disease indicated, the severity of the disease, the age and relative health of the subject, the potency of the compound administered, the mode of administration and the treatment desired. Based on these and other considerations, a clinician will be able to determine the appropriate amount to achieve the desired therapeutic effect.

In some aspects, therapeutically effective dosages of a benzonapthyridine compound of Formula (I) or Formula (VIII) include from about 0.03 to 2.5 mg/kg per body weight of a subject in need thereof. In certain aspects, the dosage of a compound of Formula (I) or Formula (VIII), administered by inhalation, is in the range from 0.05 micrograms per kilogram body weight (μg/kg) to 100 micrograms per kilogram body weight (μg/kg). In other aspects, the dosage of a compound of Formula (I) or Formula (VIII), administered orally, is in the range from 0.01 micrograms per kilogram body weight (μg/kg) to 100 milligrams per kilogram body weight (mg/kg). An oral dosage in a larger mammal, e.g. humans, is in the range from about 0.5 mg to about 100 mg of a compound of Formula (I) or Formula (VIII), conveniently administered, e.g. in divided doses up to four times a day or in controlled release form. In certain aspect, unit dosage forms for oral administration comprise from about 1 to 50 mg of a compound of Formula (I) or Formula (VIII).

Also provided herein are processes for the preparation of an immunogenic or pharmaceutical composition of the invention which comprise at least one compound of Formula (I) or Formula (VIII) provided herein, or salt, solvate, or derivative thereof. In certain aspects, such processes include admixing a benzonapthyridine compound of Formula (I) or Formula (VIII) provided herein, or salt, solvate, or derivative thereof, with one or more pharmaceutically acceptable carriers, diluents or excipients. Also provided is an immunogenic or pharmaceutical composition comprising a compound of Formula (I) or Formula (VIII) or salt, solvate, or derivative thereof, in association with at least one pharmaceutically acceptable carrier, diluent or excipient that is manufactured by mixing, granulating and/or coating methods. In other aspects, such compositions optionally contain excipients, such as preserving, stabilizing, wetting or emulsifying agents, solution promoters, salts for regulating the osmotic pressure and/or buffers. In other aspects, such compositions are sterilized.

The immunogenic or pharmaceutical composition of the invention containing at least one compound of Formula (I) or Formula (VIII) is administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) or Formula (VIII) are prepared by admixing at least one compound of Formula (I) or Formula (VIII) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof. In certain aspects, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain aspects, the amount of disintegrant used in the pharmaceutical compositions provided herein is from about 0.5 to about 15 weight percent of disintegrant, while in other aspects the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain aspects, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain aspects, tablets and capsules are prepared by uniformly admixing at least one compound of Formula (I) or Formula (VIII) (active ingredients) with liquid carriers, finely divided solid carriers, or both, and then shaping the product into the desired presentation if necessary. In certain aspects, tablets are prepared by compression. In other aspects, tablets are prepared by molding.

In certain aspects, at least one compound of Formula (I) or Formula (VIII) is orally administered as a controlled release dosage form. Such dosage forms are used to provide slow or controlled-release of one or more compounds of Formula (I) or Formula (VIII). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain aspects, controlled-release dosage forms are used to extend activity of the compound of Formula (I) or Formula (VIII), reduce dosage frequency, and increase patient compliance.

Administration of compounds of Formula (I) or Formula (VIII) as oral fluids such as solution, syrups and elixirs are prepared in unit dosage forms such that a given quantity of solution, syrups or elixirs contains a predetermined amount of a compound of Formula (I) or Formula (VIII). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

In another aspect, the immunogenic or pharmaceutical composition containing at least one compound of Formula (I) or Formula (VIII) is administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain aspects, the immunogenic or pharmaceutical composition of the invention containing at least one compound of Formula (I) or Formula (VIII) is administered transdermally. Such transdermal dosage forms include "reservoir type" or "matrix type" patches, which are applied to the skin and worn for a specific period of time to permit the penetration of a desired amount of a compound of Formula (I) or Formula (VIII). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other aspects, matrix transdermal formulations are used.

Formulations for transdermal delivery of a compound of Formula (I) or Formula (VIII) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof In certain aspects, such transdermal delivery systems include penetration enhancers to assist in delivering one or more compounds of Formula (I) or Formula (VIII) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other aspects, the pH of such a transdermal pharmaceutical composition or dosage form, or of the tissue to which the pharmaceutical composition or dosage form is applied, is adjusted to improve delivery of one or more compounds of Formula (I) or Formula (VIII). In other aspects, the polarity of a solvent carrier, its ionic strength, or tonicity are adjusted to improve delivery. In other aspects, compounds such as stearates are added to advantageously alter the hydrophilicity or lipophilicity of one or more compounds of Formula (I) or Formula (VIII) so as to improve delivery. In certain aspects, such stearates serve as a lipid vehicle for the formulation, as an emulsifying agent or surfactant, and as a delivery-enhancing or penetration-enhancing agent. In other aspects, different salts, hydrates or solvates of the compounds of Formula (I) or Formula (VIII) are used to further adjust the properties of the resulting composition.

In certain aspects at least one compound of Formula (I) or Formula (VIII) is administered by topical application of an immunogenic or pharmaceutical composition of the invention containing at least one compound of Formula (I) or Formula (VIII) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain aspects, such topical formulations include penetration enhancers to assist in delivering one or more compounds of Formula (I) or Formula (VIII) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In some aspects, an immunogenic or pharmaceutical composition of the invention containing at least one compound of Formula (I) or Formula (VIII) is administered by inhalation. Dosage forms for inhaled administration are formulated as aerosols or dry powders. Aerosol formulations for inhalation administration comprise a solution or fine suspension of at least one compound of Formula (I) or Formula (VIII) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain aspects, compounds of Formula (I) or Formula (VIII) are administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain aspects, capsules and cartridges of gelatin for use in an inhaler or insufflator are formulated containing a powder mixture of a compound of Formula (I) or Formula (VIII) and a powder base such as lactose or starch. In certain aspects, compounds of Formula (I) or Formula (VIII) are delivered to the lung using a liquid spray device, wherein such devices use extremely small nozzle holes to aerosolize liquid drug formulations that can then be directly inhaled into the lung. In other aspects, compounds of Formula (I) or Formula (VIII) are delivered to the lung using a nebulizer device, wherein a nebulizers creates an aerosols of liquid drug formulations by using ultrasonic energy to form fine particles that can be readily inhaled. In other aspects, compounds of Formula (I) or Formula (VIII) are delivered to the lung using an electrohydrodynamic ("EHD") aerosol device wherein such EHD aerosol devices use electrical energy to aerosolize liquid drug solutions or suspensions.

In certain aspects, the pharmaceutical composition containing at least one compound of Formula (I) or Formula (VIII), or pharmaceutically acceptable salts and solvates thereof, described herein, also contain one or more absorption enhancers. In certain aspects, such absorption enhancers include, but are not limited to, sodium glycocholate, sodium caprate, N-lauryl-β-D-maltopyranoside, EDTA, and mixed micelles.

In certain aspects, an immunogenic or pharmaceutical composition of the invention containing at least one compound of Formula (I) or Formula (VIII) is administered nasally. The dosage forms for nasal administration are formulated as aerosols, solutions, drops, gels or dry powders.

In certain aspects, an immunogenic or pharmaceutical composition of the invention containing at least one compound of Formula (I) or Formula (VIII) is administered rectally in the form of suppositories, enemas, ointment, creams rectal foams or rectal gels. In certain aspects such suppositories are prepared from fatty emulsions or suspensions, cocoa butter or other glycerides.

In certain aspects, an immunogenic or pharmaceutical composition of the invention containing at least one compound of Formula (I) or Formula (VIII) is administered opthamically as eye drops. Such formulations are aqueous solutions that optionally contain solubilizers, stabilizers, tonicity enhancing agents, buffers and preservatives.

In certain aspects, an immunogenic or pharmaceutical composition of the invention containing at least one compound of Formula (I) or Formula (VIII) is administered otically as ear drops. Such formulations are aqueous solutions that optionally contain solubilizers, stabilizers, tonicity enhancing agents, buffers and preservatives.

In certain aspects, an immunogenic or pharmaceutical composition of the invention containing at least one compound of Formula (I) or Formula (VIII) is formulated as a depot preparation. Such formulations are administered by implantation (for example subcutaneously or intramuscularly) or by intramuscular injection. In certain aspects, such formulations include polymeric or hydrophobic materials (for example, as an emulsion in an acceptable oil) or ion exchange resins, or as sparingly soluble derivatives, for example, as a sparingly soluble salt.

In certain aspects, an immunogenic or pharmaceutical composition of the invention containing at least one compound of Formula (I) or Formula (VIII) is formulated for sublingual administration. Formulations for sublingual administration may include a pharmaceutically acceptable carrier or vehicle.

In other aspects, the immunogenic or pharmaceutical composition described herein, is administered in combination with one or more additional therapeutic agents. If desired, the immunogenic of pharmaceutical composition described herein can further comprise one or more additional therapeutic agents, such as an antiviral agent. When co-therapy is desired, such concomitant therapy using an immunogenic or pharmaceutical composition of the invention and an antiviral agent (e.g., ribavirin), the two agents can be administered according to any suitable schedule provided that there is overlap in the pharmacological activity of the benzonapthyridine TLR7 agonist and the antiviral agent.

For example, in some aspects, the immunogenic or pharmaceutical composition described herein is administered sequentially or at the same time as one or more additional therapeutic agents. The additional therapeutic agents may include, but are not limited to antibiotics or antibacterial agents, antiemetic agents, antifungal agents, anti-inflammatory agents, antiviral agents (e.g., ribivarin), immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, -interferons, -interferons, hormones, and other toll-like receptor modulators, immunoglobulins (Igs), and antibodies modulating Ig function (such as anti-IgE (omalizumab)).

In another aspect, the invention provides a method of treating a subject that has been exposed to a hemorrhagic fever virus, such as Filoviridae (e.g., Ebola virus), comprising the step of administering to the subject a pharmaceutically effective amount of a composition comprising: (a) a benzonapthyridine small molecule immune potentiator and (b) an antiviral agent (e.g., ribavirin). In some aspects, the composition of the invention comprises a benzonapthyridine TLR7 agonist and ribavirin.

In other aspects, the invention is a method to reduce or prevent disease caused by a hemorrhagic fever virus, such as Filoviridae virus, comprising the step of administering to a subject in need thereof a pharmaceutically effective amount of a composition comprising: (a) a benzonapthyridine small molecule immune potentiator and (b) an antiviral agent.

In other aspects, the invention is a method to reduce or prevent hemorrhagic fever virus infection, such as Filoviridae virus infection, comprising the step of administering to a subject in need thereof a pharmaceutically effective amount of a composition comprising: (a) a benzonapthyridine small molecule immune potentiator and (b) an antiviral agent.

In some aspects, the activities of a benzonapthyridine TLR7 agonist of the invention and one or more therapeutic agents, such as an antiviral agent (e.g., ribivarin), can be additive or synergistic and thus, when administered concomitantly, less of the antiviral agent needs to be administered to a subject in need thereof to achieve the desired therapeutic effect. For example, the amount of an antiviral agent (e.g. ribavirin) that is required when it is co-administered with a benzonapthyridine TLR7 agonist of the invention may be less than the amount of the antiviral agent required when it is the only pharmaceutically active agent administered to a subject, e.g., for treatment of a hemorrhagic fever virus.

The invention also provides a delivery device pre-filled with an immunogenic or pharmaceutical composition disclosed herein.

The immunogenic or pharmaceutical composition provided herein may be administered to a mammal. The mammal is preferably a human, but may be, e.g., a cow, a pig, a chicken, a cat or a dog, as the pathogens covered herein may be problematic across a wide range of species. Where the immunogenic composition of the invention is for prophylactic use, the human is preferably a child (e.g., a toddler or infant) or a teenager; where the composition of the invention is for therapeutic use, the human is preferably a teenager or an adult. A immunogenic or pharmaceutical composition of the invention intended for children may also be administered to adults, e.g., to assess safety, dosage, immunogenicity, etc.

One way of checking efficacy of therapeutic treatment involves monitoring pathogen infection after administration of the immunogenic compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigens included in or administered in conjunction with the immunogenic compositions disclosed herein after administration of the immunogenic composition (and the antigen if administered separately). Typically, antigen-specific serum antibody responses are determined post-immunization but pre-challenge whereas antigen-specific mucosal antibody responses are determined post-immunization and post-challenge.

Another way of assessing the immunogenicity of the immunogenic composition disclosed herein where the antigen is a protein is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the immunogenic or pharmaceutical composition of the invention can also be determined in vivo by challenging appropriate animal models of the pathogen of interest infection.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The immunogenic or pharmaceutical composition disclosed herein that includes one or more antigens or is used in conjunction with one or more antigens may be used to treat both children and adults. Thus a human subject may be less than 1 year old, 1-5 years old, 5-15 years old, 15-55 years old, or at least 55 years old. Preferred subjects for receiving such immunogenic compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The immunogenic and pharmaceutical compositions are not suitable solely for these groups, however, and may be used more generally in a population.

The immunogenic and pharmaceutical compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

6. Processes for Making Benzonapthyridine Compounds of Formula (VIII)

The examples provided herein are offered to illustrate, but not to limit, the compounds of Formula (VIII) provided herein, and the preparation of such compounds.

Non-limiting examples of synthetic schemes used to make compounds of Formula (VIII) provided herein are illustrated in reaction schemes (I)-(XI).

Scheme (I) illustrates the synthesis of benzonaphthyridines (I-3) by coupling 2-(tert-butoxycarbonyl-amino)phenylboronic acids (I-1) with 3-halopicolinonitrile derivatives (I-2) in the presence of a palladium catalyst. By way of example only, the halo moiety of the 3-halopicolinonitrile derivatives is bromo or chloro. The $R_A$ and $R_B$ groups on benzonaphthyridines (I-3) are as described herein for substituents of Formula (VIII) at the respective positions, or $R_A$ and $R_B$ are groups that are further modified to obtain the respective substituents of Formula (VIII), as described herein.

Scheme (I)

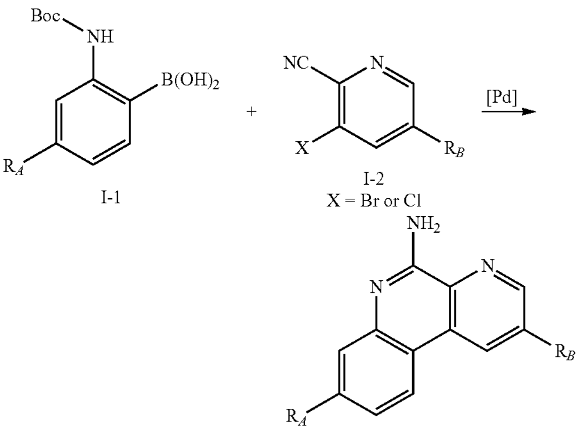

I-1 I-2 X = Br or Cl I-3

In certain aspects, the phenyl boronic acids used in the synthesis of compounds of Formula (VIII) were synthesized according to scheme (II). In scheme (II) aniline (II-1) is Boc-protected under basic conditions to give (II-2), and then converted into the boronic acids (I-1) through ortho-lithiation and reaction with trimethyl borate followed by aqueous workup.

Scheme (II)

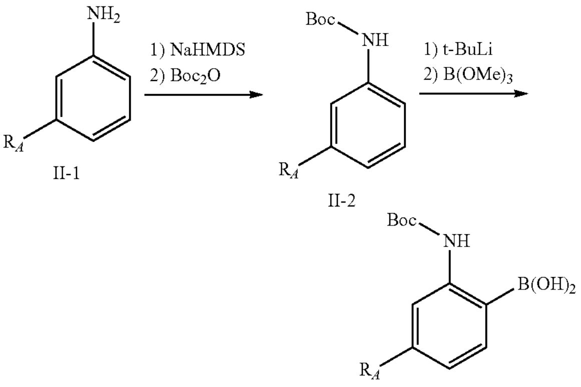

II-1 II-2 I-1

Boric acids (I-1) are used as in scheme (I) and reacted cyanopyridines (I-2) to afford benzonaphthyridines (I-3).

In certain aspects, boronic acid equivalents including, but not limited to, boronate esters were used in the synthesis of compounds of Formula (VIII). Scheme (III) illustrates the synthesis of such boronate esters (III-3), which were used as boronic acid equivalents in the synthesis of benzonaphthyridines (I-3). In scheme (III) 2-haloanilines (III-1) were Boc-protected under basic conditions to give (III-2), which were then converted into the boronate esters (III-3) using palladium-mediated catalysis. These boronate esters (III-3) were used as in scheme (I) and reacted with cyanopyridines (I-2) to afford substituted or unsubsubstituted benzonaphthyridines (I-3).

Scheme (III)

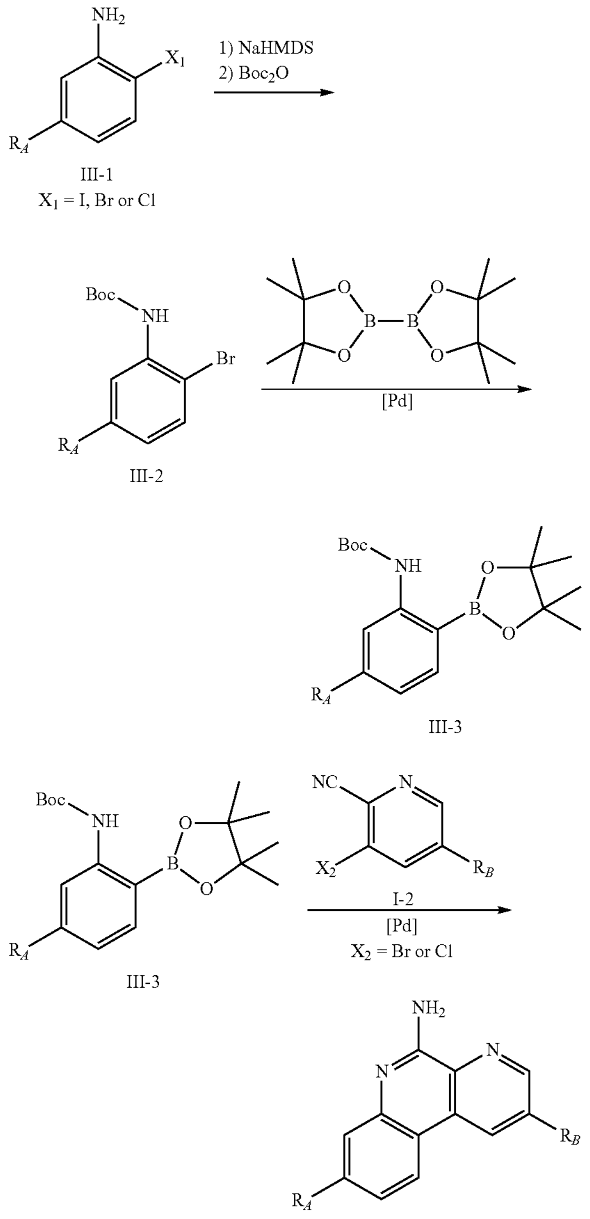

III-1

$X_1$ = I, Br or Cl

III-2

III-3

III-3

I-2

I-3

In certain aspects, 2-bromoanilines used as in scheme (III) were synthesized from their corresponding nitrobenzene compounds as illustrated below:

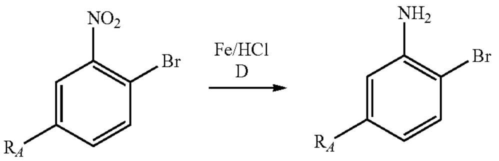

In other aspects, compounds of Formula (VIII) were synthesized using the methodologies described in scheme (IV).

Scheme (IV)

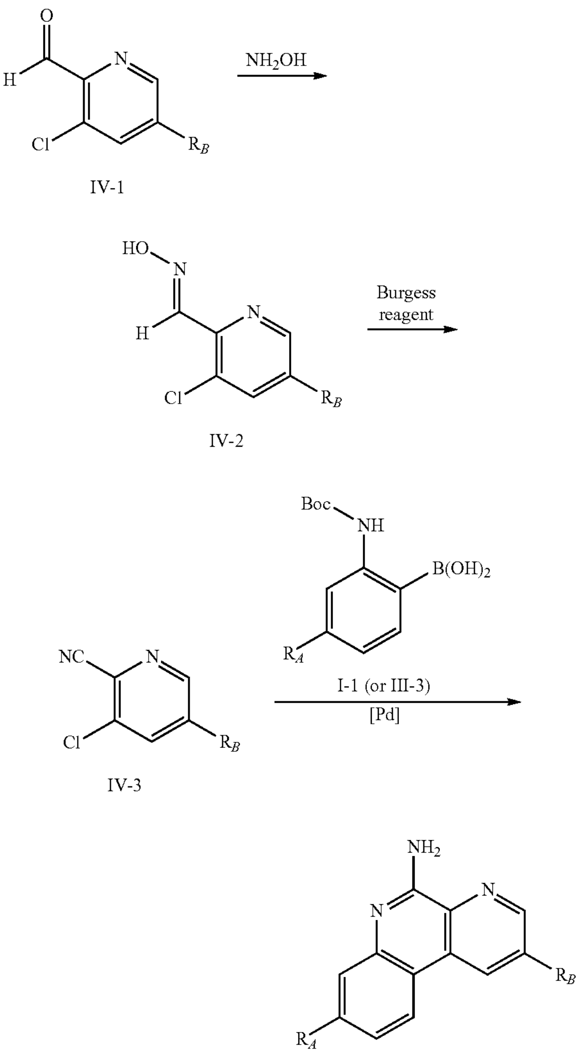

IV-1

IV-2

IV-3

I-1 (or III-3)

I-3

In scheme (IV), 3-chlorobenzaldehyde (IV-1) is first converted to the corresponding hydroxylamine (IV-2), which is then used to make the corresponding nitrile (IV-3). Using palladium-mediated conditions, as in scheme (I), derivatives of nitrile (IV-3) are coupled with boronic acids (I1) (or boronate esters (III-3) to give the benzonaphthyridine (I-3).

In other aspects, certain compounds of Formula (VIII) having carbon-linked substituents, including benzonaphthyridines with various carbon-linked substituents at the 2-position, were prepared using the synthetic route shown in scheme (V).

Scheme (V)

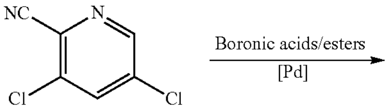

V-1

-continued

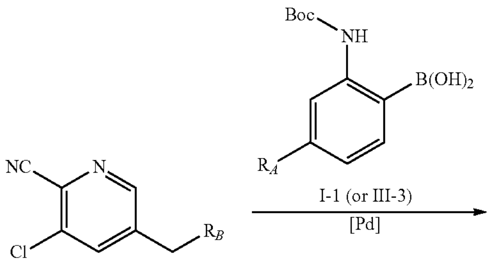

V-2

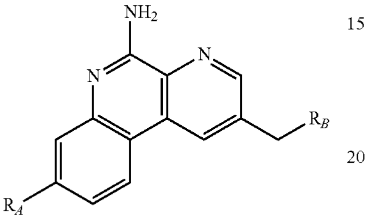

V-3

In scheme (V), a 3,5-dihalopicolinonitrile, such as, by way of example only, 3,5-dichloropicolinonitrile (V-1), is first mono-substituted using one equivalent of boronic acid/ester thereby giving the corresponding picolinonitrile (V-2). Using more vigorous palladium-mediated conditions as in scheme (I), derivatives of nitrile (V-2) are coupled with boronic acids (I-1) (or boronate esters (III-3) to give the benzonaphthyridine (V-3) having carbon-linked substituents at the 2-position. In certain aspects the carbon-linked substituent is an alkene, while in other aspects such alkenes are further modified by hydrogenation to give benzonaphthyridines with alkyl groups at the 2-position.

In other aspects, certain compounds of Formula (VIII) having various substituents, including benzonaphthyridines with various substituents at the 2-position, were synthesized using the methodologies described in scheme (VI).

Scheme (VI)

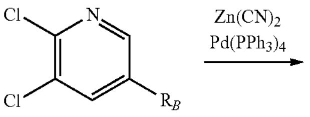

VI-1

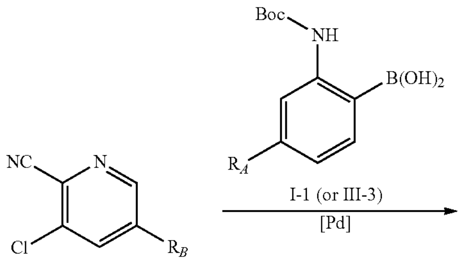

VI-2

-continued

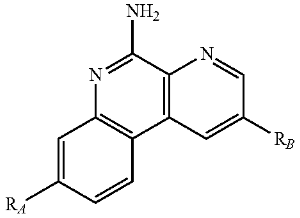

I-3

In scheme (VI), a 2,3-dihalopyridines substituted at the 5 position (VI-1), such as, by way of example only, (5,6-dichloropyridin-3-yl)methanol, is first converted to the corresponding nitrile (VI-2). Using palladium-mediated conditions as in scheme (I), derivatives of nitrile (VI-2) are coupled with boronic acids (I-1) (or boronate esters (III-3) to give the benzonaphthyridine (I-3).

In other aspects, certain compounds of Formula (VIII) were synthesized using the methodologies described in scheme (VII).

Scheme (VII)

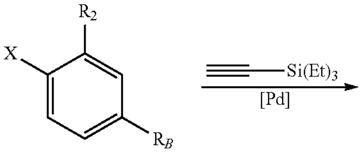

X = Br or I
VII-1

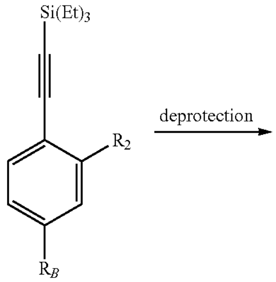

VII-2

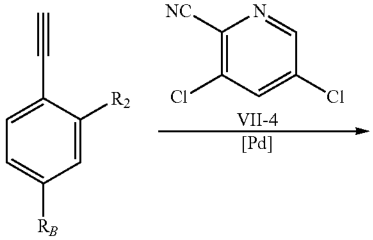

VII-3

-continued

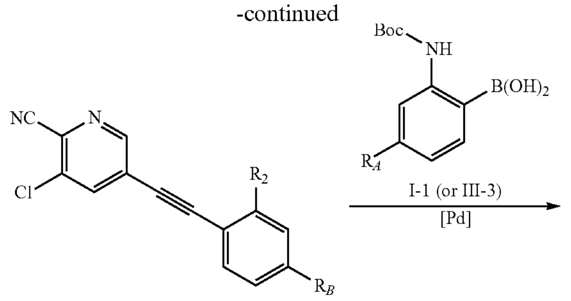

VII-5

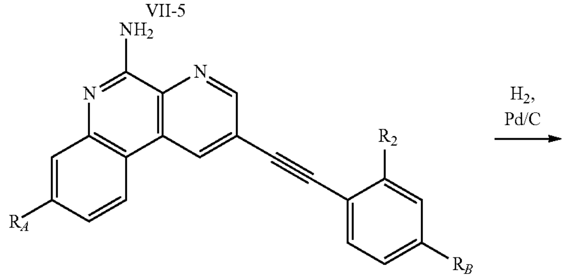

VII-6

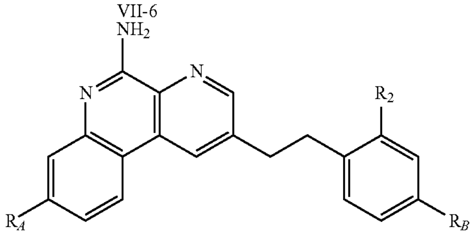

VII-7

In scheme (VII), aryl bromides or aryl iodides (VII-1) are coupled with triethyl(ethynyl)silane (or its equivalents) using palladium-mediated conditions to afford (VII-2). After deprotection of the silyl protection group, acetylene derivatives (VII-3) are coupled with 3,5-dichloropicolinonitrile (VII-4) using palladium-mediated conditions to afford 3-chloro-2-cyanopyridines (VII-5). Derivatives of (VII-5) such as, by way of example only, 3-chloro-5-(phenylethynyl)picolinonitrile are coupled with boronic acids (I-1) (or boronate esters (III-3) to give the benzonaphthyridine (VII-6). Compound (VII-6) is then subjected under hydrogenation conditions to give benzonaphthyridines (VII-7). $R_2$ is as described herein and the $R_A$ and $R_B$ groups on benzonaphthyridines (VII-7) are as described herein for substituents of Formula (VIII) at the respective positions, or $R_A$ and $R_B$ are groups that are further modified to obtain the respective substituents of Formula (VIII), as described herein.

In other aspects, certain compounds of Formula (VIII) were synthesized using the methodologies described in scheme (VIII).

Scheme (VIII)

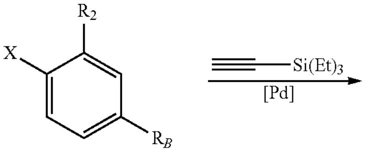

X = Br or I
VIII-1

-continued

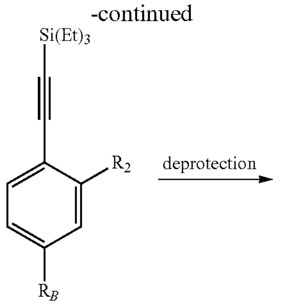

VIII-2

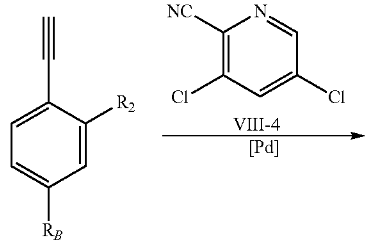

VIII-3

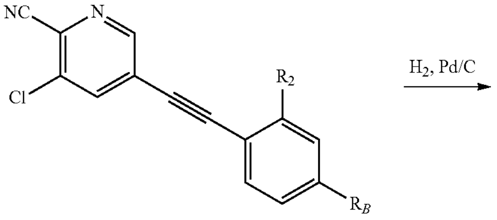

VIII-5

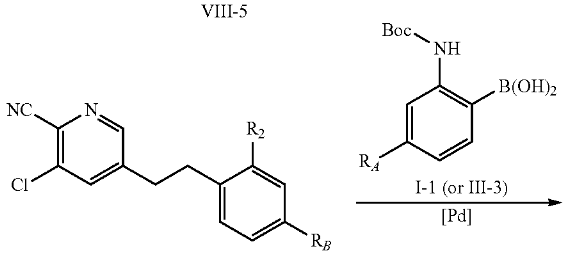

VIII-6

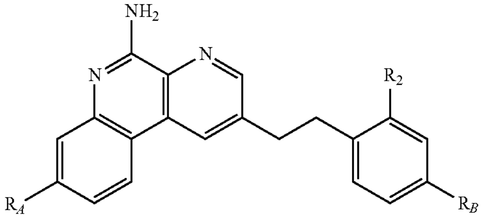

VIII-7

In scheme (VIII), aryl bromides or aryl iodides (VIII-1) are coupled with triethyl(ethynyl)silane (or its equivalents) using palladium-mediated conditions to afford (VIII-2). After deprotection of the silyl protection group, acetylene derivatives (VIII-3) are coupled with 3,5-dichloropicolinonitrile (VIII-4) using palladium-mediated conditions to afford 3-chloro-2-cyanopyridines (VIII-5). Derivatives of (VIII-5) such as, by way of example only, 3-chloro-5-(phenylethynyl)picolinonitrile are reduced to the corresponding 3-chloro-5-phenethylpicolinonitrile (VIII-6) under hydrogenation conditions. Compound (VIII-6) is coupled with boronic acids (I-1) (or boronate esters (III-3) to give benzonaphthyridines (VIII-7). $R_2$ is as described herein and the $R_A$ and $R_B$ groups on benzonaphthyridines (VII-7) are as described herein for substituents of Formula (VIII) at the respective positions, or $R_A$ and $R_B$ are groups that are further modified to obtain the respective substituents of Formula (VIII), as described herein.

In other aspects, certain compounds of Formula (VIII) were synthesized using the methodologies described in scheme (IX).

Scheme (IX)

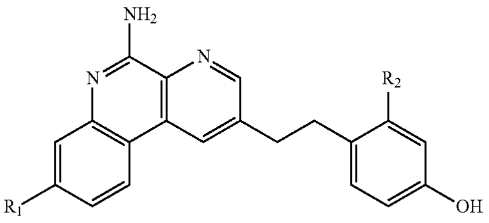

IX-1

+

X—$L_3R_7$
or
X—$L_3R_5$
or
X—$L_1R_5$
or
X—$L_3L_4R_7$
or
X—$L_3L_4L_3R_7$
or
X—$L_3L_4R_5$
or
X—$L_3L_4L_3R_5$
where X = Br or I NaH
DMF, rt

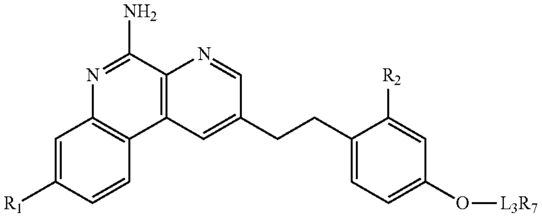

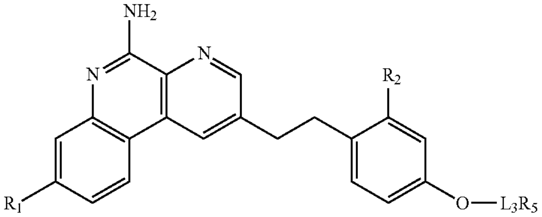

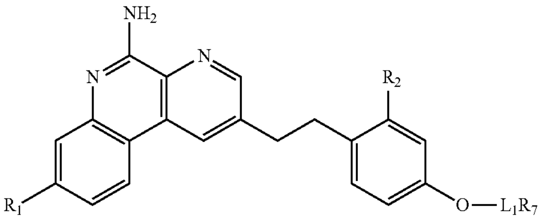

-continued

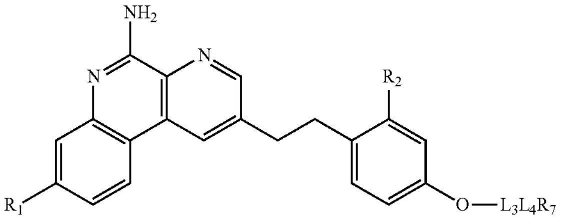

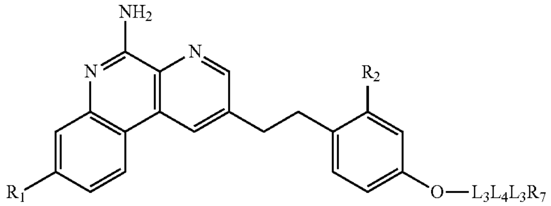

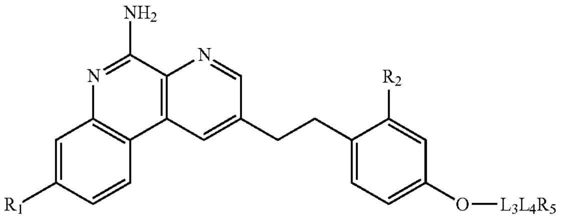

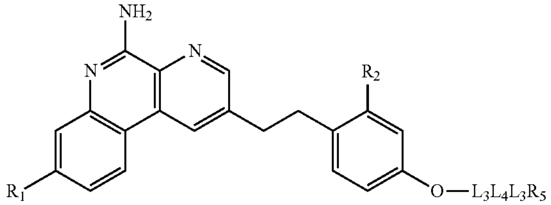

In scheme (IX) compound (IX-1) bearing a phenol group is alkylated with various electrophiles, where $R^1$, $R^2$, $L^1$, $L^3$, $L^4$, $R^5$ and $R^7$ are as defined herein.

The examples provided herein are offered to illustrate, but not to limit, the compounds of Formula (VIII) provided herein, and the preparation of such compounds.

EXEMPLIFICATION

The invention now being generally described, it will be more readily understood by reference to the following examples, which are included merely for purposes of illustration of certain aspects and aspects of the present invention, and are not intended to limit the invention.

Examples 1-197 illustrate methods for preparing certain benzonapthyridine compounds of Formula (I) that are useful in the compositions and methods of the invention. The skilled person would be able to make a wide range of other compounds for use in the instant methods based upon these examples.

Example 1

Benzo[f][1,7]naphthyridin-5-amine

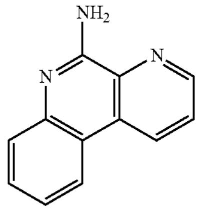 [SMILES: Nc1nc2ccccc2c2cccnc12]

A solution of 2-(tert-butoxycarbonylamino)phenylboronic acid (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-80% ethyl acetate in hexane to give a white solid. $^1H$ NMR (acetone d-6): δ 9.04 (d, 1H), 8.91 (d, 1H), 8.45 (d, 1H), 7.86 (dd, 1H), 7.53-7.62 (m, 2H), 7.35 (t, 1H), 6.65 (br, 2H). LRMS [M+H]=196.1.

Example 3

9-chlorobenzo[f][1,7]naphthyridin-5-amine

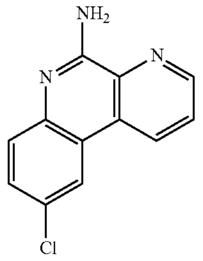 [SMILES: Nc1nc2ccc(Cl)cc2c2cccnc12]

Step 1: tert-butyl 2-bromo-4-chlorophenylcarbamate

To a solution of 2-bromo-4-chloroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified y by flash chromatography on a COMBIFLASH® system (ISCO) using 0-5% ethyl acetate in hexane to give the product as light yellow oil.

Step 2: tert-butyl 4-chloro-2-(4,4,5,5-tetramethyl-1,3,2-dioxaborolan-2-yl)phenyl-carbamate Tert-butyl 2-bromo-4-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-10% ethyl acetate in hexane to give tert-butyl 4-chloro-2-(4,4,5,5-tetramethyl-1,3,2-dioxaborolan-2-yl)phenyl-carbamate.

Step 3: 9-chlorobenzo[f][1,7]naphthyridin-5-amine

A solution of tert-butyl 4-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane and then re-purified using 0-5% methanol in dichloromethane to give a solid. $^1H$ NMR (acetone d-6): δ 9.08 (d, 1H), 8.96 (d, 1H), 8.45 (s, 1H), 7.86-7.89 (dd, 1H), 7.60 (d, 1H), 7.54 (d, 1H), 6.78 (br, 2H). LRMS [M+H]=230.1

Example 4

8-chlorobenzo[f][1,7]naphthyridin-5-amine

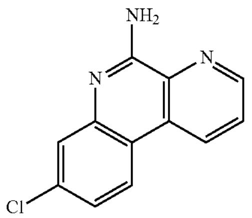 [SMILES: Nc1nc2cc(Cl)ccc2c2cccnc12]

Step 1: tert-butyl 2-bromo-5-chlorophenylcarbamate

To a solution of 2-bromo-5-chloroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-chloro-2-(4,4,5,5-tetramethyl-1,3,2-dioxaborolan-2-yl)phenyl-carbamate Tert-butyl 2-bromo-5-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-5% ethyl acetate in hexane to give tert-butyl 5-chloro-2-(4,4,5,5-tetramethyl-1,3,2-dioxaborolan-2-yl)phenyl-carbamate.

Step 3: 8-chlorobenzo[f][1,7]naphthyridin-5-amine

A solution of tert-butyl 5-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% methanol in dichloromethane to give a semipure solid, which was then stirred in hot 10% ethyl acetate in hexane, filtered, and dried to give a pure solid. $^1H$ NMR (acetone d-6): δ 9.03 (d, 1H), 8.93 (d, 1H), 8.46 (d, 1H), 7.85-7.88 (dd, 1H), 7.57 (s, 1H), 7.32 (d, 1H), 6.94 (br, 2H). LRMS [M+H]=230.1

Example 5

8-methylbenzo[f][1,7]naphthyridin-5-amine

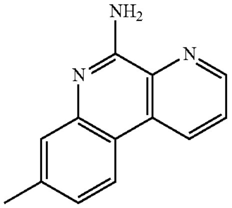 [SMILES: Cc1ccc2c(c1)nc(N)c1ncccc12]

Step 1: tert-butyl 2-bromo-5-methylphenylcarbamate

To a solution of 2-bromo-5-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl)phenylcarbamate.

Step 3: 8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-40% ethyl acetate in toluene to give a pure solid. $^1H$ NMR (acetone d-6): δ 8.98 (d, 1H), 8.87 (d, 1H), 8.32 (d, 1H), 7.79-7.82 (dd, 1H), 7.42 (s, 1H), 7.18 (d, 1H), 6.6 (br, 2H), 2.45 (s, 3H). LRMS [M+H]=210.1

Example 6

9-methylbenzo[f][1,7]naphthyridin-5-amine

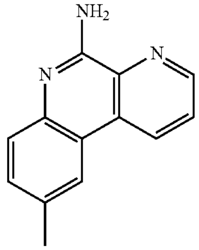 [SMILES: Cc1ccc2nc(N)c3ncccc3c2c1]

Step 1: tert-butyl 2-bromo-4-methylphenylcarbamate

To a solution of 2-bromo-4-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 4-methyl-2-(4,4,5,5-tetramethyl-1,3,2-dioxaborolan-2-yl)phenylcarbamate Tert-butyl 2-bromo-4-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 4-methyl-2-(4,4,5,5-tetramethyl-1,3,2-dioxaborolan-2-yl)phenylcarbamate.

Step 3: 9-methylbenzo[f][1,7]naphthyridin-5-amine

A solution of tert-butyl 4-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% methanol in dichloromethane to give a semipure solid, which was then swirled in hot ethyl acetate, filtered, and dried to give a pure solid. $^1H$ NMR (acetone d-6): δ 9.02 (d, 1H), 8.89 (d, 1H), 8.25 (s, 1H), 7.80-7.84 (dd, 1H), 7.52 (d, 1H), 7.40 (d, 1H), 6.5 (br, 2H), 2.48 (s, 3H). LRMS [M+H]=210.2

Example 7

10-methylbenzo[f][1,7]naphthyridin-5-amine

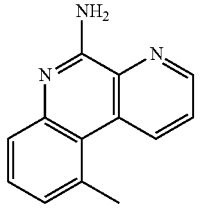 [SMILES: Cc1cccc2nc(N)c3ncccc3c12]

Step 1: tert-butyl 2-bromo-3-methylphenylcarbamate

To a solution of 2-bromo-3-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 3-methyl-2-(4,4,5,5-tetramethyl-1,3,2-dioxaborolan-2-yl)phenylcarbamate Tert-butyl 2-bromo-3-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to tert-butyl 3-methyl-2-(4,4,5,5-tetramethyl-1,3,2-dioxaborolan-2-yl)phenylcarbamate.

Step 3: 10-methylbenzo[f][1,7]naphthyridin-5-amine

A solution of tert-butyl 3-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1H$ NMR (acetone d-6): δ 9.22 (d, 1H), 8.90 (d, 1H), 7.82-7.85 (dd, 1H), 7.54 (d, 1H), 7.45 (t, 1H), 7.19 (d, 1H), 6.6 (br, 2H), 2.98 (s, 3H). LRMS [M+H]=210.2.

Example 8

Ethyl 5-aminobenzo[f][1,7]naphthyridine-9-carboxylate

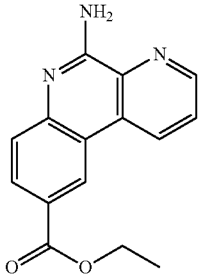 [SMILES: CCOC(=O)c1ccc2nc(N)c3ncccc3c2c1]

Step 1: ethyl 3-bromo-4-(tert-butoxycarbonylamino)benzoate

To a solution of 4-amino-3-bromobenzoate (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: Ethyl 4-(tert-butoxycarbonylamino)-3-(4,4,5,5-tetramethyl-1,3,2-dioxaborolan-2-yl)benzoate Ethyl 3-bromo-4-(tert-butoxycarbonylamino)benzoate (from step 1) (1.0 eq.), 4,4,4',4',5,5,5',5'-octamethyl-2,2'-bi (1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give ethyl 4-(tert-butoxycarbonylamino)-3-(4,4,5,5-tetramethyl-1,3,2-dioxaborolan-2-yl)benzoate.

Step 3: ethyl 5-aminobenzo[f][1,7]naphthyridine-9-carboxylate

A solution of ethyl 4-(tert-butoxycarbonylamino)-3-(4,4,5,5-tetramethyl-1,3,2-dioxaborolan-2-yl)benzoate (from step 2) (1.0 eq.) and 3-bromopicolino-nitrile (1.0 eq.) in toluene/ethanol (10:1, 0.23 M) was mixed with tetrakis (triphenyl-phosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1H$ NMR (acetone d-6): δ 9.11 (d, 1H), 9.05 (s, 1H), 8.95 (d, 1H), 8.14 (d, 1H), 7.89-7.92 (dd, 1H), 7.63 (d, 1H), 4.38 (q, 2H), 1.40 (t, 3H). LRMS [M+H]=268.2.

Example 9

5-aminobenzo[f][1,7]naphthyridine-9-carboxylic acid

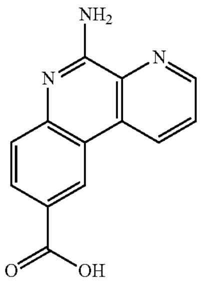 [SMILES: Nc1nc2ccc(C(=O)O)cc2c2cccnc12]

Ethyl 5-aminobenzo[f][1,7]naphthyridine-9-carboxylate (Example 8) (1.0 eq.) was mixed with 1N NaOH (2.0 eq.) in ethanol (0.12 M). The reaction was heated to 80° C. and stirred for 36 hours. The solvent was removed en vacuo. The residue was suspended in water, and the pH was adjusted to neutral using 5% citric acid aqueous solution. The suspension was centrifuged (2500 rpm, 5 min), and the supernatant was removed. The resulting solids was re-suspended in water by vortexing, centrifuged (2500 rpm, 5 min), and the supernatant was removed. The re-suspension, centrifugation, and removal of supernatant steps were repeated with hot methanol, hot ethyl acetate, and ether to give a pure solid. $^1H$ NMR (DMSO): δ 12.86 (s, 1H), 9.15 (d, 1H), 9.00 (s, 1H), 8.97 (d, 1H), 8.07 (d, 1H), 7.88-7.91 (dd, 1H), 7.56-7.59 (m, 3H). LRMS [M+H]=240.1

Example 10

8-methoxybenzo[f][1,7]naphthyridin-5-amine

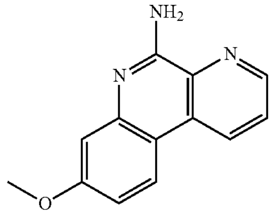 [SMILES: COc1ccc2c(c1)nc(N)c1ncccc12]

Step 1: 2-bromo-5-methoxyaniline

A solution of 1-bromo-4-methoxy-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous $MgSO_4$, and concentrated en vacuo. The crude material was purified by flash chromatography on a COMBIFLASH® system (ISCO) using 0-15% ethyl acetate in hexane to give the product as oil.

Step 2: tert-butyl 2-bromo-5-methoxyphenylcarbamate

To a solution of 2-bromo-5-methoxyaniline (1.0 eq.) (from step 1) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 3: tert-butyl 5-methoxy-2-(4,4,5,5-tetramethyl-1,3,2-dioxaborolan-2-yl)phenylcarbamate Tert-butyl 2-bromo-5-methoxyphenylcarbamate (from step 2) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-15% ether in hexane to give tert-butyl 5-methoxy-2-(4,4,5,5-tetramethyl-1,3,2-dioxaborolan-2-yl)phenylcarbamate.

Step 4: 8-methoxybenzo[f][1,7]naphthyridin-5-amine

A solution of tert-butyl 5-methoxy-2-(4,4,5,5-tetramethyl-1,3,2-dioxaborolan-2-yl)phenylcarbamate (from step 3) (1.0 eq.) and 3-bromopicolino-nitrile (1.0 eq.) in toluene/ethanol (10:1, 0.23 M) was mixed with tetrakis(triphenylphosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% methanol in dichloromethane to give a semipure solid, which was then recrystallized in ethyl acetate, filtered, and dried to give a pure solid. $^1H$ NMR (acetone d-6): δ 8.91 (d, 1H), 8.82 (d, 1H), 8.33 (d, 1H), 7.76-7.79 (dd, 1H), 7.07 (s, 1H), 6.96 (d, 1H), 6.6 (br, 2H), 3.90 (s, 3H). LRMS [M+H]=226.1

Example 11

7-fluorobenzo[f][1,7]naphthyridin-5-amine

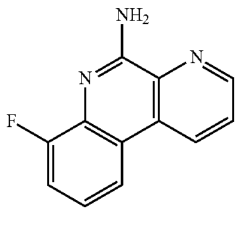 [SMILES: Nc1nc2c(F)cccc2c2cccnc12]

Step 1: tert-butyl 2-fluorophenylcarbamate

To a solution of 2-fluoroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: 2-(tert-butoxycarbonylamino)-3-fluorophenylboronic acid

To a solution of tert-butyl 2-fluorophenylcarbamate (from step 1) (1.0 eq.) in tetrahydrofuran (0.25 M) at −78° C. under $N_2$ atmosphere was added dropwise 1.7 M tert-butyllithium (2.4 eq.). The reaction was warmed to −40° C. slowly over 2 hours, and neat trimethyl borate (3.8 eq.) was added. The reaction was warmed to room temperature over 30 minutes. An aqueous solution of 1N NaOH was slowly added to the reaction and stirred for 15 minutes. The mixture was poured into ethyl acetate and acidified with 3N HCl to dissolve the solids. The aqueous layer was extracted twice with ethyl acetate, and the combined organic layers were washed with brine, dried over anhydrous $MgSO_4$, and concentrated en vacuo. The resulting solids were stirred in 1:1 ether/hexane, filtered, and dried. The solids were carried onto the next step without further purification.

Step 3: 7-fluorobenzo[f][1,7]naphthyridin-5-amine

A solution of 2-(tert-butoxycarbonylamino)-3-fluorophenylboronic acid (from step 2) (1.0 eq.) and 3-bromopicolino-nitrile (1.0 eq.) in toluene (0.44 M) was mixed with tetrakis (triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. After workup, the crude product was suspended in hot toluene, centrifuged (2500 rpm, 5 min), and the supernatant was removed. The suspension, centrifugation, and removal of supernatant steps were repeated with hot ethyl acetate, ether, and hexane to give a pure solid. $^1$H NMR (acetone d-6): δ 9.04 (d, 1H), 8.96 (d, 1H), 8.27 (d, 1H), 7.86-7.90 (dd, 1H), 7.28-7.34 (m, 2H), 6.9 (br, 2H). LRMS [M+H]=214.1

Example 12

8-(methylsulfonyl)benzo[f][1,7]naphthyridin-5-amine

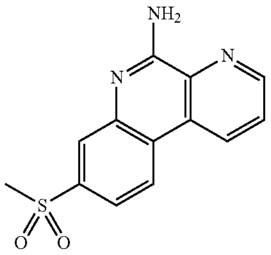 [SMILES: CS(=O)(=O)c1ccc2c(c1)nc(N)c1ncccc12]

Step 1: 2-bromo-5-(methylsulfonyl)aniline

A solution of 1-bromo-4-(methylsulfonyl)-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous $MgSO_4$, and concentrated en vacuo. The crude material was purified by triturating in 1:1 hexane/ether to give a light yellow solid.

Step 2: tert-butyl 2-bromo-5-(methylsulfonyl)phenylcarbamate

To a solution of 2-bromo-5-(methylsulfonyl)aniline (from step 1) (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give tert-butyl 2-bromo-5-(methylsulfonyl) phenylcarbamate.

Step 3: tert-butyl 5-(methylsulfonyl)-2-(4,4,5,5-tetramethyl-1,3,2-dioxaborolan-2-yl)phenylcarbamate Tert-butyl 2-bromo-5-(methylsulfonyl)phenylcarbamate (from step 2) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-50% ethyl acetate in hexane to give a solid which was then triturated in 10% ether/hexane to give tert-butyl 5-(methylsulfonyl)-2-(4,4,5,5-tetramethyl-1,3,2-dioxaborolan-2-yl)phenylcarbamate as a white solid.

Step 4: 8-(methylsulfonyl)benzo[f][1,7]naphthyridin-5-amine

A solution of tert-butyl 5-(methylsulfonyl)-2-(4,4,5,5-tetramethyl-1,3,2-dioxaborolan-2-yl)phenylcarbamate (from step 3) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-5% methanol in dichloromethane to give a solid which was then triturated in 1:1 hexane/ethyl acetate to give 8-(methylsulfonyl)benzo[f][1,7]naphthyridin-5-amine. $^1$H NMR (acetone d-6): δ 9.16 (d, 1H), 9.03 (d, 1H), 8.71 (d, 1H), 8.11 (s, 1H), 7.93-7.96 (dd, 1H), 7.81 (d, 1H), 7.0 (br, 2H), 3.19 (s, 3H). LRMS [M+H]=274.1

Example 13

8-(trifluoromethyl)benzo[f][1,7]naphthyridin-5-amine

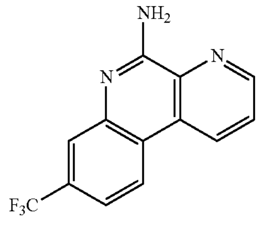 [SMILES: Nc1nc2cc(C(F)(F)F)ccc2c2cccnc12]

Step 1: tert-butyl 2-bromo-5-(trifluoromethyl)phenylcarbamate

To a solution of 2-bromo-5-(trifluoromethyl)aniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 2-(4,4,5,5-tetramethyl-1,3,2-dioxaborolan-2-yl)-5-(trifluoromethyl)phenylcarbamate Tert-butyl 2-bromo-5-(trifluoromethyl)phenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give an impure product which was carried onto the next step without further purification.

Step 3: 8-(trifluoromethyl)benzo[f][1,7]naphthyridin-5-amine

A solution of tert-butyl 2-(4,4,5,5-tetramethyl-1,3,2-dioxaborolan-2-yl)-5-(trifluoromethyl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-(trifluoromethyl)benzo[f][1,7]naphthyridin-5-amine. $^1$H NMR (acetone d-6): δ 9.13 (d, 1H), 9.00 (d, 1H), 8.67 (d, 1H), 7.91-7.94 (dd, 1H), 7.86 (s, 1H), 7.58 (d, 1H), 6.9 (br, 2H). LRMS [M+H]=264.1

Example 14

8-fluorobenzo[f][1,7]naphthyridin-5-amine

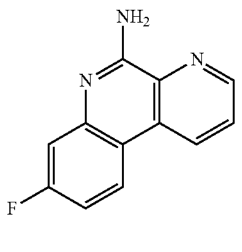 [SMILES: Nc1nc2cc(F)ccc2c2cccnc12]

Step 1: tert-butyl 2-bromo-5-fluorophenylcarbamate

To a solution of 2-bromo-5-fluoroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-fluoro-2-(4,4,5,5-tetramethyl-1,3,2-dioxaborolan-2-yl)phenylcarbamate Tert-butyl 2-bromo-5-fluorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-5% ether in hexane to give the product as a yellow solid.

Step 3: 8-fluorobenzo[f][1,7]naphthyridin-5-amine

A solution of tert-butyl 5-fluoro-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-fluorobenzo[f][1,7]naphthyridin-5-amine. $^1$H NMR (acetone d-6): δ 9.00 (d, 1H), 8.90 (d, 1H), 8.46-8.50 (dd, 1H), 7.83-7.87 (dd, 1H), 7.26 (d, 1H), 7.15 (t, 1H), 6.9 (br, 2H). LRMS [M+H]=214.1

Example 15

5-aminobenzo[f][1,7]naphthyridin-3(4H)-one

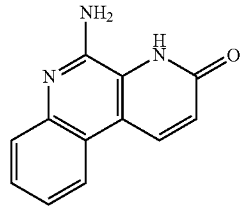 [SMILES: Nc1nc2ccccc2c2ccc(=O)[nH]c12]

Step 1: 3-bromo-2-cyanopyridine 1-oxide

To a solution of 3-bromopicolinonitrile (1.0 eq.) in chloroform (0.3 M) was added 77% meta-chloroperbenzoic acid (mCPBA) (1.8 eq.) and heated at 60° C. for 2 days. After cooling to room temperature, $Ca(OH)_2$ (2.5 eq.) was added, and the resulting precipitate was stirred for 30 minutes. The precipitate was filtered and washed with 5% methanol in dichloromethane. The filtrate was washed with saturated aqueous $NaHCO_3$ solution. The aqueous layer was extracted several times with 3% methanol in dichloromethane. The combined organic layers were dried over anhydrous $MgSO_4$ and concentrated en vacuo. The crude product was stirred in hot hexane/ethyl acetate (1:1), filtered, and dried to give the desired product as a white solid.

Step 2: 3-bromo-6-oxo-1,6-dihydropyridine-2-carbonitrile

A solution of 3-bromo-2-cyanopyridine 1-oxide (from step 1) in acetic anhydride (0.5M) was heated at 150° C. for 24 hours. The reaction was cooled to room temperature, and the solvent was removed en vacuo. The residue was purified by a COMBIFLASH® system (ISCO) using 0-90% ethyl acetate in hexane to give the O-acetate which was hydrolyzed in 2N NaOH/methanol (1:1, 0.2 M) at room temperature for 2 hours. The resulting mixture was diluted with water and acidified with 5% citric acid. The pale yellow precipitate was filtered and washed with 9:1 hexane/ethyl acetate and ether to give 3-bromo-6-oxo-1,6-dihydropyridine-2-carbonitrile.

Step 3: 3-bromo-6-(tert-butyldimethylsilyloxy)picolinonitrile

A solution of 3-bromo-6-oxo-1,6-dihydropyridine-2-carbonitrile (from step 2) (1.0 eq.), tert-butyldimethylsilylchloride (TBSCl) (1.8 eq.), and imidazole (2.5 eq.) in DMF (0.2 M) was heated to 60° C. and stirred overnight. The reaction mixture was diluted with water and extracted with ether. The combined organic layers were dried over anhydrous $MgSO_4$ and concentrated en vacuo. The residue was purified by a COMBIFLASH® system (ISCO) using 0-20% ethyl acetate in hexane to give 3-bromo-6-(tert-butyldimethylsilyloxy) picolinonitrile.

Step 4: 3-(tert-butyldimethylsilyloxy)benzo[f][1,7] naphthyridin-5-amine

A solution of 2-(tert-butoxycarbonylamino)phenylboronic acid (1.0 eq.) and 3-bromo-6-(tert-butyldimethylsilyloxy)picolinonitrile (from step 3) (1.0 eq.) in toluene/ethanol (10:1, 0.2 M) was mixed with tetrakis(triphenyl-phosphine) palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-50% ethyl acetate in hexane to give a solid.

Step 5: 5-aminobenzo[f][1,7]naphthyridin-3(4H)-one

To a solution of 3-(tert-butyldimethylsilyloxy)benzo[f][1,7]naphthyridin-5-amine (from step 4) (1.0 eq.) in tetrahydrofuran (0.05 M) was added tetra-n-butylammonium fluoride (TBAF) (1.0 eq.) and acetic acid (1.0 eq.). The reaction was stirred for 15 minutes, and then concentrated en vacuo. The crude residue was suspended in water and neutralized by addition of saturated aqueous $NaHCO_3$ solution to pH 7. The solids were filtered, washed with acetone, and dried to give 5-aminobenzo[f][1,7]naphthyridin-3(4H)-one. $^1H$ NMR (DMSO d-6): δ 8.59 (d, 1H), 8.20 (d, 1H), 7.49 (d, 1H), 7.37-7.41 (dd, 1H), 7.23-7.27 (dd, 1H), 6.88 (br, 2H), 6.79 (d, 1H). LRMS [M+H]=212.1

Example 16

3-methoxybenzo[f][1,7]naphthyridin-5-amine

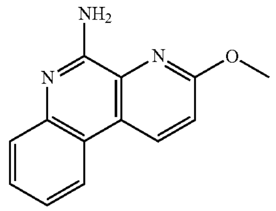 [SMILES: COc1ccc2c(n1)c(N)nc1ccccc12]

Step 1: 3-bromo-6-methoxypicolinonitrile

A solution of 3-bromo-6-oxo-1,6-dihydropyridine-2-carbonitrile (from Example 15/Step 2) (1.0 eq.), silver carbonate (1.3 eq.), and iodomethane (1.2 eq.) in toluene (0.2 M) was stirred in the dark at room temperature overnight. The solvent was concentrated en vacuo, and the resulting residue was purified by a COMBIFLASH® system (ISCO) using 0-80% ethyl acetate in hexane to give 3-bromo-6-methoxypicolinonitrile.

Step 2: 3-methoxybenzo[f][1,7]naphthyridin-5-amine

A solution of 2-(tert-butoxycarbonylamino)phenylboronic acid (1.0 eq.) and 3-bromo-6-methoxypicolinonitrile (from step 3) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane to give 3-methoxybenzo[f][1,7]naphthyridin-5-amine as a yellow solid. $^1$H NMR (acetone d-6): δ 8.91 (d, 1H), 8.34 (d, 1H), 7.63 (d, 1H), 7.51-7.53 (dd, 1H), 7.27-7.33 (m, 2H), 6.65 (br, 2H), 4.11 (s, 3H). LRMS [M+H]=226.1

Example 17

3-butoxybenzo[f][1,7]naphthyridin-5-amine

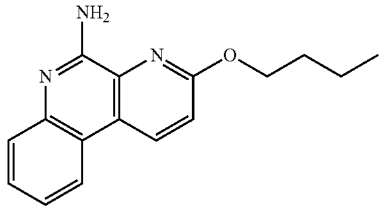 [SMILES: CCCCOc1ccc2c(n1)c(N)nc1ccccc12]

Step 1: 3-bromo-6-butoxypicolinonitrile

A solution of 3-bromo-6-oxo-1,6-dihydropyridine-2-carbonitrile (from Example 15/Step 2) (1.0 eq.), potassium carbonate (1.3 eq.), and 1-iodobutane (1.2 eq.) in acetone (0.3 M) was stirred at 70° C. overnight. The solvent was concentrated en vacuo, and the resulting residue was taken up in water and ethyl acetate. The aqueous layer was extracted with ethyl acetate three times. The combined organic layers were washed with brine, dried over anhydrous $MgSO_4$, and concentrated en vacuo. The crude product was purified by a COMBIFLASH® system (ISCO) using 0-30% ethyl acetate in hexane to give a colorless solid.

Step 2: 3-butoxybenzo[f][1,7]naphthyridin-5-amine

A solution of 2-(tert-butoxycarbonylamino)phenylboronic acid (1.0 eq.) and 3-bromo-6-butoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% ethyl acetate in methanol to give 3-butoxybenzo[f][1,7]naphthyridin-5-amine as a white solid. $^1$H NMR (acetone d-6): δ 8.91 (d, 1H), 8.34 (d, 1H), 7.61 (d, 1H), 7.48-7.52 (dd, 1H), 7.27-7.33 (m, 2H), 6.51 (br, 2H), 6.55 (t, 2H), 1.81-1.88 (m, 2H), 1.50-1.59 (m, 2H), 1.00 (t, 3H). LRMS [M+H]=268.1

Example 18

3-(benzyloxy)benzo[f][1,7]naphthyridin-5-amine

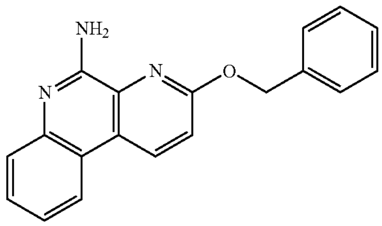 [SMILES: Nc1nc2ccccc2c2ccc(OCc3ccccc3)nc12]

Step 1: 6-(benzyloxy)-3-bromopicolinonitrile

A solution of 3-bromo-6-oxo-1,6-dihydropyridine-2-carbonitrile (from Example 15/Step 2) (1.0 eq.), silver carbonate (1.3 eq.), and benzyl bromide (1.2 eq.) in toluene (0.16 M) was stirred in the dark at 50° C. overnight. The solvent was concentrated en vacuo, and the resulting residue was purified by a COMBIFLASH® system (ISCO) using 0-20% ethyl acetate in hexane to give 6-(benzyloxy)-3-bromopicolinonitrile.

Step 2: 3-(benzyloxy)benzo[f][1,7]naphthyridin-5-amine

A solution of 2-(tert-butoxycarbonylamino)phenylboronic acid (1.0 eq.) and 6-(benzyloxy)-3-bromopicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane to give 3-(benzyloxy)benzo[f][1,7]naphthyridin-5-amine as a yellow solid. $^1$H NMR (acetone d-6): δ 8.95 (d, 1H), 8.35 (d, 1H), 7.58-7.63 (m, 2H), 7.49-7.53 (dd, 1H), 7.30-7.44 (m, 5H), 6.61 (br, 2H), 5.64 (s, 2H). LRMS [M+H]=302.1

Example 19

3-methylbenzo[f][1,7]naphthyridin-5-amine

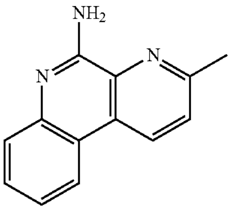 [SMILES: Cc1ccc2c(n1)c(N)nc1ccccc12]

Step 1: 5-bromo-2-methylpyridine 1-oxide

To a solution of 5-bromo-2-methylpyridine (1.0 eq.) in chloroform (0.38 M) was added 77% meta-chloroperbenzoic acid (mCPBA) (4.0 eq.) and heated at 60° C. for 20 hours. After cooling to room temperature, $Ca(OH)_2$ (5.3 eq.) was added, and the resulting precipitate was stirred for 30 minutes. The precipitate was filtered and washed with 3:1 $CHCl_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-methylpicolinonitrile

To a solution of 5-bromo-2-methylpyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBI-FLASH® system (ISCO) using 0-50% ethyl acetate in hexane to give 3-bromo-6-methylpicolinonitrile.

Step 3: 3-methylbenzo[f][1,7]naphthyridin-5-amine

A solution of 2-(tert-butoxycarbonylamino)phenylboronic acid (1.0 eq.) and 3-bromo-6-methylpicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-70% ethyl acetate in hexane to give 3-methylbenzo[f][1,7]naphthyridin-5-amine as a yellow solid. $^1$H NMR (methanol d-4): δ 8.85 (d, 1H), 8.38 (d, 1H), 7.72 (d, 1H), 7.53-7.61 (m, 2H), 7.34-7.38 (dd, 1H), 2.76 (s, 3H). LRMS [M+H]=210.1

Example 20

3-chlorobenzo[f][1,7]naphthyridin-5-amine

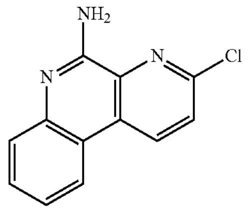 [SMILES: Nc1nc2ccccc2c2ccc(Cl)nc12]

Step 1: 5-bromo-2-chloropyridine 1-oxide

To a solution of 5-bromo-2-chloropyridine (1.0 eq.) in chloroform (0.38 M) was added 77% meta-chloroperbenzoic acid (mCPBA) (4.0 eq.) and heated at 60° C. for 20 hours. After cooling to room temperature, $Ca(OH)_2$ (5.3 eq.) was added, and the resulting precipitate was stirred for 30 minutes. The precipitate was filtered and washed with 3:1 $CHCl_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-chloropicolinonitrile

To a solution of 5-bromo-2-chloropyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBI-FLASH® system (ISCO) using 0-40% ethyl acetate in hexane to give 3-bromo-6-chloropicolinonitrile.

Step 3: 3-chlorobenzo[f][1,7]naphthyridin-5-amine

A solution of 2-(tert-butoxycarbonylamino)phenylboronic acid (1.0 eq.) and 3-bromo-6-chloropicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane to give a solid, which was then triturated in 10% ethyl acetate in hexane to give 3-chlorobenzo[f][1,7]naphthyridin-5-amine. $^1$H NMR (acetone d-6): δ 9.10 (d, 1H), 8.45 (d, 1H), 7.89 (d, 1H), 7.58-7.65 (m, 2H), 7.35-7.39 (dd, 1H), 6.67 (br, 2H). LRMS [M+H]=230.1

Example 21

$N^3$,$N^3$-dimethylbenzo[f][1,7]naphthyridine-3,5-diamine

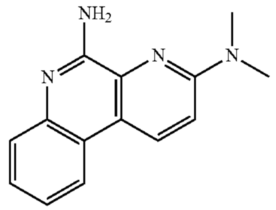 [SMILES: CN(C)c1ccc2c(n1)c(N)nc1ccccc12]

A solution of 3-chlorobenzo[f][1,7]naphthyridin-5-amine (Example 20) (1.0 eq.) was dissolved in 40% aqueous dimethylamine (0.26 M) and heated in a microwave reactor at 100° C. for 30 minutes. The reaction mixture was concentrated en vacuo, and the residue was purified by a COMBIFLASH® system (ISCO) using 0-90% ethyl acetate in hexane to give $N^3$,$N^3$-dimethylbenzo[f][1,7]naphthyridine-3,5-diamine. $^1$H NMR (methanol d-4): δ 8.63 (d, 1H), 8.20 (d, 1H), 7.55 (d, 1H), 7.41-7.45 (dd, 1H), 7.29-7.33 (dd, 1H), 7.27 (d, 1H), 3.26 (s, 6H). LRMS [M+H]=239.1

Example 22

$N^3$-butylbenzo[f][1,7]naphthyridine-3,5-diamine

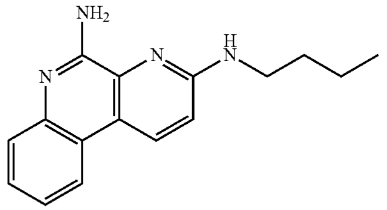 [SMILES: CCCCNc1ccc2c(n1)c(N)nc1ccccc12]

A solution of 3-chlorobenzo[f][1,7]naphthyridin-5-amine (Example 20) (1.0 eq.) was dissolved in n-butylamine (0.1 M) and heated at 110° C. overnight. The reaction mixture was concentrated en vacuo, and the residue was purified by a COMBIFLASH® system (ISCO) using 0-90% ethyl acetate in hexane to give $N^3$-butylbenzo[f][1,7]naphthyridine-3,5-diamine. $^1$H NMR (methanol d-4): δ 8.42 (d, 1H), 8.13 (d, 1H), 7.53 (d, 1H), 7.38-7.42 (dd, 1H), 7.25-7.29 (dd, 1H), 6.96 (d, 1H), 3.48 (t, 2H), 1.63-1.71 (m, 2H), 1.43-1.52 (m, 2H), 0.99 (t, 3H). LRMS [M+H]=267.2

Example 23

3-vinylbenzo[f][1,7]naphthyridin-5-amine

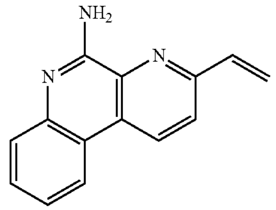 [SMILES: C=Cc1ccc2c(n1)c(N)nc1ccccc12]

A solution of 3-chlorobenzo[f][1,7]naphthyridin-5-amine (Example 20) (1.0 eq.), 4,4,5,5-tetramethyl-2-vinyl-1,3,2-dioxaborolane (1.2 eq.), tetrakis(triphenyl-phosphine)palladium (5 mol %), and 2N aqueous potassium carbonate solution (2.0 eq.) in toluene/ethanol (4:1, 0.1 M) was heated to 100° C. and stirred overnight. After cooling to ambient temperature, the reaction content was diluted with ethyl acetate and water. The two phases were separated, and the aqueous layer was extracted with ethyl acetate three times. The combined organic layers were washed with brine, dried over anhydrous $MgSO_4$, and concentrated en vacuo. The crude material was purified by flash chromatography on a COMBIFLASH® system (ISCO) using 0-50% ethyl acetate in hexane to give a solid, which was then triturated in 10% ethyl acetate in hexane to give 3-vinylbenzo[f][1,7]naphthyridin-5-amine. $^1$H NMR (acetone d-6): δ 8.99 (d, 1H), 8.42 (d, 1H), 8.01 (d, 1H), 7.53-7.62 (m, 2H), 7.30-7.35 (dd, 1H), 7.03-7.10 (dd, 1H), 6.77 (br, 2H), 6.56 (d, 1H), 5.66 (d, 1H). LRMS [M+H]=222.1

Example 24

3-ethylbenzo[f][1,7]naphthyridin-5-amine

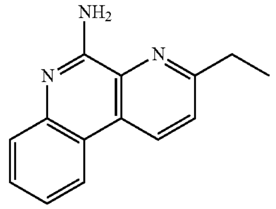 [SMILES: CCc1ccc2c(n1)c(N)nc1ccccc12]

To a solution of 3-vinylbenzo[f][1,7]naphthyridin-5-amine (Example 23) in ethyl acetate/ethanol (1:1, 0.07 M) was added 10% wt palladium on carbon (0.2 eq.). Hydrogen gas was introduced via a balloon, and the reaction was stirred overnight. The mixture was filtered through a pad of celite, washing with dichloromethane. The filtrate was concentrated en vacuo giving 3-ethylbenzo[f][1,7]naphthyridin-5-amine as a white solid. $^1$H NMR (acetone d-6): δ 8.93 (d, 1H), 8.41 (d, 1H), 7.76 (d, 1H), 7.61 (d, 1H), 7.51-7.55 (dd, 1H), 7.30-7.34 (dd, 1H), 6.55 (br, 2H), 6.03 (q, 2H), 1.41 (t, 3H). LRMS [M+H]=224.1

Example 25

3-fluorobenzo[f][1,7]naphthyridin-5-amine

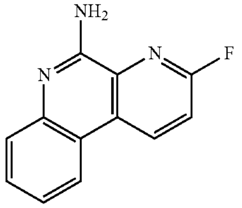 [SMILES: Nc1nc2ccccc2c2ccc(F)nc12]

A solution of 3-chlorobenzo[f][1,7]naphthyridin-5-amine (Example 20) (1.0 eq.), potassium fluoride (3.0 eq.), and 18-crown-6 (0.2 eq.) in N-methylpyrrolidone (NMP) (0.4 M) was heated in a microwave reactor at 210° C. for 80 minutes. After cooling to room temperature, the crude reaction mixture was purified by HPLC using 10-50% acetonitrile in water to give 3-fluorobenzo[f][1,7]naphthyridin-5-amine. $^1$H NMR (acetone d-6): δ 11.40 (br, 2H), 9.38-9.42 (dd, 1H), 8.60 (d, 1H), 7.89-7.92 (dd, 1H), 7.81-7.83 (m, 2H), 7.59-7.66 (m, 1H). LRMS [M+H]=214.1

Example 26

2-(trifluoromethyl)benzo[f][1,7]naphthyridin-5-amine

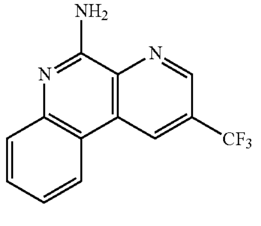 [SMILES: Nc1nc2ccccc2c2cc(C(F)(F)F)cnc12]

Step 1: 3-chloro-5-(trifluoromethyl)picolinaldehyde oxime

A solution of 3-chloro-5-(trifluoromethyl)picolinaldehyde (1.0 eq.), hydroxylamine hydrochloride (5.0 eq.), and pyridine (4.0 eq.) in ethanol was heated to 95° C. and stirred for 1 hour. The reaction was cooled to room temperature and diluted with ethyl acetate and water. The organic layer was washed with brine, water, dried over anhydrous $MgSO_4$, and concentrated en vacuo to give a solid that was carried onto the next step without further purification.

Step 2: 3-chloro-5-(trifluoromethyl)picolinonitrile

A solution of 3-chloro-5-(trifluoromethyl)picolinaldehyde oxime (1.0 eq.) and Burgess reagent (1.5 eq.) in tetrahydrofuran (0.5 M) was heated to 65° C. and stirred for 1 hour. The reaction was cooled to room temperature and diluted with ethyl acetate and water. The organic layer was washed with water, brine, dried over anhydrous $MgSO_4$, and concentrated en vacuo to give a solid that was carried onto the next step without further purification.

Step 3: 2-(trifluoromethyl)benzo[f][1,7]naphthyridin-5-amine

A solution of 2-(tert-butoxycarbonylamino)phenylboronic acid (1.0 eq.) and 3-chloro-5-(trifluoromethyl)picolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane to give 2-(trifluoromethyl)benzo[f][1,7]naphthyridin-5-amine. $^1H$ NMR (acetone d-6): δ 9.44 (s, 1H), 9.20 (s, 1H), 8.65-8.63 (d, 1H), 7.70-7.61 (m, 2H), 7.44-7.36 (m, 1H), 6.84 (br, 2H). LRMS [M+H]=264.2

Example 27

2-methoxybenzo[f][1,7]naphthyridin-5-amine

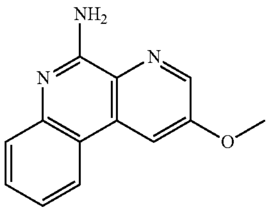 [SMILES: COc1cnc2c(N)nc3ccccc3c2c1]

Step 1: 3-chloro-5-methoxypicolinonitrile

To a solution of 3,5-dichloropicolinonitrile (1.0 eq.) in dimethyl formamide (DMF) (0.5 M) was added sodium methoxide (1.5 eq.) and heated to 75° C. After stirring for 14 hours, the reaction was diluted with ethyl acetate and water.

The organic layer was washed with saturated aqueous $NaHCO_3$ three times, water twice, dried over anhydrous $MgSO_4$, and concentrated en vacuo. The crude residue was purified by a COMBIFLASH® system (ISCO) using 15% ethyl acetate in hexane to give a mixture of two methoxy regioisomers, one of which was the desired product. The mixture was carried onto the next step without further purification.

Step 2: 2-methoxybenzo[f][1,7]naphthyridin-5-amine

A solution of 2-(tert-butoxycarbonylamino)phenylboronic acid (1.0 eq.) and 3-chloro-5-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 50-100% ethyl acetate in hexane to give 2-methoxybenzo[f][1,7]naphthyridin-5-amine.

Example 28

2-(benzyloxy)benzo[f][1,7]naphthyridin-5-amine

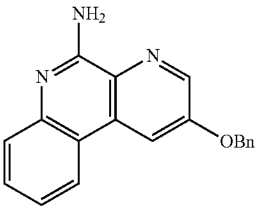 [SMILES: Nc1nc2ccccc2c2cc(OCc3ccccc3)cnc12]

Step 1: 3-(benzyloxy)-5-bromopyridine

A solution of 5-bromopyridin-3-ol (1.0 eq.), benzyl bromide (1.2 eq.), and silver carbonate (1.3 eq.) in toluene (0.1 M) was heated to 50° C. and stirred for 18 hours. After cooling to room temperature, the reaction mixture was filtered, eluting with ethyl acetate. The filtrate was concentrated en vacuo into a residue that was purified by a COMBIFLASH® system (ISCO) using 20% ethyl acetate in hexane to give 3-(benzyloxy)-5-bromopyridine.

Step 2: 3-(benzyloxy)-5-bromopyridine 1-oxide

A solution of 3-(benzyloxy)-5-bromopyridine (from step 1) (1.0 eq.) and meta-chloroperbenzoic acid (mCPBA) (4.0 eq.) in dichloromethane (0.1 M) was stirred at room temperature for 18 hours. The reaction was quenched with saturated aqueous $NaHCO_3$ solution and extracted with dichloromethane three times. The combined organic layers were dried over anhydrous $MgSO_4$ and concentrated en vacuo. The crude residue was purified by a COMBI- FLASH® system (ISCO) using 0-100% ethyl acetate in hexane to give 3-(benzyloxy)-5-bromopyridine 1-oxide.

Step 3: 5-(benzyloxy)-3-bromopicolinonitrile

To a solution of 53-(benzyloxy)-5-bromopyridine 1-oxide (from step 2) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBI-FLASH® system (ISCO) using 0-40% ethyl acetate in hexane to give a mixture of two benzoxy regioisomers, one of which was the desired product. The mixture was carried onto the next step without further purification.

Step 4: 2-(benzyloxy)benzo[f][1,7]naphthyridin-5-amine

A solution of 2-(tert-butoxycarbonylamino)phenylboronic acid (1.0 eq.) and 5-(benzyloxy)-3-bromopicolinonitrile (from step 3) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 50-100% ethyl acetate in hexane to give 2-(benzyloxy)benzo[f][1,7]naphthyridin-5-amine. $^1$H NMR (acetone d-6): δ 8.36 (s, 1H), 7.86 (s, 1H), 7.59-7.56 (d, 2H), 7.46-7.42 (dd, 2H), 7.40-7.37 (d, 1H), 7.20-7.15 (dd, 1H), 7.12-7.09 (d, 1H), 6.88-6.86 (d, 1H), 6.77-6.73 (dd, 1H), 5.51 (s, 2H), 4.74 (br, 2H). LRMS [M+H]=302.3.

Example 29

2-vinylbenzo[f][1,7]naphthyridin-5-amine

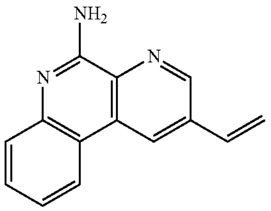 [SMILES: C=Cc1cnc2c(N)nc3ccccc3c2c1]

Step 1: 3-chloro-5-vinylpicolinonitrile

A solution of 3,5-dichloropicolinonitrile (1.0 eq.), 4,4,5,5-tetramethyl-2-vinyl-1,3,2-dioxaborolane (1.0 eq.), tetrakis (triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-80% ethyl acetate in hexane to give a white solid.

Step 2: 2-vinylbenzo[f][1,7]naphthyridin-5-amine

A solution of 2-(tert-butoxycarbonylamino)phenylboronic acid (1.0 eq.) and 3-chloro-5-vinylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude material was purified by flash chromatography on a COMBIFLASH® system (ISCO) using 0-80% ethyl acetate in hexane to give 2-vinylbenzo[f][1,7]naphthyridin-5-amine as a yellow solid. $^1$H NMR (methanol-d4 -$CDCl_3$): δ 8.87 (d, 1H), 8.69 (d, 1H), 8.28 (d, 1H), 7.49-7.58 (m, 2H), 7.32 (dt, 1H), 6.90 (dd, 1H), 6.09 (d, 1H), 5.54 (d, 1H). LRMS [M+H]=222.1.

Example 30

2-ethylbenzo[f][1,7]naphthyridin-5-amine

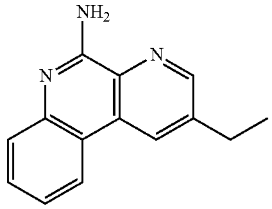 [SMILES: CCc1cnc2c(N)nc3ccccc3c2c1]

To a solution of 2-vinylbenzo[f][1,7]naphthyridin-5-amine (Example 29) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and purified by a COMBIFLASH® system (ISCO) using 0-80% ethyl acetate in hexane to give 2-ethylbenzo[f][1,7]naphthyridin-5-amine as a solid. $^1$H NMR (methanol-d4): δ 8.78-8.81 (m, 2H), 8.45 (d, 1H), 7.55-7.63 (m, 2H), 7.35-7.40 (m, 1H), 2.97 (q, 2H), 1.43 (t, 2H). LRMS [M+H]=224.1.

Example 31

2-phenylbenzo[f][1,7]naphthyridin-5-amine

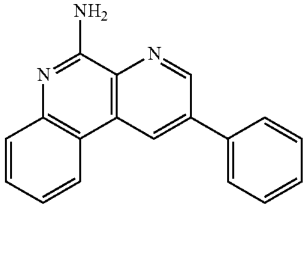 [SMILES: Nc1nc2ccccc2c2cc(-c3ccccc3)cnc12]

Step 1: 3-chloro-5-phenylpicolinonitrile

A solution of 3,5-dichloropicolinonitrile (1.0 eq.), 4,4,5,5-tetramethyl-2-phenyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-80% ethyl acetate in hexane to give a white solid.

Step 2: 2-phenylbenzo[f][1,7]naphthyridin-5-amine

A solution of 2-(tert-butoxycarbonylamino)phenylboronic acid (1.0 eq.) and 3-chloro-5-phenylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-phenylbenzo[f][1,7]naphthyridin-5-amine as a white solid. $^1H$ NMR (dmso-d6): δ 9.13 (d, 1H), 9.03 (d, 1H), 8.56 (d, 1H), 7.98 (d, 2H), 7.43-7.56 (m, 5H), 7.27 (m, 1H), 7.13 (bs, 2H). LRMS [M+H]=272.2.

Example 32

(E)-2-styrylbenzo[f][1,7]naphthyridin-5-amine

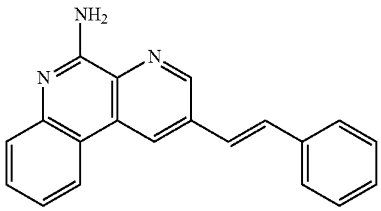 [SMILES: Nc1nc2ccccc2c2cc(/C=C/c3ccccc3)cnc12]

Step 1: (E)-3-chloro-5-styrylpicolinonitrile

A solution of 3,5-dichloropicolinonitrile (1.0 eq.), (E)-4,4,5,5-tetramethyl-2-styryl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vacuo. The crude product was purified by flash chromatography on a COMBIFLASH® system (ISCO) using 0-80% ethyl acetate in hexane to give a white solid.

Step 2: (E)-2-styrylbenzo[f][1,7]naphthyridin-5-amine

A solution of 2-(tert-butoxycarbonylamino)phenylboronic acid (1.0 eq.) and (E)-3-chloro-5-styrylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-styrylbenzo[f][1,7]naphthyridin-5-amine as a brown solid. $^1H$ NMR (dmso-d6): δ 9.22 (d, 1H), 9.06 (d, 1H), 8.51 (d, 1H), 7.78 (d, 1H), 7.66 (d, 2H), 7.46-7.56 (m, 3H), 7.70 (t, 2H), 7.26-7.32 (m, 2H), 7.08 (bs, 2H). LRMS [M+H]=298.2.

Example 33

2-phenethylbenzo[f][1,7]naphthyridin-5-amine

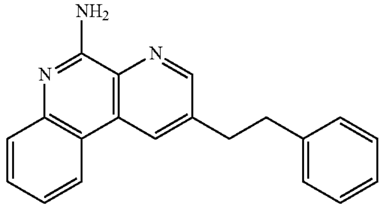 [SMILES: Nc1nc2ccccc2c2cc(CCc3ccccc3)cnc12]

To a solution of (E)-2-styrylbenzo[f][1,7]naphthyridin-5-amine (Example 32) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-phenethylbenzo[f][1,7]naphthyridin-5-amine as a yellow solid. $^1H$ NMR ($CDCl_3$): δ 8.54 (d, 1H), 8.32 (d, 1H), 8.10 (dd, 1H), 7.63 (dd, 1H), 7.51 (m, 1H), 7.03-7.32 (m, 6H), 6.16 (bs, 2H), 3.11 (t, 2H), 2.97 (t, 2H). LRMS [M+H]=300.1.

Example 34

(E)-2-(3-methoxyprop-1-enyl)benzo[f][1,7]naphthyridin-5-amine

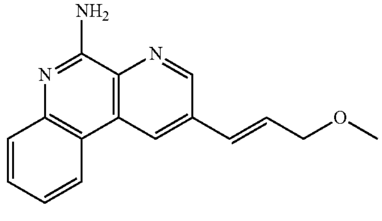 [SMILES: COC/C=C/c1cnc2c(N)nc3ccccc3c2c1]

Step 1: (E)-3-chloro-5-(3-methoxyprop-1-enyl)picolinonitrile

A solution of 3,5-dichloropicolinonitrile (1.0 eq.), (E)-2-(3-methoxyprop-1-enyl)-4,4,5,5-tetramethyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vacuo. The crude product was purified by flash chromatography on a COMBIFLASH® system (ISCO) using 0-80% ethyl acetate in hexane to give (E)-3-chloro-5-(3-methoxyprop-1-enyl)picolinonitrile as a white solid.

Step 2: (E)-2-(3-methoxyprop-1-enyl)benzo[f][1,7]naphthyridin-5-amine

A solution of 2-(tert-butoxycarbonylamino)phenylboronic acid (1.0 eq.) and (E)-3-chloro-5-(3-methoxyprop-1-enyl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-(3-methoxyprop-1-enyl)benzo[f][1,7]naphthyridin-5-amine as a yellow solid. $^1H$ NMR (dmso-d6): δ 9.24 (d, 1H), 9.18 (d, 1H), 8.54 (d, 1H), 7.52-7.58 (m, 2H), 7.31 (m, 1H), 7.11 (bs, 2H), 6.86-7.00 (m, 2H), 4.18 (d, 2H), 3.36 (s, 3H). LRMS [M+H]=266.2.

Example 35

2-(3-methoxypropyl)benzo[f][1,7]naphthyridin-5-amine

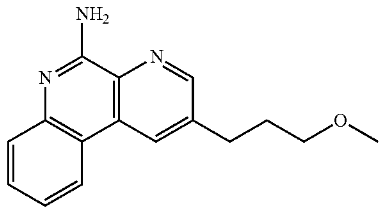 [SMILES: COCCCc1cnc2c(N)nc3ccccc3c2c1]

To a solution of (E)-2-(3-methoxyprop-1-enyl)benzo[f][1,7]naphthyridin-5-amine (Example 34) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-(3-methoxypropyl)benzo[f][1,7]naphthyridin-5-amine as a white solid. $^1H$ NMR ($CDCl_3$): δ 8.64 (d, 1H), 8.46 (d, 1H), 8.19 (d, 1H), 7.66 (d, 1H), 7.53 (m, 1H), 7.31 (m, 1H), 6.56 (bs, 2H), 3.37 (t, 2H), 3.31 (s, 3H), 2.91 (t, 2H), 1.93-2.00 (m, 2H). LRMS [M+H]=268.1.

Example 36

2-(prop-1-en-2-yl)benzo[f][1,7]naphthyridin-5-amine

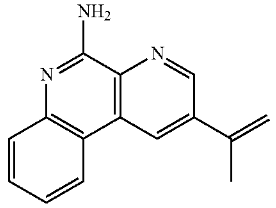 [SMILES: C=C(C)c1cnc2c(N)nc3ccccc3c2c1]

Step 1: 3-chloro-5-(prop-1-en-2-yl)picolinonitrile

A solution of 3,5-dichloropicolinonitrile (1.0 eq.), 4,4,5,5-tetramethyl-2-(prop-1-en-2-yl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vacuo. The crude product was purified by flash chromatography on a COMBIFLASH® system (ISCO) using 0-80% ethyl acetate in hexane to give 3-chloro-5-(prop-1-en-2-yl)picolinonitrile as a white solid.

Step 2: 2-(prop-1-en-2-yl)benzo[f][1,7]naphthyridin-5-amine

A solution of 2-(tert-butoxycarbonylamino)phenylboronic acid (1.0 eq.) and 3-chloro-5-(prop-1-en-2-yl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-(prop-1-en-2-yl)benzo[f][1,7]naphthyridin-5-amine as a white solid. $^1H$ NMR (dmso-d6): δ 9.03 (d, 1H), 8.96 (d, 1H), 8.55 (d, 1H), 7.47-7.53 (m, 2H), 7.25 (m, 1H), 7.07 (bs, 2H) 5.80 (s, 1H), 5.36 (s, 1H), 2.27 (s, 3H). LRMS [M+H]=236.2.

Example 37

2-isopropylbenzo[f][1,7]naphthyridin-5-amine

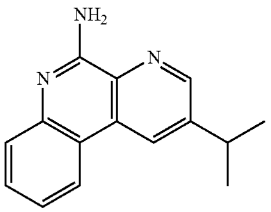 [SMILES: CC(C)c1cnc2c(N)nc3ccccc3c2c1]

To a solution of 2-(prop-1-en-2-yl)benzo[f][1,7]naphthyridin-5-amine (Example 36) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-isopropylbenzo[f][1,7]naphthyridin-5-amine as a yellow solid. $^1$H NMR ($CDCl_3$): δ 8.69 (d, 1H), 8.49 (d, 1H), 8.25 (dd, 1H), 7.65 (dd, 1H), 7.53 (m, 1H), 7.31 (m, 1H), 6.02 (bs, 2H), 3.15 (septet, 1H), 1.37 (d, 6H). LRMS [M+H]=238.2.

Example 38

1-methylbenzo[f][1,7]naphthyridin-5-amine

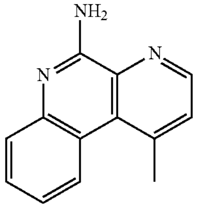 [SMILES: Cc1ccnc2c(N)nc3ccccc3c12]

Step 1: 5-bromo-2-chloro-4-methylpyridine 1-oxide

A solution of 5-bromo-2-chloro-4-methylpyridine (1.0 eq.) and meta-chloroperbenzoic acid (mCPBA) (2.5 eq.) in chloroform (0.1 M) was stirred at 50° C. overnight. After cooling to room temperature, $Ca(OH)_2$ (2.5 eq.) was added to the reaction mixture. The precipitate was filtered and washed with 5% methanol in dichloromethane and ethyl acetate. The filtrate was washed with saturated aqueous $Na_2S_2O_3$ solution and saturated aqueous $NaHCO_3$ solution. The combined organic layers were washed with brine, dried over anhydrous $MgSO_4$, and concentrated en vacuo into a pale solid that was carried onto the next step without further purification.

Step 2: 3-bromo-6-chloro-4-methylpicolinonitrile

To a solution of 5-bromo-2-chloro-4-methylpyridine 1-oxide (from step 1) (1.0 eq.) in acetonitrile (0.2 M) was added TMSCN (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-chloro-4-methylpicolinonitrile.

Step 3: 3-chloro-1-methylbenzo[f][1,7]naphthyridin-5-amine

A solution of 2-(tert-butoxycarbonylamino)phenylboronic acid (1.0 eq.) and 3-bromo-6-chloro-4-methylpicolinonitrile (from step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 3-chloro-1-methylbenzo[f][1,7]naphthyridin-5-amine as a white solid. $^1$H NMR (dmso-d6): δ 8.44 (d, 1H), 7.83 (s, 1H), 7.50-7.58 (m, 2H), 7.02 (bs, 2H), 2.98 (s, 3H). LRMS [M+H]=244.1.

Step 4: 1-methylbenzo[f][1,7]naphthyridin-5-amine

To a solution of 3-chloro-1-methylbenzo[f][1,7]naphthyridin-5-amine (from step 3) in ethyl acetate/methanol (1:2, 0.03 M) was added 10% wt palladium on carbon (0.2 eq.). The reaction vessel was shaken on a hydrogen Parr apparatus under 50 psi of hydrogen overnight. The mixture was filtered through a pad of celite, washing with dichloromethane. The filtrate was concentrated en vacuo and purified by a COMBIFLASH® system (ISCO) using 0-80% ethyl acetate in hexane to give 1-methylbenzo[f][1,7]naphthyridin-5-amine as a white solid. $^1$H NMR ($CDCl_3$): δ 8.63 (d, 1H), 8.44 (d, 1H), 7.71 (dd, 1H), 7.54 (m, 1H), 7.45 (d, 1H), 7.30 (m, 1H), 6.20 (bs, 2H), 3.01 (s, 3H). LRMS [M+H]=210.1.

Example 40 pyrido[3,2-f][1,7]naphthyridin-6-amine

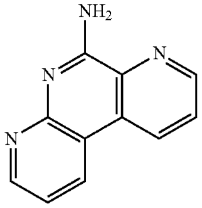 [SMILES: Nc1nc2ncccc2c2cccnc12]

A solution of tert-butyl 3-(4,4,5,5-tetramethyl-1,3,2-dioxaborolan-2-yl)pyridin-2-ylcarbamate (1.0 eq.) and 3-bromopicolinonitrile (1.0 eq.), tetrakis(triphenyl-phosphine) palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give pyrido[3,2-f][1,7]naphthyridin-6-amine as a white solid. $^1$H NMR (dmso-d6): δ 9.14 (dd, 1H), 8.98 (dd, 1H), 8.90 (dd, 1H), 7.93 (dd, 1H), 7.60 (bs, 2H), 7.30 (dd, 1H). LRMS [M+H]=197.

Example 41

2-ethyl-8-methylbenzo[f][1,7]naphthyridin-5-amine

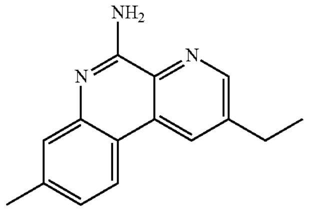 [SMILES: CCc1cnc2c(N)nc3cc(C)ccc3c2c1]

Step 1: 8-methyl-2-vinylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/step 2) (1.0 eq.) and 3-chloro-5-vinylpicolinonitrile (from Example 29/Step 1) (1.0 eq.), tetrakis(triphenyl-phosphine) palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 8-methyl-2-vinylbenzo[f][1,7]naphthyridin-5-amine as a yellow solid.

Step 2: 2-ethyl-8-methylbenzo[f][1,7]naphthyridin-5-amine

To a solution of 8-methyl-2-vinylbenzo[f][1,7]naphthyridin-5-amine (from the previous step) in ethyl acetate/methanol (1:4, 0.05 M) was added 10% wt palladium on carbon (0.2 eq.). Hydrogen gas was introduced via a ballon, and the reaction was stirred for 3 hours. The mixture was filtered through a pad of celite and washed with dichloromethane. The filtrate was concentrated en vaccuo and purified by a COMBIFLASH® system (ISCO) using 0-80% ethyl acetate in hexane to give 2-ethyl-8-methylbenzo[f][1,7]naphthyridin-5-amine as an offwhite solid. $^1$H NMR ($CDCl_3$): δ 8.61 (d, 1H), 8.42 (d, 1H), 8.10 (d, 1H), 7.44 (s, 1H), 7.12 (dd, 1H), 6.00 (bs, 2H), 2.84 (q, 2H), 2.45 (s, 3H), 1.33 (t, 3H). LRMS [M+H]=238.1.

Example 42

(5-amino-8-methylbenzo[f][1,7]naphthyridin-2-yl) methanol

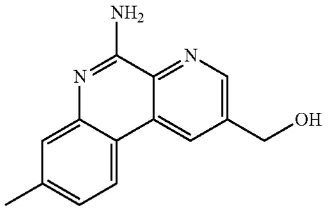 [SMILES: Cc1ccc2c(c1)nc(N)c1ncc(CO)cc12]

Step 1: ethyl 5-chloro-6-cyanonicotinate

A solution of ethyl 5,6-dichloronicotinate (1 eq), zinc cyanide (0.75 eq) and tetrakis(triphenyl-phosphine)palladium (0.10 eq.) in DMF (0.3 M) was degassed and then heated at 100° C. for 3 hours. Solvent was removed en vaccuo to obtain a crude residue. The crude material was purified by flash chromatography on a COMBIFLASH® system (ISCO) using 0-80% ethyl acetate in hexane to give ethyl 5-chloro-6-cyanonicotinate as a white solid.

Step 2: ethyl 5-amino-8-methylbenzo[f][1,7]naphthyridine-2-carboxylate

A solution of tert-butyl 5-methyl-2-(4,4,5,5-tetramethyl-1,3,2-dioxaborolan-2-yl)phenylcarbamate (from Example 5/step 2) (1.0 eq.) and ethyl 5-chloro-6-cyanonicotinate (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give ethyl 5-amino-8-methylbenzo[f][1,7]naphthyridine-2-carboxylate.

Step 3: 2-ethyl-8-methylbenzo[f][1,7]naphthyridin-5-amine

To a stirred solution of ethyl 5-amino-8-methylbenzo[f][1,7]naphthyridine-2-carboxylate (from the previous step) in THF (0.2 M) cooled in an ice-water bath was added 1 N solution of super hydride in THF (10 eq.). Upon completion of the reaction the reaction was quenched with 1 N HCl, and extracted with EtOAc. Combined organic extracts were concentrated en vaccuo to obtain a crude residue. The crude material was purified by flash chromatography on a COMBIFLASH® system (ISCO) using 0-80% ethyl acetate in hexane to give (5-amino-8-methylbenzo[f][1,7]naphthyridin-2-yl)methanol as a white solid. $^1$H NMR ($CDCl_3$): δ 8.68 (d, 1H), 8.52 (d, 1H), 8.04 (d, 1H), 7.44 (s, 1H), 7.12 (dd, 1H), 6.00 (bs, 2H), 4.90 (s, 2H), 2.45 (s, 3H). LRMS [M+H]=240.1

Example 43

8-methyl-2-propylbenzo[f][1,7]naphthyridin-5-amine

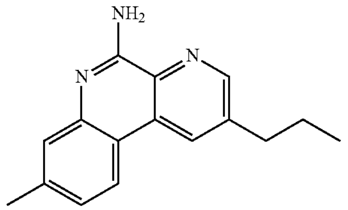 [SMILES: CCCc1cnc2c(N)nc3cc(C)ccc3c2c1]

Step 1: (E)-3-chloro-5-(prop-1-enyl)picolinonitrile

A solution of 3,5-dichloropicolinonitrile (1.0 eq.), (E)-4,4,5,5-tetramethyl-2-(prop-1-enyl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo to obtain a crude residue. The crude material was purified by flash chromatography on a COMBIFLASH® system (ISCO) using 0-80% ethyl acetate in hexane to give a white solid (E)-3-chloro-5-(prop-1-enyl)picolinonitrile.

Step 2: (E)-8-methyl-2-(prop-1-enyl)benzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/Step 2) (1.0 eq.) and (E)-3-chloro-5-(prop-1-enyl)picolinonitrile (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give (E)-8-methyl-2-(prop-1-enyl)benzo[f][1,7]naphthyridin-5-amine as a yellow solid.

Step 3: 8-methyl-2-propylbenzo[f][1,7]naphthyridin-5-amine

To a solution of (E)-8-methyl-2-(prop-1-enyl)benzo[f][1,7]naphthyridin-5-amine (from the previous step) in ethyl acetate/methanol (1:4, 0.05 M) was added 10% wt palladium on carbon (0.2 eq.). Hydrogen gas was introduced via a ballon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give 8-methyl-2-propylbenzo[f][1,7]naphthyridin-5-amine as offwhite solid. $^1H$ NMR ($CDCl_3$): δ 8.59 (d, 1H), 8.41 (d, 1H), 8.10 (d, 1H), 7.43 (s, 1H), 7.13 (dd, 1H), 5.94 (bs, 2H), 2.78 (t, 2H), 2.44 (s, 3H), 1.75 (m, 2H), 0.95 (t, 3H). LRMS [M+H]=252.1

Example 44

2-(2-(1H-indol-5-yl)ethyl)-8-methylbenzo[f][1,7]naphthyridin-5-amine

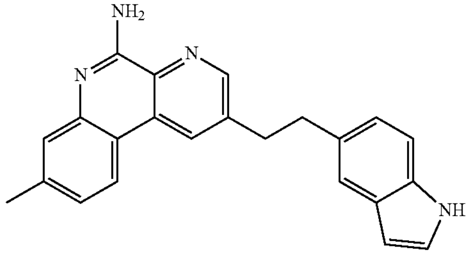 [SMILES: Cc1ccc2c(c1)nc(N)c1ncc(CCc3ccc4[nH]ccc4c3)cc12]

Step 1: 5-((triethylsilyl)ethynyl)-1H-indole

To a scintillation vial was added -iodo-1H-indole (1.1 eq.), triethyl(ethynyl)silane (1 eq.), triethylamine (5 eq.), and anhydrous DMF (0.2 M). Vacuumed and nitrogen flushed for three times. CuI (0.1 eq.) and bis(triphenylphosphine)dichloro-palladium(II) (0.1 eq) were added. The vial was sealed and heated at 60° C. overnight. Upon completion of the reaction as monitored by TLC, the content of the vial was loaded onto a silica gel column pretreated with hexanes. Column was washed with hexanes and diethylether until all eluents containing product were collected. Carefully distill off hexanes and ether using rotary evaporator with minim heating afforded product 5-((triethylsilyl)ethynyl)-1H-indole as colorless oil, which was carried directly on to the next step.

Step 2: 5-ethynyl-1H-indole

To a stirred solution of 5-((triethylsilyl)ethynyl)-1H-indole (from the previous step) in THF (0.2 M) cooled at 0° C. was treated with a solution (0.5 eq.) of tetrabutylammonium fluoride in a dropwise fashion. The reaction mixture turned black and was continued to stir for 30 minutes before warming up to rt. TLC showed full conversion. The reaction was quenched with water and was extracted with diethylether. Combined organic layers were dried over anhydrous $Na_2SO_4$ and concentrated using rotary evaporator with minim heating. Chromatography (silica gel, diethylether) afforded the product 5-ethynyl-1H-indole as colorless oil.

Step 3: 5-(OH-indol-5-yl)ethynyl)-3-chloropicolinonitrile

To a round bottom flask capped with septa was added 5-ethynyl-1H-indole (from the previous step) (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium(II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 5-((1H-indol-5-yl)ethynyl)-3-chloropicolinonitrile.

Step 4: 2-((1H-indol-5-yl)ethynyl)-8-methylbenzo[f][1,7]naphthyridin-5-amine

To a round bottom flask with refluxing condenser were added 5-((1H-indol-5-yl)ethynyl)-3-chloropicolinonitrile (from the previous step) (1 eq.), tert-butyl 2-(4,4,5,5-tetramethyl-1,3,2-dioxaborolan-2-yl)phenylcarbamate (from Example 5/Step 2) (1.25 eq.), $K_3PO_4$ (2 eq.), tris(dibenzylideneacetone)dipalladium(0) (0.05 eq.), and 2-Dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried ($Na_2SO_4$) and concentrated. Flash chromatography (silica gel, 0-50% EtOAc in $CH_2Cl_2$) afforded the product 2-((1H-indol-5-yl)ethynyl)-8-methylbenzo[f][1,7]naphthyridin-5-amine as a yellow solid.

Step 5: 2-(2-(2,3-dihydrobenzofuran-5-yl)ethyl)-8-methylbenzo[f][1,7]naphthyridin-5-amine To a round bottom flask was added 2-((1H-indol-5-yl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The content were vacuumed followed by hydrogen flush for three times. The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in $CH_2Cl_2$) afforded the product 2-(2-(2,3-Dihydrobenzo furan-5-yl)ethyl)-8-methylbenzo[f][1,7]naphthyridin-5-amine as a yellow solid. $^1$H NMR ($CDCl_3$): δ 8.54 (d, 1H), 8.34 (d, 1H), 8.28 (s, 1H), 7.99 (d, 1H), 7.64-7.56 (m, 1H), 7.50-7.35 (m, 1H), 7.24 (d, 1H), 7.12 (t, 1H), 7.08 (dd, 1H), 6.92 (dd, 1H), 6.41 (s, 1H), 6.01 (bs, 2H), 3.16-3.12 (m, 2H), 3.10-3.05 (m, 2H), 2.43 (s, 3H). LRMS [M+H]=353.2

Example 45

2-(4-ethoxyphenethyl)-8-methylbenzo[f][1,7]naphthyridin-5-amine

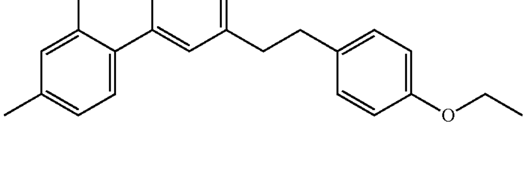

Step 1: 3-chloro-5-((4-ethoxyphenyl)ethynyl)picolinonitrile

To a round bottom flask capped with septa was added 1-ethoxy-4-ethynylbenzene (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium (II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-ethoxyphenyl)ethynyl)picolinonitrile.

Step 2: 2-((4-ethoxyphenyl)ethynyl)-8-methylbenzo[f][1,7]naphthyridin-5-amine

To a round bottom flask with refluxing condenser were added 3-chloro-5-((4-ethoxyphenyl)ethynyl)picolinonitrile (from the previous step) (1 eq.), tert-butyl 5-methyl-2-(4,4,5,5-tetramethyl-1,3,2-dioxaborolan-2-yl)phenylcarbamate (from Example 5/Step 2) (1.25 eq.), $K_3PO_4$ (2 eq.), tris(dibenzylideneacetone)dipalladium(0) (0.05 eq.), and 2-dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried ($Na_2SO_4$) and concentrated. Flash chromatography (silica gel, 0-50% EtOAc in $CH_2Cl_2$) afforded the product 2-((4-ethoxyphenyl)ethynyl)-8-methylbenzo[f][1,7]naphthyridin-5-amine.

Step 3: 2-(4-ethoxyphenethyl)-8-methylbenzo[f][1,7]naphthyridin-5-amine

To a round bottom flask was added 2-((4-ethoxyphenyl)ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The contents were degassed under vacuum followed by hydrogen flush (three times). The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in $CH_2Cl_2$) afforded the product as a yellow solid. Further recrystallization using toluene afforded product 2-(4-ethoxyphenethyl)-8-methylbenzo[f][1,7]naphthyridin-5-amine as a white fine crystal. $^1$H NMR ($CDCl_3$): δ 8.52 (d, 1H), 8.30 (d, 1H), 8.10 (d, 1H), 7.46 (s, 1H), 7.12 (dd, 1H), 7.06 (d, 2H), 6.75 (d, 2H), 5.95 (bs, 2H), 3.93 (q, 2H), 3.11-3.05 (dd, 2H), 2.95-2.90 (dd, 2H), 2.44 (s, 3H), 1.33 (t, 3H). LRMS [M+H]=358.2

Example 46

8-methyl-2-(4-phenoxyphenethyl)benzo[f][1,7]naphthyridin-5-amine

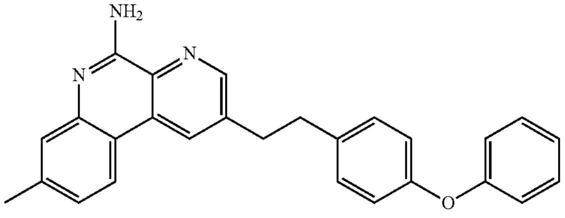 [SMILES: Cc1ccc2c(c1)nc(N)c1ncc(CCc3ccc(Oc4ccccc4)cc3)cc12]

Step 1: 3-chloro-5-((4-phenoxyphenyl)ethynyl)picolinonitrile

3-Chloro-5-((4-phenoxyphenyl)ethynyl)picolinonitrile was prepared from 1-ethynyl-4-phenoxybenzene (commercially available) following the procedures described for Example 45, step 1.

Step 2: 8-methyl-2-((4-phenoxyphenyl)ethynyl)benzo[f][1,7]naphthyridin-5-amine

8-Methyl-2-((4-phenoxyphenyl)ethynyl)benzo[f][1,7]naphthyridin-5-amine was prepared from 3-chloro-5-((4-phenoxyphenyl)ethynyl)picolinonitrile (from the previous step) following the procedures described for Example 45, step 2.

Step 3: 8-methyl-2-(4-phenoxyphenethyl)benzo[f][1,7]naphthyridin-5-amine

8-Methyl-2-(4-phenoxyphenethyl)benzo[f][1,7]naphthyridin-5-amine was prepared from 8-methyl-2-((4-phenoxyphenyl)ethynyl)benzo[f][1,7]naphthyridin-5-amine (from the previous step) following the procedures described for Example 45, step 3. $^1$H NMR ($CDCl_3$): δ 8.54 (d, 1H), 8.30 (d, 1H), 8.01 (d, 1H), 7.45 (s, 1H), 7.25-7.20 (m, 2H), 7.12 (dd, 1H), 7.07-6.84 (m, 8H), 6.00 (bs, 2H), 3.13-3.08 (dd, 2H), 2.99-2.94 (dd, 2H), 2.44 (s, 3H). LRMS [M+H]=406.2

Example 47

2-(2,4-dimethylphenethyl)benzo[f][1,7]naphthyridin-5-amine

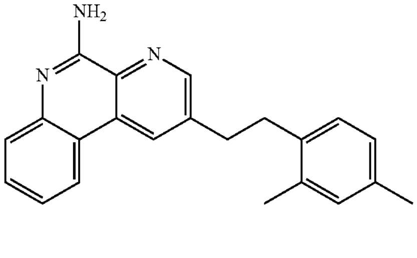 [SMILES: Cc1ccc(CCc2cnc3c(N)nc4ccccc4c3c2)c(C)c1]

Step 1: ((2,4-dimethylphenyl)ethynyl)triethylsilane ((2,4-Dimethylphenyl)ethynyl)triethylsilane was prepared from 1-iodo-2,4-dimethylbenzene (commercially available) following the procedures described for Example 44, step 1.

Step 2: 1-ethynyl-2,4-dimethylbenzene

1-Ethynyl-2,4-dimethylbenzene was prepared from ((2,4-dimethylphenyl)ethynyl)triethylsilane (from the previous step) following the procedures described for Example 44, step 2.

Step 3: 3-chloro-5-((2,4-dimethylphenyl)ethynyl)picolinonitrile

3-Chloro-5-((2,4-dimethylphenyl)ethynyl)picolinonitrile was prepared from 1-ethynyl-2,4-dimethylbenzene (from the previous step) following the procedures described for Example 44, step 3.

Step 4: 2-((2,4-dimethylphenyl)ethynyl)benzo[f][1,7]naphthyridin-5-amine 2-((2,4-Dimethylphenyl)ethynyl)benzo[f][1,7]naphthyridin-5-amine was prepared from 3-chloro-5-((2,4-dimethylphenyl)ethynyl)-picolinonitrile (from the previous step) following the procedures described for Example 44, step 4.

Step 5: 2-(2,4-dimethylphenethyl)benzo[f][1,7]naphthyridin-5-amine 2-(2,4-Dimethylphenethyl)benzo[f][1,7]naphthyridin-5-amine was prepared from 2-((2,4-dimethylphenyl)ethynyl)benzo[f][1,7]naphthyridin-5-amine (from the previous step) following the procedures described for Example 44, step 5. $^1$H NMR ($CDCl_3$): δ 8.60 (d, 1H), 8.33 (d, 1H), 8.14 (d, 1H), 7.67 (d, 1H), 7.54 (t, 1H), 7.31 (t, 1H), 6.96-6.86 (m, 3H), 6.29 (bs, 2H), 3.04-3.10 (dd, 2H), 2.97-2.91 (dd, 2H), 2.24 (s, 3H), 2.20 (s, 3H). LRMS [M+H]=328.2.

Example 48

2-(2,4-dimethylphenethyl)-8-methylbenzo[f][1,7]naphthyridin-5-amine

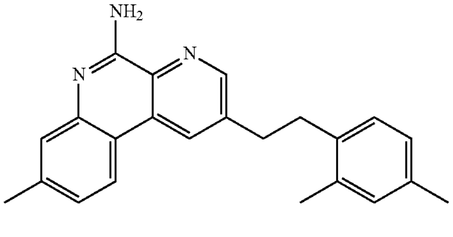

Step 1: 2-((2,4-dimethylphenyl)ethynyl)-8-methylbenzo[f][1,7]naphthyridin-5-amine 2-((2,4-Dimethylphenyl)ethynyl)-8-methylbenzo[f][1,7]naphthyridin-5-amine was prepared from 3-chloro-5-((2,4-dimethylphenyl)ethynyl)picolinonitrile (from Example 47/Step 3) and tert-butyl 5-methyl-2-(4,4,5,5-tetramethyl-1, 3,2-dioxaborolan-2-yl)phenylcarbamate (from Example 5/Step 2) following the procedures described for Example 44, step 4.

Step 2: 2-(2,4-dimethylphenethyl)-8-methylbenzo[f][1,7]naphthyridin-5-amine 2-(2,4-Dimethylphenethyl)-8-methylbenzo[f][1,7]naphthyridin-5-amine was prepared from 1-ethynyl-4-phenoxybenzene (from the previous step) following the procedures described for Example 44, step 5. $^1$H NMR ($CDCl_3$): δ 8.56 (d, 1H), 8.28 (d, 1H), 8.00 (d, 1H), 7.46 (s, 1H), 7.14 (dd, 1H), 6.95-6.85 (m, 3H), 6.26 (bs, 2H), 3.08-3.02 (dd, 2H), 2.96-2.90 (dd, 2H), 2.45 (s, 3H), 2.23 (s, 3H), 2.19 (s, 3H). LRMS [M+H]=342.2

Example 49

2-(4-methoxy-2-methylphenethyl)-8-methylbenzo[f][1,7]naphthyridin-5-amine

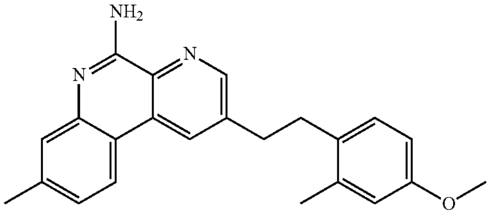

Step 1: 3-chloro-5-((4-methoxy-2-methylphenyl)ethynyl)picolinonitrile

3-Chloro-5-((4-methoxy-2-methylphenyl)ethynyl)picolinonitrile was prepared from 1-ethynyl-4-methoxy-2-methylbenzene (commercially available) following the procedure described for Example 44/Step 3.

Step 2: 2-((4-methoxy-2-methylphenyl)ethynyl)-8-methylbenzo[f][1,7]naphthyridin-5-amine 2-((4-Methoxy-2-methylphenyl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 44, step 4.

Step 3: 2-(4-methoxy-2-methylphenethyl)-8-methylbenzo[f][1,7]naphthyridin-5-amine 2-(4-Methoxy-2-methylphenethyl)-8-methylbenzo[f][1,7]naphthyridin-5-amine was prepared from 2-((4-methoxy-2-methylphenyl)ethynyl)-8-methylbenzo[f][1,7]naphthyridin-5-amine (from the previous step) following the procedures described for Example 44, step 5. $^1$H NMR ($CDCl_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

Example 50

4-(2-(5-amino-8-methylbenzo[f][1,7]naphthyridin-2-yl)ethyl)-3-methylphenol

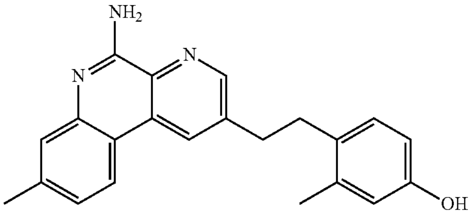 [SMILES: Cc1ccc2c(c1)nc(N)c1ncc(CCc3ccc(O)cc3C)cc12]

To a stirred solution of 2-(4-methoxy-2-methylphenethyl)-8-methylbenzo[f][1,7]naphthyridin-5-amine (Example 49) in methylene chloride (0.2 M) in an ice-water bath was added 1 N solution of $BBr_3$ (2 eq) in $CH_2Cl_2$ in a drop-wise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-$d_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2

Example 51

2-(2-(2,3-dihydrobenzofuran-5-yl)ethyl)-8-methylbenzo[f][1,7]naphthyridin-5-amine

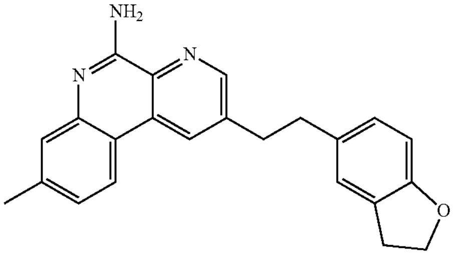 [SMILES: Cc1ccc2c(c1)nc(N)c1ncc(CCc3ccc4c(c3)CCO4)cc12]

Step 1: ((2,3-dihydrobenzofuran-5-yl)ethynyl)triethylsilane ((2,3-Dihydrobenzofuran-5-yl)ethynyl)triethylsilane was prepared from 5-iodo-2,3-dihydrobenzofuran (commercially available) following the procedures described for Example 44, step 1.

Step 2: 5-ethynyl-2,3-dihydrobenzofuran

5-Ethynyl-2,3-dihydrobenzo furan was prepared from ((2,3-dihydrobenzofuran-5-yl)ethynyl)triethylsilane (from the previous step) following the procedures described for Example 44/Step 2.

Step 3: 3-chloro-5-((2,3-dihydrobenzofuran-5-yl) ethynyl)picolinonitrile

3-Chloro-5-((2,3-dihydrobenzo furan-5-yl)ethynyl)picolinonitrile was prepared from 5-ethynyl-2,3-dihydrobenzofuran (from the previous step) following the procedures described for Example 44/Step 3.

Step 4: 2-(2,3-dihydrobenzofuran-5-yl)ethynyl)-8-methylbenzo[f][1,7]naphthyridin-5-amine 2-((2,3-Dihydrobenzo furan-5-yl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 44/Step 4.

Step 5: 2-(2-(2,3-dihydrobenzofuran-5-yl)ethyl)-8-methylbenzo[f][1,7]naphthyridin-5-amine 2-(2-(2,3-Dihydrobenzo furan-5-yl)ethyl)-8-methylbenzo[f][1,7]naphthyridin-5-amine was prepared from 2-((2,3-dihydrobenzo furan-5-yl)ethynyl)-8-methylbenzo[f][1,7]naphthyridin-5-amine (from the previous step) following the procedures described for Example 44/Step 5. $^1$H NMR ($CDCl_3$): δ 8.62 (d, 1H), 8.40 (d, 1H), 8.11 (d, 1H), 7.53 (s, 1H), 7.21 (dd, 1H), 6.99 (s, 1H), 6.95 (dd, 1H), 6.74 (d, 1H), 6.05 (bs, 2H), 4.57 (t, 2H), 3.19-3.13 (m, 4H), 3.03-2.98 (dd, 2H), 2.54 (s, 3H). LRMS [M+H]=356.2

Example 52

2-(5-amino-8-methylbenzo[f][1,7]naphthyridin-2-yl) ethanol

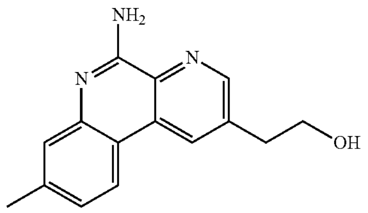 [SMILES: Cc1ccc2c(c1)nc(N)c1ncc(CCO)cc12]

Step 1: (Z)-3-chloro-5-(2-ethoxyvinyl)picolinonitrile (Z)-3-Chloro-5-(2-ethoxyvinyl)picolinonitrile was prepared from (Z)-2-(2-ethoxyvinyl)-4,4,5,5-tetramethyl-1,3,2-dioxaborolane (commercially available) following the procedures described for Example 43/Step 1.

Step 2: (Z)-2-(2-ethoxyvinyl)-8-methylbenzo[f][1,7] naphthyridin-5-amine (Z)-2-(2-Ethoxyvinyl)-8-methylbenzo[f][1,7]naphthyridin-5-amine was prepared from (Z)-3-chloro-5-(2-ethoxyvinyl)picolinonitrile (from the previous step) following the procedures described for Example 43/Step 2.

Step 3: 2-(5-amino-8-methylbenzo[f][1,7]naphthyridin-2-yl)ethanol

A solution of (Z)-2-(2-ethoxyvinyl)-8-methylbenzo[f][1,7]naphthyridin-5-amine (from the previous step) in a mixture of 2:5 conc. HCl and dioxane (0.1 M) was heated at 60° C. overnight. Upon cooling down to rt, the reaction mixture was treated with excess $NaHCO_3$ saturated solution, followed by extraction with EtOAc. Combined organic extracts were concentrated and was taken up in THF (0.2 M), and was treated with 1 N super hydride solution in THF (10 eq.) at 0° C. The reaction mixture was allowed to warm to room temperature and stirred overnight. The reaction was worked up following the procedures described for Example 42/Step 3, to afford 2-(5-amino-8-methylbenzo[f][1,7]naphthyridin-2-yl)ethanol as white solid. $^1$H NMR ($CDCl_3$): δ 8.61 (d, 1H), 8.47 (d, 1H), 8.01 (d, 1H), 7.41 (s, 1H), 7.10 (d, 1H), 6.40 (s, 1H), 6.01 (bs, 2H), 4.01 (t, 2H), 3.06 (t, 2H), 2.43 (s, 3H). LRMS [M+H]=254.1

Example 53

3-methyl-9-phenyl-9,10-dihydrobenzo[f]furo[2,3-b] [1,7]naphthyridin-6-amine

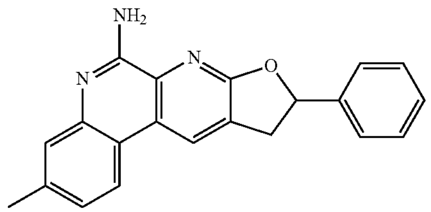 [SMILES: Cc1ccc2c(c1)nc(N)c1nc3c(cc12)CC(c1ccccc1)O3]

Step 1: 5-bromo-2-chloro-3-methylpyridine 1-oxide

5-Bromo-2-chloro-3-methylpyridine 1-oxide was prepared from 5-bromo-2-chloro-3-methylpyridine (commercially available) following the procedures described for Example 19/Step 1.

Step 2: 3-bromo-6-chloro-5-methylpicolinonitrile

3-Bromo-6-chloro-5-methylpicolinonitrile was prepared from (Z)-3-chloro-5-(2-ethoxyvinyl)picolinonitrile (from the previous step) following the procedures described for Example 19/Step 2.

Step 3: 3-bromo-6-chloro-5-(2-hydroxy-2-phenylethyl)picolinonitrile

A solution of 3-bromo-6-chloro-5-methylpicolinonitrile (from the previous step) in THF (0.2 M) was cooled to −78° C. LDA (2N solution, 2 eq) was added dropwise. The reaction was kept stirring at −78° C. for 1 hour, followed by addition of benzaldehyde (1 eq). The reaction was kept stirring at −78° C. for another 30 minutes before allowing it to slowly warm to room temperature. The reaction was quenched with sat. $NH_4Cl$ and extracted with EtOAc. Combined organic washes were concentrated. Flash chromatography (silica gel, 20-50% EtOAc in hexanes) afforded the product 3-bromo-6-chloro-5-(2-hydroxy-2-phenylethyl)picolinonitrile as a yellow solid.

Step 4: 3-methyl-9-phenyl-9,10-dihydrobenzo[f]furo [2,3-b][1,7]naphthyridin-6-amine 3-Methyl-9-phenyl-9,10-dihydrobenzo[f]furo[2,3-b][1,7] naphthyridin-6-amine was prepared from 3-bromo-6- chloro-5-methylpicolinonitrile (from the previous step) following the procedures described for Example 44/Step 4. $^1H$ NMR ($CDCl_3$): δ 8.45 (s, 1H), 7.98 (d, 1H), 7.45 (s, 1H), 7.40-7.28 (m, 5H), 7.12 (d, 1H), 5.93 (t, 1H), 5.93 (brs, 2H), 3.86 (dd, 1H), 3.40 (dd, 1H), 2.44 (s, 3H). LRMS [M+H]=328.1

Example 54

8-methylbenzo[f][1,7]naphthyridine-2,5-diamine

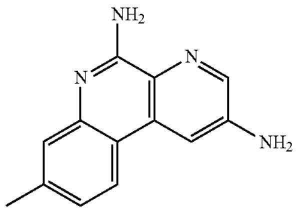 [SMILES: Cc1ccc2c(c1)nc(N)c1ncc(N)cc12]

Step 1: tert-butyl 5,6-dichloropyridin-3-ylcarbamate

To a solution of 5,6-dichloropyridin-3-amine (commercially available) in THF (0.2 M) stirred at 0° C. was added $(BOC)_2O$ (1.2 eq). The reaction mixture was heated at 40° C. until full conversion as monitored by TLC. The reaction mixture was then concentrated. Flash chromatography (silica gel, 20-50% EtOAc in hexanes) of the crude afforded tert-butyl 5,6-dichloropyridin-3-ylcarbamate.

Step 2: tert-butyl 5-chloro-6-cyanopyridin-3-ylcarbamate

Tert-butyl 5-chloro-6-cyanopyridin-3-ylcarbamate was prepared from tert-butyl 5,6-dichloropyridin-3-ylcarbamate (from the previous step) following the procedures described for Example 42/Step 1.

Step 3: 8-methylbenzo[f][1,7]naphthyridine-2,5-diamine 8-methylbenzo[f][1,7]naphthyridine-2,5-diamine was prepared (as minor product) together with tert-butyl 5-amino-8-methylbenzo[f][1,7]naphthyridin-2-ylcarbamate (as major product) from tert-butyl 5-chloro-6-cyanopyridin-3-ylcarbamate (from the previous step) following the procedures described for Example 5/Step 2. $^1H$ NMR (DMSO-$d_6$): δ 10.11 (s, 1H), 9.02 (s, 1H), 8.82 (d, 1H), 8.06 (d, 1H), 7.34 (s, 1H), 7.15 (dd, 1H), 6.99 (s, 2H), 2.44 (s, 3H). LRMS [M+H]=225.1

Example 55

1-(5-amino-8-methylbenzo[f][1,7]naphthyridin-2-yl) propan-2-ol

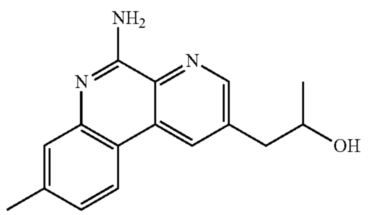 [SMILES: Cc1ccc2c(c1)nc(N)c1ncc(CC(C)O)cc12]

Step 1: 3-bromo-5-methylpicolinonitrile

3-Bromo-5-methylpicolinonitrile was prepared from 2,3-dibromo-5-methylpyridine (commercially available) following the procedures described for Example 42/Step 1.

Step 2: 3-bromo-5-(2-hydroxypropyl)picolinonitrile

3-Bromo-5-(2-hydroxypropyl)picolinonitrile was prepared from 3-bromo-5-methylpicolinonitrile (from the previous step) and acetaldehyde following the procedures described for Example 53/Step 3.

Step 3: 1-(5-amino-8-methylbenzo[f][1,7]naphthyridin-2-yl)propan-2-ol 1-(5-Amino-8-methylbenzo[f][1,7]naphthyridin-2-yl) propan-2-ol was prepared from 3-bromo-5-(2-hydroxypropyl)picolinonitrile (from the previous step) following the procedures described for Example 53, step 4. $^1H$ NMR (methanol-$d_4$): δ 8.72 (d, 1H), 8.68 (d, 1H), 8.24 (d, 1H), 7.38 (s, 1H), 7.18 (dd, 1H), 4.16-4.07 (m, 1H), 3.05-2.99 (m, 2H), 2.97-2.90 (m, 2H), 2.47 (s, 3H), 1.28 (d, 3H). LRMS [M+H]=268.1

Example 56

2-(5-amino-8-methylbenzo[f][1,7]naphthyridin-2-yl) acetonitrile

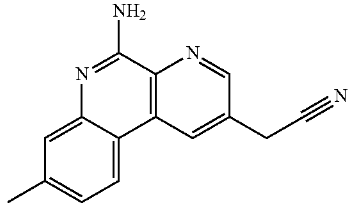 [SMILES: Cc1ccc2c(c1)nc(N)c1ncc(CC#N)cc12]

Step 1: 2,3-dichloro-5-((methoxymethoxy)methyl)pyridine

To a stirred solution of (5,6-dichloropyridin-3-yl)methanol (commercially available) in $CH_2Cl_2$ (0.2 M) at 0° C. was added triethylamine (3 eq.) and chloro(methoxy)methane (2 eq.). After stirring at 0° C. for 3 hours the reaction mixture was concentrated and the crude was purified by chromatography (silica gel, 50% EtOAc in hexanes) to afford 2,3-dichloro-5-((methoxymethoxy)methyl)pyridine as a colorless oil.

Step 2: 3-chloro-5-((methoxymethoxy)methyl)picolinonitrile

3-Chloro-5-((methoxymethoxy)methyl)picolinonitrile was prepared from 2,3-dichloro-5-((methoxymethoxy) methyl)pyridine (from the previous step) following the procedures described for Example 42/Step 1.

Step 3: 3-chloro-5-(hydroxymethyl)picolinonitrile

To a stirred solution of 2,3-dichloro-5-((methoxymethoxy)methyl)pyridine (from the previous step) in methanol (0.2 M) was added conc. HCl (10 eq). After stirring at room temperature overnight the reaction mixture was concentrated under vacuum and the resulting crude was purified by chromatography (silica gel, 20-50% EtOAc in hexanes) to afford 3-chloro-5-(hydroxymethyl) picolinonitrile.

Step 4: 3-chloro-5-(chloromethyl)picolinonitrile

To a stirred solution of 3-chloro-5-(hydroxymethyl)picolinonitrile (from the previous step) in $CH_2Cl_2$ (0.2 M) at 0° C. was added thionyl chloride (10 eq). After stirring at room temperature overnight the reaction mixture was concentrated under vacuum and the resulting crude was purified by chromatography (silica gel, 20-50% EtOAc in hexanes) to afford 3-chloro-5-(chloromethyl)picolinonitrile as a colorless oil.

Step 5: 3-chloro-5-(cyanomethyl)picolinonitrile

To a solution of 3-chloro-5-(chloromethyl)picolinonitrile (from the previous step) in DMSO (0.2 M) was added sodium cyanide (1.25 eq). The reaction mixture was heated at 130° C. under microwave irradiation. The reaction mixture taken up in water and EtOAc, and extracted with EtOAc. Organic phases were dried over anhydrous $Na_2SO_4$, and concentrated. Flash chromatography (silica gel, 20-50% EtOAc in hexanes) of the crude afforded 3-chloro-5-(cyanomethyl)picolinonitrile.

Step 6: 2-(5-amino-8-methylbenzo[f][1,7]naphthyridin-2-yl)acetonitrile 2-(5-amino-8-methylbenzo[f][1,7]naphthyridin-2-yl)acetonitrile was prepared from 3-chloro-5-(cyanomethyl)picolinonitrile (from the previous step) following the procedures described for Example 44/Step 4. $^1H$ NMR (methanol-$d_4$): δ 8.79 (d, 1H), 8.78 (d, 1H), 8.20 (d, 1H), 7.66 (s, 2H), 7.36 (s, 1H), 7.18 (dd, 1H), 4.15 (d, 2H), 2.43 (s, 3H). LRMS [M+H]=249.1

Example 57

N-(5-amino-8-methylbenzo[f][1,7]naphthyridin-2-yl)acetamide

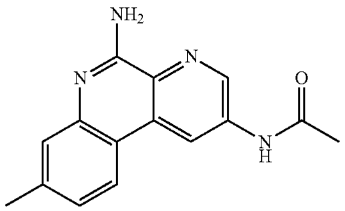 [SMILES: CC(=O)Nc1cnc2c(N)nc3cc(C)ccc3c2c1]

Step 1: N-(5,6-dichloropyridin-3-yl)acetamide

To a stirred solution of 5,6-dichloropyridin-3-amine (commercially available) and triethyl amine (3 eq) in $CH_2Cl_2$ (0.2 M) at 0° C. was added acetyl chloride (2 eq). After stirring at room temperature overnight the reaction mixture was concentrated under vacuum and the resulting crude residue was purified by chromatography (silica gel, 20-50% EtOAc in hexanes) to afford N-(5,6-dichloropyridin-3-yl)acetamide.

Step 2: N-(5-chloro-6-cyanopyridin-3-yl)acetamide

N-(5-chloro-6-cyanopyridin-3-yl)acetamide was prepared from N-(5,6-dichloropyridin-3-yl)acetamide (from the previous step) following the procedures described for Example 42/Step 1.

Step 3: N-(5-amino-8-methylbenzo[f][1,7]naphthyridin-2-yl)acetamide

N-(5-amino-8-methylbenzo[f][1,7]naphthyridin-2-yl)acetamide was prepared from N-(5-chloro-6-cyanopyridin-3-yl)acetamide (from the previous step) following the procedures described for Example 44/Step 4. $^1H$ NMR (DMSO-$d_6$): δ 10.99 (s, 1H), 8.18 (d, 1H), 8.95 (d, 1H), 8.12 (d, 1H), 7.44 (s, 1H), 7.35 (dd, 1H), 2.43 (s, 3H), 2.16 (s, 3H). LRMS [M+H]=267.1

Example 58

2-(5-amino-8-methylbenzo[f][1,7]naphthyridin-2-yl)-1-(2,4-dimethylphenyl)ethanol

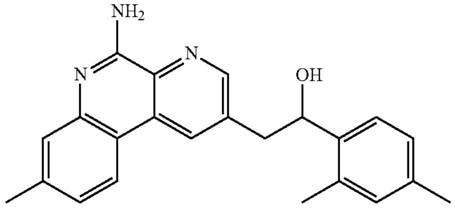

Step 1: 3-bromo-5-(2-(2,4-dimethylphenyl)-2-hydroxyethyl)picolinonitrile 3-bromo-5-(2-(2,4-dimethylphenyl)-2-hydroxyethyl)picolinonitrile was prepared from 3-bromo-5-methylpicolinonitrile (Example 55/Step 1) and 2,4-dimethylbenzaldehyde following the procedures described for Example 53/Step 3.

Step 2: 2-(5-amino-8-methylbenzo[f][1,7]naphthyridin-2-yl)-1-(2,4-dimethylphenyl)ethanol 2-(5-Amino-8-methylbenzo[f][1,7]naphthyridin-2-yl)-1-(2,4-dimethylphenyl)ethanol was prepared from 3-bromo-5-(2-(2,4-dimethylphenyl)-2-hydroxyethyl)picolinonitrile (from the previous step) following the procedures described for Example 53/Step 4. $^1H$ NMR ($CDCl_3$): δ 8.67 (d, 1H), 8.45 (d, 1H), 8.06 (d, 1H), 7.57 (s, 1H), 7.42 (d, 1H), 7.23 (d, 1H), 7.11 (d, 1H), 7.01 (s, 1H), 5.31 (dd, 1H), 3.28-3.25 (m, 2H), 2.53 (s, 3H), 2.35 (s, 3H), 2.33 (s, 3H). LRMS [M+H]=358.2

Example 59

2-(2-(6-methoxy-4-methylpyridin-3-yl)ethyl)-8-methylbenzo[f][1,7]naphthyridin-5-amine

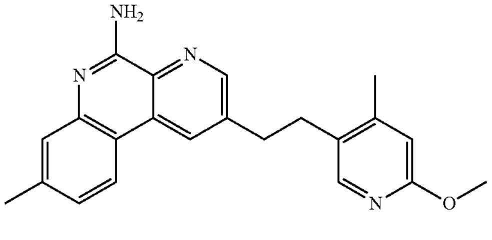

Step 1: 2-methoxy-4-methyl-5-((triethylsilyl)ethynyl)pyridine

2-Methoxy-4-methyl-5-((triethylsilyl)ethynyl)pyridine was prepared from 5-bromo-2-methoxy-4-methylpyridine (commercially available) following the procedures described for Example 44/Step 1.

Step 2: 5-ethynyl-2-methoxy-4-methylpyridine

5-Ethynyl-2-methoxy-4-methylpyridine was prepared from 2-methoxy-4-methyl-5-((triethylsilyl)ethynyl)pyridine (from the previous step) following the procedures described for Example 44/Step 2.

Step 3: 3-chloro-5-((6-methoxy-4-methylpyridin-3-yl)ethynyl)picolinonitrile

3-Chloro-5-((6-methoxy-4-methylpyridin-3-yl)ethynyl) picolinonitrile was prepared from 5-ethynyl-2-methoxy-4-methylpyridine (from the previous step) following the procedures described for Example 44/Step 3.

Step 4: 2-((6-methoxy-4-methylpyridin-3-yl)ethynyl)-8-methylbenzo[f][1,7]naphthyridin-5-amine 2-(6-Methoxy-4-methylpyridin-3-yl)ethynyl)-8-methylbenzo[f][1,7]naphthyridin-5-amine was prepared from 3-chloro-5-((6-methoxy-4-methylpyridin-3-yl)ethynyl)picolinonitrile (from the previous step) following the procedures described for Example 44/Step 4.

Step 5: 2-(2-(6-methoxy-4-methylpyridin-3-yl) ethyl)-8-methylbenzo[f][1,7]naphthyridin-5-amine 2-(2-(6-Methoxy-4-methylpyridin-3-yl)ethyl)-8-methylbenzo[f][1,7]naphthyridin-5-amine was prepared from 2-((6-methoxy-4-methylpyridin-3-yl)ethynyl)-8-methylbenzo[f][1,7]naphthyridin-5-amine (from the previous step) following the procedures described for Example 44/Step 5. $^1$H NMR ($CDCl_3$): δ 8.65 (d, 1H), 8.43 (d, 1H), 8.13 (d, 1H), 7.87 (s, 1H), 7.57 (s, 1H), 7.24 (dd, 1H), 6.60 (s, 1H), 6.39 (bs, 2H), 3.91 (s, 3H), 3.17-3.11 (dd, 2H), 3.03-2.98 (dd, 2H), 2.54 (s, 3H), 2.28 (s, 3H). LRMS [M+H]=359.2

Example 60

4-(4-(2-(5-amino-8-methylbenzo[f][1,7]naphthyridin-2-yl)ethyl)phenyl)butan-1-ol

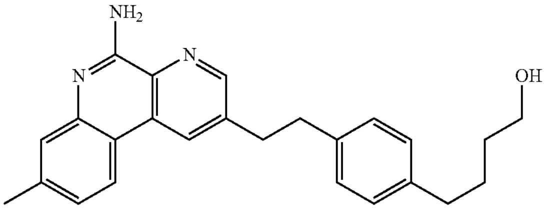 [SMILES: Cc1ccc2c(c1)nc(N)c1ncc(CCc3ccc(CCCCO)cc3)cc12]

Step 1: 4-(4-((trimethylsilyl)ethynyl)phenyl)but-3-yn-1-ol 4-(4-((trimethylsilyl)ethynyl)phenyl)but-3-yn-1-ol was prepared from ((4-bromophenyl)ethynyl)trimethylsilane (commercially available) and but-3-yn-1-ol (commercially available) following the procedures described for Example 44/Step 1.

Step 2: 4-(4-ethynylphenyl)but-3-yn-1-ol 4-(4-ethynylphenyl)but-3-yn-1-ol was prepared from 4-(4-((trimethylsilyl)ethynyl)phenyl)but-3-yn-1-ol following the procedures described for Example 44/Step 2.

Step 3: 5-((4-(4-hydroxybut-1-ynyl)phenyl)ethynyl)-3-methylpicolinonitrile 5-((4-(4-hydroxybut-1-ynyl)phenyl)ethynyl)-3-methylpicolinonitrile was prepared from 4-(4-ethynylphenyl)but-3-yn-1-ol (from the previous step) following the procedures described for Example 44/Step 3.

Step 4: 4-(4-((5-amino-8-methylbenzo[f][1,7]naphthyridin-2-yl)ethynyl)phenyl)but-2-yn-1-ol 4-(4-((5-amino-8-methylbenzo[f][1,7]naphthyridin-2-yl) ethynyl)phenyl)but-2-yn-1-ol was prepared from 5-((4-(4-hydroxybut-1-ynyl)phenyl)ethynyl)-3-methylpicolinonitrile (from the previous step) following the procedures described for Example 44/Step 4.

Step 5: 4-(4-(2-(5-amino-8-methylbenzo[f][1,7] naphthyridin-2-yl)ethyl)phenyl)butan-1-ol 4-(4-(2-(5-amino-8-methylbenzo[f][1,7]naphthyridin-2-yl)ethyl)phenyl)butan-1-ol was prepared from 4-(4-((5-amino-8-methylbenzo[f][1,7]naphthyridin-2-yl)ethynyl) phenyl)but-2-yn-1-ol (from the previous step) following the procedures described for Example 44/Step 5. $^1$H NMR ($CDCl_3$): δ 8.58 (d, 1H), 8.36 (d, 1H), 8.07 (d, 1H), 7.53 (s, 1H), 7.20 (dd, 1H), 7.10 (dd, 4H), 6.20 (bs, 2H), 3.68 (t, 2H), 3.20-3.15 (dd, 2H), 3.06-3.01 (dd, 2H), 2.64 (t, 2H), 2.52 (s, 3H), 1.75-1.57 (m, 4H). LRMS [M+H]=386.2

Example 61 methyl 3-(4-(2-(5-amino-8-methylbenzo[f][1,7] naphthyridin-2-yl)ethyl)phenyl)propanoate

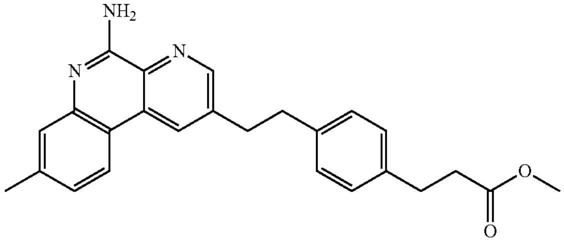

Step 1: methyl 3-(4-iodophenyl)propanoate

To a stirred solution of 3-(4-iodophenyl)propanoic acid (commercially available) in toluene and methanol (9:1, 0.2 M) 0° C. was added (diazomethyl)trimethylsilane (1 N solution in $Et_2O$, 2 eq). After stirring at room temperature overnight the reaction mixture was concentrated under vacuum and the resulting crude residue was purified by chromatography (silica gel, 20-50% EtOAc in hexanes) to afford methyl 3-(4-iodophenyl)propanoate.

Step 2: methyl 3-(4-ethynylphenyl)propanoate

Methyl 3-(4-ethynylphenyl)propanoate was prepared from methyl 3-(4-iodophenyl)propanoate (from the previous step) following the procedures described for Example 44/Steps 1 and 2.

Step 3: methyl 3-(4-((5-chloro-6-cyanopyridin-3-yl)ethynyl)phenyl)propanoate

Methyl 3-(4-((5-chloro-6-cyanopyridin-3-yl)ethynyl)phenyl)propanoate was prepared from methyl 3-(4-ethynylphenyl)propanoate (from the previous step) following the procedures described for Example 44/Step 3.

Step 4: methyl 3-(4-((5-amino-8-methylbenzo[f][1,7]naphthyridin-2-yl)ethynyl)phenyl)propanoate Methyl 3-(4-((5-amino-8-methylbenzo[f][1,7]naphthyridin-2-yl)ethynyl)phenyl)propanoate was prepared from methyl 3-(4-((5-chloro-6-cyanopyridin-3-yl)ethynyl)phenyl)propanoate (from the previous step) following the procedures described for Example 44/Step 4.

Step 5: methyl 3-(4-(2-(5-amino-8-methylbenzo[f][1,7]naphthyridin-2-yl)ethyl)phenyl)propanoate Methyl 3-(4-(2-(5-amino-8-methylbenzo[f][1,7]naphthyridin-2-yl)ethyl)phenyl)propanoate was prepared from methyl 3-(4-((5-amino-8-methylbenzo[f][1,7]naphthyridin-2-yl)ethynyl)phenyl)propanoate (from the previous step) following the procedures described for Example 44/Step 5. $^1$H NMR (DMSO-$d_6$): δ 8.83 (d, 1H), 8.72 (d, 1H), 8.32 (d, 1H), 7.35 (s, 1H), 7.21-7.12 (m, 5H), 7.05 (br s, 2H), 7.05 (dd, 2H), 3.57 (s, 3H), 3.19-3.13 (dd, 2H), 3.06-3.00 (dd, 2H), 2.81 (t, 2H), 2.60 (t, 2H), 2.45 (s, 3H). LRMS [M+H]=400.2

Example 62

3-(4-(2-(5-amino-8-methylbenzo[f][1,7]naphthyridin-2-yl)ethyl)phenyl)propan-1-ol

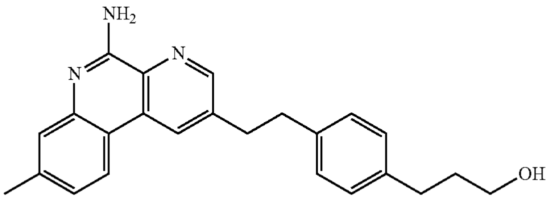 [SMILES: Cc1ccc2c(c1)nc(N)c1ncc(CCc3ccc(CCCO)cc3)cc12]

3-(4-(2-(5-amino-8-methylbenzo[f][1,7]naphthyridin-2-yl)ethyl)phenyl)propan-1-ol was prepared from methyl 3-(4-(2-(5-amino-8-methylbenzo[f][1,7]naphthyridin-2-yl)ethyl)phenyl)propanoate (from Example 61) following the procedures described for Example 42/Step 3. $^1$H NMR of the TFA salt: (DMSO-$d_6$): δ 9.56 (s, 1H), 9.24 (s, 1H), 8.92 (d, 1H), 8.81 (d, 1H), 8.43 (d, 1H), 7.44 (d, 1H), 7.35 (d, 1H), 7.13 (dd, 2H), 7.05 (dd, 2H), 3.32 (t, 2H), 3.18-3.12 (dd, 2H), 3.02-2.95 (dd, 2H), 2.50 (t, 2H), 2.44 (s, 3H), 1.65-1.57 (m, 2H). LRMS [M+H]=372.2

Example 63

4-(4-(2-(5-amino-8-methylbenzo[f][1,7]naphthyridin-2-yl)ethyl)phenyl)-2-methylbutan-2-ol

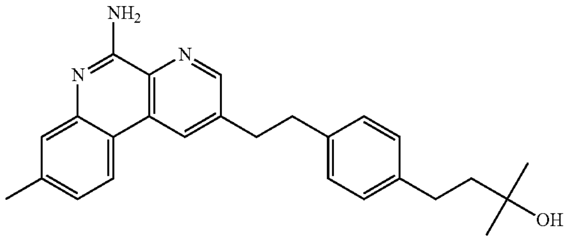 [SMILES: Cc1ccc2c(c1)nc(N)c1ncc(CCc3ccc(CCC(C)(C)O)cc3)cc12]

To a solution of methyl 3-(4-(2-(5-amino-8-methylbenzo[f][1,7]naphthyridin-2-yl)ethyl)phenyl)propanoate (from Example 61) in THF (0.2 M) at 0° C. was added in a dropwise fashion a solution of methylmagnesium bromide in THF (1.0 M, 2 eq). After stirring at room temperature overnight the reaction mixture was concentrated under vacuum and the resulting crude residue was purified by chromatography (silica gel, 50-100% EtOAc in hexanes) to afford 4-(4-(2-(5-amino-8-methylbenzo[f][1,7]naphthyridin-2-yl)ethyl)phenyl)-2-methylbutan-2-ol. $^1$H NMR ($CDCl_3$): δ 8.64 (d, 1H), 8.34 (d, 1H), 8.06 (t, 1H), 7.57 (d, 1H), 7.30-7.20 (m, 2H), 7.18-7.07 (m, 4H), 6.67 (bs, 2H), 3.24-3.16 (dd, 2H), 3.08-3.01 (dd, 2H), 2.73-2.66 (m, 2H), 2.53 (s, 3H), 1.82-1.75 (m, 2H), 1.31 (s, 3H), 1.29 (s, 3H). LRMS [M+H]=400.2

Example 64

2-(4-(aminomethyl)phenethyl)-8-methylbenzo[f][1,7]naphthyridin-5-amine

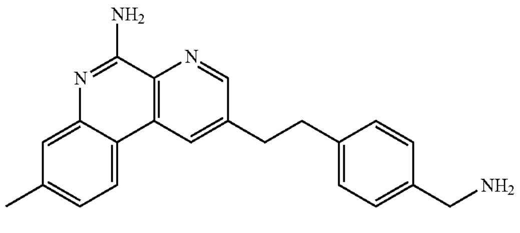 [SMILES: Cc1ccc2c(c1)nc(N)c1ncc(CCc3ccc(CN)cc3)cc12]

Step 1: 4-(2-(5-amino-8-methylbenzo[f][1,7]naphthyridin-2-yl)ethyl)benzonitrile 4-(2-(5-amino-8-methylbenzo[f][1,7]naphthyridin-2-yl)ethyl)benzonitrile was prepared from 4-ethynylbenzonitrile (commercially available) following the procedures described for Example 44/Steps 3 to 5.

Step 2: 2-(4-(aminomethyl)phenethyl)-8-methylbenzo[f][1,7]naphthyridin-5-amine

To a solution of 4-(2-(5-amino-8-methylbenzo[f][1,7]naphthyridin-2-yl)ethyl)benzonitrile (from the previous step) in ethanol and ammonium hydroxide (4:1, 0.2 M) stirred at room temperature was added raney nickel (10 eq). The reaction mixture was stirred under hydrogen atmosphere until the conversion was complete as shown by TLC. The reaction mixture was filtered through a short celite pad. The celite pad was washed with EtOAc. Combined organic extracts were concentrated under vacuum and the resulting crude residue was purified by chromatography (silica gel, 50-100% EtOAc in hexanes) to afford product 2-(4-(aminomethyl)phenethyl)-8-methylbenzo[f][1,7]naphthyridin-5-amine. $^1$H NMR of the TFA salt: (methanol-$d_4$): δ 8.81 (d, 1H), 8.79 (d, 1H), 8.38 (d, 1H), 7.51 (s, 1H), 7.44 (dd, 1H), 7.36 (dd, 4H), 4.07 (s, 2H), 3.29 (s, 2H), 3.20-3.14 (dd, 2H), 2.55 (s, 3H). LRMS [M+H]=343.2

Example 65

(E)-ethyl 3-(4-(2-(5-amino-8-methylbenzo[f][1,7]naphthyridin-2-yl)ethyl)-3-methylphenyl)acrylate

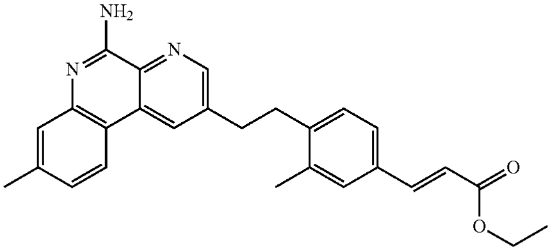 [SMILES: CCOC(=O)/C=C/c1ccc(CCc2cnc3c(N)nc4cc(C)ccc4c3c2)c(C)c1]

Step 1: (4-(2-(5-amino-8-methylbenzo[f][1,7]naphthyridin-2-yl)ethyl)-3-methylphenyl)methanol (4-(2-(5-amino-8-methylbenzo[f][1,7]naphthyridin-2-yl)ethyl)-3-methylphenyl)methanol was prepared from methyl 4-(2-(5-amino-8-methylbenzo[f][1,7]naphthyridin-2-yl)ethyl)-3-methylbenzoate (Example 115) following the procedures described for Example 42/Step 3.

Step 2: 4-(2-(5-amino-8-methylbenzo[f][1,7]naphthyridin-2-yl)ethyl)-3-methylbenzaldehyde To a solution of (4-(2-(5-amino-8-methylbenzo[f][1,7]naphthyridin-2-yl)ethyl)-3-methylphenyl)methanol (from the previous step) in DMSO was added 2-iodoxybenzoic acid (IBX, 2.5 eq). The reaction was stirred at room temperature for 3 hours before being diluted with water. Extraction with EtOAc followed by concentration gave a crude residue which was purified by chromatography (silica gel, 100% EtOAc in hexanes) to afford 4-(2-(5-amino-8-methylbenzo[f][1,7]naphthyridin-2-yl)ethyl)-3-methylbenzaldehyde.

Step 3: (E)-ethyl 3-(4-(2-(5-amino-8-methylbenzo[f][1,7]naphthyridin-2-yl)ethyl)-3-methylphenyl)acrylate To a suspension of NaH (3 eq) in THF (0.2 M) stirred at 0° C. was added ethyl 2-(diethoxyphosphoryl)acetate (commercially available) (3 eq). After stirring for 30 minutes, a solution of 4-(2-(5-amino-8-methylbenzo[f][1,7]naphthyridin-2-yl)ethyl)-3-methylbenzaldehyde (from the previous step) in THF (0.2 M) was added dropwise. The reaction was allowed to warm to room temperature and stirred overnight. The reaction was quenched with sat. NH4Cl solution, and was extracted with EtOAc. Combined organic extracts were dried and concentrated to give a crude residue which was purified by chromatography (silica gel, 50-100% EtOAc in hexanes) to afford (E)-ethyl 3-(4-(2-(5-amino-8-methylbenzo[f][1,7]naphthyridin-2-yl)ethyl)-3-methylphenyl)acrylate as a white solid. $^1$H NMR: ($CDCl_3$): δ 8.54 (d, 1H), 8.29 (d, 1H), 7.99 (d, 1H), 7.57 (d, 1H), 7.44 (s, 1H), 7.23 (dd, 1H), 7.11 (dd, 1H), 7.05 (d, 1H), 6.33 (d, 1H), 5.93 (s, 2H), 4.19 (q, 2H), 3.10-2.95 (m, 4H), 2.44 (s, 3H), 2.23 (s, 3H), 1.26 (t, 3H). LRMS [M+H]=426.2

Example 66 ethyl 3-(4-(2-(5-amino-8-methylbenzo[f][1,7]naphthyridin-2-yl)ethyl)-3-methylphenyl)propanoate

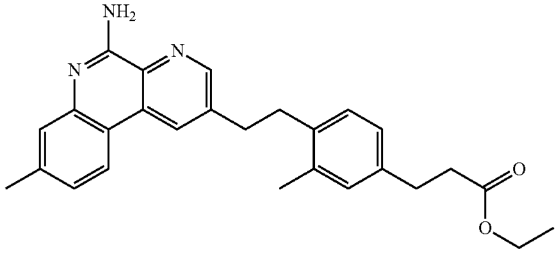 [SMILES: CCOC(=O)CCc1ccc(CCc2cnc3c(N)nc4cc(C)ccc4c3c2)c(C)c1]

Ethyl 3-(4-(2-(5-amino-8-methylbenzo[f][1,7]naphthyridin-2-yl)ethyl)-3-methylphenyl)propanoate was prepared from (E)-ethyl 3-(4-(2-(5-amino-8-methylbenzo[f][1,7]naphthyridin-2-yl)ethyl)-3-methylphenyl)acrylate (from Example 65) following the procedures described for Example 44/Step 5. $^1$H NMR: ($CDCl_3$): δ 8.55 (d, 1H), 8.26 (d, 1H), 7.99 (d, 1H), 7.45 (s, 1H), 7.12 (dd, 1H), 6.98-6.88 (m, 3H), 6.02 (s, 2H), 4.06 (q, 2H), 3.04 (dd, 2H), 2.93 (dd, 2H), 2.83 (t, 2H), 2.53 (t, 2H), 2.44 (s, 3H), 2.19 (s, 3H), 1.17 (t, 3H). LRMS [M+H]=428.2

Example 67

2-(4-(2-(5-amino-8-methylbenzo[f][1,7]naphthyridin-2-yl)ethyl)-3-methylbenzyl)propane-1,3-diol

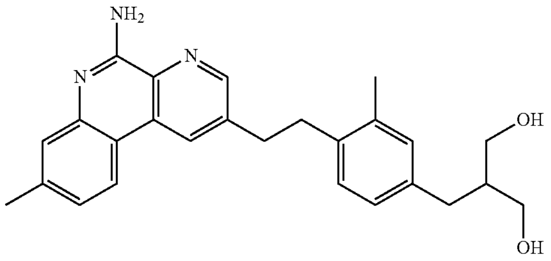 [SMILES: Cc1ccc2c(c1)nc(N)c1ncc(CCc3ccc(CC(CO)CO)cc3C)cc12]

Step 1: diethyl 2-(4-(2-(5-amino-8-methylbenzo[f][1,7]naphthyridin-2-yl)ethyl)-3-methylbenzyl)malonate To a stirred solution of (4-(2-(5-amino-8-methylbenzo[f][1,7]naphthyridin-2-yl)ethyl)-3-methylphenyl)methanol (from Example 65/Step 1) (0.2 M) and diethyl malonate (2 eq) in dry toluene was added tributylphosphine (2 eq) and $N^1,N^1,N^2,N^2$-tetramethyldiazene-1,2-dicarboxamide (2 eq). The reaction mixture was stirred at 120° C. overnight. Upon completion of the reaction, the reaction mixture was concentrated under vacuum and the resulting crude residue was purified by chromatography (silica gel, 50-100% EtOAc in hexanes) to afford diethyl 2-(4-(2-(5-amino-8-methylbenzo[f][1,7]naphthyridin-2-yl)ethyl)-3-methylbenzyl)malonate as a white solid.

Step 2: 2-(4-(2-(5-amino-8-methylbenzo[f][1,7]naphthyridin-2-yl)ethyl)-3-methylbenzyl)propane-1,3-diol 2-(4-(2-(5-Amino-8-methylbenzo[f][1,7]naphthyridin-2-yl)ethyl)-3-methylbenzyl)propane-1,3-diol was prepared from diethyl 2-(4-(2-(5-amino-8-methylbenzo[f][1,7]naphthyridin-2-yl)ethyl)-3-methylbenzyl)malonate (from the previous step) following the procedures described for Example 42/Step 3. $^1$H NMR: (methanol-$d_4$): δ 8.51 (d, 1H), 8.39 (d, 1H), 8.05 (d, 1H), 7.45 (s, 1H), 7.10 (dd, 1H), 6.91-6.87 (m, 2H), 6.83 (dd, 1H), 3.42 (d, 4H), 3.08-3.02 (m, 2H), 2.96-2.91 (m, 2H), 2.47 (d, 2H), 2.38 (s, 3H), 2.13 (s, 3H). LRMS [M+H]=416.2

Example 68

3-(4-(2-(5-amino-8-methylbenzo[f][1,7]naphthyridin-2-yl)ethyl)-3-methylphenyl)propanoic acid

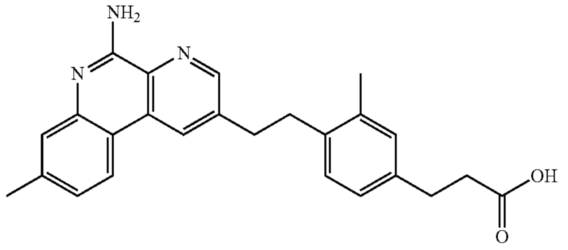 [SMILES: Cc1ccc2c(c1)nc(N)c1ncc(CCc3ccc(CCC(=O)O)cc3C)cc12]

A solution of ethyl 3-(4-(2-(5-amino-8-methylbenzo[f][1,7]naphthyridin-2-yl)ethyl)-3-methylphenyl)propanoate (from Example 66) in 1 N NaOH, THF and methanol (1:5:2, 0.1 N) was heated at 60° C. for 3 hours. After cooling to room temperature the reaction mixture was neutralized with 1 N HCl to pH 7, and was concentrated to give a crude residue which was purified by chromatography (silica gel, 0-20% methanol in dichloromethane) to afford (E)-ethyl 3-(4-(2-(5-amino-8-methylbenzo[f][1,7]naphthyridin-2-yl)ethyl)-3-methylphenyl)acrylate as a white solid. $^1$H NMR: (methanol-$d_4$): δ 8.73 (d, 1H), 8.54 (d, 1H), 8.20 (d, 1H), 7.45 (s, 1H), 7.37 (d, 1H), 7.00-6.97 (m, 2H), 6.92 (d, 1H), 3.19 (t, 2H), 3.04 (t, 2H), 2.81 (t, 2H), 2.53 (t, 2H), 2.50 (s, 3H), 2.25 (s, 3H). LRMS [M+H]=400.2

Example 69

5-amino-2-(4-methoxy-2-methylphenethyl)benzo[f][1,7]naphthyridine-8-carbaldehyde

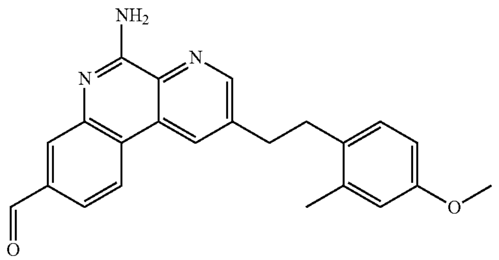 [SMILES: COc1ccc(CCc2cnc3c(N)nc4cc(C=O)ccc4c3c2)c(C)c1]

5-amino-2-(4-methoxy-2-methylphenethyl)benzo[f][1,7]naphthyridine-8-carbaldehyde was prepared from (5-amino-2-(4-methoxy-2-methylphenethyl)benzo[f][1,7]naphthyridin-8-yl)methanol (from Example 108) following the procedures described for Example 65/Step 2. $^1$H NMR: ($CDCl_3$): δ 10.19 (s, 1H), 8.74 (d, 1H), 8.43 (d, 1H), 8.32 (d, 1H), 8.18 (d, 1H), 7.88 (dd, 1H), 7.00 (d, 1H), 6.76 (d, 1H), 6.70 (dd, 1H), 6.30 (s, 2H), 3.80 (s, 3H), 3.16 (dd, 2H), 3.02 (dd, 2H), 2.29 (s, 3H). LRMS [M+H]=372.2

Example 70 ethyl 4-(2-(5-amino-8-methylbenzo[f][1,7]naphthyridin-2-yl)ethyl)benzoate

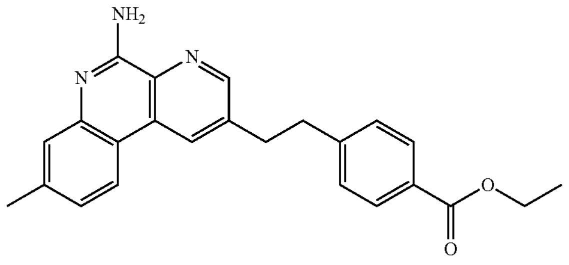

Step 1: ethyl 4-((5-chloro-6-cyanopyridin-3-yl)ethynyl)benzoate

A solution of 3,5-dichloropicolinonitrile (commercially available) (1.0 eq.), ethyl 4-ethynylbenzoate (commercially available) (1.0 eq.), trans-dichlororbis(triphenylphosphine) palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-20% ethyl acetate in hexane to give ethyl 4-((5-chloro-6-cyanopyridin-3-yl)ethynyl)benzoate as a white solid.

Step 2: ethyl 4-((5-amino-8-methylbenzo[f][1,7]naphthyridin-2-yl)ethynyl)benzoate A solution of ethyl 4-((5-chloro-6-cyanopyridin-3-yl)ethynyl)benzoate (from the previous step) (1.0 eq.), tert-butyl 5-methyl-2-(4,4,5,5-tetramethyl-1,3,2-dioxaborolan-2-yl)phenylcarbamate (from Example 5/Step 2) (2.6 eq.), tetrakis(triphenylphosphine)palladium (10 mol %), and potassium carbonate (5.3 eq.) in toluene/ethanol (2:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)benzoate.

Step 3: ethyl 4-(2-(5-amino-8-methylbenzo[f][1,7]naphthyridin-2-yl)ethyl)benzoate A solution of ethyl 4-((5-amino-8-methylbenzo[f][1,7]naphthyridin-2-yl)ethynyl)benzoate (from the previous step) (1.0 eq.) in THF/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give ethyl 4-(2-(5-amino-8-methylbenzo[f][1,7]naphthyridin-2-yl)ethyl)benzoate. $^{1}H$ NMR (Acetone-$d_6$): δ 8.80 (s, 1H), 8.69 (s, 1H), 8.25 (d, 1H), 7.90 (d, 2H), 7.40-7.42 (m, 3H), 7.12 (d, 1H), 6.55 (br, 2H), 4.28 (q, 2H), 3.2-3.3 (m, 4H), 2.44 (s, 3H), 1.31 (t, 3H). LRMS [M+H]=386.2

Example 71

8-methyl-2-(4-methylphenethyl)benzo[f][1,7]naphthyridin-5-amine

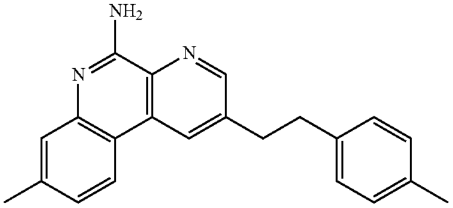

Step 1: 3-chloro-5-(p-tolylethynyl)picolinonitrile

A solution of 3,5-dichloropicolinonitrile (commercially available) (1.0 eq.), 1-ethynyl-4-methylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by stirring in hot ether/hexane mixtures and filtered to give 3-chloro-5-(p-tolylethynyl)picolinonitrile.

Step 2: 8-methyl-2-(p-tolylethynyl)benzo[f][1,7]naphthyridin-5-amine

A solution of 3-chloro-5-(p-tolylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.2 eq.), tetrakis(triphenylphosphine)palladium (10 mol %), and 2N sodium carbonate aqueous solution (4.0 eq.) in toluene/ethanol (2:1, 0.2 M) was stirred at 100° C. overnight. After cooling to ambient temperature, the reaction mixture was diluted with 2% MeOH in DCM. The two phases were separated, and the aqueous layer was extracted with 2% MeOH in DCM twice. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give 8-methyl-2-(p-tolylethynyl)benzo[f][1,7]naphthyridin-5-amine.

Step 3: 8-methyl-2-(4-methylphenethyl)benzo[f][1,7]naphthyridin-5-amine

A solution of 8-methyl-2-(p-tolylethynyl)benzo[f][1,7]naphthyridin-5-amine (from the previous step) (1.0 eq.) in EtOH/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give 8-methyl-2-(4-methylphenethyl)benzo[f][1,7]naphthyridin-5-amine. $^{1}H$ NMR (Acetone-$d_6$): δ 8.74 (s, 1H), 8.68 (s, 1H), 8.24 (d, 1H), 7.41 (s, 1H), 7.13-7.15 (m, 3H), 7.06 (d, 2H), 6.6 (br, 2H), 3.19 (t, 2H), 3.06 (t, 2H), 2.44 (s, 3H), 2.25 (s, 3H). LRMS [M+H]=328.1

Example 72

2-(4-(2-(5-amino-8-methylbenzo[f][1,7]naphthyridin-2-yl)ethyl)phenyl)propan-2-ol

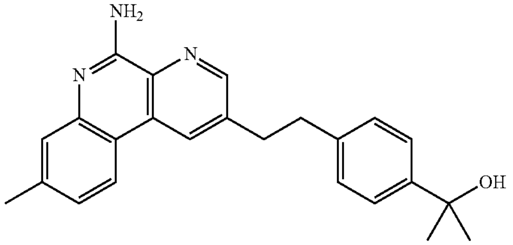 [SMILES: Cc1ccc2c(c1)nc(N)c1ncc(CCc3ccc(C(C)(C)O)cc3)cc12]

To a solution of ethyl 4-(2-(5-amino-8-methylbenzo[f][1,7]naphthyridin-2-yl)ethyl)benzoate (from Example 70) (1.0 eq.) in DCM at 0° C. was added 3.0 M methyl magnesium iodide (10 eq.) in ether and warmed to room temperature overnight. The reaction was cooled to 0° C. and quenched with 1N HCl aqueous solution and ether. After stirring for 15 minutes, the reaction mixture was neutralized with saturated aqueous sodium bicarbonate solution. The two phases were separated, and the aqueous layer was extracted with ether. The combined organic layers were washed with brine, dried over anhydrous $MgSO_4$, and concentrated en vaccuo. The crude material was purified by RP-HPLC using a 10-50% MeCN in water gradient followed by extraction in DCM to give 2-(4-(2-(5-amino-8 methylbenzo[f][1,7]naphthyridin-2-yl)ethyl)phenyl)propan-2-ol. $^{1}H$ NMR (Acetone-$d_6$): δ 8.73 (m, 2H), 8.22 (d, 1H), 7.40-7.44 (m, 3H), 7.20 (d, 2H), 7.12 (d, 1H), 6.5 (br, 2H), 3.94 (s, 1H), 3.21 (t, 2H), 3.08 (t, 2H), 2.44 (s, 3H), 1.47 (s, 6H). LRMS [M+H]=372.2

Example 73

(4-(2-(5-amino-8-methylbenzo[f][1,7]naphthyridin-2-yl)ethyl)phenyl)methanol

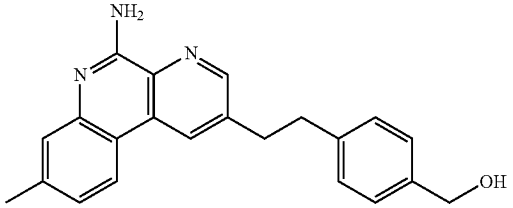 [SMILES: Cc1ccc2c(c1)nc(N)c1ncc(CCc3ccc(CO)cc3)cc12]

To a solution of ethyl 4-(2-(5-amino-8-methylbenzo[f][1,7]naphthyridin-2-yl)ethyl)benzoate (Example 70) (1.0 eq.) in THF (0.1 M) at 0° C. was added 1.0 M lithium triethylborohydride in THF (10 eq.) and warmed to room temperature over 2 hours. 1N HCl aqueous solution was added slowly to quench the reaction, and the mixture was heated to reflux for 30 minutes. The reaction mixture was neutralized with saturated aqueous sodium bicarbonate solution. The two phases were separated, and the aqueous layer was extracted with ethyl acetate (EA). The combined organic layers were washed with brine, dried over anhydrous $MgSO_4$, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)phenyl)methanol. $^1$H NMR (Acetone-$d_6$): δ 8.77 (s, 1H), 8.69 (s, 1H), 8.26 (d, 1H), 7.40 (s, 1H), 7.21-7.28 (m, 4H), 7.13 (d, 1H), 6.5 (br, 2H), 4.56 (s, 2H), 4.1 (br t, 1H), 3.10-3.23 (m, 4H), 2.44 (s, 3H). LRMS [M+H]=344.2

Example 74 ethyl 4-(2-(5-amino-8-methylbenzo[f][1,7]naphthyridin-2-yl)ethyl)-3-methylbenzoate

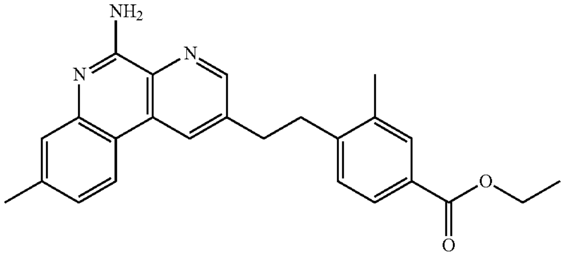 [SMILES: CCOC(=O)c1ccc(CCc2cnc3c(N)nc4cc(C)ccc4c3c2)c(C)c1]

Step 1: ethyl 4-bromo-3-methylbenzoate

To a solution of 4-bromo-3-methylbenzoic acid (commercially available) (1.0 eq.) in EtOH (0.3 M) was added thionyl chloride (1.5 eq.) and heated to reflux for 2 hours. The solvent was concentrated en vaccuo, and the residue was diluted in ether and neutralized with saturated aqueous sodium bicarbonate solution. The two phases were separated, and the aqueous layer was extracted with ether. The combined organic layers were washed with brine, dried over anhydrous $MgSO_4$, and concentrated en vaccuo to give ethyl 4-bromo-3-methylbenzoate.

Step 2: ethyl 3-methyl-4-((triethylsilyl)ethynyl)benzoate

A solution of ethyl 4-bromo-3-methylbenzoate (from the previous step) (1.0 eq.), triethyl(ethynyl)silane (1.1 eq.), trans-dichlorobis(triphenylphosphine)palladium (II) (10 mol %), copper (I) iodide (20 mol %), and triethylamine (5.0 eq.) in DMF (0.3 M) was stirred at 60° C. overnight. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-5% ethyl acetate in hexane to give ethyl 3-methyl-4-((triethylsilyl)ethynyl)benzoate as a yellow oil.

Step 3: ethyl 4-ethynyl-3-methylbenzoate

To a solution of ethyl 3-methyl-4-((triethylsilyl)ethynyl)benzoate (from the previous step) (1.0 eq.) in THF (0.3 M) at 0° C. was added dropwise 1.0 M TBAF in THF (1.2 eq.). After stirring for 10 minutes at 0° C., the reaction was quenched with saturated aqueous sodium bicarbonate solution. The two phases were separated, and the aqueous layer was extracted with ether. The combined organic layers were washed with brine, dried over anhydrous $MgSO_4$, and concentrated en vaccuo. The crude material was purified by flash chromatography on a COMBIFLASH® system (ISCO) using 0-5% ethyl acetate in hexane to give ethyl 4-ethynyl-3-methylbenzoate as a white solid.

Step 4: ethyl 4-((5-chloro-6-cyanopyridin-3-yl)ethynyl)-3-methylbenzoate

A solution of 3,5-dichloropicolinonitrile (1.0 eq.), ethyl 4-ethynyl-3-methylbenzoate (from the previous step) (1.0 eq.), trans-dichlorobis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-10% ethyl acetate in hexane to give ethyl 4-((5-chloro-6-cyanopyridin-3-yl)ethynyl)-3-methylbenzoate as a white solid.

Step 5: ethyl 4-((5-amino-8-methylbenzo[f][1,7]naphthyridin-2-yl)ethynyl)-3-methylbenzoate A solution of ethyl 4-((5-chloro-6-cyanopyridin-3-yl)ethynyl)-3-methylbenzoate (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and potassium carbonate (3.0 eq.) in toluene/ethanol (9:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)-3-methylbenzoate.

Step 6: ethyl 4-(2-(5-amino-8-methylbenzo[f][1,7]naphthyridin-2-yl)ethyl)-3-methylbenzoate A solution of ethyl 4-((5-amino-8-methylbenzo[f][1,7]naphthyridin-2-yl)ethynyl)-3-methylbenzoate (from the previous step) (1.0 eq.) in THF/ethyl acetate (1:1, 0.05M) was flushed with nitrogen and added 10% palladium on carbon (10 wt %). The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 30-100% EA in hexane to give ethyl 4-(2-(5-amino-8-methylbenzo[f][1,7]naphthyridin-2-yl)ethyl)-3-methylbenzoate. $^1H$ NMR (Acetone-$d_6$): δ 8.79 (s, 1H), 8.71 (s, 1H), 8.24 (d, 1H), 7.80 (s, 1H), 7.73 (d, 1H), 7.40 (s, 1H), 7.31 (d, 1H), 7.12 (d, 1H), 6.5 (br, 2H), 4.29 (q, 2H), 3.19-3.22 (m, 4H), 2.44 (s, 3H), 2.39 (s, 3H), 1.31 (t, 3H). LRMS [M+H]=400.2

Example 75

4-(2-(5-amino-8-methylbenzo[f][1,7]naphthyridin-2-yl)ethyl)-3-methylbenzoic acid

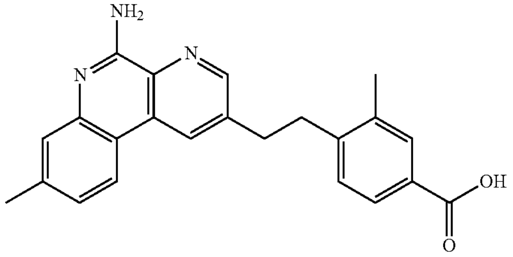 [SMILES: Cc1ccc2c(c1)nc(N)c1ncc(CCc3ccc(C(=O)O)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in EtOH was added 1N aqueous sodium hydroxide (1.5 eq.) and heated to 80° C. for 5 hours. The reaction mixture was neutralized by adding 1N aqueous HCl (1.5 eq.) and concentrated en vaccuo. The crude material was purified by RP-HPLC using a 10-50% MeCN in water gradient followed by concentration en vaccuo to give the TFA salt. $^1H$ NMR (DMSO-$d_6$) of the TFA salt: δ 7.94-7.96 (m, 2H), 7.55 (d, 1H), 7.00 (s, 1H), 6.91 (d, 1H), 6.62-6.66 (m, 2H), 6.39 (d, 1H), 2.36-2.5 (m, 4H), 1.73 (s, 3H), 1.54 (s, 3H). LRMS [M+H]=372.2

Example 76

(4-(2-(5-amino-8-methylbenzo[f][1,7]naphthyridin-2-yl)ethyl)-3-methylphenyl)methanol

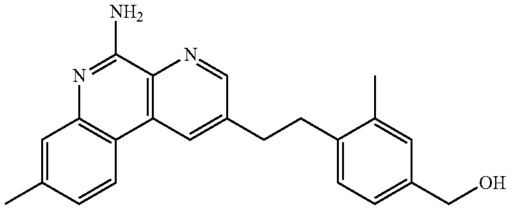 [SMILES: Cc1ccc2c(c1)nc(N)c1ncc(CCc3ccc(CO)cc3C)cc12]

To a solution of ethyl 4-(2-(5-amino-8-methylbenzo[f][1,7]naphthyridin-2-yl)ethyl)-3-methylbenzoate (from Example 74) (1.0 eq.) in THF (0.1M) at −78° C. was added 1.0 M DIBAL-H in toluene (10 eq.) and warmed to room temperature over 2 hours. 1.5 M Rochelle salt aqueous solution was added slowly to quench the reaction followed by addition of EA, and the mixture was stirred for 45 minutes. The two phases were separated, and the aqueous layer was extracted twice with EA. The combined organic layers were washed with brine, dried over anhydrous $MgSO_4$, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)-3-methylphenyl)methanol. $^1H$ NMR (Acetone-$d_6$): δ 8.77 (s, 1H), 8.71 (s, 1H), 8.25 (d, 1H), 7.41 (s, 1H), 7.10-7.15 (m, 4H), 6.5 (br, 2H), 4.54 (s, 2H), 4.05 (br, 1H), 3.08-3.18 (m, 4H), 2.44 (s, 3H), 2.31 (s, 3H). LRMS [M+H]=358.2

Example 77

8-methyl-2-(2,4,6-trimethylphenethyl)benzo[f][1,7]naphthyridin-5-amine

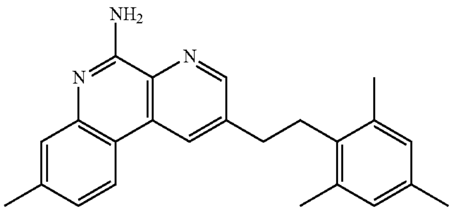

Step 1: 3-chloro-5-(mesitylethynyl)picolinonitrile

A solution of 3,5-dichloropicolinonitrile (1.0 eq.), 2-ethynyl-1,3,5-trimethylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBI- FLASH® system (ISCO) using 0-10% ethyl acetate in hexane to give 3-chloro-5-(mesitylethynyl)picolinonitrile a as white solid.

Step 2: 2-(mesitylethynyl)-8-methylbenzo[f][1,7] naphthyridin-5-amine

A solution of 3-chloro-5-(mesitylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 5/Step 2) (1.1 eq.), tetrakis(triphenylphosphine)palladium (8 mol %), and 2N aqueous sodium carbonate solution (3.0 eq.) in toluene/ethanol (4:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give 2-(mesitylethynyl)-8-methylbenzo[f][1,7] naphthyridin-5-amine.

Step 3: 8-methyl-2-(2,4,6-trimethylphenethyl)benzo [f][1,7]naphthyridin-5-amine

A solution of 2-(mesitylethynyl)-8-methylbenzo[f][1,7] naphthyridin-5-amine (from the previous step) (1.0 eq.) in EtOH (0.05M) was flushed with nitrogen and added palladium on carbon (10 wt %). The reaction vessel was evacuated, flushed with hydrogen, and stirred overnight at rt. The reaction mixture was filtered through celite, washed with 2% MeOH in DCM, and concentrated en vaccuo. The crude material was purified by flash chromatography on a COMBIFLASH® system (ISCO) using 0-50% ethyl acetate in hexane to give 8-methyl-2-(2,4,6-trimethylphenethyl)benzo [f][1,7]naphthyridin-5-amine. $^1H$ NMR (Acetone-$d_6$): δ 8.73-8.74 (m, 2H), 8.25 (d, 1H), 7.42 (s, 1H), 7.14 (d, 1H), 6.83 (s, 2H), 6.55 (br, 2H), 3.07 (m, 4H), 2.47 (s, 3H), 2.29 (s, 6H), 2.22 (s, 3H). LRMS [M+H]=356.2

Example 78

2-(4-(2-(5-amino-8-methylbenzo[f][1,7]naphthyridin-2-yl)ethyl)-3-methylphenyl)propan-2-ol

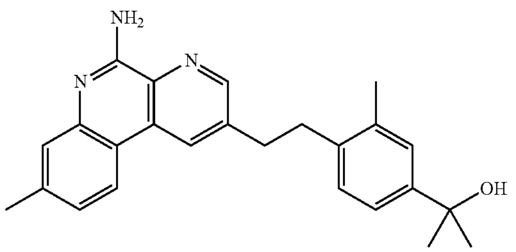

To a solution of ethyl 4-(2-(5-amino-8-methylbenzo[f][1,7]naphthyridin-2-yl)ethyl)-3-methylbenzoate (from Example 74) (1.0 eq.) in DCM at 0° C. was added 3.0 M methyl magnesium iodide (10 eq.) in ether and warmed to room temperature overnight. The reaction was cooled to 0° C. and quenched with water. After stirring for 15 min, the reaction mixture was neutralized with saturated aqueous sodium bicarbonate solution and added EA. The two phases were separated, and the aqueous layer was extracted three times with EA. The combined organic layers were washed with brine, dried over anhydrous $MgSO_4$, and concentrated en vaccuo. The crude material was purified by flash chromatography on a COMBIFLASH® system (ISCO) using 0-5% MeOH in DCM to give a 2-(4-(2-(5-amino-8-methylbenzo[f][1,7]naphthyridin-2-yl)ethyl)-3-methylphenyl)propan-2-ol. $^1H$ NMR (Acetone-$d_6$): δ 8.72-8.75 (m, 2H), 8.23 (d, 1H), 7.41 (s, 1H), 7.32 (s, 1H), 7.25 (d, 1H), 7.12-7.14 (m, 2H), 6.6 (br, 2H), 3.91 (s, 1H), 3.07-3.18 (m, 4H), 2.44 (s, 3H), 2.31 (s, 3H), 1.48 (s, 6H). LRMS [M+H]=386.2

Example 79

8-methyl-2-(4-propoxyphenethyl)benzo[f][1,7]naphthyridin-5-amine

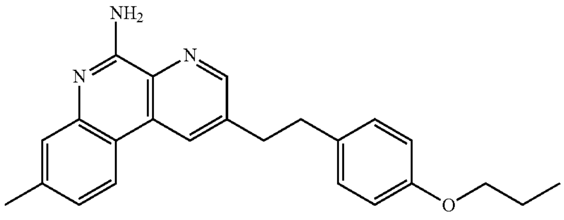 [SMILES: CCCOc1ccc(CCc2cnc3c(N)nc4cc(C)ccc4c3c2)cc1]

Step 1: 3-chloro-5-((4-propoxyphenyl)ethynyl)picolinonitrile

A solution of 3,5-dichloropicolinonitrile (1.0 eq.), 1-ethynyl-4-propoxybenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-10% ethyl acetate in hexane to give 3-chloro-5-((4-propoxyphenyl)ethynyl)picolinonitrile as a white solid.

Step 2: 3-chloro-5-(4-propoxyphenethyl)picolinonitrile

A solution of 3-chloro-5-((4-propoxyphenyl)ethynyl)picolinonitrile (from the previous step) (1.0 eq.) in EtOH (0.05M) was flushed with nitrogen and added platinum (VI) oxide (0.5 eq.). The reaction vessel was evacuated, flushed with hydrogen, and stirred for 5 hours at room temperature. The reaction mixture was filtered through celite, washed with 2% MeOH in DCM, and concentrated en vaccuo. The crude material was purified by flash chromatography on a COMBIFLASH® system (ISCO) using 0-15% ethyl acetate in hexane to give 3-chloro-5-(4-propoxyphenethyl)picolinonitrile.

Step 3: 8-methyl-2-(4-propoxyphenethyl)benzo[f][1,7]naphthyridin-5-amine

A solution of 3-chloro-5-(4-propoxyphenethyl)picolinonitrile (from the previous step) (1.0 eq.), tert-butyl 5-methyl- 2-(4,4,5,5-tetramethyl-1,3,2-dioxaborolan-2-yl)phenylcarbamate (from Example 5/Step 2) (1.1 eq.), tetrakis (triphenylphosphine)palladium (8 mol %), and 2N aqueous sodium carbonate solution (3.0 eq.) in toluene (0.2 M) was stirred at 100° C. overnight. After cooling to ambient temperature, the reaction mixture was diluted with 2% MeOH in DCM. The two phases were separated. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give 8-methyl-2-(4-propoxyphenethyl)benzo[f][1,7]naphthyridin-5-amine. $^1H$ NMR (Acetone-$d_6$): δ 8.74 (s, 1H), 8.67 (s, 1H), 8.24 (d, 1H), 7.41 (s, 1H), 7.15-7.17 (m, 3H), 6.81 (d, 2H), 6.5 (br, 2H), 3.87 (t, 2H), 3.18 (t, 2H), 3.04 (t, 2H), 2.44 (s, 3H), 1.73 (m, 2H), 0.99 (t, 3H). LRMS [M+H]=372.2

Example 80

(E)-ethyl 3-(5-amino-2-(4-methoxy-2-methylphenethyl)benzo[f][1,7]naphthyridin-8-yl)acrylate

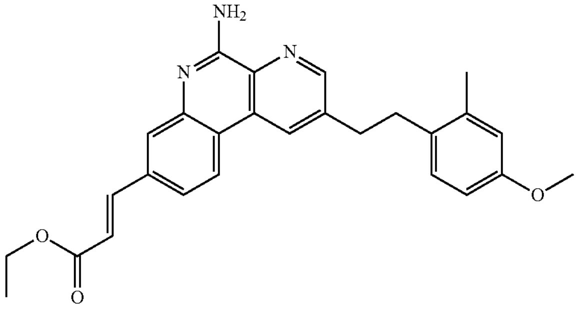

(E)-ethyl 3-(5-amino-2-(4-methoxy-2-methylphenethyl) benzo[f][1,7]naphthyridin-8-yl)acrylate was prepared from 5-amino-2-(4-methoxy-2-methylphenethyl)benzo[f][1,7] naphthyridine-8-carbaldehyde (from Example 69) and ethyl 2-(diethoxyphosphoryl)acetate (commercially available) following the procedures described for Example 65/Step 3. LRMS [M+H]=442.2

Example 81

(E)-3-(5-amino-2-(4-methoxy-2-methylphenethyl) benzo[f][1,7]naphthyridin-8-yl)acrylic acid

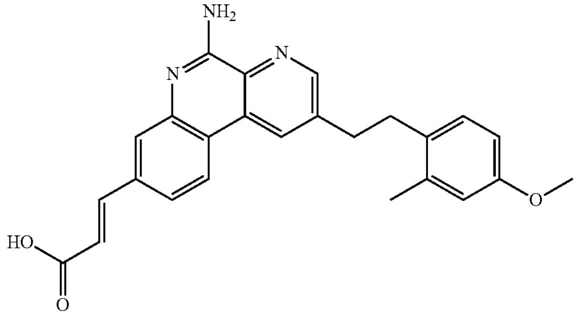 [SMILES: COc1ccc(CCc2cnc3c(N)nc4cc(/C=C/C(=O)O)ccc4c3c2)c(C)c1]

(E)-3-(5-amino-2-(4-methoxy-2-methylphenethyl)benzo [f][1,7]naphthyridin-8-yl)acrylic acid was prepared from (E)-ethyl 3-(5-amino-2-(4-methoxy-2-methylphenethyl) benzo[f][1,7]naphthyridin-8-yl)acrylate (from Example 80) following the procedures described for Example 68. $^1H$ NMR of TFA salt (DMSO-$d_6$): δ 12.66 (s, 1H), 9.09 (s, 1H), 8.88 (s, 1H), 8.66 (d, 1H), 7.95 (d, 1H), 7.91 (s, 1H), 7.75 (d, 1H), 7.10 (d, 1H), 6.77-6.71 (m, 2H), 6.68 (dd, 1H), 3.70 (s, 3H), 3.16 (t, 2H), 3.00 (t, 2H), 2.30 (s, 3H). LRMS [M+H]=414.2

Example 82 ethyl 3-(5-amino-2-(4-methoxy-2-methylphenethyl) benzo[f][1,7]naphthyridin-8-yl)propanoate

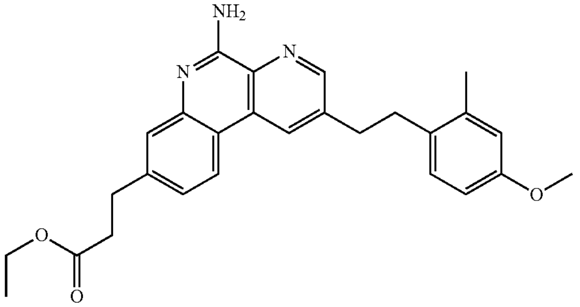 [SMILES: CCOC(=O)CCc1ccc2c(c1)nc(N)c1ncc(CCc3ccc(OC)cc3C)cc12]

Ethyl 3-(5-amino-2-(4-methoxy-2-methylphenethyl) benzo[f][1,7]naphthyridin-8-yl)propanoate was prepared from (E)-ethyl 3-(5-amino-2-(4-methoxy-2-methylphenethyl)benzo[f][1,7]naphthyridin-8-yl)acrylate (from Example 80) following the procedures described for Example 44/Step 5. $^1H$ NMR ($CDCl_3$): δ 8.63 (d, 1H), 8.37 (d, 1H), 8.13 (d, 1H), 7.56 (d, 1H), 7.24 (dd, 1H), 7.02 (d, 1H), 6.75 (d, 1H), 6.69 (dd, 1H), 6.15 (br s, 2H), 4.17 (q, 2H), 3.79 (s, 3H), 3.12 (dd, 4H), 2.99 (dd, 2H), 2.75 (t, 2H), 2.29 (s, 3H), 1.27 (t, 2H), 0.99 (t, 3H). LRMS [M+H]=444.2

Example 83

3-(5-amino-2-(4-methoxy-2-methylphenethyl)benzo [f][1,7]naphthyridin-8-yl)propanoic acid

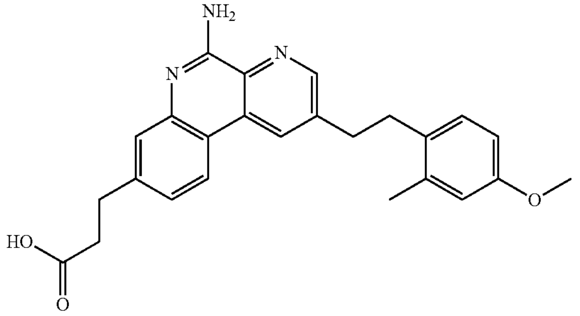 [SMILES: COc1ccc(CCc2cnc3c(N)nc4cc(CCC(=O)O)ccc4c3c2)c(C)c1]

3-(5-Amino-2-(4-methoxy-2-methylphenethyl)benzo[f] [1,7]naphthyridin-8-yl)propanoic acid was prepared from ethyl 3-(5-amino-2-(4-methoxy-2-methylphenethyl)benzo [f][1,7]naphthyridin-8-yl)propanoate (from Example 82) following the procedures described for Example 68. $^1H$ NMR (DMSO-$d_6$): δ 12.18 (s, 1H), 8.84 (d, 1H), 8.70 (d, 1H), 8.36 (d, 1H), 7.39 (d, 1H), 7.20 (dd, 1H), 7.09 (m, 2H), 6.74 (d, 1H), 6.68 (dd, 1H), 3.70 (s, 3H), 3.09 (dd, 2H), 2.96 (dd, 4H), 2.63 (t, 2H), 2.27 (s, 3H). LRMS [M+H]=416.2

Example 84

3-(5-amino-2-(4-methoxy-2-methylphenethyl)benzo[f][1,7]naphthyridin-8-yl)propan-1-ol

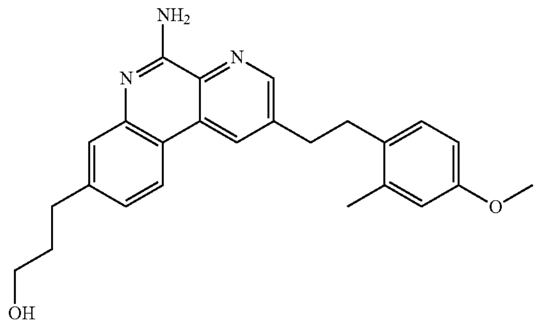 [SMILES: COc1ccc(CCc2cnc3c(N)nc4cc(CCCO)ccc4c3c2)c(C)c1]

3-(5-Amino-2-(4-methoxy-2-methylphenethyl)benzo[f][1,7]naphthyridin-8-yl)propan-1-ol was prepared from ethyl 3-(5-amino-2-(4-methoxy-2-methylphenethyl)benzo[f][1,7]naphthyridin-8-yl)propanoate (from Example 82) following the procedures described for Example 42/Step 3. $^1$H NMR ($CDCl_3$): δ 8.54 (d, 1H), 8.30 (d, 1H), 8.05 (d, 1H), 7.48 (d, 1H), 7.15 (dd, 1H), 6.93 (d, 1H), 6.66 (d, 1H), 6.61 (dd, 1H), 5.98 (br s, 2H), 3.71 (s, 3H), 3.66 (t, 2H), 3.03 (dd, 2H), 2.91 (dd, 2H), 2.81 (t, 2H), 2.20 (s, 3H), 1.98-1.90 (m, 2H). LRMS [M+H]=402.2

Example 85

(5-aminobenzo[f][1,7]naphthyridin-8-yl)methanol

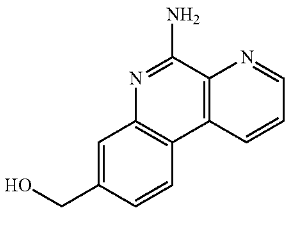 [SMILES: Nc1nc2cc(CO)ccc2c2cccnc12]

Step 1: 2-(tert-butoxycarbonylamino)-4-(methoxycarbonyl)phenylboronic acid

A solution of 2-amino-4-(methoxycarbonyl)phenylboronic acid hydrochloride (commercially available) (1.0 eq.), triethylamine (3.0 eq.), di-tert-butyl dicarbonate (1.1 eq.), and DMAP (0.1 eq.) in $CH_3CN$ (0.3 M) was stirred at 40° C. overnight. After cooling to ambient temperature, the reaction mixture was concentrated en vaccuo to obtain a crude residue. The crude material was purified by flash chromatography on a COMBIFLASH® system (ISCO) using 0-30% MeOH/DCM to give 2-(tert-butoxycarbonylamino)-4-(methoxycarbonyl)phenylboronic acid as a brown solid.

Step 2: methyl 5-aminobenzo[f][1,7]naphthyridine-8-carboxylate

A solution of 2-(tert-butoxycarbonylamino)-4-(methoxycarbonyl)phenylboronic acid (from the previous step) (1.0 eq.) and 3-bromopicolinonitrile (1.0 eq.), tetrakis(triphenylphosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was filtered to collect the precipitate. The precipitate was rinsed with EtOAc to give methyl 5-aminobenzo[f][1,7]naphthyridine-8-carboxylate as a pale brown solid.

Step 3: (5-aminobenzo[f][1,7]naphthyridin-8-yl)methanol

To a solution of methyl 5-aminobenzo[f][1,7]naphthyridine-8-carboxylate (from the previous step) (1.0 eq.) in EtOH (0.03M) was added $NaBH_4$ (10 eq.) at 25° C. The solution was heated to 80° C. for 5 hours. After cooling to ambient temperature, the reaction mixture was concentrated en vaccuo. The residue was portionized between saturated $NaHCO_3$ and EtOAc. The layers were separated and aqueous layer was extracted with EtOAc twice. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give (5-aminobenzo[f][1,7]naphthyridin-8-yl)methanol as an off white solid: $^1$H NMR (methanol-d4): δ 8.82 (dd, 1H), 8.77 (dd, 1H), 7.26 (d, 1H), 7.70 (dd, 1H), 7.50 (d, 1H), 7.27 (dd, 1H), 4.66 (s, 2H). LRMS [M+H]=226.1.

Example 86

5-aminobenzo[f][1,7]naphthyridin-8-ol

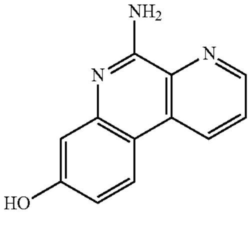 [SMILES: Nc1nc2cc(O)ccc2c2cccnc12]

To a solution of 8-methoxybenzo[f][1,7]naphthyridin-5-amine (from Example 10) (1.0 eq.) in DCM (0.04 M) was added $BBr_3$ (2.5 eq.) dropwise under $N_2$ at −20° C. The reaction was allowed to warm to ambient temperature over 30 minutes. The reaction was then stirred overnight. The reaction was quenched with saturated $NaHCO_3$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-20% MeOH/DCM to give 5-aminobenzo[f][1,7]naphthyridin-8-ol as a yellow solid: $^1$H NMR (acetone-$d_6$): δ 8.90 (dd, 1H), 8.83 (dd, 1H), 8.32 (d, 1H), 7.83 (dd, 1H), 7.11 (br s, 2H), 7.10 (d, 1H), 6.96 (dd, 1H), 5.86 (br s, 1H). LRMS [M+H]=212.1.

Example 87

5-aminobenzo[f][1,7]naphthyridine-8-carbaldehyde

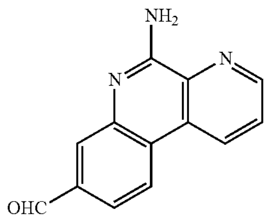 [SMILES: Nc1nc2cc(C=O)ccc2c2cccnc12]

A solution of (5-aminobenzo[f][1,7]naphthyridin-8-yl) methanol (from Example 85) (1.0 eq.) and activated $MnO_2$ (20 eq.) in DCM (0.1 M) was stirred at ambient temperature over night. The reaction mixture was diluted with DCM. The $MnO_2$ was filtered off, and the filtrate was concentrated en vaccuo to obtain a crude residue. The crude material was purified by flash chromatography on a COMBIFLASH® system (ISCO) using 0-10% MeOH/DCM to give 5-aminobenzo[f][1,7]naphthyridine-8-carbaldehyde as a yellow solid: $^1H$ NMR (acetone-$d_6$): δ 10.19 (s, 1H), 9.14 (dd, 1H), 9.01 (dd, 1H), 8.63 (d, 1H), 8.14 (d, 1H), 7.93 (dd, 1H), 7.81 (dd, 1H), 6.96 (br s, 2H). LRMS [M+H]=224.1

Example 88

1-(5-aminobenzo[f][1,7]naphthyridin-8-yl)ethanol

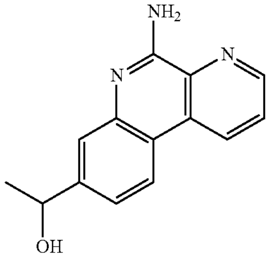 [SMILES: CC(O)c1ccc2c(c1)nc(N)c1ncccc12]

To a solution of 5-aminobenzo[f][1,7]naphthyridine-8-carbaldehyde (from Example 87) (1.0 eq.) in THF (0.02M) was added MeLi (2.5 eq.) at −78° C. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-5% MeOH/DCM to give 145-aminobenzo [f][1,7]naphthyridin-8-yl)ethanol as a yellow solid: $^1H$ NMR (methanol-$d_4$): δ 8.94 (dd, 1H), 8.88 (dd, 1H), 8.38 (d, 1H), 7.81 (dd, 1H), 7.62 (d, 1H), 7.41 (dd, 1H), 4.97 (q, 1H), 1.53 (d, 3H). LRMS [M+H]=240.1.

Example 89

1-(5-aminobenzo[f][1,7]naphthyridin-8-yl)ethanone

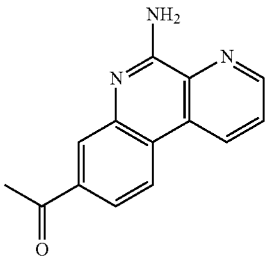 [SMILES: CC(=O)c1ccc2c(c1)nc(N)c1ncccc12]

A solution 1-(5-aminobenzo[f][1,7]naphthyridin-8-yl) ethanol (from Example 88) (1.0 eq.) and activated $MnO_2$ (20 eq.) in DCM (0.1 M) was stirred at ambient temperature over night. The reaction mixture was diluted with DCM. The $MnO_2$ was filtered off, and the filtrate was concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanone as a yellow solid: $^1H$ NMR (acetone-$d_6$): δ 9.11 (dd, 1H), 8.99 (dd, 1H), 8.56 (d, 1H), 8.20 (d, 1H), 7.94-7.88 (m, 2H), 6.90 (br s, 2H), 2.70 (s, 3H). LRMS [M+H]=238.1.

Example 90

8-isopropylbenzo[f][1,7]naphthyridin-5-amine

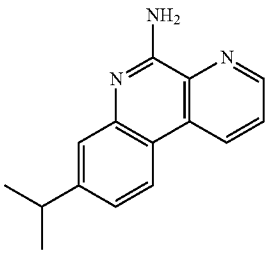 [SMILES: CC(C)c1ccc2c(c1)nc(N)c1ncccc12]

Step 1: 2-(5-aminobenzo[f][1,7]naphthyridin-8-yl) propan-2-ol

To a solution of methyl 5-aminobenzo[f][1,7]naphthyridine-8-carboxylate (from Example 85/Step 2) (1.0 eq.) in THF (0.02M) was added MeLi (10 eq.) at −78° C. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give 2-(5-aminobenzo[f][1,7]naphthyridin-8-yl)propan-2-ol as a yellow oil.

Step 2: 8-(prop-1-en-2-yl)benzo[f][1,7]naphthyridin-5-amine

A solution of 2-(5-aminobenzo[f][1,7]naphthyridin-8-yl) propan-2-ol (from the previous step) (1.0 eq.) and p-TsOH (2 eq.) in toluene (0.01 M) was stirred at 90° C. for 6 hours. The reaction was quenched by saturated $NaHCO_3$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-5% MeOH/DCM to give 8-(prop-1-en-2-yl)benzo[f][1,7]naphthyridin-5-amine as a yellow solid.

Step 3: 8-isopropylbenzo[f][1,7]naphthyridin-5-amine

A mixture of 8-(prop-1-en-2-yl)benzo[f][1,7]naphthyridin-5-amine (from the previous step) (1.0 eq) and Pd/C (wet, 10% wt) in EtOH was stirred under $H_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-isopropylbenzo[f][1,7]naphthyridin-5-amine as a yellow solid: $^1H$ NMR (acetone-$d_6$): δ 8.98 (dd, 1H), 8.88 (dd, 1H), 8.37 (d, 1H), 7.83 (dd, 1H), 7.49 (d, 1H), 7.27 (dd, 1H), 6.66 (br s, 2H), 3.10-3.00 (m, 1H), 1.33 (d, 6H). LRMS [M+H]=238.1.

Example 91

8-vinylbenzo[f][1,7]naphthyridin-5-amine

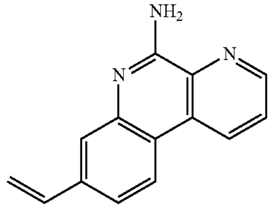 [SMILES: C=Cc1ccc2c(c1)nc(N)c1ncccc12]

To a solution of methyl triphenyl phosphonium iodide (6.0 eq.) was added nBuLi (7.0 eq.) at −78° C. The reaction mixture was allowed to warm to 0° C. and stirred for 30 minutes (deep orange color). The reaction was again cooled down to −78° C. and 5-aminobenzo[f][1,7]naphthyridine-8-carbaldehyde (from Example 87) (1.0 eq.) in THF was introduced dropwised to the reaction. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-50% EtOAc/Hexanes to give 8-vinylbenzo[f][1,7]naphthyridin-5-amine as a white solid: $^1H$ NMR (acetone-$d_6$): $^1H$ NMR (acetone-$d_6$): δ 9.00 (dd, 1H), 8.90 (dd, 1H), 8.41 (d, 1H), 7.84 (dd, 1H), 7.65 (d, 1H), 7.52 (dd, 1H), 6.91 (dd, 1H), 6.77 (br s, 2H), 5.97 (dd, 1H), 5.34 (dd, 1H). LRMS [M+H]=222.1.

Example 92

8-ethylbenzo[f][1,7]naphthyridin-5-amine

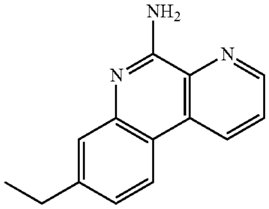 [SMILES: CCc1ccc2c(c1)nc(N)c1ncccc12]

A mixture of 8-vinylbenzo[f][1,7]naphthyridin-5-amine (1.0 eq) (from Example 91) and Pd/C (wet, 10% wt) in EtOH was stirred under $H_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-ethylbenzo[f][1,7]naphthyridin-5-amine as a white foam: $^1H$ NMR (acetone-$d_6$): δ 8.98 (dd, 1H), 8.88 (dd, 1H), 8.35 (d, 1H), 7.82 (dd, 1H), 7.46 (d, 1H), 7.22 (dd, 1H), 6.63 (br s, 2H), 2.78 (q, 2H), 1.30 (t, 3H). LRMS [M+H]=224.1.

Example 93

8-(methoxymethyl)benzo[f][1,7]naphthyridin-5-amine

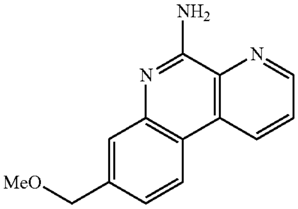 [SMILES: COCc1ccc2c(c1)nc(N)c1ncccc12]

Step 1: tert-butyl 2-chloro-5-(methoxymethyl)phenylcarbamate

To a solution of 2-chloro-5-(methoxymethyl)aniline (commercially available) (1.0 eq.) in THF (0.2M) at 0° C. under $N_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-30% EtOAc/Hexanes to give tert-butyl 2-chloro-5-(methoxymethyl)phenylcarbamate as a colorless oil.

Step 2: tert-butyl 5-(methoxymethyl)-2-(4,4,5,5-tetramethyl-1,3,2-dioxaborolan-2-yl)phenylcarbamate Tert-butyl 2-chloro-5-(methoxymethyl)phenylcarbamate (from the previous step) (1.0 eq.), 4,4,4',4',5,5,5',5'-octamethyl-2,2'-bi(1,3,2-dioxaborolane) (3.0 eq.), $Pd_2dba_3$ (2.5%), XPhos (10%), and KOAc (3 eq.) were mixed in dioxane (0.2 M) under $N_2$ atmosphere. The reaction was heated to 110° C. and stirred overnight. The resulting suspension was cooled to ambient temperature, diluted with ether, filtered through celite, and the filtrate was concentrated en vaccuo. The combined organic layers were washed with brine, dried over anhydrous $MgSO_4$, and concentrated en vaccuo. The crude material was purified by flash chromatography on a COMBIFLASH® system (ISCO) using 0-20% EtOAc/Hexanes to give tert-butyl 5-(methoxymethyl)-2-(4,4,5,5-tetramethyl-1,3,2-dioxaborolan-2-yl)phenylcarbamate as a white foam.

Step 3: 8-(methoxymethyl)benzo[f][1,7]naphthyridin-5-amine

A solution of tert-butyl 5-(methoxymethyl)-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis (triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with 2% MeOH in DCM and water. The two phases were separated, and the aqueous layer was extracted twice with 2% MeOH in DCM. The combined organic layers were washed with brine, dried over anhydrous $MgSO_4$, and concentrated en vaccuo. The crude material was purified by flash chromatography on a COMBIFLASH® system (ISCO) using 0-100% EtOAc/Hexanes to give 8-(methoxymethyl)benzo[f][1,7]naphthyridin-5-amine as a white solid: $^1H$ NMR (methanol-$d_4$): δ 8.97 (dd, 1H), 8.91 (dd, 1H), 8.41 (dd, 1H), 7.83 (dd, 1H), 7.59 (d, 1H), 7.37 (dd, 1H), 4.62 (s, 2H), 3.45 (s, 3H). LRMS [M+H]=240.1.

Example 94

(5-amino-2-phenethylbenzo[f][1,7]naphthyridin-8-yl)methanol

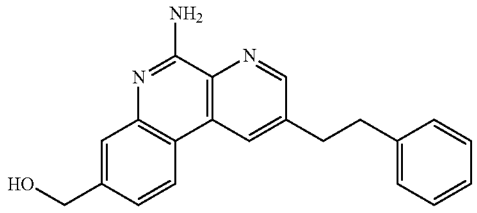 [SMILES: Nc1nc2cc(CO)ccc2c2cc(CCc3ccccc3)cnc12]

Step 1: methyl 5-amino-2-phenethylbenzo[f][1,7]naphthyridine-8-carboxylate

A solution of 2-(tert-butoxycarbonylamino)-4-(methoxycarbonyl)phenylboronic acid (from Example 85/Step 1) (1.0 eq.) and 2-chloro-6-phenethylnicotinonitrile (prepared from (E)-3-chloro-5-styrylpicolinonitrile (from Example 32/Step 1) following the procedure described in Example 114/Step 3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-60% EtOAc/Hexanes to give methyl 5-amino-2-phenethylbenzo[f][1,7]naphthyridine-8-carboxylate as a white solid.

Step 2: (5-amino-2-phenethylbenzo[f][1,7]naphthyridin-8-yl)methanol

To a solution of methyl 5-amino-2-phenethylbenzo[f][1,7]naphthyridine-8-carboxylate (from the previous step) (1.0 eq.) in THF (0.03M) was added Super-H (10 eq.) at 0° C. The solution was allowed to warm to ambient temperature over 30 min. The reaction was quenched by water until no bubbling. The layers were separated and aqueous layer was extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give (5-amino-2-phenethylbenzo[f][1,7]naphthyridin-8-yl)methanol as an off white solid: $^1H$ NMR (methanol-$d_4$): δ 8.63 (dd, 1H), 8.56 (dd, 1H), 8.24 (d, 1H), 7.57 (d, 1H), 7.35 (dd, 1H), 7.27-7.15 (m, 5H), 4.75 (s, 2H), 3.20 (t, 2H), 3.06 (t, 2H). LRMS [M+H]=330.1.

Example 95

(5-amino-2-(4-methoxyphenethyl)benzo[f][1,7]naphthyridin-8-yl)methanol

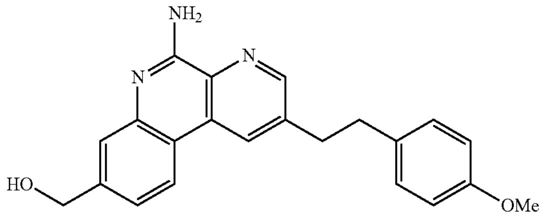 [SMILES: COc1ccc(CCc2cnc3c(N)nc4cc(CO)ccc4c3c2)cc1]

Step 1: methyl 5-amino-2-(4-methoxyphenethyl)benzo[f][1,7]naphthyridine-8-carboxylate A solution of 2-(tert-butoxycarbonylamino)-4-(methoxycarbonyl)phenylboronic acid (from Example 85/Step 1) (1.0 eq.) and 2-chloro-6-(4-methoxyphenethyl)nicotinonitrile (prepared from reaction of 3,5-dichloropicolinonitrile with 1-ethynyl-4-methoxybenzene following the procedure described in Example 44/Step 3 and reduction of the product following the procedure described in Example 114/Step 3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-80% EtOAc/Hexanes to give methyl 5-amino-2-(4-methoxyphenethyl)benzo[f][1,7]naphthyridine-8-carboxylate as a white solid.

Step 2: (5-amino-2-(4-methoxyphenethyl)benzo[f][1,7]naphthyridin-8-yl)methanol

To a solution of methyl 5-amino-2-(4-methoxyphenethyl)benzo[f][1,7]naphthyridine-8-carboxylate (from the previous step) (1.0 eq.) in THF (0.03M) was added Super-H (10 eq.) at 0° C. The solution was allowed to warm to ambient temperature over 30 minutes. The reaction was quenched by water until no bubbling. The layers were separated and aqueous layer was extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-100% EtOAc/Hexanes to give (5-amino-2-(4-methoxyphenethyl)benzo[f][1,7]naphthyridin-8-yl)methanol as an off white solid (31%): $^1$H NMR (acetone-$d_6$): δ 8.79 (d, 1H), 8.70 (d, 1H), 8.35 (d, 1H), 7.61 (d, 1H), 7.33 (dd, 1H), 7.13 (d, 2H), 6.83 (d, 2H), 6.62 (br s, 2H), 4.47 (s, 2H), 4.40 (br s, 1H), 3.75 (s, 3H), 3.22 (t, 2H), 3.06 (t, 2H). LRMS [M+H]=360.2.

Example 96 benzo[f][1,7]naphthyridine-5,8-diamine

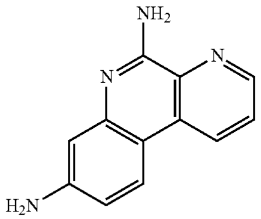 [SMILES: Nc1ccc2c(c1)nc(N)c1ncccc12]

Step 1: tert-butyl 2-bromo-5-nitrophenylcarbamate

To a solution of 2-bromo-5-nitroaniline (commercially available) (1.0 eq.) in THF (0.2M) at 0° C. under $N_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-30% EtOAc/Hexanes to give tert-butyl 2-bromo-5-nitrophenylcarbamate as a colorless oil.

Step 2: tert-butyl 5-nitro-2-(4,4,5,5-tetramethyl-1,3,2-dioxaborolan-2-yl)phenyl carbamate Tert-butyl 2-bromo-5-nitrophenylcarbamate (from the previous step) (1.0 eq.), 4,4,4',4',5,5,5',5'-octamethyl-2,2'-bi(1,3,2-dioxaborolane) (1.8 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vaccuo. The residue was purified by flash chromatography on a COMBIFLASH® system (ISCO) using 0-30% EtOAc/Hexanes to give tert-butyl 5-nitro-2-(4,4,5,5-tetramethyl-1,3,2-dioxaborolan-2-yl)phenyl carbamate as a white foam.

Step 3: 8-nitrobenzo[f][1,7]naphthyridin-5-amine

A solution of tert-butyl 5-nitro-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis(triphenyl-phosphine) palladium (5 mol %) and 2N aqueous potassium carbonate solution (2.0 eq.). The reaction was heated to 100° C. and stirred overnight. After cooling to ambient temperature, the reaction mixture was filtered to collect the precipitate. The precipitate was rinsed with EtOAc to give 8-nitrobenzo[f][1,7]naphthyridin-5-amine as a yellow solid.

Step 4: benzo[f][1,7]naphthyridine-5,8-diamine

A mixture of 8-nitrobenzo[f][1,7]naphthyridin-5-amine (from the previous step) (1.0 eq) and Pd/C (wet, 10% wt) in EtOH was stirred under $H_2$ balloon overnight. The reaction mixture was diluted with DCM. The insoluble solid was filtered off through celite, and the filtrate was concentrated en vaccuo to obtain a crude residue. The crude material was washed with acetone to give benzo[f][1,7]naphthyridine-5,8-diamine as an off white solid: $^1$H NMR (methanol-$d_4$): δ 8.73 (dd, 1H), 8.71 (dd, 1H), 8.11 (d, 1H), 7.69 (dd, 1H), 6.86 (d, 1H), 6.82 (dd, 1H). LRMS [M+H]=211.1.

Example 97

8-(aminomethyl)benzo[f][1,7]naphthyridin-5-amine

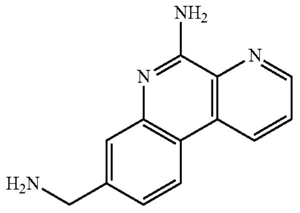 [SMILES: NCc1ccc2c(c1)nc(N)c1ncccc12]

Step 1: 2-(tert-butoxycarbonylamino)-4-cyanophenylboronic acid

The titled compound was prepared according to the procedure described in Example 85/Step 1, but using 2-amino-4-cyanophenylboronic acid hydrochloride (commercially available) as the starting material. The crude material was purified by flash chromatography on a COMBIFLASH® system (ISCO) using 0-30% MeOH/DCM to give 2-(tert-butoxycarbonylamino)-4-cyanophenylboronic acid as an off white solid.

Step 2:
5-aminobenzo[f][1,7]naphthyridine-8-carbonitrile

The titled compound was prepared according to the procedure described in Example 96/Step 3, but using 2-(tert-butoxycarbonylamino)-4-cyanophenylboronic acid (from the previous step) as the starting material. The crude material was rinsed with 1:1 EtOAc/Hexanes to give 5-aminobenzo[f][1,7]naphthyridine-8-carbonitrile as a pale yellow solid.

Step 4: benzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH/ammonia (2:1) was stirred under $H_2$ balloon overnight. The reaction mixture was diluted with DCM. The insoluble solid was filtered off through celite, and the filtrate was concentrated en vaccuo to obtain a crude residue. The crude material was washed with 10% MeOH/DCM and 70% EtOAc/Hexanes to give benzo[f][1,7]naphthyridine-5,8-diamine as an off white solid: $^1$H NMR (methanol-$d_4$): δ 8.97 (dd, 1H), 8.90 (dd, 1H), 8.41 (d, 1H), 7.83 (dd, 1H), 7.57 (d, 1H), 7.39 (dd, 1H), 3.96 (s, 2). LRMS [M+H]=229.1.

Example 98

3-fluoro-8-methylbenzo[f][1,7]naphthyridin-5-amine

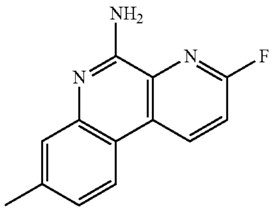 [SMILES: Cc1ccc2c(c1)nc(N)c1nc(F)ccc12]

Step 1:
3-chloro-8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 5/Step 2) (1.0 eq.) and 3-bromo-6-chloropicolinonitrile (from Example 20/Step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous $MgSO_4$, and concentrated en vaccuo. The crude material was purified by flash chromatography on a COMBI-FLASH® system (ISCO) using 0-40% EtOAc/Hexanes to give 3-chloro-8-methylbenzo[f][1,7]naphthyridin-5-amine as a pale yellow solid.

Step 2:
3-fluoro-8-methylbenzo[f][1,7]naphthyridin-5-amine

A mixture of 3-chloro-8-methylbenzo[f][1,7]naphthyridin-5-amine (from the previous step) (1.0 eq.) potassium fluoride (4.0 eq.), and 18-crown-6 (0.4 eq.) in NMP (0.1M) was heated in microwave reactor at 210° C. for 2 hours. After cooling to ambient temperature, the reaction residue was purified by flash chromatography on a COMBI-FLASH® system (ISCO) using 0-30% EtOAc/Hexanes to give 3-fluoro-8-methylbenzo[f][1,7]naphthyridin-5-amine as a white solid. $^1$H NMR (acetone-$d_6$): δ 9.20 (dd, 1H), 8.32 (d, 1H), 7.58 (dd, 1H), 7.46 (d, 1H), 7.21 (dd, 1H), 6.51 (br s, 2H), 2.47 (s, 3H). LRMS [M+H]=228.1.

Example 99

(5-amino-3-fluorobenzo[f][1,7]naphthyridin-8-yl)methanol

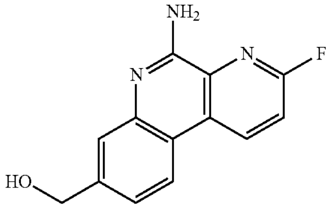 [SMILES: Nc1nc2cc(CO)ccc2c2ccc(F)nc12]

Step 1: tert-butyl 5-((tert-butyldimethylsilyloxy)methyl)-2-(4,4,5,5-tetramethyl-1,3,2-dioxaborolan-2-yl)phenylcarbamate The titled compound was prepared according to the procedure described in Example 93/Step 1 and 2, but using 5-((tert-butyldimethylsilyloxy)methyl)-2-chloroaniline (commercially available) as the starting material. The crude material was purified by flash chromatography on a COMBIFLASH® system (ISCO) using 0-20% EtOAc/Hexanes to give tert-butyl 5-((tert-butyldimethylsilyloxy)methyl)-2-(4,4,5,5-tetramethyl-1,3,2-dioxaborolan-2-yl)phenylcarbamate as a white foam.

Step 2: 8-((tert-butyldimethylsilyloxy)methyl)-3-chlorobenzo[f][1,7]naphthyridin-5-amine The titled compound was prepared according to the procedure described in Example 98/Step 1, but using tert-butyl 5-((tert-butyldimethylsilyloxy)methyl)-2-(4,4,5,5-tetramethyl-1,3,2-dioxaborolan-2-yl)phenylcarbamate (from the previous step) as the starting material. The crude material was purified by flash chromatography on a COMBI-FLASH® system (ISCO) using 0-15% EtOAc/Hexanes to give 8-((tert-butyldimethylsilyloxy)methyl)-3-chlorobenzo[f][1,7]naphthyridin-5-amine as a pale yellow solid.

Step 3: (5-amino-3-chlorobenzo[f][1,7]naphthyridin-8-yl)methanol

A solution of 8-((tert-butyldimethylsilyloxy)methyl)-3-chlorobenzo[f][1,7]naphthyridin-5-amine (from the previous step) (1.0 eq.) and TBAF (1.1 eq.) in THF was stirred at ambient temperature overnight. The reaction was quenched with saturated $NaHCO_3$. The two phases were separated, and the aqueous layer was extracted twice with $Et_2O$. The combined organic layers were washed with brine, dried over anhydrous $MgSO_4$, and concentrated en vaccuo. The crude material was purified by flash chromatography on a COM- BIFLASH® system (ISCO) using 0-5% MeOH/DCM to give (5-amino-3-chlorobenzo[f][1,7]naphthyridin-8-yl) methanol as a white solid.

Step 4: (5-amino-3-fluorobenzo[f][1,7]naphthyridin-8-yl)methanol

The titled compound was prepared according to the procedure described in Example 98/Step 2, but using (5-amino-3-chlorobenzo[f][1,7]naphthyridin-8-yl)methanol (from the previous step) as the starting material. The crude material was purified by flash chromatography on a COMBIFLASH® system (ISCO) using 0-40% EtOAc/Hexanes to give (5-amino-3-fluorobenzo[f][1,7]naphthyridin-8-yl) methanol as a white solid. $^1$H NMR (methanol-$d_4$): δ 9.15 (dd, 1H), 8.38 (d, 1H), 7.64 (d, 1H), 7.55 (dd, 1H), 7.41 (dd, 1H), 4.77 (s, 2H). LRMS [M+H]=244.1.

Example 100

3-chlorobenzo[f][1,7]naphthyridine-5,8-diamine

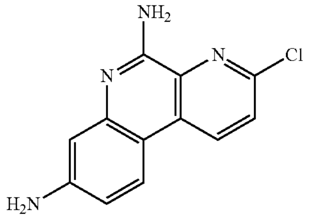 [SMILES: Nc1ccc2c(c1)nc(N)c1nc(Cl)ccc12]

Step 1: 3-chloro-8-nitrobenzo[f][1,7]naphthyridin-5-amine

The titled compound was prepared according to the procedure described in Example 98/Step 1, but using tert-butyl 5-nitro-2-(4,4,5,5-tetramethyl-1,3,2-dioxaborolan-2-yl)phenylcarbamate (commercially available) as the starting material. The crude material was purified by flash chromatography on a COMBIFLASH® system (ISCO) using 0-40% EtOAc/Hexanes to give 3-chloro-8-nitrobenzo[f][1,7]naphthyridin-5-amine as a pale yellow solid.

Step 2: 3-chlorobenzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH was stirred under $H_2$ balloon overnight. The reaction mixture was diluted with DCM. The insoluble solid was filtered off through celite, and the filtrate was concentrated en vaccuo to obtain a crude residue. The crude material was purified by flash chromatography on a COMBIFLASH® system (ISCO) using 0-100% EtOAc/Hexanes to give 3-chlorobenzo[f][1,7]naphthyridine-5,8-diamine as a white solid. $^1$H NMR (methanol-$d_4$): δ 8.75 (d, 1H), 8.08 (dd, 1H), 7.70 (d, 1H), 6.84-6.81 (m, 2H). LRMS [M+H]=245.1.

Example 101

3-fluorobenzo[f][1,7]naphthyridine-5,8-diamine

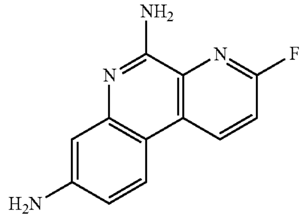 [SMILES: Nc1ccc2c(c1)nc(N)c1nc(F)ccc12]

The titled compound was prepared according to the procedure described in Example 98/Step 2, but using 3-chlorobenzo[f][1,7]naphthyridine-5,8-diamine (from Example 100) as the starting material. The crude material was purified by flash chromatography on a COMBIFLASH® system (ISCO) using 0-7% MeOH/DCM to give 3-fluorobenzo[f][1,7]naphthyridine-5,8-diamine as a white solid. $^1$H NMR (methanol-$d_4$): δ 8.93 (dd, 1H), 8.09 (d, 1H), 7.44 (dd, 1H), 6.86-6.83 (m, 2H). LRMS [M+H]=229.1.

Example 102

8-isobutylbenzo[f][1,7]naphthyridin-5-amine

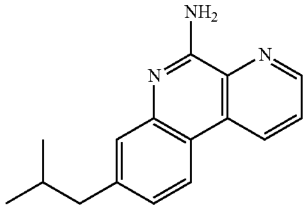 [SMILES: CC(C)Cc1ccc2c(c1)nc(N)c1ncccc12]

8-Isobutylbenzo[f][1,7]naphthyridin-5-amine was prepared from 5-aminobenzo[f][1,7]naphthyridine-8-carbaldehyde (from Example 87) with isopropyl(triphenyl)phosphonium bromide following the procedures described for Example 91 (wittig reaction) and Example 92 (reduction). $^1$H NMR (acetone-$d_6$): δ 8.98 (dd, 1H), 8.88 (dd, 1H), 8.35 (d, 1H), 7.82 (dd, 1H), 7.44 (d, 1H), 7.18 (dd, 1H), 6.73 (br s, 2H), 2.63 (d, 2H), 2.04-1.94 (m, 1H), 0.94 (d, 6H). LRMS [M+H]=252.1.

Example 103

(E)-8-(prop-1-enyl)benzo[f][1,7]naphthyridin-5-amine

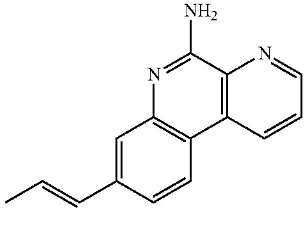 [SMILES: C/C=C/c1ccc2c(c1)nc(N)c1ncccc12]

(E)-8-(prop-1-enyl)benzo[f][1,7]naphthyridin-5-amine was prepared from 5-aminobenzo[f][1,7]naphthyridine-8-carbaldehyde (from Example 87) with ethyl(triphenyl)phosphonium bromide following the procedures described for Example 91. $^1$H NMR (acetone-$d_6$): δ 8.98 (dd, 1H), 8.88 (dd, 1H), 8.36 (d, 1H), 7.83 (dd, 1H), 7.54 (d, 1H), 7.43 (dd, 1H), 6.67 (br s, 2H), 6.60-6.42 (m, 2H), 1.92 (dd, 3H). LRMS [M+H]=236.1.

Example 104

8-propylbenzo[f][1,7]naphthyridin-5-amine

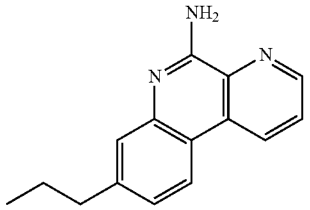 [SMILES: CCCc1ccc2c(c1)nc(N)c1ncccc12]

8-Propylbenzo[f][1,7]naphthyridin-5-amine was prepared from (E)-8-(prop-1-enyl)benzo[f][1,7]naphthyridin-5-amine (from Example 103) following the procedures described for Example 92. $^1$H NMR (acetone-$d_6$): δ 8.99 (dd, 1H), 8.88 (dd, 1H), 8.35 (d, 1H), 7.83 (dd, 1H), 7.45 (d, 1H), 7.21 (dd, 1H), 6.64 (br s, 2H), 2.74 (t, 2H), 1.74 (qt, 2H), 0.98 (t, 3H). LRMS [M+H]=238.1.

Example 105

8-(2-cyclopropylethyl)benzo[f][1,7]naphthyridin-5-amine

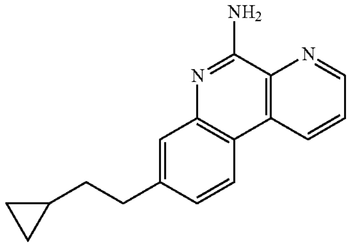 [SMILES: Nc1nc2cc(CCC3CC3)ccc2c2cccnc12]

8-(2-Cyclopropylethyl)benzo[f][1,7]naphthyridin-5-amine was prepared from 5-aminobenzo[f][1,7]naphthyridine-8-carbaldehyde (from Example 87) with (cyclopropylmethyl)triphenylphosphonium bromide following the procedures described for Example 91 (wittig reaction) and Example 92 (reduction). $^1$H NMR (acetone-$d_6$): δ 8.99 (dd, 1H), 8.88 (dd, 1H), 8.35 (d, 1H), 7.83 (dd, 1H), 7.47 (d, 1H), 7.23 (dd, 1H), 6.64 (br s, 2H), 1.60 (q, 2H), 1.34-1.25 (m, 1H), 0.91-0.72 (m, 2H), 0.45-0.41 (m, 2H), 0.11-0.07 (m, 2H). LRMS [M+H]=264.1.

Example 106

8-phenethylbenzo[f][1,7]naphthyridin-5-amine

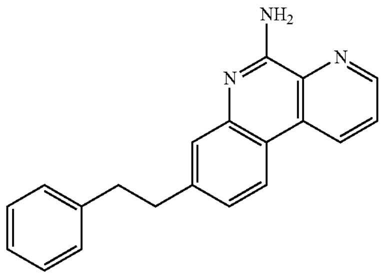 [SMILES: Nc1nc2cc(CCc3ccccc3)ccc2c2cccnc12]

8-Phenethylbenzo[f][1,7]naphthyridin-5-amine was prepared from 5-aminobenzo[f][1,7]naphthyridine-8-carbaldehyde (from Example 87) with benzyltriphenylphosphonium bromide following the procedures described for Example 91 (wittig reaction) and Example 92 (reduction). $^1$H NMR (acetone-$d_6$): δ 8.99 (dd, 1H), 8.88 (dd, 1H), 8.35 (d, 1H), 7.83 (dd, 1H), 7.49 (d, 1H), 7.29-7.15 (dd, 6H), 6.70 (br s, 2H), 3.10-3.00 (m, 4H). LRMS [M+H]=300.1.

Example 107

(5-amino-2-(4-bromophenethyl)benzo[f][1,7]naphthyridin-8-yl)methanol

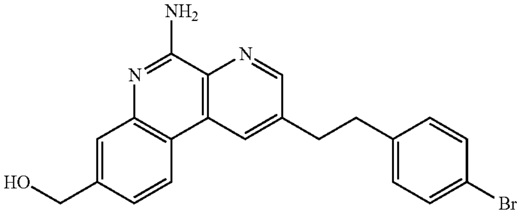 [SMILES: Nc1nc2cc(CO)ccc2c2cc(CCc3ccc(Br)cc3)cnc12]

(5-Amino-2-(4-bromophenethyl)benzo[f][1,7]naphthyridin-8-yl)methanol was prepared from (5-amino-2-(4-methoxyphenethyl)benzo[f][1,7]naphthyridin-8-yl)methanol (from Example 95) following the procedures described for Example 86. $^1$H NMR (acetone-$d_6$): δ 8.81 (d, 1H), 8.72 (d, 1H), 8.40 (d, 1H), 7.68 (d, 1H), 7.39 (dd, 1H), 7.08 (d, 2H), 6.74 (d, 2H), 6.66 (br s, 2H), 4.49 (s, 2H), 3.21 (t, 2H), 3.03 (t, 2H). LRMS [M+H]=408.1.

Example 108

(5-amino-2-(4-methoxy-2-methylphenethyl)benzo[f][1,7]naphthyridin-8-yl)methanol

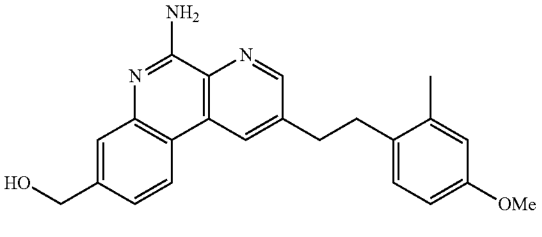 [SMILES: COc1ccc(CCc2cnc3c(N)nc4cc(CO)ccc4c3c2)c(C)c1]

(5-Amino-2-(4-methoxy-2-methylphenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (Example 99/Step 1) and 3-chloro-5-((4-methoxy-2-methylphenyl)ethynyl)picolinonitrile (from Example 49/Step 1) following the procedures described for Example 44/Step 4 and deprotection of TBS group following the procedure describes from Example 99/Step 3. $^1$H NMR (acetone-$d_6$): δ 8.79 (s, 1H), 8.73 (s, 1H), 8.35 (d, 1H), 7.61 (s, 1H), 7.33 (d, 1H), 7.09 (d, 1H), 6.75 (d, 1H), 6.68 (dd, 1H), 6.57 (br s, 2H), 4.47 (d, 2H), 4.32 (t, 1H), 3.58 (s, 3H), 3.17 (t, 2H), 3.04 (t, 2H), 2.30 (s, 3H). LRMS [M+H]=374.2.

Example 109

2-(4-methoxy-2-methylphenethyl)-8-pentylbenzo[f][1,7]naphthyridin-5-amine

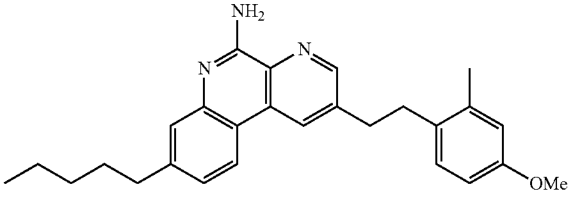 [SMILES: CCCCCc1ccc2c(c1)nc(N)c1ncc(CCc3ccc(OC)cc3C)cc12]

and

Example 110

8-(2-cyclopropylethyl)-2-(4-methoxy-2-methylphenethyl)benzo[f][1,7]naphthyridin-5-amine

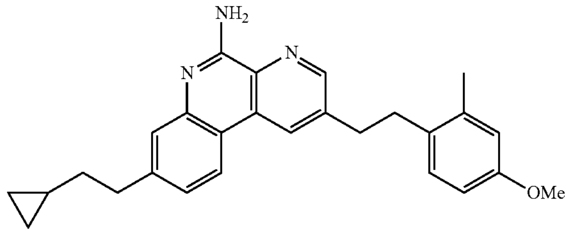 [SMILES: COc1ccc(CCc2cnc3c(N)nc4cc(CCC5CC5)ccc4c3c2)c(C)c1]

Step 1: tert-butyl 5-bromo-2-chlorophenylcarbamate

The titled compound was prepared according to the procedure described in Example 5/Step 1, but using 5-bromo-2-chloroaniline (commercially available) as the starting material. The crude material was purified by flash chromatography on a COMBIFLASH® system (ISCO) using 0-40% EtOAc/Hexanes to give tert-butyl 5-bromo-2-chlorophenylcarbamate as a pale yellow solid.

Step 2: (E)-tert-butyl 2-chloro-5-(2-cyclopropylvinyl)phenylcarbamate

A solution of tert-butyl 5-bromo-2-chlorophenylcarbamate (from the previous step) (1.0 eq.) and (E)-2-(2-cyclopropylvinyl)-4,4,5,5-tetramethyl-1,3,2-dioxaborolane (commercially available) (1.0 eq.) in toluene (0.2 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with EtOAc and water. The two phases were separated, and the aqueous layer was extracted twice with EtOAc. The combined organic layers were washed with brine, dried over anhydrous $MgSO_4$, and concentrated en vaccuo. The crude product was purified by flash chromatography on a COMBIFLASH® system (ISCO) using 0-5% EtOAc/Hexanes to give (E)-tert-butyl 2-chloro-5-(2-cyclopropylvinyl)phenylcarbamate as a pale yellow solid.

Step 3: (E)-tert-butyl 5-(2-cyclopropylvinyl)-2-(4,4,5,5-tetramethyl-1,3,2-dioxaborolan-2-yl)phenylcarbamate The titled compound was prepared according to the procedure described in Example 93/Step 2, but using (E)-tert-butyl 2-chloro-5-(2-cyclopropylvinyl)phenylcarbamate (from previous step) as the starting material. The crude product was purified by flash chromatography on a COMBIFLASH® system (ISCO) using 0-10% EtOAc/Hexanes to give (E)-tert-butyl 5-(2-cyclopropylvinyl)-2-(4,4,5,5-tetramethyl-1,3,2-dioxaborolan-2-yl)phenylcarbamate as a pale yellow solid.

Step 4: 2-(4-methoxy-2-methylphenethyl)-8-pentylbenzo[f][1,7]naphthyridin-5-amine and 8-(2-cyclopropylethyl)-2-(4-methoxy-2-methylphenethyl)benzo[f][1,7]naphthyridin-5-amine The titled compounds were prepared according to the procedure described in Example 44/Step 4 (Suzuki coupling) and 5 (reduction), but using (E)-tert-butyl 5-(2-cyclopropylvinyl)-2-(4,4,5,5-tetramethyl-1,3,2-dioxaborolan-2-yl)phenylcarbamate (from previous step) and 3-chloro-5-((4-methoxy-2-methylphenyl)ethynyl)picolinonitrile (from Example 49/Step 1) as the starting material. The crude product was purified by flash chromatography on a COMBIFLASH® system (ISCO) using 0-40% EtOAc/Hexanes to give Example 109 as a white solid: $^1$H NMR (acetone-$d_6$): δ 8.76 (d, 1H), 8.70 (d, 1H), 8.29 (d, 1H), 7.44 (d, 1H), 7.18 (dd, 1H), 7.08 (d, 1H), 6.74 (d, 1H), 6.68 (dd, 1H), 6.59 (br s, 2H), 3.74 (s, 3H), 3.18 (t, 2H), 3.04 (t, 2H), 2.75 (t, 2H), 2.29 (s, 3H), 1.75-1.68 (m, 2H), 1.40-1.35 (m, 4H), 0.90 (s, 3H); LRMS [M+H]=414.3; and Example 110 as an off white solid: $^1$H NMR (acetone-$d_6$): δ 8.76 (d, 1H), 8.70 (d, 1H), 8.28 (d, 1H), 7.45 (d, 1H), 7.19 (dd, 1H), 7.08 (d, 1H), 6.74 (d, 1H), 6.67 (dd, 1H), 6.55 (br s, 2H), 3.73 (s, 3H), 3.16 (t, 2H), 3.03 (t, 2H), 2.29 (s, 3H), 1.60 (q, 2H), 1.29-1.28 (m, 1H), 0.89-0.74 (m, 2H), 0.44-0.41 (m, 2H), 0.10-0.07 (m, 2H). LRMS [M+H]=412.3.

Example 111

(5-amino-2-(2,4,6-trimethylphenethyl)benzo[f][1,7]naphthyridin-8-yl)methanol

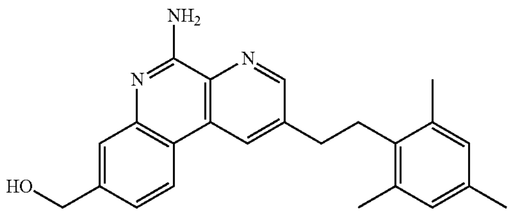 [SMILES: Cc1cc(C)c(CCc2cnc3c(N)nc4cc(CO)ccc4c3c2)c(C)c1]

(5-Amino-2-(2,4,6-trimethylphenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1), 2-ethynyl-1,3,5-trimethylbenzene (commercially available) and 3-chloro-5-(mesitylethynyl)picolinonitrile (from Example 77/step 1) following the procedures described for Example 44/Step 4, Example 99/step 3 (deprotection of TBS) and Example 77/step 3 (reduction). $^1$H NMR (acetone-$d_6$): δ 8.77 (s, 2H), 8.34 (d, 1H), 7.61 (s, 1H), 7.33 (d, 1H), 6.84 (s, 2H), 6.60 (br s, 2H), 4.77 (d, 2H), 4.35 (t, 1H), 3.08 (s, 3H), 2.84 (s, 6H), 2.30-2.29 (m, 4H). LRMS [M+H]=372.2.

Example112

(5-amino-2-(4-propoxyphenethyl)benzo[f][1,7]naphthyridin-8-yl)methanol

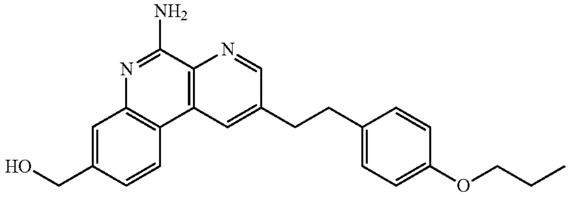 [SMILES: CCCOc1ccc(CCc2cnc3c(N)nc4cc(CO)ccc4c3c2)cc1]

(5-Amino-2-(4-propoxyphenethyl)benzo[f][1,7]naphthyridin-8-yl)methanol was prepared from 8-((tert-butyldimethylsilyloxy)methyl)-3-chlorobenzo[f][1,7]naphthyridin-5-amine (from Example 99/step 1) and 3-chloro-5-(4-propoxyphenethyl)picolinonitrile (from Example 79/step 2) following the procedures described for Example 44/Step 4 and Example 99/step 3 (deprotection of TBS). $^1$H NMR (acetone-$d_6$): δ 8.79 (d, 1H), 8.70 (d, 1H), 8.35 (d, 1H), 7.61 (d, 1H), 7.33 (dd, 1H), 7.17 (d, 2H), 6.83 (d, 2H), 6.57 (br s, 2H), 4.77 (d, 2H), 4.34 (t, 1H), 3.89 (t, 2H), 3.22 (t, 2H), 3.06 (t, 2H), 1.83-1.70 (m, 2H), 1.00 (t, 3H). LRMS [M+H]=388.2.

Example 113

(2-(2-(1H-indol-5-yl)ethyl)-5-aminobenzo[f][1,7]naphthyridin-8-yl)methanol

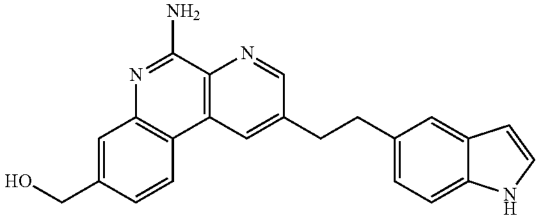 [SMILES: Nc1nc2cc(CO)ccc2c2cc(CCc3ccc4[nH]ccc4c3)cnc12]

(2-(2-(1H-indol-5-yl)ethyl)-5-aminobenzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1) and 5-((1H-indol-5-yl)ethynyl)-3-chloropicolinonitrile (from Example 44/step 3) following the procedures described for Example 44/Step 4 and Example 99/step 3 (deprotection of TBS). $^1$H NMR (acetone-$d_6$): δ 10.19 (t, 1H), 8.83 (d, 1H), 8.71 (d, 1H), 8.35 (d, 1H), 7.60 (d, 1H), 7.46 (d, 1H), 7.36-7.27 (m, 3H), 7.04 (dd, 1H), 6.57 (br s, 2H), 6.38 (dt, 1H), 4.77 (d, 2H), 4.36 (t, 1H), 3.29 (t, 2H), 3.19 (t, 2H). LRMS [M+H]=369.2.

Example 114

N-(4-(2-(5-amino-8-methylbenzo[f][1,7]naphthyridin-2-yl)ethyl)phenyl)acetamide

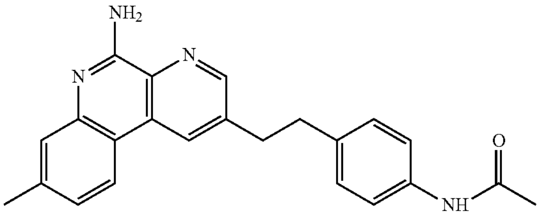 [SMILES: CC(=O)Nc1ccc(CCc2cnc3c(N)nc4cc(C)ccc4c3c2)cc1]

Step 1: N-(4-ethynylphenyl)acetamide

To a solution of 4-ethynylaniline (commercially available) (1.0 eq.), and triethylamine (1.0 eq.) in methylene chloride (0.04 M), acetyl chloride (1.5 eq.) was added slowly. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give N-(4-ethynylphenyl)acetamide as a white solid.

Step 2: N-(4-((5-chloro-6-cyanopyridin-3-yl)ethynyl)phenyl)acetamide

A solution of 3,5-dichloropicolinonitrile (1.0 eq.), N-(4-ethynylphenyl)acetamide (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-80% ethyl acetate in hexane to give N-(4-((5-chloro-6-cyanopyridin-3-yl)ethynyl)phenyl)acetamide as a white solid.

Step 3: N-(4-(2-(5-chloro-6-cyanopyridin-3-yl)ethyl)phenyl)acetamide

To a solution of N-(4-((5-chloro-6-cyanopyridin-3-yl)ethynyl)phenyl)acetamide (from the previous step) in ethyl acetate/methanol (1:4, 0.05 M) was added 10% wt palladium on carbon (0.2 eq.). Hydrogen gas was introduced via a ballon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give N-(4-(2-(5-chloro-6-cyanopyridin-3-yl)ethyl)phenyl)acetamide.

Step 4: N-(4-(2-(5-amino-8-methylbenzo[f][1,7]naphthyridin-2-yl)ethyl)phenyl)acetamide A solution of N-(4-(2-(5-chloro-6-cyanopyridin-3-yl)ethyl)phenyl)acetamide (from the previous step) (1.0 eq.), tert-butyl 4-methyl-2-(4,4,5,5-tetramethyl-1,3,2-dioxaborolan-2-yl)phenylcarbamate (from Example 5/Step 2) (1.5 eq.), Tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/$H_2O$ (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give N-(4-(2-(5-amino-8-methylbenzo[f][1,7]naphthyridin-2-yl)ethyl)phenyl)acetamide as a white solid. $^1$H NMR ($CDCl_3$): δ 8.51 (s, 1H), 8.32 (s, 1H), 8.01 (d, 1H), 7.44 (s, 1H), 7.33-7.36 (m, 2H), 7.03-7.19 (m, 3H), 5.98 (br, 2H), 3.07-3.11 (m, 2H), 2.94-2.98 (m, 2H), 2.44 (s, 3H), 2.10 (s, 3H). LRMS [M+H]=371.2.

Example 115 methyl 4-(2-(5-amino-8-methylbenzo[f][1,7]naphthyridin-2-yl)ethyl)-3-methylbenzoate

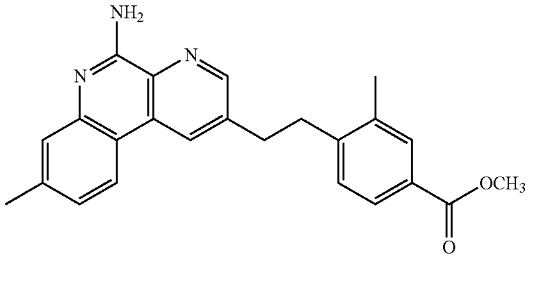 [SMILES: COC(=O)c1ccc(CCc2cnc3c(N)nc4cc(C)ccc4c3c2)c(C)c1]

Step 1: methyl 3-methyl-4-((triethylsilyl)ethynyl)benzoate

A solution of methyl 4-bromo-3-methylbenzoate (1.0 eq.), triethyl(ethynyl)silane (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-50% ethyl acetate in hexane to give methyl 3-methyl-4-((triethylsilyl)ethynyl)benzoate as a white solid.

Step 2: methyl 4-ethynyl-3-methylbenzoate

To a solution of methyl 3-methyl-4-((triethylsilyl)ethynyl)benzoate (from the previous step) (1.0 eq.) in THF (0.2 M), was added TBAF (0.2 eq.) slowly at 0° C. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give methyl 4-ethynyl-3-methylbenzoate as a white solid.

Step 3: methyl 4-((5-chloro-6-cyanopyridin-3-yl)ethynyl)-3-methylbenzoate

A solution of 3,5-dichloropicolinonitrile (1.0 eq.), methyl 4-ethynyl-3-methylbenzoate (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-80% ethyl acetate in hexane to give methyl 4-((5-chloro-6-cyanopyridin-3-yl)ethynyl)-3-methylbenzoate as a white solid.

Step 4: methyl methyl 4-((5-amino-8-methylbenzo[f][1,7]naphthyridin-2-yl)ethynyl)-3-methylbenzoate A solution of methyl 4-((5-chloro-6-cyanopyridin-3-yl)ethynyl)-3-methylbenzoate (from the previous step) (1.0 eq.), tert-butyl 4-methyl-2-(4,4,5,5-tetramethyl-1,3,2-dioxaborolan-2-yl)phenylcarbamate (From Example 5/Step 2) (1.5 eq.), tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/$H_2O$ (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give methyl methyl-4-((5-amino-8-methylbenzo[f][1,7]naphthyridin-2-yl)ethynyl)-3-methylbenzoate as a white solid.

Step 5: methyl 4-(2-(5-amino-8-methylbenzo[f][1,7]naphthyridin-2-yl)ethyl)-3-methylbenzoate To a solution of methyl methyl 4-((5-amino-8-methylbenzo[f][1,7]naphthyridin-2-yl)ethynyl)-3-methylbenzoate (from the previous step) in ethyl acetate/methanol (1:4, 0.05 M) was added 10% wt palladium on carbon (0.2 eq.). Hydrogen gas was introduced via a ballon, and the reaction was stirred for 3 hours. The mixture was filtered through a pad of celite, washing with dichloromethane. The filtrate was concentrated en vaccuo and purified by a COMBI-FLASH® system (ISCO) using 0-80% ethyl acetate in hexane to give methyl 4-(2-(5-amino-8-methylbenzo[f][1,7]naphthyridin-2-yl)ethyl)-3-methylbenzoate. $^1H$ NMR ($CDCl_3$): δ 8.61 (s, 1H), 8.40 (s, 1H), 8.09 (d, 1H), 7.83 (s, 1H), 7.81 (d, 1H), 7.54 (s, 1H), 7.18-7.20 (m, 2H), 6.17 (br, 2H), 3.92 (s, 3H), 3.10-3.16 (m, 4H), 2.53 (s, 3H), 2.36 (s, 3H). LRMS [M+H]=386.2.

Example 116

4-(2-(5-amino-8-methylbenzo[f][1,7]naphthyridin-2-yl)ethyl)-N,3-dimethylbenzamide

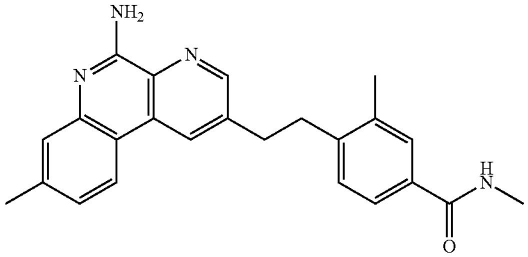

Step 1: 4-(2-(5-amino-8-methylbenzo[f][1,7]naphthyridin-2-yl)ethyl)-3-methylbenzoic acid A solution of methyl 4-(2-(5-amino-8-methylbenzo[f][1,7]naphthyridin-2-yl)ethyl)-3-methylbenzoate (from Example 115) (1.0 eq.), and 1N sodium hydroxide (1.5 eq.) in methanol (0.04 M) was stirred at 60° C. for 4 hours. After cooling to ambient temperature, the reaction mixture was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-50% ethyl acetate in hexane to give 4-(2-(5-amino-8-methylbenzo[f][1,7]naphthyridin-2-yl)ethyl)-3-methylbenzoic acid as a white solid.

Step 2: 4-(2-(5-amino-8-methylbenzo[f][1,7]naphthyridin-2-yl)ethyl)-3-methylbenzoyl chloride A solution of 4-(2-(5-amino-8-methylbenzo[f][1,7]naphthyridin-2-yl)ethyl)-3-methylbenzoic acid (from the previous step) in thionyl chloride was stirred at 60° C. for 3 hour. After cooling to ambient temperature, the reaction mixture was concentrated en vaccuo. The crude material was used for next step without purification.

Step 3: 4-(2-(5-amino-8-methylbenzo[f][1,7]naphthyridin-2-yl)ethyl)-N,3-dimethylbenzamide To a solution of 4-(2-(5-amino-8-methylbenzo[f][1,7]naphthyridin-2-yl)ethyl)-3-methylbenzoyl chloride (from the previous step) (Example 5) and triethylamine (2.5 eq.) in ether (0.05 M) was added methanamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give 4-(2-(5-amino-8-methylbenzo[f][1,7]naphthyridin-2-yl)ethyl)-N,3-dimethylbenzamide as a white solid. $^1H$ NMR ($CDCl_3$): δ 8.62 (s, 1H), 8.32 (s, 1H), 8.04 (d, 1H), 7.60 (s, 1H), 7.46-7.52 (m, 2H), 7.09-7.11 (m, 2H), 6.05 (br, 2H), 3.09-3.17 (m, 4H), 3.00 (d, 3H), 2.52 (s, 3H), 2.33 (s, 3H). LRMS [M+H]=385.2.

Example 117

4-(2-(5-amino-8-methylbenzo[f][1,7]naphthyridin-2-yl)ethyl)-N-(2-(dimethylamino)ethyl)-N,3-dimethylbenzamide

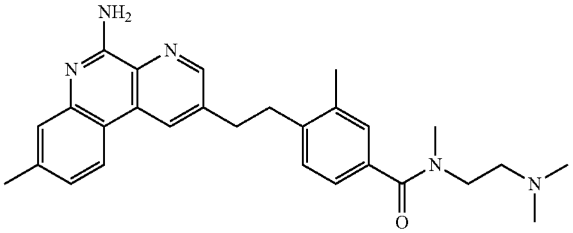

To a solution of 4-(2-(5-amino-8-methylbenzo[f][1,7]naphthyridin-2-yl)ethyl)-3-methylbenzoyl chloride (Example 116/Step 2) and triethylamine (2.5 eq.) in ether (0.05 M) was added $N^1,N^1,N^2$-trimethylethane-1,2-diamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBI-FLASH® system (ISCO) using 0-80% ethyl acetate in hexane to give 4-(2-(5-amino-8-methylbenzo[f][1,7]naphthyridin-2-yl)ethyl)-N-(2-(dimethylamino)ethyl)-N,3-dimethylbenzamide as a white solid. $^1H$ NMR ($CDCl_3$): δ 8.66 (s, 1H), 8.37 (s, 1H), 8.07 (d, 1H), 7.63 (s, 1H), 7.09-7.30 (m, 4H), 3.90 (br, 2H), 3.01-3.19 (m, 4H), 3.08 (s, 6H), 2.72 (br, 5H), 2.52 (s, 3H), 2.33 (s, 3H). LRMS [M+H]=456.3.

Example 118

2-(4-methoxyphenethyl)benzo[f][1,7]naphthyridin-5-amine

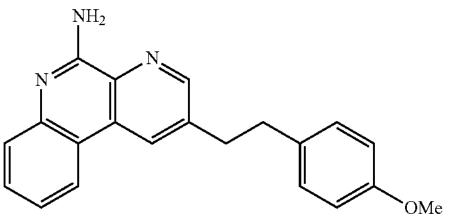 [SMILES: COc1ccc(CCc2cnc3c(N)nc4ccccc4c3c2)cc1]

2-(4-Methoxyphenethyl)benzo[f][1,7]naphthyridin-5-amine was prepared from 1-ethynyl-4-methoxybenzene (Example 116/Step 2) following the procedures described for Example 45/Steps 1 to 3. $^{1}$H NMR ($CDCl_3$): δ 8.69 (s, 1H), 8.47 (s, 1H), 8.27 (d, 1H), 7.80 (d, 2H), 7.58-7.66 (m, 1H), 7.33-7.42 (m, 1H), 7.15 (d, 2H), 6.90 (d, 2H), 6.25 (br, 2H), 3.86 (s, 3H), 3.13-3.23 (m, 2H), 2.97-3.10 (m, 2H). LRMS [M+H]=330.2.

Example 119

2-(4-methoxy-2-methylphenethyl)benzo[f][1,7]naphthyridin-5-amine

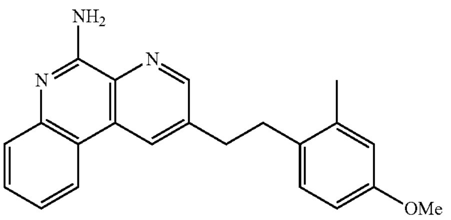 [SMILES: COc1ccc(CCc2cnc3c(N)nc4ccccc4c3c2)c(C)c1]

2-(4-Methoxy-2-methylphenethyl)benzo[f][1,7]naphthyridin-5-amine was prepared from 1-ethynyl-4-methoxy-2-methylbenzene (commercially available) following the procedures described for Example 45/Step 1 to 3. $^{1}$H NMR ($CDCl_3$): δ 8.60 (s, 1H), 8.37 (s, 1H), 8.18 (d, 1H), 7.69 (d, 1H), 7.49-7.57 (m, 1H), 7.24-7.34 (m, 1H), 6.98 (d, 1H), 6.56-6.70 (m, 2H), 6.00 (br, 2H), 3.70 (s, 3H), 3.00-3.09 (m, 2H), 2.83-2.96 (m, 2H), 2.20 (s, 3H). LRMS [M+H]=344.2.

Example 120

4-(2-(5-amino-8-methylbenzo[f][1,7]naphthyridin-2-yl)ethyl)-3-methylbenzamide

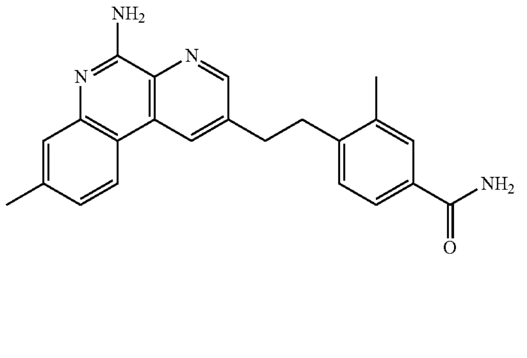 [SMILES: Cc1ccc2c(c1)nc(N)c1ncc(CCc3ccc(C(N)=O)cc3C)cc12]

4-(2-(5-Amino-8-methylbenzo[f][1,7]naphthyridin-2-yl)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and ammonia following the procedures described for Example 117. $^{1}$H NMR ($CDCl_3$): δ 8.60 (s, 1H), 8.35 (s, 1H), 8.05 (d, 1H), 7.65 (s, 1H), 7.51-7.53 (m, 2H), 7.13-7.21 (m, 2H), 3.09-3.16 (m, 4H), 2.51 (s, 3H), 2.34 (s, 3H). LRMS [M+H]=371.2

Example 121

4-(2-(5-amino-8-methylbenzo[f][1,7]naphthyridin-2-yl)ethyl)-N,N,3-trimethylbenzamide

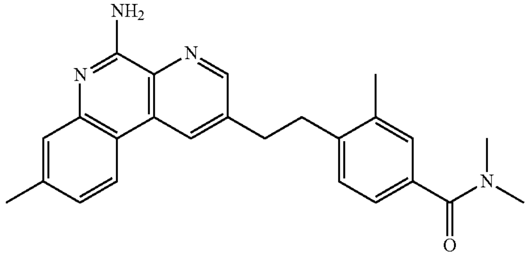

4-(2-(5-Amino-8-methylbenzo[f][1,7]naphthyridin-2-yl)ethyl)-N,N,3-trimethylbenzamide was prepared from 4-(2-(5-amino-8-methylbenzo[f][1,7]naphthyridin-2-yl)ethyl)-3-methylbenzoyl chloride (Example 116/Step 2) and dimethylamine following the procedures described for Example 117. $^{1}$H NMR ($CDCl_3$): δ 8.68 (s, 1H), 8.32 (s, 1H), 8.04 (d, 1H), 7.66 (s, 1H), 7.31 (d, 1H), 7.06-7.18 (m, 3H), 3.08-3.19 (m, 4H), 2.96 (d, 3H), 2.54 (s, 3H), 2.33 (s, 3H), 2.05 (s, 3H). LRMS [M+H]=399.2

Example 122

4-(2-(5-amino-8-methylbenzo[f][1,7]naphthyridin-2-yl)ethyl)-N-(2-hydroxyethyl)-3-methylbenzamide

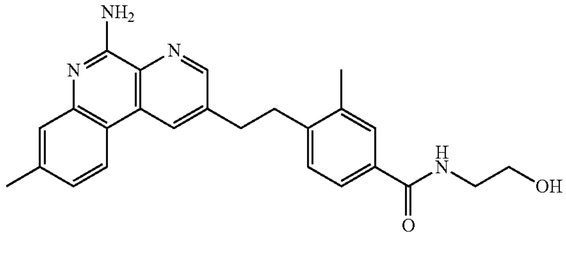 [SMILES: Cc1ccc2c(c1)nc(N)c1ncc(CCc3ccc(C(=O)NCCO)cc3C)cc12]

4-(2-(5-Amino-8-methylbenzo[f][1,7]naphthyridin-2-yl)ethyl)-N-(2-hydroxyethyl)-3-methylbenzamide was prepared from 4-(2-(5-amino-8-methylbenzo[f][1,7]naphthyridin-2-yl)ethyl)-3-methylbenzoyl chloride (Example 116/Step 2) and 2-aminoethanol following the procedures described for Example 117. $^{1}$H NMR ($CDCl_3$): δ 8.59 (s, 1H), 8.34 (s, 1H), 8.04 (d, 1H), 7.50-7.62 (m, 3H), 7.08-7.25 (m, 2H), 3.80 (t, 2H), 3.63 (t, 2H), 3.07-3.16 (m, 4H), 2.51 (s, 3H), 2.32 (s, 3H). LRMS [M+H]=415.2

Example 123

4-(2-(5-amino-8-methylbenzo[f][1,7]naphthyridin-2-yl)ethyl)-N-(2-(dimethylamino)ethyl)-3-methylbenzamide

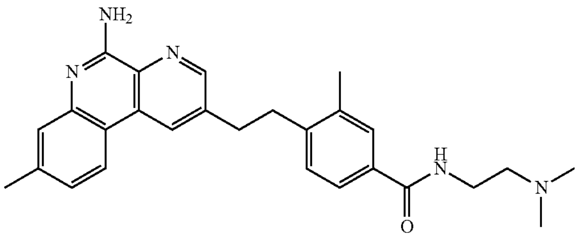

4-(2-(5-Amino-8-methylbenzo[f][1,7]naphthyridin-2-yl)ethyl)-N-(2-(dimethylamino)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and $N^1,N^1$-dimethylethane-1,2-diamine following the procedures described for Example 117. $^1H$ NMR (methanol-$d_4$): δ 8.60 (s, 1H), 8.39 (s, 1H), 8.08 (d, 1H), 7.68 (s, 1H), 7.57-7.59 (m, 2H), 7.19-7.22 (m, 2H), 3.57-3.61 (m, 2H), 3.07-3.16 (m, 4H), 2.64-2.67 (m, 2H), 2.52 (s, 3H), 2.38 (s, 6H), 2.35 (s, 3H). LRMS [M+H]=442.3

Example 124

(4-(2-(5-amino-8-methylbenzo[f][1,7]naphthyridin-2-yl)ethyl)-3-methylphenyl)(pyrrolidin-1-yl)methanone

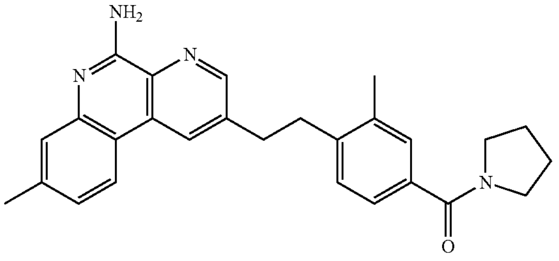 [SMILES: Cc1ccc2c(c1)nc(N)c1ncc(CCc3ccc(C(=O)N4CCCC4)cc3C)cc12]

(4-(2-(5-Amino-8-methylbenzo[f][1,7]naphthyridin-2-yl)ethyl)-3-methylphenyl)(pyrrolidin-1-yl)methanone was prepared from 4-(2-(5-amino-8-methylbenzo[f][1,7]naphthyridin-2-yl)ethyl)-3-methylbenzoyl chloride (Example 116/Step 2) and pyrrolidine following the procedures described for Example 117. $^1H$ NMR (methanol-$d_4$): δ 8.60 (s, 1H), 8.42 (s, 1H), 8.09 (d, 1H), 7.34 (s, 1H), 7.23 (s, 1H), 7.05-7.15 (m, 3H), 3.49 (t, 2H), 3.27 (t, 2H), 3.05-3.17 (m, 4H), 2.42 (s, 3H), 2.26 (s, 3H), 1.88-1.91 (m, 2H), 1.73-1.77 (m, 2H). LRMS [M+H]=425.2

Example 125

4-(2-(5-amino-8-methylbenzo[f][1,7]naphthyridin-2-yl)ethyl)-N-(2-(diethylamino)ethyl)-3-methylbenzamide

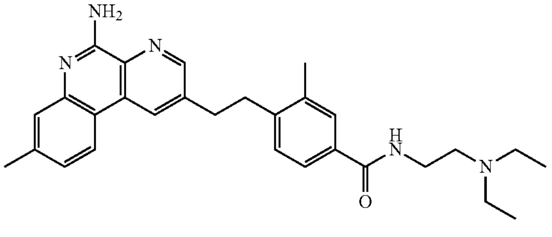 [SMILES: CCN(CC)CCNC(=O)c1ccc(CCc2cnc3c(N)nc4cc(C)ccc4c3c2)c(C)c1]

4-(2-(5-Amino-8-methylbenzo[f][1,7]naphthyridin-2-yl)ethyl)-N-(2-(diethylamino)ethyl)-3-methylbenzamide was prepared from 4-(2-(5-amino-8-methylbenzo[f][1,7]naphthyridin-2-yl)ethyl)-3-methylbenzoyl chloride (Example 116/Step 2) and $N^1,N^1$-diethylethane-1,2-diamine following the procedures described for Example 117. $^1H$ NMR (methanol-$d_4$): δ 8.55 (s, 1H), 8.48 (s, 1H), 8.10 (d, 1H), 7.56 (s, 1H), 7.47-7.50 (m, 1H), 7.33 (s, 1H), 7.10-7.14 (m, 2H), 3.44 (t, 2H), 3.25 (t, 2H), 3.08-3.14 (m, 4H), 2.62-2.72 (m, 4H), 2.42 (s, 3H), 2.27 (s, 3H), 1.05 (t, 6H). LRMS [M+H]=470.3

Example 126

(4-(2-(5-amino-8-methylbenzo[f][1,7]naphthyridin-2-yl)ethyl)-3-methylphenyl)(4-ethylpiperazin-1-yl)methanone

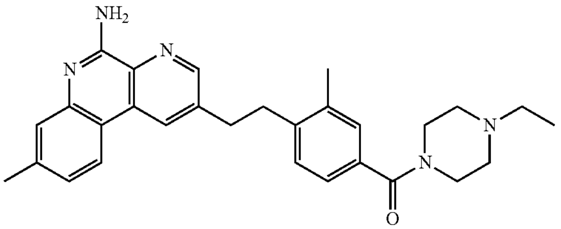 [SMILES: CCN1CCN(C(=O)c2ccc(CCc3cnc4c(N)nc5cc(C)ccc5c4c3)c(C)c2)CC1]

(4-(2-(5-Amino-8-methylbenzo[f][1,7]naphthyridin-2-yl)ethyl)-3-methylphenyl)(4-ethylpiperazin-1-yl)methanone was prepared from 4-(2-(5-amino-8-methylbenzo[f][1,7]naphthyridin-2-yl)ethyl)-3-methylbenzoyl chloride (Example 116/Step 2) and 1-ethylpiperazine following the procedures described for Example 117. $^1H$ NMR (Methanol-$d_4$): δ 8.59 (s, 1H), 8.37 (s, 1H), 8.06 (d, 1H), 7.32 (s, 1H), 7.00-7.12 (m, 4H), 3.67 (br, 2H), 3.06-3.13 (m, 4H), 2.45 (br, 4H), 2.37 (q, 2H), 2.41 (s, 3H), 2.26 (s, 3H), 2.19 (br, 2H), 1.04 (t, 3H). LRMS [M+H]=468.3

Example 127

(4-(2-(5-amino-8-methylbenzo[f][1,7]naphthyridin-2-yl)ethyl)-3-methylphenyl)(piperazin-1-yl)methanone

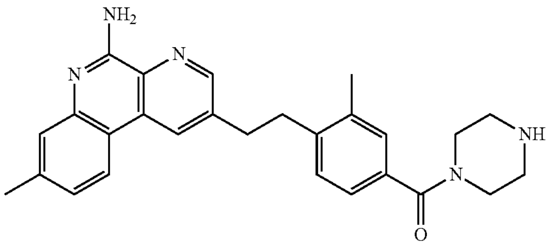 [SMILES: Cc1ccc2c(c1)nc(N)c1ncc(CCc3ccc(C(=O)N4CCNCC4)cc3C)cc12]

(4-(2-(5-Amino-8-methylbenzo[f][1,7]naphthyridin-2-yl)ethyl)-3-methylphenyl)(piperazin-1-yl)methanone was prepared from 4-(2-(5-amino-8-methylbenzo[f][1,7]naphthyridin-2-yl)ethyl)-3-methylbenzoyl chloride (Example 116/Step 2) and piperazine following the procedures described for Example 117. $^1$H NMR (methanol-$d_4$): δ 8.66 (s, 1H), 8.55 (s, 1H), 8.19 (d, 1H), 7.38 (s, 1H), 7.21-7.23 (m, 2H), 7.10-7.15 (m, 2H), 3.66 (br, 6H), 3.08-3.18 (m, 6H), 2.45 (s, 3H), 2.30 (s, 3H). LRMS [M+H]=440.2

Example 128

4-(2-(5-amino-8-methylbenzo[f][1,7]naphthyridin-2-yl)ethyl)-3-methyl-N-(2-(pyrrolidin-1-yl)ethyl)benzamide

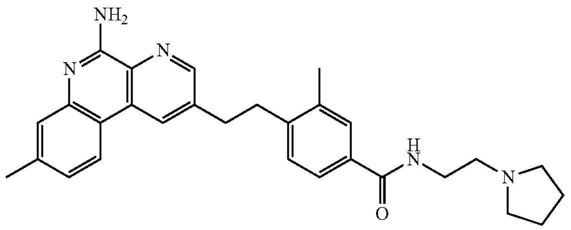 [SMILES: Cc1ccc2c(c1)nc(N)c1ncc(CCc3ccc(C(=O)NCCN4CCCC4)cc3C)cc12]

4-(2-(5-Amino-8-methylbenzo[f][1,7]naphthyridin-2-yl)ethyl)-3-methyl-N-(2-(pyrrolidin-1-yl)ethyl)benzamide was prepared from 4-(2-(5-amino-8-methylbenzo[f][1,7]naphthyridin-2-yl)ethyl)-3-methylbenzoyl chloride (Example 116/Step 2) and 2-(pyrrolidin-1-yl)ethanamine following the procedures described for Example 117. $^1$H NMR ($CDCl_3$): δ 8.58 (s, 1H), 8.38 (s, 1H), 8.07 (d, 1H), 7.64 (s, 1H), 7.51-7.55 (m, 2H), 7.12-7.20 (m, 2H), 6.26 (br, 2H), 3.61 (dd, 2H), 3.05-3.12 (m, 4H), 2.81 (t, 2H), 2.69 (br, 4H), 2.50 (s, 3H), 2.33 (s, 3H), 1.83-1.85 (m, 4H). LRMS [M+H]=468.3

Example 129

4-(2-(5-amino-8-methylbenzo[f][1,7]naphthyridin-2-yl)ethyl)-N-(2-aminoethyl)-3-methylbenzamide

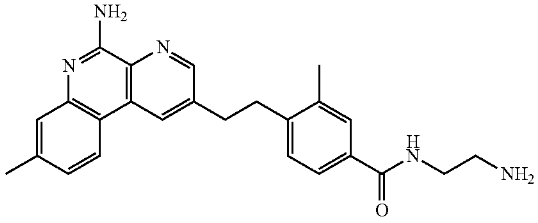 [SMILES: Cc1ccc2c(c1)nc(N)c1ncc(CCc3ccc(C(=O)NCCN)cc3C)cc12]

4-(2-(5-Amino-8-methylbenzo[f][1,7]naphthyridin-2-yl)ethyl)-N-(2-aminoethyl)-3-methylbenzamide was prepared from 4-(2-(5-amino-8-methylbenzo[f][1,7]naphthyridin-2-yl)ethyl)-3-methylbenzoyl chloride (Example 116/Step 2) and ethane-1,2-diamine following the procedures described for Example 117. $^1$H NMR ($CDCl_3$): δ 8.59 (s, 1H), 8.37 (s, 1H), 8.07 (d, 1H), 7.63 (s, 1H), 7.51 (br, 2H), 7.12-7.21 (m, 2H), 6.25 (br, 2H), 3.48-3.52 (m, 2H), 3.08-3.15 (m, 4H), 2.94 (t, 2H), 2.51 (s, 3H), 2.34 (s, 3H). LRMS [M+H]=414.2

Example 130

4-(2-(5-aminobenzo[f][1,7]naphthyridin-2-yl)ethyl)-N-(2-(dimethylamino)ethyl)-N,3-dimethylbenzamide

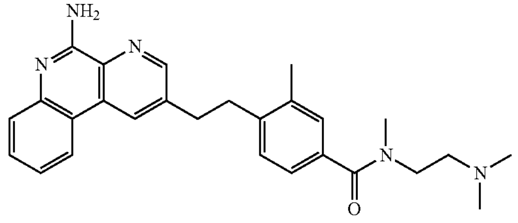 [SMILES: Cc1cc(C(=O)N(C)CCN(C)C)ccc1CCc1cnc2c(N)nc3ccccc3c2c1]

4-(2-(5-Aminobenzo[f][1,7]naphthyridin-2-yl)ethyl)-N-(2-(dimethylamino)ethyl)-N,3-dimethylbenzamide was prepared from 4-(2-(5-aminobenzo[f][1,7]naphthyridin-2-yl)ethyl)-3-methylbenzoyl chloride (Example 116/Step 2) and $N^1$,$N^1$,$N^2$-trimethylethane-1,2-diamine following the procedures described for Example 117. $^1$H NMR (methanol-$d_4$): δ 8.84 (s, 1H), 8.63 (s, 1H), 8.39 (d, 1H), 7.76-7.83 (m, 2H), 7.60-7.64 (m, 1H), 7.37 (s, 1H), 7.19-7.29 (m, 2H), 3.96 (t, 2H), 3.48 (t, 2H), 3.32 (t, 2H), 3.20 (t, 2H), 3.09 (s, 3H), 3.06 (s, 6H), 2.42 (s, 3H). LRMS [M+H]=442.3

Example 131

4-(2-(5-amino-8-methylbenzo[f][1,7]naphthyridin-2-yl)ethyl)-N-(2-(dimethylamino)ethyl)-N-methylbenzamide

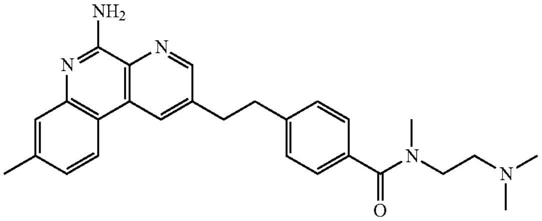

4-(2-(5-Amino-8-methylbenzo[f][1,7]naphthyridin-2-yl)ethyl)-N-(2-(dimethylamino)ethyl)-N-methylbenzamide was prepared from 4-(2-(5-amino-8-methylbenzo[f][1,7]naphthyridin-2-yl)ethyl)-3-methylbenzoyl chloride (Example 116/Step 2) and $N^1,N^1,N^2$-trimethylethane-1,2-diamine following the procedures described for Example 117. $^1H$ NMR ($CDCl_3$): δ 8.64 (s, 1H), 8.36 (s, 1H), 8.05 (d, 1H), 7.60 (s, 1H), 7.41 (d, 2H), 7.31 (d, 1H), 7.21 (d, 2H), 3.91 (t, 2H), 3.44 (t, 2H), 3.25 (t, 2H), 3.12 (t, 2H), 3.03 (s, 3H), 3.01 (s, 6H), 2.53 (s, 3H). LRMS [M+H]=442.3

Example 132

2-(4-(2-(5-aminobenzo[f][1,7]naphthyridin-2-yl)ethyl)-3-methylphenyl)propan-2-ol

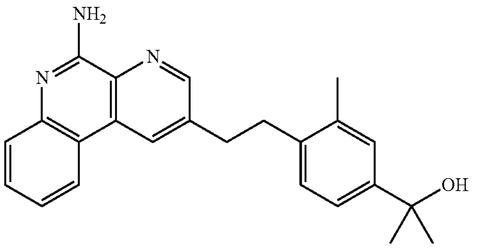 [SMILES: Cc1cc(C(C)(C)O)ccc1CCc1cnc2c(N)nc3ccccc3c2c1]

2-(4-(2-(5-Aminobenzo[f][1,7]naphthyridin-2-yl)ethyl)-3-methylphenyl)propan-2-ol was prepared following the procedures described for Example 78, but using methyl 4-(2-(5-aminobenzo[f][1,7]naphthyridin-2-yl)ethyl)-3-methylbenzoate which was prepared analogous to Example 115 but using tert-butyl 2-(4,4,5,5-tetramethyl-1,3,2-dioxaborolan-2-yl)phenylcarbamate in Step 4. LRMS [M+H]=372.2

Example 133

2-(4-butoxyphenethyl)-8-methylbenzo[f][1,7]naphthyridin-5-amine

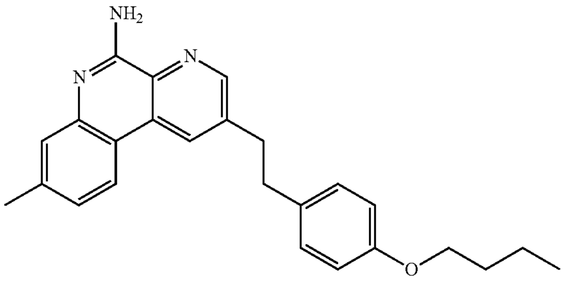 [SMILES: CCCCOc1ccc(CCc2cnc3c(N)nc4cc(C)ccc4c3c2)cc1]

2-(4-Butoxyphenethyl)-8-methylbenzo[f][1,7]naphthyridin-5-amine was prepared following the procedures described for Example 45/Steps 1 to 3, but using 1-butoxy-4-ethynylbenzene (commercially available) with 3,5-dichloropicolinonitrile (commercially available) in step 1. $^1H$ NMR (Acetone-$d_6$): δ 8.75 (s, 1H), 8.68 (s, 1H), 8.28 (d, 1H), 7.42 (s, 1H), 7.10-7.18 (m, 3H), 6.84 (d, 2H), 6.58 (br, 2H), 3.94 (t, 2H), 3.21 (t, 2H), 3.05 (t, 2H), 2.46 (s, 3H), 1.65-1.75 (m, 2H), 1.41-1.58 (m, 2H), 0.94 (s, 3H). LRMS [M+H]=386.2.

Example 134

2-(2-(biphenyl-4-yl)ethyl)-8-methylbenzo[f][1,7]naphthyridin-5-amine

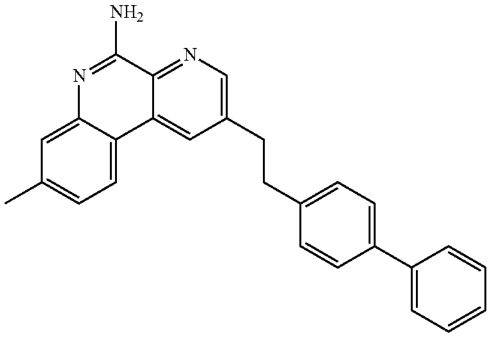 [SMILES: Cc1ccc2c(c1)nc(N)c1ncc(CCc3ccc(-c4ccccc4)cc3)cc12]

2-(2-(Biphenyl-4-yl)ethyl)-8-methylbenzo[f][1,7]naphthyridin-5-amine was prepared following the procedures described for Example 45/Steps 1 to 3, but using 4-ethynylbiphenyl (commercially available) with 3,5-dichloropicolinonitrile (commercially available) in Step 1. $^1H$ NMR (Acetone-$d_6$): δ 8.80 (s, 1H), 8.75 (s, 1H), 8.26 (d, 2H), 7.55-7.69 (m, 4H), 7.30-7.46 (m, 4H), 7.13 (d, 2H), 6.58 (br, 2H), 3.30 (t, 2H), 3.18 (t, 2H), 2.45 (s, 3H). LRMS [M+H]=390.2

Example 135

2-((1,3-dihydroisobenzofuran-1-yl)methyl)-8-methylbenzo[f][1,7]naphthyridin-5-amine

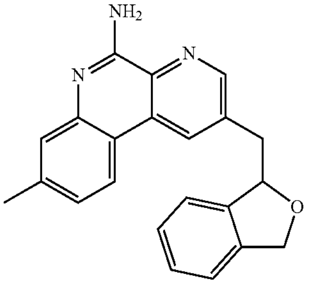 [SMILES: Cc1ccc2c(c1)nc(N)c1ncc(CC3OCc4ccccc43)cc12]

Step 1: 2-((5-amino-8-methylbenzo[f][1,7]naphthyridin-2-yl)ethynyl)phenyl)methanol 2-((5-Amino-8-methylbenzo[f][1,7]naphthyridin-2-yl)ethynyl)phenyl)methanol was prepared following the procedures described for Example 45/Steps 1 to 2, but using (2-ethynylphenyl)methanol (commercially available) with 3,5-dichloropicolinonitrile (commercially available) in Step 1.

Step 2: 2-((1,3-dihydroisobenzofuran-1-yl)methyl)-8-methylbenzo[f][1,7]naphthyridin-5-amine To a solution of 2-((5-amino-8-methylbenzo[f][1,7]naphthyridin-2-yl)ethynyl)phenyl)methanol (1.0 equiv.) (from the previous step) in ethanol (0.05 M) was added 10% wt palladium on carbon (0.2 equiv. by weight). Hydrogen gas was then introduced via a balloon, and the reaction was allowed to stir for 18 hours. At this point, the mixture was filtered through a pad of celite, washing with methanol. The volatiles were removed in vacuo and the resulting residue was purified by a COMBIFLASH® system (ISCO) using 0-60% ethyl acetate in hexanes to give 2-((1,3-dihydroisobenzofuran-1-yl)methyl)-8-methylbenzo[f][1,7]naphthyridin-5-amine as a solid. $^1$H NMR (Acetone-$d_6$): δ 8.78 (s, 1H), 8.74 (s, 1H), 8.24 (d, 2H), 7.40-7.44 (m, 2H), 7.20-7.34 (m, 3H), 6.61 (br, 2H), 5.63-5.69 (m, 1H), 4.89-5.00 (dd, 2H), 3.51-3.56 (dd, 1H), 3.28-3.34 (dd, 1H), 2.46 (s, 3H). LRMS [M+H]=342.1

Example 136

8-methyl-2-(4-(2-methylallyloxy)phenethyl)benzo[f][1,7]naphthyridin-5-amine

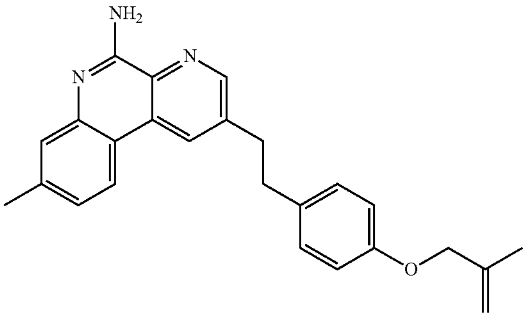 [SMILES: C=C(C)COc1ccc(CCc2cnc3c(N)nc4cc(C)ccc4c3c2)cc1]

To a solution of 4-(2-(5-amino-8-methylbenzo[f][1,7]naphthyridin-2-yl)ethyl)phenol (from Example 170) (1.0 equiv.) in dimethylformamide (0.10 M) was added anhydrous potassium carbonate (1.5 euiv.) followed by methallyl bromide (1.2 equiv.). The resulting mixture was allowed to stir for 18 hours at 100° C. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-60% ethyl acetate in hexanes to provide 8-methyl-2-(4-(2-methylallyloxy)phenethyl)benzo[f][1,7]naphthyridin-5-amine as a solid. $^1$H NMR (Acetone-$d_6$): δ 8.75 (s, 1H), 8.68 (s, 1H), 8.27 (d, 1H), 7.41 (s, 1H), 7.12-7.19 (m, 3H), 6.87 (d, 2H), 6.60 (br, 2H), 5.06 (s, 1H), 4.93 (s, 1H), 4.43 (s, 2H), 3.20 (t, 2H), 3.05 (t, 2H), 2.45 (s, 3H), 1.79 (s, 3H). LRMS [M+H]=384.2

Example 137

2-(4-(isopentyloxy)phenethyl)-8-methylbenzo[f][1,7]naphthyridin-5-amine

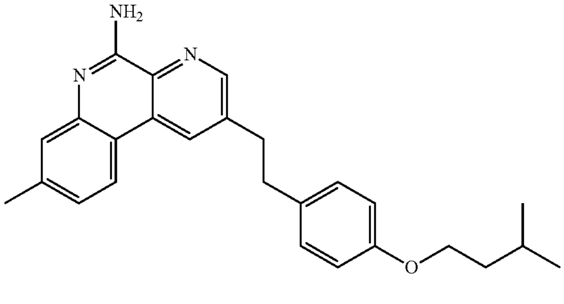 [SMILES: Cc1ccc2c(c1)nc(N)c1ncc(CCc3ccc(OCCC(C)C)cc3)cc12]

2-(4-(Isopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using 1-bromo-3-methylbutane. $^1$H NMR (Acetone-$d_6$): δ 8.72 (s, 1H), 8.69 (s, 1H), 8.26 (d, 1H), 7.43 (s, 1H), 7.12-7.18 (m, 3H), 6.84 (d, 2H), 6.50 (br, 2H), 3.98 (t, 2H), 3.21 (t, 2H), 3.06 (t, 2H), 2.46 (s, 3H), 1.78-1.87 (m, 1H), 1.61-1.67 (dd, 2H), 0.96 (s, 3H), 0.95 (3H). LRMS [M+H]=400.2

Example 138

4-(2-(5-amino-8-methylbenzo[f][1,7]naphthyridin-2-yl)ethyl)phenyl propyl carbonate

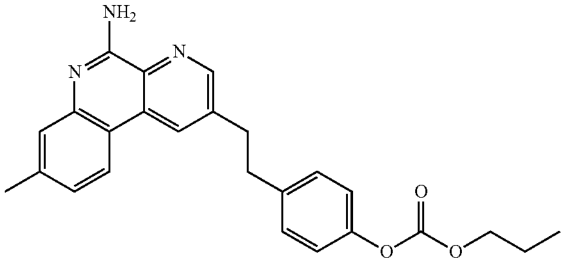 [SMILES: CCCOC(=O)Oc1ccc(CCc2cnc3c(N)nc4cc(C)ccc4c3c2)cc1]

To a solution of 4-(2-(5-amino-8-methylbenzo[f][1,7]naphthyridin-2-yl)ethyl)phenol (from Example 170) (1.0 equiv.) and triethyl amine (2 equiv.) in dichloromethane (0.10 M) at 0° C. was added ethyl chloroformate (1.2 equiv.). The resulting mixture was allowed to stir for 30 minutes at 0° C., after which it was diluted with water and dichloromethane. The biphasic layers were separated and the aqueous layer was washed twice with dichloromethane. The combined organic layers were dried over anhydrous $Na_2SO_4$ and the volatiles were removed in vacuo. The resulting residue was purified by a COMBIFLASH® system (ISCO) using 0-50% ethyl acetate in hexanes to provide 4-(2-(5-amino-8-methylbenzo[f][1,7]naphthyridin-2-yl)ethyl)phenyl ethyl carbonate as a solid. $^1$H NMR (Acetone-$d_6$): δ 8.78 (s, 1H), 8.73 (s, 1H), 8.28 (d, 1H), 7.43 (s, 1H), 7.33 (d, 2H), 7.10-7.17 (m, 3H), 6.64 (br, 2H), 4.18 (t, 2H), 3.25 (t, 2H), 3.14 (t, 2H), 2.45 (s, 3H), 1.68-1.77 (m, 2H), 0.97 (t, 3H). LRMS [M+H]=416.2

Example 139 ethyl 5-(4-(2-(5-amino-8-methylbenzo[f][1,7]naphthyridin-2-yl)ethyl)phenoxy)pentanoate

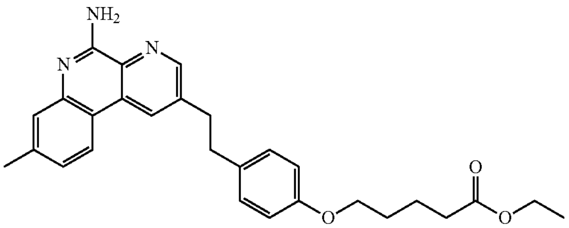 [SMILES: CCOC(=O)CCCCOc1ccc(CCc2cnc3c(N)nc4cc(C)ccc4c3c2)cc1]

To a solution of 4-(2-(5-amino-8-methylbenzo[f][1,7]naphthyridin-2-yl)ethyl)phenol (from Example 170) (1.0 equiv.) in dimethylformamide (0.10 M) 22° C. was added 60% dispersion of sodium hydride in mineral oil (1.5 euiv.)

and the resulting mixture was allowed to stir for 30 min. At this point, ethyl 5-bromopentanoate (1.2 equiv.) was added to this mixture. The reaction mixture was then allowed to stir for 18 hours. after which it was diluted with ethyl acetate and water. The biphasic layers were separated and the organic layer was washed twice with water. The organic layer was dried over anhydrous $Na_2SO_4$ and the volatiles were removed in vacuo. The resulting residue was purified by RP-HPLC using a 10-50% MeCN in water gradient. The resulting trifluoroacetate salt was then converted to the free base form by utilizing a StratoSpheres™ PL-SO3H SPE ion exchange resin, delivering ethyl 5-(4-(2-(5-amino-8-methylbenzo[f][1,7]naphthyridin-2-yl)ethyl)phenoxy)pentanoate as a solid. $^1$H NMR (Acetone-$d_6$): δ 8.80 (s, 1H), 8.74 (s, 1H), 8.33 (d, 1H), 7.47 (s, 1H), 7.24 (d, 1H), 7.17 (d, 2H), 6.85 (d, 2H), 4.10 (q, 2H), 3.97 (t, 2H), 3.25 (t, 2H), 3.07 (t, 2), 2.50 (s, 3H), 2.37 (t, 3H), 1.74-1.84 (m, 4H), 1.21 (t, 3H). LRMS [M+H]=458.2

Example 140

2-(4-(cyclopentyloxy)phenethyl)-8-methylbenzo[f][1,7]naphthyridin-5-amine

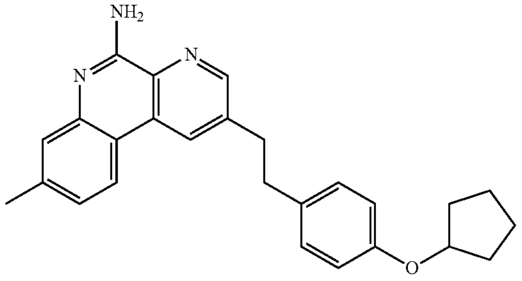 [SMILES: Cc1ccc2c(c1)nc(N)c1ncc(CCc3ccc(OC4CCCC4)cc3)cc12]

2-(4-(Cyclopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using bromocyclopentane. $^1$H NMR (Acetone-$d_6$): δ 8.75 (d, 2H), 8.30 (d, 1H), 7.45 (s, 1H), 7.20 (d, 1H), 7.14 (d, 2H), 6.79 (d, 2H), 4.73-4.81 (m, 1H), 3.22 (t, 2H), 3.05 (t, 2H), 2.47 (s, 3H), 1.85-1.96 (m, 2H), 1.70-1.79 (m, 4H), 1.56-1.64 (m, 2H). LRMS [M+H]=398.2

Example 141

2-(4-(cyclobutylmethoxy)phenethyl)-8-methylbenzo[f][1,7]naphthyridin-5-amine

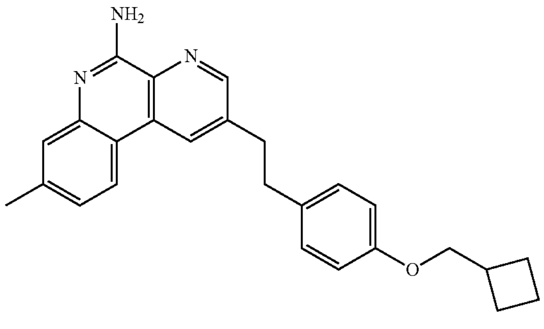 [SMILES: Cc1ccc2c(c1)nc(N)c1ncc(CCc3ccc(OCC4CCC4)cc3)cc12]

2-(4-(Cyclobutylmethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 136, but using (bromomethyl)cyclobutane. $^1$H NMR (Acetone-$d_6$): δ 8.79 (s, 1H), 8.73 (s, 1H), 8.33 (d, 1H), 7.47 (s, 1H), 7.26 (d, 1H), 7.16 (d, 2H), 6.82 (d, 2H), 3.90 (d, 2H), 3.23 (t, 2H), 3.06 (t, 2H), 2.68-2.79 (m, 1H), 2.49 (s, 3H), 2.05-2.14 (m, 2H), 1.80-1.98 (m, 4H). LRMS [M+H]=398.2

Example 142

8-methyl-2-(4-(2-morpholinoethoxy)phenethyl)benzo[f][1,7]naphthyridin-5-amine

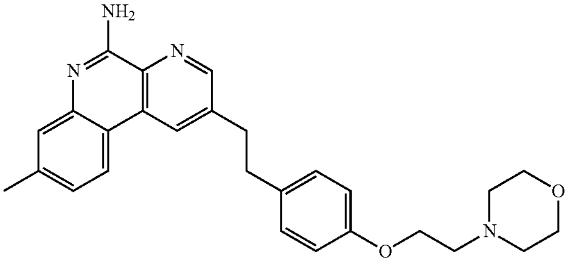 [SMILES: Cc1ccc2c(c1)nc(N)c1ncc(CCc3ccc(OCCN4CCOCC4)cc3)cc12]

8-Methyl-2-(4-(2-morpholino ethoxy)phenethyl)benzo[f][1,7]naphthyridin-5-amine was prepared from 4-(2-(5-amino-8-methylbenzo[f][1,7]naphthyridin-2-yl)ethyl)phenol (from Example 170) following the procedure described for Example 139, but using 4-(2-bromoethyl)morpholine. $^1$H NMR (Acetone-$d_6$): δ 8.78 (s, 1H), 8.72 (s, 1H), 8.30 (d, 1H), 7.46 (s, 1H), 7.17-7.24 (m, 3H), 6.85 (d, 2H), 4.08 (t, 2H), 3.56-3.62 (m, 4H), 3.45-3.53 (m, 2H), 3.24 (t, 2H), 3.07 (t, 2H), 2.73 (t, 2H), 2.52-2.56 (m, 2H), 2.49 (s, 3H). LRMS [M+H]=443.2

Example 143

2-(4-(2-(5-amino-8-methylbenzo[f][1,7]naphthyridin-2-yl)ethyl)phenoxy)-1-phenylethanone

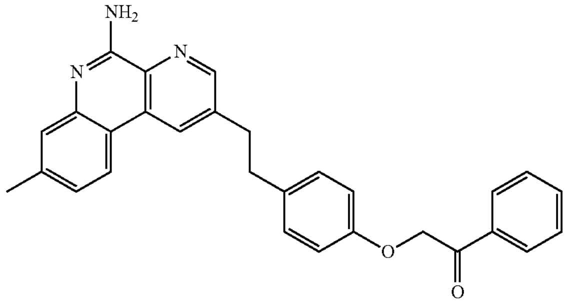 [SMILES: Cc1ccc2c(c1)nc(N)c1ncc(CCc3ccc(OCC(=O)c4ccccc4)cc3)cc12]

2-(4-(2-(5-Amino-8-methylbenzo[f][1,7]naphthyridin-2-yl)ethyl)phenoxy)-1-phenylethanone was prepared from 4-(2-(5-amino-8-methylbenzo[f][1,7]naphthyridin-2-yl)ethyl)phenol (from Example 170) following the procedure described for Example 139, but using 2-bromo-1-phenylethanone. $^1$H NMR (Acetone-$d_6$): δ 8.76 (s, 1H), 8.71 (s, 1H), 8.27 (d, 1H), 8.06 (d, 2H), 7.67 (t, 1H), 7.57 (t, 2H), 7.43 (s, 1H), 7.17 (d, 3H), 6.90 (d, 2H), 5.45 (s, 2H), 3.21 (t, 2H), 3.06 (t, 2H), 2.45 (s, 3H). LRMS [M+H]=448.2

Example 144

5-(4-(2-(5-amino-8-methylbenzo[f][1,7]naphthyridin-2-yl)ethyl)phenoxy)pentanoic acid

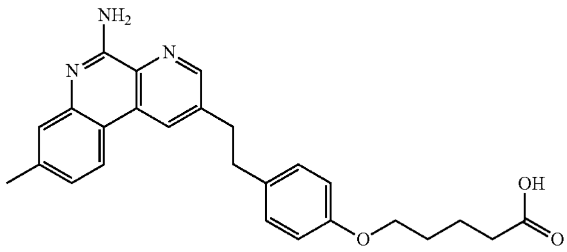 [SMILES: Cc1ccc2c(c1)nc(N)c1ncc(CCc3ccc(OCCCCC(=O)O)cc3)cc12]

To a solution of ethyl 5-(4-(2-(5-amino-8-methylbenzo[f][1,7]naphthyridin-2-yl)ethyl)phenoxy)pentanoate (1.0 equiv.) (from Example 139) in ethanol (0.10 M) was added anhydrous sodium hydroxide (2.0 equiv.) and the resulting mixture was allowed to stir at 80° C. for 2 hours. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 5-(4-(2-(5-amino-8-methylbenzo[f][1,7]naphthyridin-2-yl)ethyl)phenoxy)pentanoic acid as a solid. $^1$H NMR (Methanol-$d_4$): δ 8.61 (s, 1H), 8.57 (s, 1H), 8.20 (d, 1H), 7.40 (s, 1H), 7.20 (d, 1H), 7.07 (d, 2H), 6.81 (d, 2H), 3.93 (t, 2H), 3.18 (t, 2H), 3.00 (t, 2H), 2.48 (s, 3H), 2.25 (t, 2H), 1.74-1.81 (m, 2H), 0.86-0.96 (m, 2H). LRMS [M+H]=430.2

Example 145

2-(4-(2-(5-amino-8-methylbenzo[f][1,7]naphthyridin-2-yl)ethyl)phenoxy)ethanol

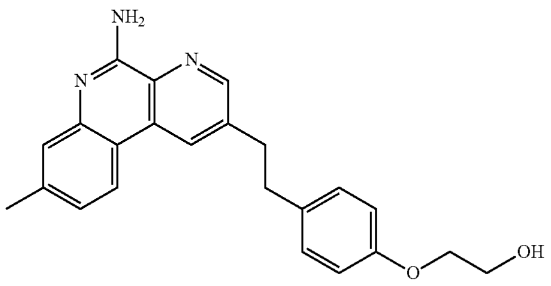 [SMILES: Cc1ccc2c(c1)nc(N)c1ncc(CCc3ccc(OCCO)cc3)cc12]

Step 1: 2-(4-(2-(tert-butyldimethylsilyloxy)ethoxy)phenethyl)-8-methylbenzo[f][1,7]naphthyridin-5-amine 2-(4-(2-(Tert-butyldimethylsilyloxy)ethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 170) following the procedure described for Example 139, but using (2-bromoethoxy)(tert-butyl)dimethylsilane.

Step 2: 2-(4-(2-(5-amino-8-methylbenzo[f][1,7]naphthyridin-2-yl)ethyl)phenoxy)ethanol To a solution of 2-(4-(2-(tert-butyldimethylsilyloxy)ethoxy)phenethyl)-8-methylbenzo[f][1,7]naphthyridin-5-amine (from the previous step) (1.0 equiv.) in tetrahydrofuran (0.10 M) was added a 1.0 M solution of tetrabutylammonium fluoride (5 equiv.) in THF and the resulting mixture was allowed to stir at 22° C. for 2 hours. At this point, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 2-(4-(2-(5-amino-8-methylbenzo[f][1,7]naphthyridin-2-yl)ethyl)phenoxy)ethanol as a solid. $^1$H NMR (Acetone-$d_6$): δ 8.76 (s, 1H), 8.67 (s, 1H), 8.28 (d, 1H), 7.40 (s, 1H), 7.15 (t, 3H), 6.84 (d, 2H), 6.54 (br, 2H), 4.00 (t, 2H), 3.83 (t, 2H), 3.21 (t, 2H), 3.05 (t, 2H), 2.45 (s, 3H). LRMS [M+H]=374.2

Example 146

2-(4-(2-(5-amino-8-methylbenzo[f][1,7]naphthyridin-2-yl)ethyl)phenoxy)-N,N-dimethylacetamide

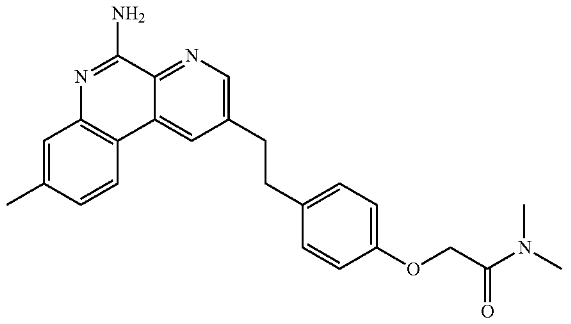

2-(4-(2-(5-Amino-8-methylbenzo[f][1,7]naphthyridin-2-yl)ethyl)phenoxy)-N,N-dimethylacetamide was prepared from 4-(2-(5-amino-8-methylbenzo[f][1,7]naphthyridin-2-yl)ethyl)phenol (from Example 170) and following the procedure described for Example 139, but using 2-bromo-N,N-dimethylacetamide. $^1$H NMR (Acetone-$d_6$): δ 8.75 (s, 1H), 8.70 (s, 1H), 8.28 (d, 1H), 7.40 (s, 1H), 7.18 (t, 3H), 6.87 (d, 2H), 6.56 (br, 2H), 4.72 (s, 2H), 3.20 (t, 2H), 3.07 (s, 3H), 3.05 (t, 2H), 2.87 (s, 3H), 2.45 (s, 3H). LRMS [M+H]=415.2

Example 147

8-methyl-2-(2-methyl-4-(2-morpholinoethoxy)phenethyl)benzo[f][1,7]naphthyridin-5-amine

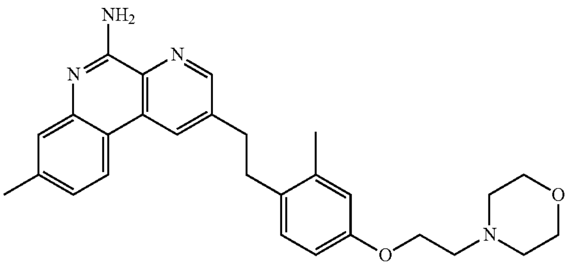 [SMILES: Cc1ccc2c(c1)nc(N)c1ncc(CCc3ccc(OCCN4CCOCC4)cc3C)cc12]

8-Methyl-2-(2-methyl-4-(2-morpholinoethoxy)phenethyl)benzo[f][1,7]naphthyridin-5-amine was prepared following an analogous procedure to the preparation described for Example 139, but using 4-(2-(5-amino-8-methylbenzo[f][1,7]naphthyridin-2-yl)ethyl)-3-methylphenol (from Example 50) and 4-(2-bromoethyl)morpholine. $^1$H NMR (Acetone-d$_6$): δ 8.73 (d, 2H), 8.26 (d, 1H), 7.44 (s, 1H), 7.17 (d, 1H), 7.05 (d, 1H), 6.76 (s, 1H), 6.67 (d, 1), 4.04-4.08 (m, 3H), 3.60-3.62 (m, 4H), 3.30 (s, 1H), 3.16 (t, 2H), 3.04 (t, 2H), 2.71 (t, 2H), 2.50-2.52 (m, 2H), 2.47 (s, 3H), 2.28 (s, 3H). LRMS [M+H]=457.3

Example 148

2-(2-(4-(2-(5-amino-8-methylbenzo[f][1,7]naphthyridin-2-yl)ethyl)-3-methylphenoxy)ethoxy)ethanol

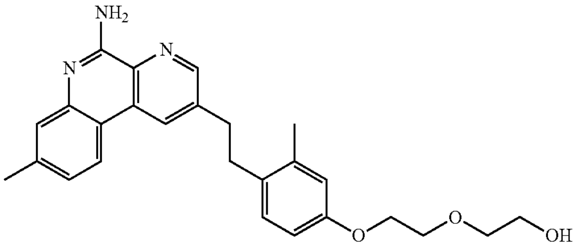 [SMILES: Cc1ccc2c(c1)nc(N)c1ncc(CCc3ccc(OCCOCCO)cc3C)cc12]

Step 1: 2-(4-(2-(2-(tert-butyldimethylsilyloxy)ethoxy)ethoxy)-2-methylphenethyl)-8-methylbenzo[f][1,7]naphthyridin-5-amine 2-(4-(2-(2-(Tert-butyldimethylsilyloxy)ethoxy)ethoxy)-2-methylphenethyl)-8-methylbenzo[f][1,7]naphthyridin-5-amine was prepared following an analogous procedure to the preparation described for Example 145/Step 1, but using 4-(2-(5-amino-8-methylbenzo[f][1,7]naphthyridin-2-yl)ethyl)-3-methylphenol (from Example 50) with tert-butyl(2-(2-chloroethoxy)ethoxy)dimethylsilane.

Step 2: 2 (2 (4 (2 (5 Amino-8-methylbenzo[f][1,7]naphthyridin-2-yl)ethyl)-3-methylphenoxy)ethoxy)ethanol 2-(2-(4-(2-(5-Amino-8-methylbenzo[f][1,7]naphthyridin-2-yl)ethyl)-3-methylphenoxy)ethoxy)ethanol was prepared from 2-(4-(2-(2-(tert-butyldimethylsilyloxy)ethoxy)ethoxy)-2-methylphenethyl)-8-methylbenzo[f][1,7]naphthyridin-5-amine (from the previous step) following the procedures described for Example 145/Step 2. $^1$H NMR (Acetone-d$_6$): δ 8.74 (s, 1H), 8.69 (s, 1H), 8.27 (d, 1H), 7.41 (s, 1H), 7.14 (d, 1H), 7.06 (d, 1H), 6.75 (s, 1H), 6.69 (d, 1), 6.54 (br, 2H), 4.07 (t, 2H), 3.79 (t, 2H), 3.64 (t, 2H), 3.59 (t, 2H), 3.16 (t, 2H), 3.03 (t, 2H), 2.45 (s, 3H), 2.29 (s, 3H). LRMS [M+H]=432.2

Example 149 diethyl 3-(4-(2-(5-amino-8-methylbenzo[f][1,7]naphthyridin-2-yl)ethyl)-3-methylphenoxy)propylphosphonate

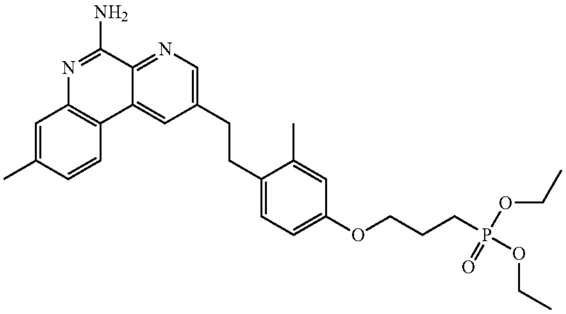 [SMILES: CCOP(=O)(CCCOc1ccc(CCc2cnc3c(N)nc4cc(C)ccc4c3c2)c(C)c1)OCC]

Diethyl 3-(4-(2-(5-amino-8-methylbenzo[f][1,7]naphthyridin-2-yl)ethyl)-3-methylphenoxy)propylphosphonate was prepared following an analogous procedure to the preparation described for Example 139, but using 4-(2-(5-amino-8-methylbenzo[f][1,7]naphthyridin-2-yl)ethyl)-3-methylphenol (from Example 50) with diethyl 3-bromopropylphosphonate. $^1$H NMR (Acetone-d$_6$): δ 9.52 (s, 1H), 9.47 (s, 1H), 9.03 (d, 1H), 8.21 (s, 1H), 7.93 (d, 1H), 7.84 (d, 1H), 7.60 (br, 2H), 7.53 (s, 1), 7.45 (d, 1H), 4.76-4.91 (m, 6H), 3.93 (t, 2H), 3.81 (t, 2H), 3.24 (s, 3H), 3.06 (s, 3H), 2.76-2.86 (m, 2H), 2.61-2.72 (m, 2H), 2.07 (t, 6H). LRMS [M+H]=522.2

Example 150

3-(4-(2-(5-amino-8-methylbenzo[f][1,7]naphthyridin-2-yl)ethyl)-3-methylphenoxy)propylphosphonic acid

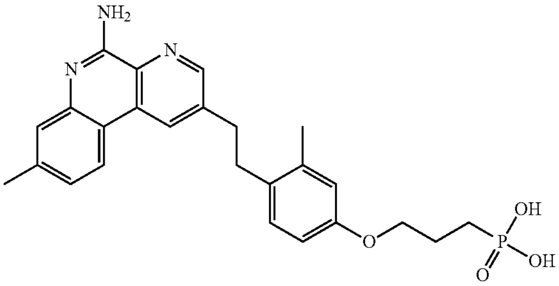 [SMILES: Cc1ccc2c(c1)nc(N)c1ncc(CCc3ccc(OCCCP(=O)(O)O)cc3C)cc12]

A 12 N solution of hydrochloric acid (0.10 M) was added to diethyl 3-(4-(2-(5-amino-8-methylbenzo[f][1,7]naphthyridin-2-yl)ethyl)-3-methylphenoxy)propylphosphonate (from Example 149) and the resulting mixture was allowed to stir at 100° C. for 18 hours. At this point, hydrochloric acid was removed under reduced pressure and the resulting residue was purified by RP-HPLC using a 10-50% MeCN in water gradient. The resulting trifluoroacetate salt was then converted to the free base form by the addition of a saturated aqueous solution of sodium bicarbonate, followed by washing three times with ethyl acetate. The combined organic layers were dried with anhydrous $Na_2SO_4$, and the volatiles were removed in vacuo to deliver 3-(4-(2-(5-amino-8-methylbenzo[f][1,7]naphthyridin-2-yl)ethyl)-3-methylphenoxy)propylphosphonic acid as a solid. $^1$H NMR (Dimethylsulfoxide-d$_6$): δ 9.72 (br, 1H), 9.01 (s, 1H), 8.96 (br, 1H), 8.85 (s, 1H), 8.54 (d, 1H), 7.54 (s, 1H), 7.42 (d, 1H), 7.08 (d, 1), 6.74 (s, 1H), 6.66 (d, 1H), 3.95 (t, 2H), 3.14 (t, 2H), 2.97 (t, 2H), 2.50 (s, 3H), 2.27 (s, 3H), 1.81-1.91 (m, 2H), 1.56-1.67 (m, 2H). LRMS [M+H]=466.2

Example 151

2-(4-butoxy-2-methylphenethyl)-8-methylbenzo[f][1,7]naphthyridin-5-amine

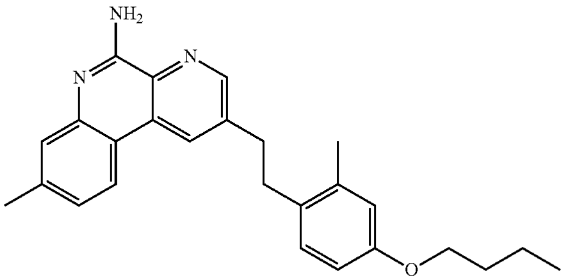 [SMILES: CCCCOc1ccc(CCc2cnc3c(N)nc4cc(C)ccc4c3c2)c(C)c1]

2-(4-Butoxy-2-methylphenethyl)-8-methylbenzo[f][1,7]naphthyridin-5-amine was prepared following an analogous procedure to the preparation described for Example 139, but using 4-(2-(5-amino-8-methylbenzo[f][1,7]naphthyridin-2-yl)ethyl)-3-methylphenol (from Example 50) with 1-bromobutane. $^1$H NMR (Acetone-$d_6$): δ 8.75 (s, 1H), 8.71 (s, 1H), 8.28 (d, 1H), 7.43 (s, 1H), 7.15 (d, 1H), 7.07 (d, 1H), 6.75 (s, 1H), 6.69 (d, 1H), 6.54 (br, 2H) 3.95 (t, 2H), 3.16 (t, 2H), 3.04 (t, 2H), 2.47 (s, 3H), 2.30 (s, 3H), 1.69-1.77 (m, 2H), 1.43-1.54 (m, 2H), 0.97 (t, 3H). LRMS [M+H]=400.2

Example 152

2-(4-(2-(5-aminobenzo[f][1,7]naphthyridin-2-yl)ethyl)-3-methylphenoxy)ethanol

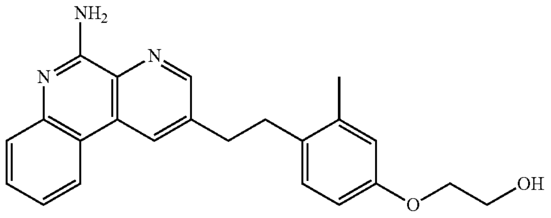 [SMILES: Cc1cc(OCCO)ccc1CCc1cnc2c(N)nc3ccccc3c2c1]

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 145, but using 2-(4-Methoxy-2-methylphenethyl)benzo[f][1,7]naphthyridin-5-amine (from Example 119).

Step 2: 2-(4-(2-(5-Aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared from 4-(2-(5-aminobenzo[f][1,7]naphthyridin-2-yl)ethyl)-3-methylphenol (from the previous step) following the procedures described for Example 145/Steps 1 to 2. LRMS [M+H]=374.2

Example 153

2-(4-(2-(5-aminobenzo[f][1,7]naphthyridin-2-yl)ethyl)-3-methylphenoxy)ethanol

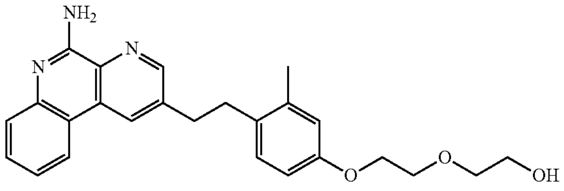 [SMILES: Cc1cc(OCCOCCO)ccc1CCc1cnc2c(N)nc3ccccc3c2c1]

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 50, but using 2-(4-Methoxy-2-methylphenethyl)benzo[f][1,7]naphthyridin-5-amine (from Example 119).

Step 2: 2-(4-(2-(5-aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared following the procedures described for Example 148/Steps 1 to 2. LRMS [M+H]=418.2

Example 154 ethyl 5-(4-(2-(5-amino-8-methylbenzo[f][1,7]naphthyridin-2-yl)ethyl)-3-methylphenoxy)pentanoate

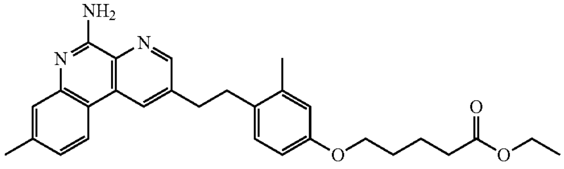 [SMILES: CCOC(=O)CCCCOc1ccc(CCc2cnc3c(N)nc4cc(C)ccc4c3c2)c(C)c1]

Ethyl 5-(4-(2-(5-amino-8-methylbenzo[f][1,7]naphthyridin-2-yl)ethyl)-3-methylphenoxy)pentanoate was prepared from 4-(2-(5-amino-8-methylbenzo[f][1,7]naphthyridin-2-yl)ethyl)-3-methylphenol (from Example 50) following the procedure described for Example 139, but using ethyl 5-bromopentanoate. $^1$H NMR ($CDCl_3$): δ 8.64 (s, 1H), 8.27 (s, 1H), 8.02 (d, 1H), 7.66 (s, 1H), 7.32 (d, 1H), 6.91 (d, 1H), 6.66 (s, 1H), 6.63 (d, 1H), 4.13 (q, 2H), 3.93 (t, 2H), 3.14 (t, 2H), 2.99 (t, 2H), 2.54 (s, 3H), 2.38 (t, 2H), 2.25 (s, 3H), 1.79-1.83 (m, 4H), 1.26 (t, 3H). LRMS [M+H]=472.3

Example 155

5-(4-(2-(5-amino-8-methylbenzo[f][1,7]naphthyridin-2-yl)ethyl)-3-methylphenoxy)pentanoic acid

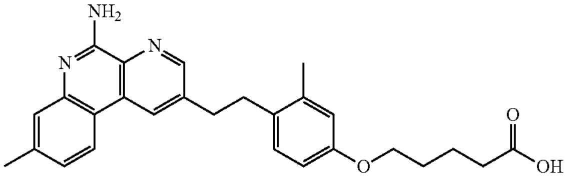 [SMILES: Cc1ccc2c(c1)nc(N)c1ncc(CCc3ccc(OCCCCC(=O)O)cc3C)cc12]

5-(4-(2-(5-Amino-8-methylbenzo[f][1,7]naphthyridin-2-yl)ethyl)-3-methylphenoxy)pentanoic acid was prepared from ethyl 5-(4-(2-(5-amino-8-methylbenzo[f][1,7]naphthyridin-2-yl)ethyl)-3-methylphenoxy)pentanoate (from the previous step) following the procedure described for Example 144. $^1$H NMR ($CDCl_3$): δ 8.52 (s, 1H), 8.27 (s, 1H), 8.02 (d, 1H), 7.65 (s, 1H), 7.32 (d, 1H), 6.86 (d, 1H), 6.72 (s, 1H), 6.63 (d, 1H), 3.95 (t, 2H), 3.15 (t, 2H), 2.99 (t, 2H), 2.54 (s, 3H), 2.45 (t, 2H), 2.23 (s, 3H), 1.79-1.83 (m, 4H). LRMS [M+H]=444.2

Example 156

2-(4-(2-(5-amino-8-methylbenzo[f][1,7]naphthyridin-2-yl)ethyl)-3-methylphenoxy)ethanol

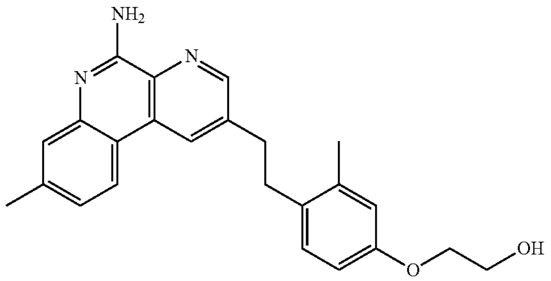 [SMILES: Cc1ccc2c(c1)nc(N)c1ncc(CCc3ccc(OCCO)cc3C)cc12]

2-(4-(2-(5-Amino-8-methylbenzo[f][1,7]naphthyridin-2-yl)ethyl)-3-methylphenoxy)ethanol was prepared following the procedures described for Example 145/Steps 1 to 2, but using 4-(2-(5-amino-8-methylbenzo[f][1,7]naphthyridin-2-yl)ethyl)-3-methylphenol (from Example 50). $^1$H NMR (Acetone-$d_6$): δ 8.76 (s, 1H), 8.69 (s, 1H), 8.28 (d, 1H), 7.40 (s, 1H), 7.15 (d, 1H), 7.09 (d, 1H), 6.75 (s, 1H), 6.68 (d, 1H), 6.57 (br, 2H), 4.00 (t, 2H), 3.79-3.88 (m, 2H), 3.17 (t, 2H), 3.04 (t, 2H), 2.46 (s, 2H), 2.29 (s, 2H). LRMS [M+H]=388.5.

Example 157

4-(2-(5-amino-8-methylbenzo[f][1,7]naphthyridin-2-yl)ethyl)phenyl ethyl carbonate

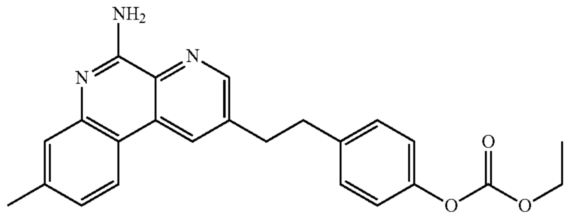 [SMILES: CCOC(=O)Oc1ccc(CCc2cnc3c(N)nc4cc(C)ccc4c3c2)cc1]

4-(2-(5-Amino-8-methylbenzo[f][1,7]naphthyridin-2-yl)ethyl)phenyl ethyl carbonate was prepared from 4-(2-(5-amino-8-methylbenzo[f][1,7]naphthyridin-2-yl)ethyl)phenol (from Example 170) following the procedure described for Example 138, but using ethyl carbonochloridate. LRMS [M+H]=402.2

Example 158 methyl 4-(4-(2-(5-amino-8-methylbenzo[f][1,7]naphthyridin-2-yl)ethyl)phenoxy)butanoate

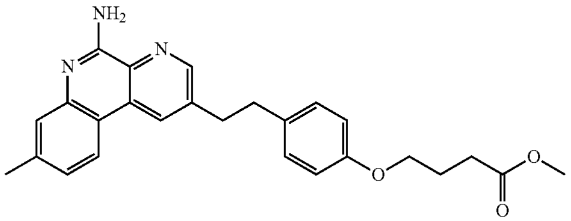

Methyl 4-(4-(2-(5-amino-8-methylbenzo[f][1,7]naphthyridin-2-yl)ethyl)phenoxy)butanoate was prepared from 4-(2-(5-amino-8-methylbenzo[f][1,7]naphthyridin-2-yl)ethyl) phenol (from Example 170) following the procedure described for the preparation of Example 139, but using methyl 4-bromobutanoate. $^1$H NMR (Acetone-$d_6$): δ 8.74 (s, 1H), 8.67 (s, 1H), 8.24 (d, 1H), 7.39 (s, 1H), 7.09-7.19 (m, 3H), 6.82 (d, 2H), 6.53 (br, 2H), 3.97 (t, 2H), 3.60 (s, 3H), 3.19 (t, 2H), 3.04 (t, 2H), 2.48 (t, 2H), 2.44 (s, 3H), 0.84-0.91 (m, 2H). LRMS [M+H]=430.2.

Example 159

4-(4-(2-(5-amino-8-methylbenzo[f][1,7]naphthyridin-2-yl)ethyl)phenoxy)butanoic acid

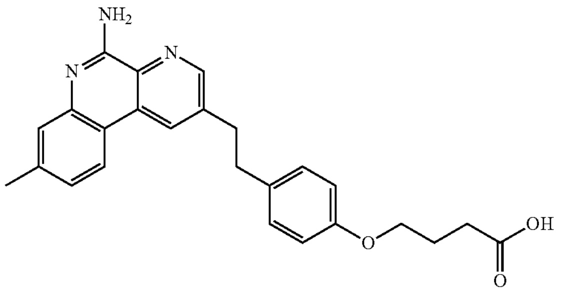 [SMILES: Cc1ccc2c(c1)nc(N)c1ncc(CCc3ccc(OCCCC(=O)O)cc3)cc12]

4-(4-(2-(5-Amino-8-methylbenzo[f][1,7]naphthyridin-2-yl)ethyl)phenoxy)butanoic acid was prepared from methyl 4-(4-(2-(5-amino-8-methylbenzo[f][1,7]naphthyridin-2-yl) ethyl)phenoxy)butanoate (from the previous step) following the procedure described for Example 144. $^1$H NMR (Acetone-$d_6$): δ 7.47 (s, 1H), 7.41 (s, 1H), 7.09 (d, 1H), 6.21 (s, 1H), 6.18 (d, 1H), 5.82 (d, 2H), 5.52 (d, 2H), 2.66 (t, 2H), 1.99 (t, 2H), 1.77 (t, 2H), 1.28 (s, 3H), 1.17 (t, 2H), 0.70-0.79 (m, 2H). LRMS [M+H]=416.2.

Example 160

4-(4-(2-(5-amino-8-methylbenzo[f][1,7]naphthyridin-2-yl)ethyl)-3-methylphenoxy)butanoic acid

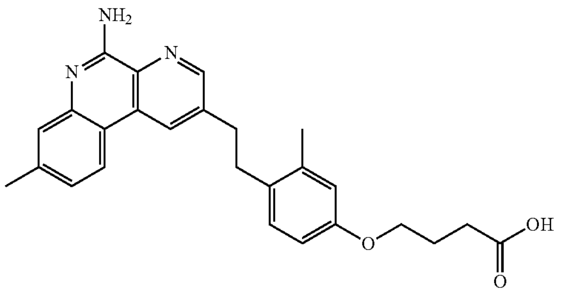 [SMILES: Cc1ccc2c(c1)nc(N)c1ncc(CCc3ccc(OCCCC(=O)O)cc3C)cc12]

Step 1: methyl 4-(4-(2-(5-amino-8-methylbenzo[f][1,7]naphthyridin-2-yl)ethyl)-3-methylphenoxy) butanoate Methyl 4-(4-(2-(5-amino-8-methylbenzo[f][1,7]naphthyridin-2-yl)ethyl)-3-methylphenoxy)butanoate was prepared following the same procedure described for the preparation of Example 158, but using 4-(2-(5-amino-8-methylbenzo[f][1,7]naphthyridin-2-yl)ethyl)-3-methylphenol (from Example 50).

Step 2: 4-(4-(2-(5-Amino-8-methylbenzo[f][1,7]naphthyridin-2-yl)ethyl)-3-methylphenoxy)butanoic acid 4-(4-(2-(5-Amino-8-methylbenzo[f][1,7]naphthyridin-2-yl)ethyl)-3-methylphenoxy)butanoic acid was prepared from methyl 4-(4-(2-(5-amino-8-methylbenzo[f][1,7]naphthyridin-2-yl)ethyl)-3-methylphenoxy)butanoate (from the previous step) following the procedure described for Example 144. $^1$H NMR (Acetone-$d_6$): δ 8.38 (s, 1H), 8.24 (s, 1H), 7.90 (d, 1H), 6.90 (s, 1H), 6.68 (d, 1H), 6.54-6.63 (m, 2H), 6.27 (d, 1H), 6.20 (d, 1H), 3.40 (t, 2H), 2.62 (t, 2H), 2.47 (t, 2H), 1.99 (s, 3H), 1.80 (s, 2H), 1.45 (t, 2H), 1.27-1.39 (m, 2H). LRMS [M+H]=430.2.

Example 161

2-(4-(isopentyloxy)-2-methylphenethyl)-8-methylbenzo[f][1,7]naphthyridin-5-amine

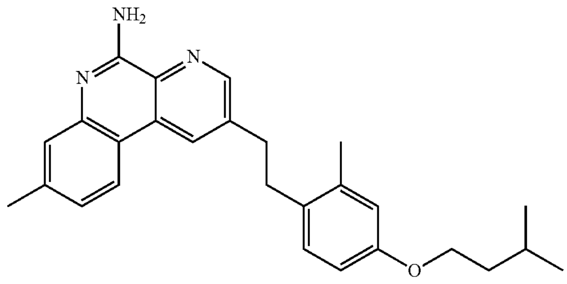 [SMILES: Cc1ccc2c(c1)nc(N)c1ncc(CCc3ccc(OCCC(C)C)cc3C)cc12]

2-(4-(Isopentyloxy)-2-methylphenethyl)-8-methylbenzo[f][1,7]naphthyridin-5-amine was prepared from 4-(2-(5-amino-8-methylbenzo[f][1,7]naphthyridin-2-yl)ethyl)-3-methylphenol (from Example 50) following the procedure described for Example 136, but using 1-bromo-3-methylbutane. $^1$H NMR (Acetone-$d_6$): δ 8.75 (s, 1H), 8.72 (s, 1H), 8.29 (d, 1H), 7.43 (s, 1H), 7.17 (D, 1H), 7.10 (d, 1H), 6.76 (d, 1H), 6.68 (d, 1H), 6.56 (br, 2H), 4.00 (t, 2H), 3.17 (t, 2H), 3.07 (t, 2H), 2.48 (s, 3H), 1.76-1.91 (m, 1H), 1.60-1.71 (m, 2H), 0.96 (s, 6H). LRMS [M+H]=414.2.

Example 162

4-(2-(5-amino-8-methylbenzo[f][1,7]naphthyridin-2-yl)ethyl)phenyl hexyl carbonate

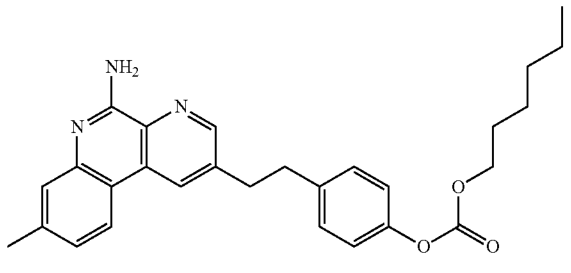 [SMILES: CCCCCCOC(=O)Oc1ccc(CCc2cnc3c(N)nc4cc(C)ccc4c3c2)cc1]

4-(2-(5-Amino-8-methylbenzo[f][1,7]naphthyridin-2-yl)ethyl)phenyl hexyl carbonate was prepared from 4-(2-(5-amino-8-methylbenzo[f][1,7]naphthyridin-2-yl)ethyl)phenol (from Example 170) following the procedures described for Example 138, but using hexyl carbonochloridate. LRMS [M+H]=458.2.

Example 163

2-(2,4,6-trimethylphenethyl)benzo[f][1,7]naphthyridin-5-amine

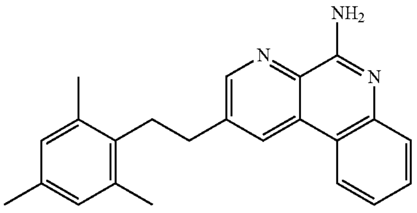 [SMILES: Cc1cc(C)c(CCc2cnc3c(N)nc4ccccc4c3c2)c(C)c1]

Step 1: 2-(mesitylethynyl)benzo[f][1,7]naphthyridin-5-amine 2-(Mesitylethynyl)benzo[f][1,7]naphthyridin-5-amine was prepared from 3-chloro-5-(mesitylethynyl)picolinonitrile (Example 77/Step 1) and tert-butyl 2-(4,4,5,5-tetramethyl-1,3,2-dioxaborolan-2-yl)phenylcarbamate (commercially available) following the procedures described for Example 45/Step 1.

Step 2: 2-(2,4,6-Trimethylphenethyl)benzo[f][1,7]naphthyridin-5-amine 2-(2,4,6-Trimethylphenethyl)benzo[f][1,7]naphthyridin-5-amine was prepared from 2-(mesitylethynyl)benzo[f][1,7]naphthyridin-5-amine (from the previous step) following the procedures described for Example 45/Step 2 to 3. $^1$H NMR (Acetone-$d_6$): δ 8.80 (s, 2H), 8.38 (d, 1H), 7.60 (d, 2H), 7.54 (d, 2H), 7.31 (t, 1H), 6.84 (s, 2H), 6.61 (br, 2H), 3.08 (s, 2H), 2.30 (s, 6H), 2.23 (s, 3H). LRMS [M+H]=342.2.

Example 164

(5-amino-2-(2,4-dimethylphenethyl)benzo[f][1,7]naphthyridin-8-yl)methanol

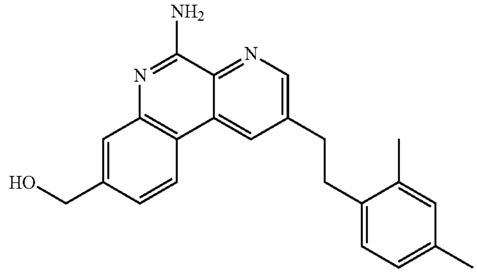 [SMILES: Cc1ccc(CCc2cnc3c(N)nc4cc(CO)ccc4c3c2)c(C)c1]

Step 1: methyl 5-amino-2-((2,4-dimethylphenyl)ethynyl)benzo[f][1,7]naphthyridine-8-carboxylate Methyl 5-amino-2-((2,4-dimethylphenyl)ethynyl)benzo[f][1,7]naphthyridine-8-carboxylate was prepared from 3-chloro-5-((2,4-d methylphenyl) ethynyl)picolinonitrile (from Example 47/Step 3) and 2-(tert-butoxycarbonylamino)-4-(methoxycarbonyl)phenylboronic acid (from Example 85/Step 1) following the procedures described in Example 95/step 1.

Step 2: methyl 5-amino-2-(2,4-dimethylphenethyl) benzo[f][1,7]naphthyridine-8-carboxylate Methyl 5-amino-2-(2,4-dimethylphenethyl)benzo[f][1,7] naphthyridine-8-carboxylate was prepared from methyl 5-amino-2-((2,4-dimethylphenyl)ethynyl)benzo[f][1,7] naphthyridine-8-carboxylate (from the previous step) following the procedures described in Example 44/Step 5.

Step 3: (5-amino-2-(2,4-dimethylphenethyl)benzo[f] [1,7]naphthyridin-8-yl)methanol (5-Amino-2-(2,4-dimethylphenethyl)benzo[f][1,7]naphthyridin-8-yl)methanol was prepared from methyl 5-amino-2-(2,4-dimethylphenethyl)benzo[f][1,7]naphthyridine-8-carboxylate (from the previous step) following the procedures described in Example 95/Step 2. $^1$H NMR (Acetone-$d_6$): δ 8.79 (s, 1H), 8.73 (s, 1H), 8.35 (d, 1H), 7.61 (s, 1H), 7.34 (d, 1H), 7.08 (d, 1H), 6.97 (s, 1H), 6.91 (d, 1H), 6.51 (br. 2H), 4.77 (s, 2H), 3.16-3.20 (m, 2H), 3.04-3.10 (m, 2H), 2.28 (s, 3H), 2.25 (s, 3H). LRMS [M+H]=358.2.

Example 165 diethyl 3-(2-(4-(2-(5-amino-8-methylbenzo[f][1,7] naphthyridin-2-yl)ethyl)-3-methylphenoxy)ethoxy) propylphosphonate

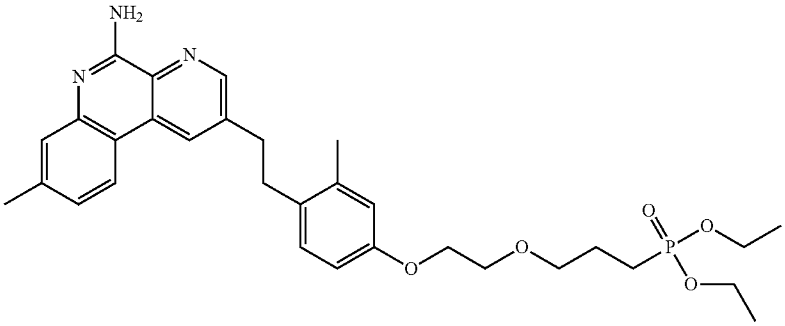 [SMILES: CCOP(=O)(CCCOCCOc1ccc(CCc2cnc3c(N)nc4cc(C)ccc4c3c2)c(C)c1)OCC]

-

Diethyl 3-(2-(4-(2-(5-amino-8-methylbenzo[f][1,7]naphthyridin-2-yl)ethyl)-3-methylphenoxy)ethoxy)propylphosphonate was prepared following the procedure described for Example 139, but using 4-(2-(5-amino-8-methylbenzo[f][1,7]naphthyridin-2-yl)ethyl)-3-methylphenol (from Example 156) and diethyl 3-(2-bromoethoxy)propylphosphonate. LRMS [M+H]=566.3.

Example 166 diethyl 3-(2-(2-(4-(2-(5-amino-8-methylbenzo[f][1,7]naphthyridin-2-yl)ethyl)-3-methylphenoxy)ethoxy) ethoxy)propylphosphonate

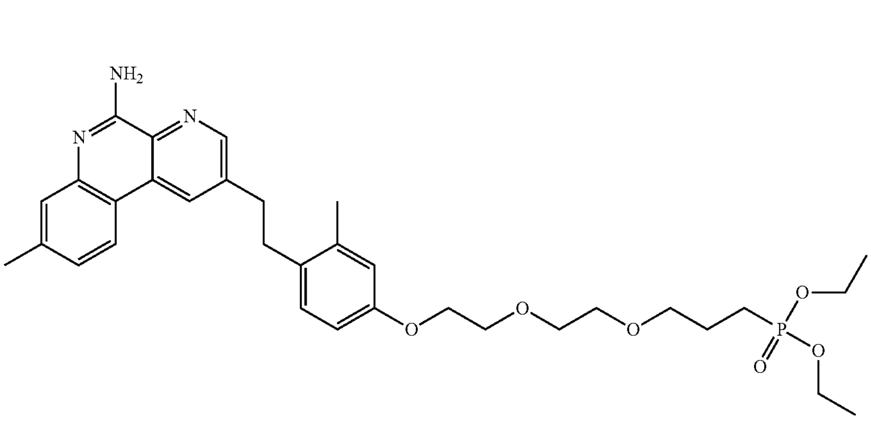 [SMILES: CCOP(=O)(CCCOCCOCCOc1ccc(CCc2cnc3c(N)nc4cc(C)ccc4c3c2)c(C)c1)OCC]

Diethyl 3-(2-(2-(4-(2-(5-amino-8-methylbenzo[f][1,7]naphthyridin-2-yl)ethyl)-3-methylphenoxy)ethoxy)ethoxy)propylphosphonate was prepared from following the procedure described for Example 139, but using 4-(2-(5-amino-8-methylbenzo[f][1,7]naphthyridin-2-yl)ethyl)-3-methylphenol (from Example 148) and diethyl 3-(2-(2-bromoethoxy)ethoxy)propylphosphonate. $^1$H NMR (Acetone-$d_6$): δ 8.75 (s, 1H), 8.70 (s, 1H), 8.26 (d, 1H), 7.42 (s, 1H), 7.16 (d, 1H), 7.09 (d, 1H), 6.77 (s, 1H), 6.71 (d, 1H), 6.58 (br, 2H), 3.95-4.11 (m, 6H), 3.76-3.80 (m, 2H), 3.63-3.67 (m, 2H), 3.55-3.58 (m, 2H), 3.57-3.51 (m, 2H), 3.14-3.18 (m, 2H), 3.04-3.05 (m, 2H), 2.46 (s, 3H), 2.29 (s, 3H), 1.71-1.87 (m, 4H), 1.22-1.29 (m, 8H). LRMS [M+H]=610.3.

Example 167

4-(2-(5-amino-8-methylbenzo[f][1,7]naphthyridin-2-yl)ethyl)-3-methylphenyl dimethylsulfamate

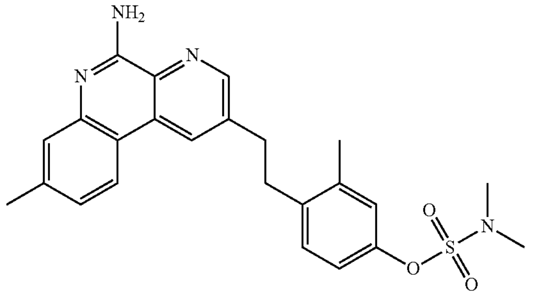

4-(2-(5-Amino-8-methylbenzo[f][1,7]naphthyridin-2-yl)ethyl)-3-methylphenyl dimethylsulfamate was prepared from 4-(2-(5-amino-8-methylbenzo[f][1,7]naphthyridin-2-yl)ethyl)-3-methylphenol (from Example 50) following the procedure described for Example 138, but using dimethylsulfamoyl chloride. $^1$H NMR (Acetone-$d_6$): δ 8.79 (s, 1H), 8.72 (s, 1H), 8.28 (d, 1H), 7.42 (s, 1H), 7.27 (d, 1H), 7.17 (s, 1H), 7.14 (t, 1H), 7.05-7.10 (d, 1H), 3.19-3.25 (m, 2H), 3.11-3.17 (m, 2H), 2.92 (s, 6H), 2.46 (s, 3H), 2.37 (s, 3H). LRMS [M+H]=451.2.

Example 168

(5-amino-2-(4-(dimethylamino)phenethyl)benzo[f][1,7]naphthyridin-8-yl)methanol

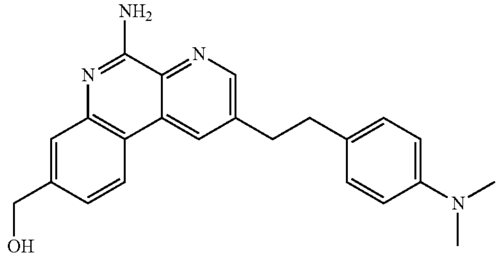 [SMILES: CN(C)c1ccc(CCc2cnc3c(N)nc4cc(CO)ccc4c3c2)cc1]

(5-Amino-2-(4-(dimethylamino)phenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 99/step 1) and 4-ethynyl-N,N-dimethylaniline (commercially available) following the procedures described in Example 45/Step 1 to 4 followed by deprotection of TBS group as in Example 99/Step 3. $^1$H NMR (Acetone-$d_6$): δ 8.78 (s, 1H), 8.73 (s, 1H), 8.35 (d, 1H), 7.61 (s, 1H), 7.31-7.35 (d, 1H), 7.08 (d, 1H), 6.68 (d, 2H), 6.50 (br, 2H), 4.78 (s, 2H), 4.34 (s, 1H), 3.16-3.20 (m, 2H), 3.03-3.10 (m, 2H), 2.83 (s, 3H), 2.80 (s, 3H). LRMS [M+H]=373.2.

Example 169

2-(4-(dimethylamino)phenethyl)-8-methylbenzo[f][1,7]naphthyridin-5-amine

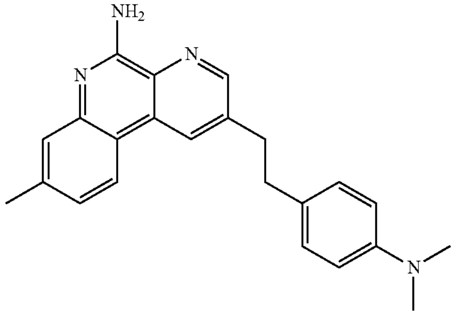

2-(4-(Dimethylamino)phenethyl)-8-methylbenzo[f][1,7]naphthyridin-5-amine was prepared following the procedures described for Example 45/Steps 1 to 3, but using 4-ethynyl-N,N-dimethylaniline in step 1. $^1$H NMR (Acetone-$d_6$) Free base: δ 8.60 (s, 1H), 8.55 (s, 1H), 8.15 (d, 1H), 7.28 (s, 1H), 7.03 (d, 1H), 6.96 (d, 2H), 6.56 (d, 2H), 6.55 (br s, 2H), 3.05 (t, 2H), 2.88 (t, 2H), 2.75 (s, 6H), 2.33 (s, 3H). LRMS [M+H]=357.2

Example 170

4-(2-(5-amino-8-methylbenzo[f][1,7]naphthyridin-2-yl)ethyl)phenol

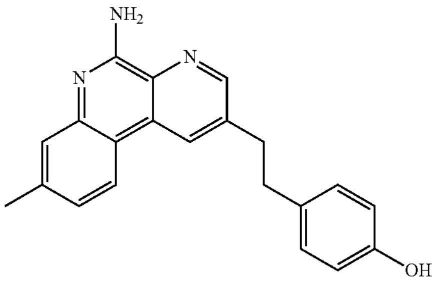 [SMILES: Cc1ccc2c(c1)nc(N)c1ncc(CCc3ccc(O)cc3)cc12]

Step 1: 2-(4-methoxyphenethyl)-8-methylbenzo[f][1,7]naphthyridin-5-amine 2-(4-methoxyphenethyl)-8-methylbenzo[f][1,7]naphthyridin-5-amine was prepared following the procedures described for Example 79/Steps 1 to 3, but using 1-ethynyl-4-methoxybenzene in Step 1.

Step 2: 4-(2-(5-Amino-8-methylbenzo[f][1,7]naphthyridin-2-yl)ethyl)phenol 4-(2-(5-Amino-8-methylbenzo[f][1,7]naphthyridin-2-yl)ethyl)phenol was prepared from 2-(4-methoxyphenethyl)-8-methylbenzo[f][1,7]naphthyridin-5-amine (from the previous step) following the procedure described for Example 50. $^1$H NMR (Methanol-$d_4$): δ 8.59

Example 171

1-(4-(2-(5-amino-8-methylbenzo[f][1,7]naphthyridin-2-yl)ethyl)phenyl)ethanone

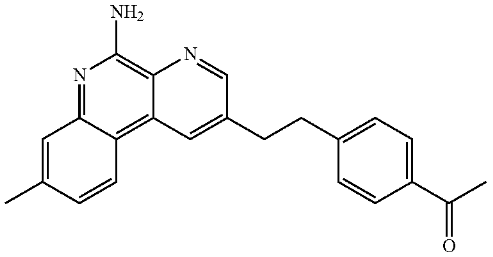 [SMILES: CC(=O)c1ccc(CCc2cnc3c(N)nc4cc(C)ccc4c3c2)cc1]

Step 1: 5-((4-acetylphenyl)ethynyl)-3-chloropicolinonitrile

To a solution of 1-(4-ethynylphenyl)ethanone (commercially available) (1 eq) 3,5-dichloropicolinonitrile (1 eq), dichlorobis(triphenylphosphine)-palladium (II) (20 mol %), copper iodide (10 mol %) and DMF:Triethylamine (10:1) (0.13 M) was stirred at ambient temperature overnight. The reaction mixture was then diluted with ethyl acetate and sodium bi-carbonate solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 5-((4-acetylphenyl)ethynyl)-3-chloropicolinonitrile was isolated as a yellow solid Step 2: 5-(4-acetylphenethyl)-3-chloropicolinonitrile To a solution of 5-((4-acetylphenyl)ethynyl)-3-chloropicolinonitrile (from the previous step) (1 eq) in ethanol (0.1 M) was added Platinum Oxide (30 mol %). Hydrogen gas was introduced via a balloon, and the reaction was stirred for 0.5 hour. The mixture was filtered through a pad of celite, washing with dichloromethane. The filtrate was concentrated en vaccuo and purified by flash chromatography on a COMBIFLASH® system (ISCO) using 0-100% ethyl acetate in hexane to give 5-(4-acetylphenethyl)-3-chloropicolinonitrile as an off-white solid.

Step 3: 1-(4-(2-(5-amino-8-methylbenzo[f][1,7]naphthyridin-2-yl)ethyl)phenyl)ethanone To a solution of 5-(4-acetylphenethyl)-3-chloropicolinonitrile (from the previous step) (1 eq) and tert-butyl 5-methyl-2-(4,4,5,5-tetramethyl-1,3,2-dioxaborolan-2-yl)phenylcarbamate (1.0 eq.), tetrakis(triphenyl-phosphine) palladium (10 mol %), and 2N aqueous sodium carbonate solution (2.0 eq.) in toluene/ethanol (1:1, 0.09 M) was heated under microwave condition using a BIOTAGE INITIATOR 2.0 at 150° C. for 20 minutes. After cooling to ambient temperature, the reaction mixture was diluted with ethanol/water. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 1-(4-(2-(5-amino-8-methylbenzo[f][1,7]naphthyridin-2-yl)ethyl)phenyl)ethanone as a yellow solid. $^1$H NMR (Methanol-$d_4$) TFA Salt: δ 8.69 (d, 2H), 8.30 (d, 1H), 7.80 (d, 2H), 7.38 (s, 1H), 7.36 (d, 1H), 7.28 (d, 2H), 3.25 (t, 2H), 3.13 (t, 2H), 2.47 (s, 3H), 2.45 (s, 3H). LRMS [M+H]=356.2

Example 172

2-(4-((dimethylamino)methyl)phenethyl)-8-methylbenzo[f][1,7]naphthyridin-5-amine

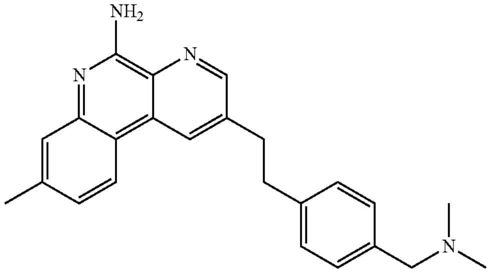

Step 1: 4-(2-(5-amino-8-methylbenzo[f][1,7]naphthyridin-2-yl)ethyl)benzaldehyde 4-(2-(5-Amino-8-methylbenzo[f][1,7]naphthyridin-2-yl)ethyl)benzaldehyde was prepared from 4-ethynylbenzaldehyde (commercially available) following the procedures described for Example 171/Steps 1 to 3.

Step 2: 2-(4-((dimethylamino)methyl)phenethyl)-8-methylbenzo[f][1,7]naphthyridin-5-amine A solution of 4-(2-(5-amino-8-methylbenzo[f][1,7]naphthyridin-2-yl)ethyl)benzaldehyde (from the previous step) (1 eq), sodium acetate (3.5 eq) and N,N'-dimethyl amine hydrochloride (3.5 eq) dissolved in 1-2, dichloroethane (0.04 M) was heated at 80° C. for 2 hours in a sealed vial. After cooling to ambient temperature, the reaction mixture was further cooled down to 0° C. and sodium tri-acetoxy borohydride (1.25 eq) was added. The reaction mixture was stirred at room temperature for one hour. The mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by preparative HPLC using 10-90% acetonitrile/water as the gradient and 2-(4-((dimethylamino)methyl)phenethyl)-8-methylbenzo[f][1,7]naphthyridin-5-amine was isolated as a off-white powder as a TFA salt. $^1$H NMR (Methanol-$d_4$) TFA Salt: δ 8.83 (s, 1H), 8.81 (s, 1H), 8.41 (d, 1H), 7.52 (s, 1H), 7.45 (d, 1H), 7.43 (s, 1H), 7.40 (m, 3H), 4.29 (s, 2H), 3.30-3.24 (m, 4H), 2.79 (s, 6H), 2.60 (s, 3H). LRMS [M+H]=371.2

Example 173

2-(4-(1-(dimethylamino)ethyl)phenethyl)-8-methylbenzo[f][1,7]naphthyridin-5-amine

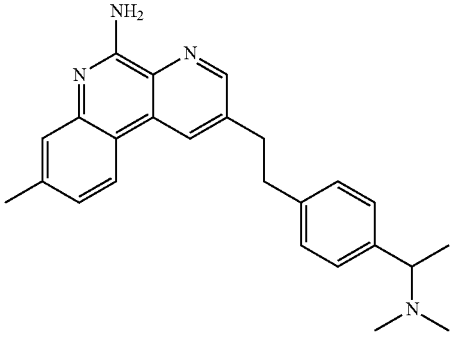

2-(4-(1-(Dimethylamino)ethyl)phenethyl)-8-methylbenzo[f][1,7]naphthyridin-5-amine was prepared from 1-(4-(2-(5-amino-8-methylbenzo[f][1,7]naphthyridin-2-yl)ethyl)phenyl)ethanone (from Example 171) following the procedures described for Example 172/Step 2. $^1$H NMR (Methanol-$d_4$) TFA_Salt: δ 8.84 (s, 1H), 8.79 (s, 1H), 8.40 (d, 1H), 7.52 (s, 1H), 7.44-7.46 (m, 2H), 7.38-7.42 (m, 3H), 4.45 (m, 1H), 3.31 (t, 2H), 3.19 (t, 2H), 2.83 (s, 3H), 2.66 (s, 3H), 2.56 (s, 3H), 1.70 (d, 3H). LRMS [M+H]=385.2

Example 174

1-(4-(2-(5-amino-8-methylbenzo[f][1,7]naphthyridin-2-yl)ethyl)phenyl)ethanone oxime

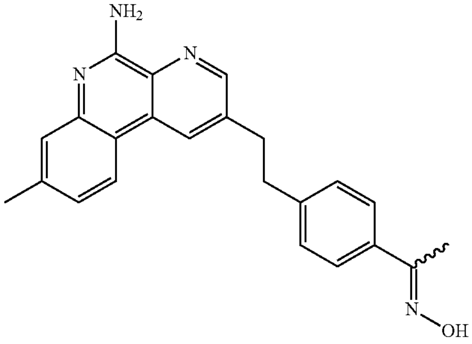

A solution of 1-(4-(2-(5-amino-8-methylbenzo[f][1,7]naphthyridin-2-yl)ethyl)phenyl)ethanone (from Example 171) (1 eq), hydroxylamine hydrochloride (2 eq) and 1 drop of HOAc, dissolved in absolute ethanol (0.028M) was stirred at room temperature for 1.5 hours. The mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 10-80% ethyl acetate in hexane to give 1-(4-(2-(5-amino-8-methylbenzo[f][1,7]naphthyridin-2-yl)ethyl)phenyl)ethanone oxime as a white solid. $^1$H NMR (Methanol-$d_4$): δ 8.56

(s, 1H), 8.52 (s, 1H), 8.12 (d, 1H), 7.45 (d, 2H), 7.31 (s, 1H), 7.12 (m, 3H), 4.51 (s, OH), 3.15 (t, 2H), 3.01 (t, 2H), 2.39 (s, 3H), 2.09 (s, 3H). LRMS [M+H]=371.2

Example 175

8-methyl-2-(4-((methylamino)methyl)phenethyl)benzo[f][1,7]naphthyridin-5-amine

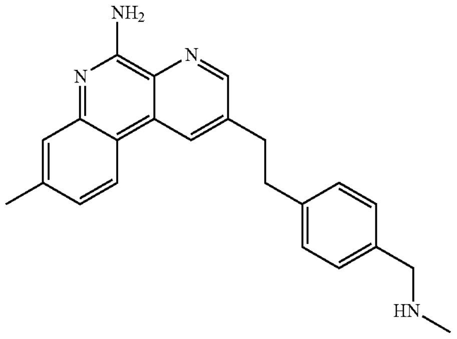

8-Methyl-2-(4-((methylamino)methyl)phenethyl)benzo[f][1,7]naphthyridin-5-amine was prepared from 4-(2-(5-Amino-8-methylbenzo[f][1,7]naphthyridin-2-yl)ethyl)benzaldehyde (from Example 172/Step 1) and methylamine following the procedures described for Example 172, step 2. $^1$H NMR (Acetone-$d_6$) TFA Salt: δ 8.95 (s, 1H), 8.88 (s, 1H), 8.43 (d, 1H), 7.58 (s, 1H), 7.54 (d, 2H), 7.42 (d, 1H), 7.37 (d, 2H), 4.30 (s, 2H), 3.32-3.37 (m, 4H), 2.75 (s, 3H), 2.55 (s, 3H). LRMS [M+H]=357.2

Example 176

(4-(2-(5-amino-8-methylbenzo[f][1,7]naphthyridin-2-yl)ethyl)benzylamino)ethanol

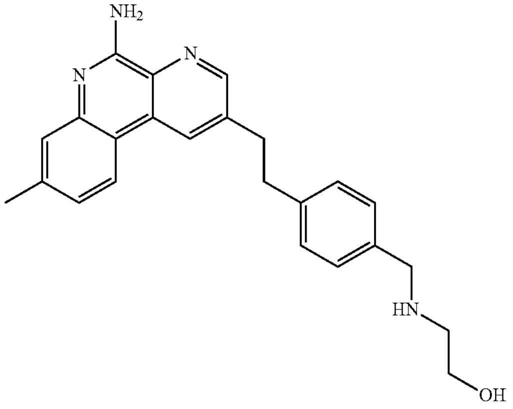 [SMILES: Cc1ccc2c(c1)nc(N)c1ncc(CCc3ccc(CNCCO)cc3)cc12]

A solution of 4-(2-(5-amino-8-methylbenzo[f][1,7]naphthyridin-2-yl)ethyl)benzaldehyde (from Example 172/Step 1) (1 eq), ethanol amine (8 eq) and 1 drop of HOAc, dissolved in absolute ethanol (0.018M) was stirred at 80° C. for 2 hours. The mixture was cooled down to 0° C. and $NaBH_4$ (3.5 eq) was added and the reaction mixture was stirred for another one hour at room temperature. The mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give a light yellow solid as a TFA salt. $^1$H NMR (Acetone-$d_6$) TFA Salt: δ 8.82 (s, 1H), 8.75 (s, 1H), 8.30 (d, 1H), 7.44 (m, 3H), 7.28 (d, 1H), 7.21 (d, 2H), 4.22 (s, 2H), 3.72 (t, 2H), 3.22 (t, 2H), 3.09 (m, 2H), 3.07 (t, 2H), 3.01 (bs, OH), 2.41 (s, 3H). LRMS [M+H]=387.2

Example 177

8-methyl-2-(4-(pyrrolidin-1-ylmethyl)phenethyl) benzo[f][1,7]naphthyridin-5-amine

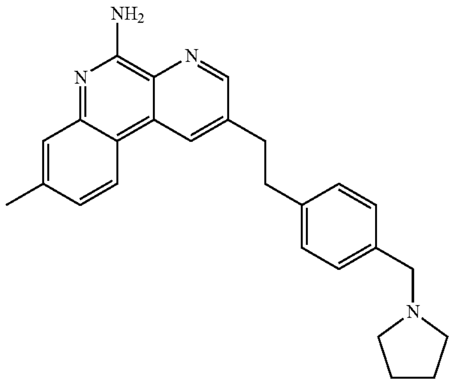 [SMILES: Cc1ccc2c(c1)nc(N)c1ncc(CCc3ccc(CN4CCCC4)cc3)cc12]

8-Methyl-2-(4-(pyrrolidin-1-ylmethyl)phenethyl)benzo [f][1,7]naphthyridin-5-amine was prepared from 4-(2-(5-Amino-8-methylbenzo[f][1,7]naphthyridin-2-yl)ethyl)benzaldehyde (from Example 172/Step 1) and pyrrolidine following the procedures described for Example 172, step 2. $^1$H NMR (Acetone-$d_6$) TFA Salt: δ 8.88 (s, 1H), 8.82 (s, 1H), 8.82 (s, 1H), 8.43 (d, 1H), 8.38 (d, 1H), 7.58 (s, 1H), 7.51 (m, 1H), 7.33 (d, 2H), 4.16 (s, 2H), 3.32-3.38 (m, 4H), 2.55 (s, 3H), 2.20-2.32 (m, 4H), 1.90-1.99 (m, 4H). LRMS [M+H]=397.2

Example 178

2-(3,4-dimethoxyphenethyl)-8-methylbenzo[f][1,7] naphthyridin-5-amine

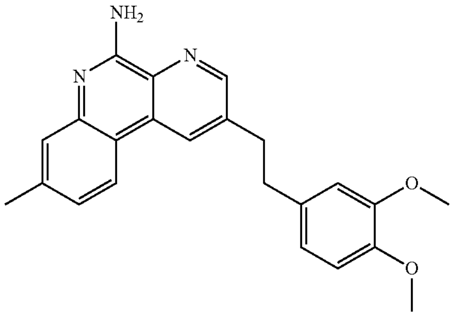

2-(3,4-Dimethoxyphenethyl)-8-methylbenzo[f][1,7] naphthyridin-5-amine was prepared from 4-ethynyl-1,2-dimethoxybenzene (commercially available) following the procedures described for Example 45/Steps 1 to 3. $^1$H NMR (Acetone-$d_6$): δ 8.64 (s, 1H), 8.56 (s, 1H), 8.14 (d, 1H), 7.29 (s, 1H), 7.03 (d, 1H), 6.77 (s, 1H), 6.71 (s, 1H), 6.62 (d, 1H), 6.45 (bs, 2H), 3.62 (s, 6H), 3.12 (t, 2H), 2.94 (t, 2H), 2.33 (s, 3H). LRMS [M+H]=374.2

Example 179

2-(1-(4-(2-(5-amino-8-methylbenzo[f][1,7]naphthyridin-2-yl)ethyl)phenyl)ethylamino)ethanol

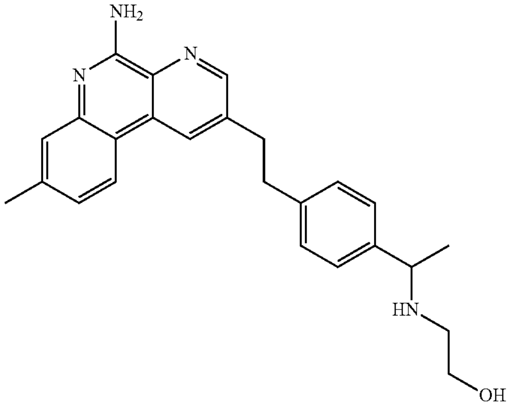

2-(1-(4-(2-(5-Amino-8-methylbenzo[f][1,7]naphthyridin-2-yl)ethyl)phenyl)ethylamino)ethanol (from Example 171) was prepared from 1-(4-(2-(5-amino-8-methylbenzo[f][1,7] naphthyridin-2-yl)ethyl)phenyl)ethanone and ethanol amine (commercially available) following the procedures described for Example 176. $^1$H NMR (Acetone-$d_6$) of TFA Salt: δ 8.78 (d, 1H), 8.29 (d, 1H), 7.83 (s, 1H), 7.45 (m, 3H), 7.28 (m, 3H), 4.22 (m, 1H), 3.52 (m, 2H), 3.23 (t, 2H), 3.09 (t, 2H), 2.85 (m, 1H), 2.65 (m, 1H), 2.41 (s, 3H), 1.61 (d, 3H). LRMS [M+H]=401.2

Example 180

1-(4-(2-(5-amino-8-methylbenzo[f][1,7]naphthyridin-2-yl)ethyl)phenyl)ethanol

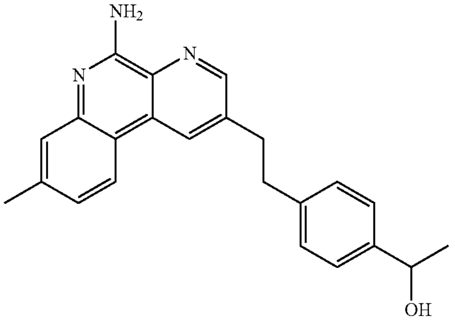 [SMILES: Cc1ccc2c(c1)nc(N)c1ncc(CCc3ccc(C(C)O)cc3)cc12]

1-(4-(2-(5-Amino-8-methylbenzo[f][1,7]naphthyridin-2-yl)ethyl)phenyl)ethanol (from Example 171) was isolated as a side product during the reductive amination as shown in Example 173. $^1$H NMR (Acetone-$d_6$) of TFA Salt: δ 8.90 (s, 1H), 8.88 (s, 1H), 8.42 (d, 1H), 7.57 (s, 1H), 7.43 (d, 1H), 7.33 (d, 2H), 7.26 (d, 2H), 4.82 (q, 1H), 3.32 (t, 2H), 3.17 (t, 2H), 3.01-2.55 (s, 3H), 1.41 (s, 3H). LRMS [M+H]=358.2

Example 181

8-methyl-2-(4-(oxazol-5-yl)phenethyl)benzo[f][1,7] naphthyridin-5-amine

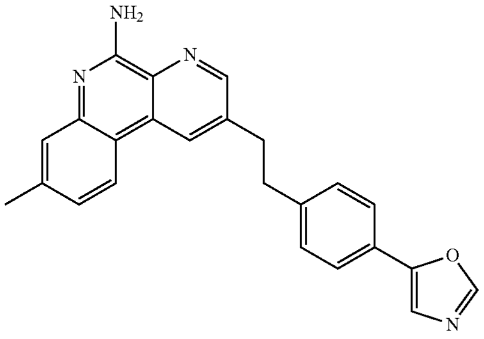 [SMILES: Cc1ccc2c(c1)nc(N)c1ncc(CCc3ccc(-c4cnco4)cc3)cc12]

8-Methyl-2-(4-(oxazol-5-yl)phenethyl)benzo[f][1,7] naphthyridin-5-amine was prepared from 5-(4-ethynylphenyl)oxazole (commercially available) following the procedures described for Example 45/Steps 1 to 3. $^{1}$H NMR (Acetone-$d_6$) of TFA Salt: 8.69 (s, 1H), 8.59 (s, 1H), 8.16 (d, 1H), 8.04 (s, 1H), 7.55 (m, 2H), 7.38 (s, 1H), 7.28 (m, 2H), 7.01 (m, 2H), 3.16 (t, 2H), 3.07 (t, 2H), 2.33 (s, 3H). LRMS [M+H]=381.2

Example 182

3-(1-(4-(2-(5-amino-8-methylbenzo[f][1,7]naphthyridin-2-yl)ethyl)phenyl)ethylamino)propanenitrile

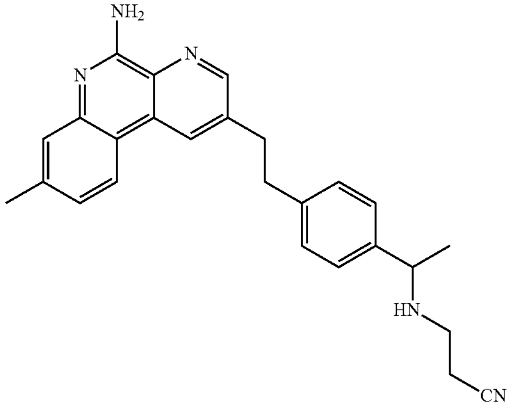 [SMILES: Cc1ccc2c(c1)nc(N)c1ncc(CCc3ccc(C(C)NCCC#N)cc3)cc12]

A solution of 1-(4-(2-(5-amino-8-methylbenzo[f][1,7] naphthyridin-2-yl)ethyl)phenyl)ethanone (from Example 171) (1 eq), 3-aminopropane nitrile (commercially available) (2.5 eq) dissolved in absolute ethanol (0.014M) was stirred at 80° C. for 2 hours. The mixture was cooled to 0° C. and $NaCNBH_3$ (2 eq) was added and the reaction mixture was stirred for another hour at room temperature. The mixture was diluted with ethyl acetate and ammonium chloride. The two phases were separated, and the aqueous layer was extracted twice with ethyl acetate. The combined organic layers were washed with brine, dried over anhydrous $MgSO_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanenitrile as a light yellow solid as a TFA salt. $^{1}$H NMR (Acetone-$d_6$): δ 8.60 (s, 1H), 8.59 (s, 1H), 8.11 (d, 1H), 7.29 (s, 1H), 7.16 (d, 2H), 7.09 (d, 2H), 7.03 (d, 1H), 6.43 (bs, 2H), 3.65 (m, 1H), 3.12 (t, 2H), 2.99 (t, 2H), 2.56 (m, 2H), 2.35 (m, 2H), 2.32 (s, 3H), 1.16 (d, 3H). LRMS [M+H]=410.2

Example 183

(2R)-2-(1-(4-(2-(5-amino-8-methylbenzo[f][1,7] naphthyridin-2-yl)ethyl)phenyl)ethylamino)propan-1-ol

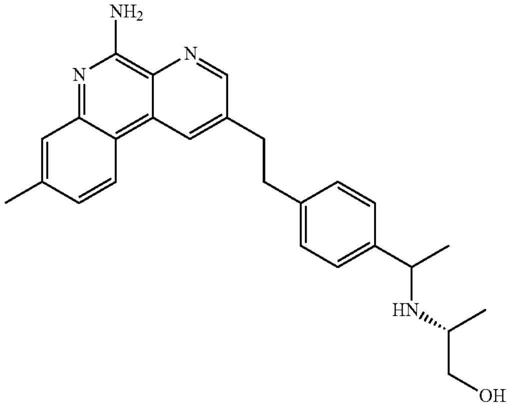

(2R)-2-(1-(4-(2-(5-amino-8-methylbenzo[f][1,7]naphthyridin-2-yl)ethyl)phenyl)ethylamino)propan-1-ol was prepared from 1-(4-(2-(5-amino-8-methylbenzo[f][1,7]naphthyridin-2-yl)ethyl)phenyl)ethanone (from Example 171) and (R)-2-aminopropan-1-ol (commercially available) following the procedures described for Example 182. $^{1}$H NMR (Acetone-$d_6$): δ 8.94 (m, 2H), 8.45 (m, 1H), 7.64 (d, 2H), 7.59 (s, 1H), 7.55 (br s, 2H), 7.41 (m, 3H), 4.65 (m, 1H), 3.81 (m, 1H), 3.35 (t, 2H), 3.25 (t, 2H), 2.56 (s, 3H), 1.73 (m, 3H), 1.29 (d, 3H), 1.23 (d, 3H). LRMS [M+H]=415.2

Example 184

8-methyl-2-(4-(1-(piperazin-1-yl)ethyl)phenethyl) benzo[f][1,7]naphthyridin-5-amine

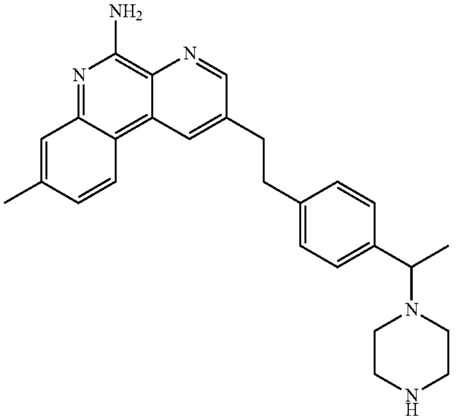 [SMILES: Cc1ccc2c(c1)nc(N)c1ncc(CCc3ccc(C(C)N4CCNCC4)cc3)cc12]

8-Methyl-2-(4-(1-(piperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and piperazine (commercially available) following the procedures described for Example 182. $^{1}H$ NMR (Methanol-$d_4$) TFA Salt: δ 8.83 (s, 1H), 8.75 (s, 1H), 8.39 (d, 1H), 7.51 (s, 1H), 7.46 (d, 1H), 7.26 (m, 4H), 3.62 (m, 1H), 3.25 (t, 2H), 3.12 (t, 2H), 2.80 (m, 4H), 2.69 (m, 4H), 2.56 (s, 3H), 1.42 (d, 3H). LRMS [M+H]=426.2

Example 185

((2S)-1-(1-(4-(2-(5-amino-8-methylbenzo[f][1,7]naphthyridin-2-yl)ethyl)phenyl)ethyl)pyrrolidin-2-yl)methanol

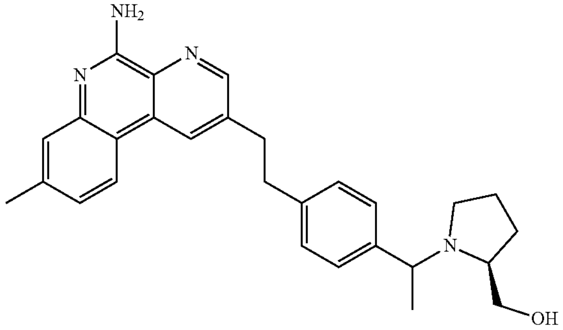 [SMILES: Cc1ccc2c(c1)nc(N)c1ncc(CCc3ccc(C(C)N4CCC[C@H]4CO)cc3)cc12]

((2S)-1-(1-(4-(2-(5-Amino-8-methylbenzo[f][1,7]naphthyridin-2-yl)ethyl)phenyl)ethyl)pyrrolidin-2-yl)methanol was prepared from 1-(4-(2-(5-amino-8-methylbenzo[f][1,7]naphthyridin-2-yl)ethyl)phenyl)ethanone (from Example 171) and (S)-pyrrolidin-2-ylmethanol (commercially available) following the procedures described for Example 182. $^{1}H$ NMR (Acetone-$d_6$) TFA Salt: δ 8.83 (s, 1H), 8.80 (s, 1H), 8.43 (d, 1H), 7.36-7.53 (m, 6H), 4.68 (m, 1H), 3.69 (m, 2H), 3.19-3.21 (m, 4H), 2.55 (m, 4H), 1.75-1.78 (m, 6H), 1.74 (d, 3H). LRMS [M+H]=441.2

Example 186

$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine

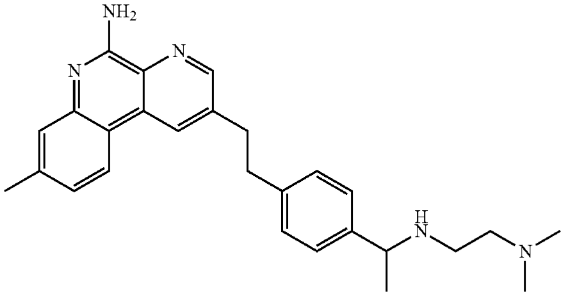

$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine was prepared from 1-(4-(2-(5-amino-8-methylbenzo[f][1,7]naphthyridin-2-yl)ethyl)phenyl)ethanone (from Example 171) and $N^1$,$N^1$-dimethylethane-1,2-diamine (commercially available) following the procedures described for Example 182. $^{1}H$ NMR (Acetone-$d_6$) TFA Salt: δ 8.85 (m, 2H), 8.43 (d, 1H), 7.52 (s, 1H), 7.48 (m, 2H), 7.40 (m, 2H), 6.69 (m, 1H), 4.39 (m, 1H), 3.42 (m, 2H), 3.18-3.25 (m, 6H), 2.87 (s, 6H), 2.56 (s, 3H), 1.69 (d, 3H). LRMS [M+H]=428.2

Example 187

3-(1-(4-(2-(5-amino-8-methylbenzo[f][1,7]naphthyridin-2-yl)ethyl)phenyl)ethylamino)propanoic acid

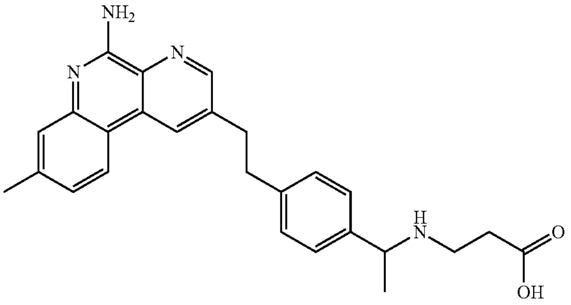 [SMILES: Cc1ccc2c(c1)nc(N)c1ncc(CCc3ccc(C(C)NCCC(=O)O)cc3)cc12]

A solution of 1-(4-(2-(5-amino-8-methylbenzo[f][1,7]naphthyridin-2-yl)ethyl)phenyl)ethanone (from Example 171) (1 eq), 3-aminopropanoic acid (commercially available) (5 eq), triethylamine (3 eq) dissolved in absolute ethanol (0.042M) was stirred at 50° C. for 3 hours. The mixture was cooled to 0° C. and $NaCNBH_3$ (1 eq) was added and the reaction mixture was stirred for another six hours at room temperature. Then another equivalent of $NaCNBH_3$ was added and the reaction mixture was stirred at 50° C. for another hour. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous $MgSO_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanoic acid a white solid as a TFA salt. $^{1}H$ NMR (Methanol-$d_4$) TFA Salt: δ 8.74 (s, 1H), 8.42 (d, 1H), 7.66 (m, 2H), 7.50 (m, 1H), 7.31 (d, 2H), 7.23 (m, 2H), 4.24 (m, 1H), 3.21 (t, 2H), 3.14 (t, 2H), 2.75-3.10 (m, 2H), 2.51 (t, 2H), 2.10 (s, 3H), 1.55 (d, 3H). LRMS [M+H]=429.2

Example 188

8-methyl-2-(4-(1-(4-methylpiperazin-1-yl)ethyl)phenethyl)benzo[f][1,7]naphthyridin-5-amine

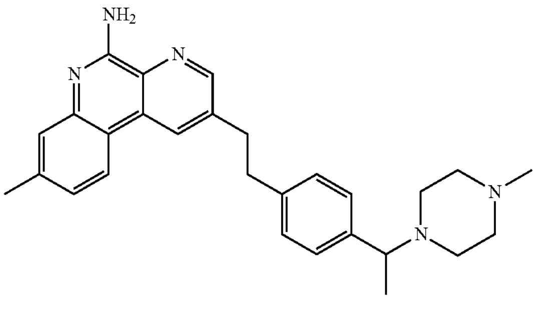

8-Methyl-2-(4-(1-(4-methylpiperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and 1-methylpiperazine (commercially available) following the procedures described for Example 182. $^1$H NMR (Acetone-$d_6$) TFA Salt: δ 8.84 (s, 1H), 8.80 (s, 1H), 8.41 (d, 1H), 7.52 (s, 1H), 7.42-7.46 (m, 3H), 7.36-7.38 (m, 2H), 3.53 (m, 1H), 3.18 (m, 2H), 3.12 (m, 2H), 2.92 (s, 2H), 2.66 (s, 2H), 2.56 (s, 2H), 2.16 (s, 3H), 1.99 (m, 2H), 1.69 (d, 3H), 1.30 (s, 3H). LRMS [M+H]=440.2

Example 189

$N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine

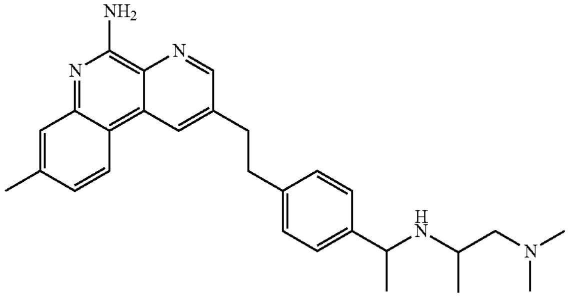

$N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine was prepared from 1-(4-(2-(5-amino-8-methylbenzo[f][1,7]naphthyridin-2-yl)ethyl)phenyl)ethanone (from Example 171) and N',N'-dimethylpropane-1,2-diamine (commercially available) following the procedures described for Example 182. $^1$H NMR (Acetone-$d_6$) TFA Salt: δ 8.83 (m, 2H), 8.40 (d, 1H), 7.46-7.51 (m, 3H), 7.43 (m, 1H), 7.37 (d, 2H), 4.54 (m, 1H), 3.74 (m, 1H), 3.19 (m, 4H), 2.90 (s, 3H), 2.77 (s, 3H), 2.55 (s, 3H), 2.41 (d, 2H), 1.66 (d, 3H), 1.39 (d, 3H). LRMS [M+H]=442.2

Example 190

8-methyl-2-(4-(1-(2-(pyridin-4-yl)ethylamino)ethyl)phenethyl)benzo[f][1,7]naphthyridin-5-amine

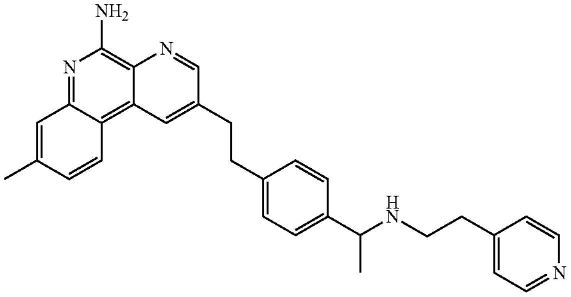 [SMILES: Cc1ccc2c(c1)nc(N)c1ncc(CCc3ccc(C(C)NCCc4ccncc4)cc3)cc12]

8-Methyl-2-(4-(1-(2-(pyridin-4-yl)ethylamino)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 171) and 2-(pyridin-4-yl)ethanamine (commercially available) following the procedures described for Example 182. $^1$H NMR (Acetone-$d_6$) TFA Salt: δ 8.94 (m, 2H), 8.92 (d, 2H), 8.73 (s, 1H), 8.43 (d, 1H), 7.60 (m, 2H), 7.40 (m, 2H), 7.16-7.26 (m, 3H), 4.55 (m, 1H), 3.55 (m, 4H), 2.56 (m, 4H), 2.12 (s, 3H), 1.73 (d, 3H) LRMS [M+H]=462.2

Example 191

$N^1$-(1-(4-(2-(5-amino-8-methylbenzo[f][1,7]naphthyridin-2-yl)ethyl)phenyl)ethyl)-$N^2$,$N^2$-diethylethane-1,2-diamine

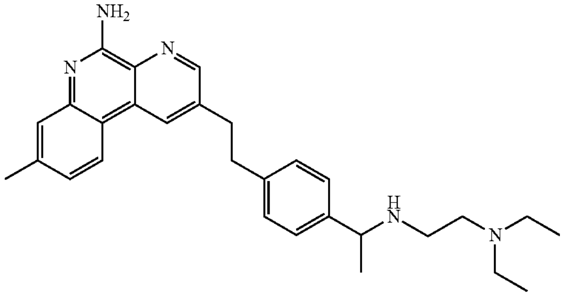 [SMILES: CCN(CC)CCNC(C)c1ccc(CCc2cnc3c(N)nc4cc(C)ccc4c3c2)cc1]

$N^1$-(1-(4-(2-(5-amino-8-methylbenzo[f][1,7]naphthyridin-2-yl)ethyl)phenyl)ethyl)-$N^2$,$N^2$-diethylethane-1,2-diamine was prepared from 1-(4-(2-(5-amino-8-methylbenzo[f][1,7]naphthyridin-2-yl)ethyl)phenyl)ethanone (from Example 171) and $N^1$,$N^1$-diethylethane-1,2-diamine (commercially available) following the procedures described for Example 182. $^1$H NMR (Acetone-$d_6$) TFA Salt: δ 8.81 (s, 1H), 8.75 (s, 1H), 8.23 (d, 1H), 7.60 (d, 2H), 7.39 (d, 2H), 7.28 (m, 2H), 4.51 (m, 1H), 3.82 (m, 1H), 3.62 (m, 1H), 3.34 (m, 4H), 3.20 (t, 2H), 2.46 (s, 3H), 2.10 (m, 4H), 1.74 (d, 3H), 1.34 (t, 6H). LRMS [M+H]=456.2

Example 192

2-(4-(dimethylamino)-2-methylphenethyl)-8-methylbenzo[f][1,7]naphthyridin-5-amine

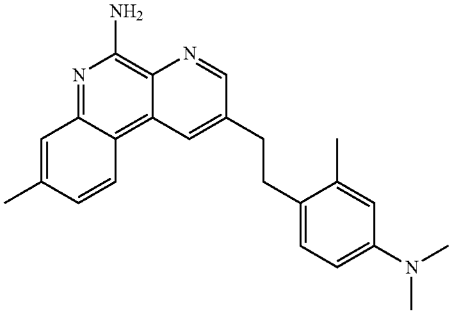

Step 1: 4-iodo-N,N,3-trimethylaniline

To a solution of 4-iodo-3-methylaniline (commercially available) (1 eq), $NaHCO_3$ (2.5 eq), and iodomethane (2.5 eq), in DMF ((0.2M) was stirred at ambient temperature overnight. The reaction mixture was then diluted with ethyl acetate and water. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-80% ethyl acetate in hexane and 4-iodo-N,N,3-trimethylaniline was isolated as a yellow solid.

Step 2: Synthesis was of N,N,3-trimethyl-4-((trimethylsilyl)ethynyl)aniline

To a solution of 4-iodo-N,N-3-trimethylaniline (from the previous step) (1 eq), ethynyltrimethylsilane (1.5 eq), dichlorobis(triphenylphosphine)-palladium (II) (20 mol %), copper iodide (20 mol %) and triethylamine (0.4 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and N,N,3-trimethyl-4-((trimethylsilyl)ethynyl)aniline was isolated as a yellow solid.

Step 3: 4-ethynyl-N,N,3-trimethylaniline

To a solution of N,N-3-trimethyl-4-((trimethylsilyl)ethynyl)aniline (from the previous step) (1 eq), $K_2CO_3$ (2.5 eq), in MeOH ((0.15M) was stirred at ambient temperature for six hours. The solids were filtered out, and the liquid was concentrated en vaccuo. The crude material was purified by flash chromatography on a COMBIFLASH® system (ISCO) using 0-80% ethyl acetate in hexane and 4-ethynyl-N,N-3-trimethylaniline was isolated as a yellow solid.

Step 4: 3-chloro-5-((4-(dimethylamino)-2-methylphenyl)ethynyl)picolinonitrile

To a solution of 4-ethynyl-N,N-3-trimethylaniline (from the previous step) (1 eq) 3,5-dichloropicolinonitrile (1.2 eq), dichlorobis(triphenylphosphine)-palladium (II) (10 mol %), copper iodide (10 mol %) and DMF: triethylamine (0.28 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 3-chloro-5-((4-(dimethylamino)-2-methylphenyl)ethynyl)picolinonitrile was isolated as a off-yellow solid.

Step 5: 2-((4-(dimethylamino)-2-methylphenyl)ethynyl)-8-methylbenzo[f][1,7]naphthyridin-5-amine A solution of tert-butyl 5-methyl-2-(4,4,5,5-tetramethyl-1,3,2-dioxaborolan-2-yl)phenylcarbamate (1.3 eq.) and 3-chloro-5-((4-(dimethylamino)-2-methylphenyl)ethynyl) picolinonitrile (from the previous step) (1.0 eq.), tetrakis (triphenyl-phosphine)palladium (10 mol %), and 2N aqueous sodium carbonate solution (2.0 eq.) in toluene/ethanol (2:1, 0.17 M) was stirred at 100° C. overnight. After cooling to ambient temperature, the reaction mixture was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 2-((4-(dimethylamino)-2-methylphenyl)ethynyl)-8-methylbenzo[f][1,7]naphthyridin-5-amine as a yellow solid.

Step 6: 2-(4-(dimethylamino)-2-methylphenethyl)-8-methylbenzo[f][1,7]naphthyridin-5-amine To a solution of 2-((4-(dimethylamino)-2-methylphenyl) ethynyl)-8-methylbenzo[f][1,7]naphthyridin-5-amine (1 eq), (from the previous step) in ethyl acetate/ethanol (1:5, 0.035 M) was added 10% wt palladium on carbon (0.2 eq.). Hydrogen gas was introduced via a balloon, and the reaction was stirred for 3.5 hours. The mixture was filtered through a pad of celite, washing with dichloromethane. The filtrate was concentrated en vaccuo and purified by preparative HPLC on a 19×50 mm ATLANTIS® 10 micron C18 (Waters Corp.) system using 10-90% Acetonitrile (0.035% TFA) in Water (0.05% TFA) to give 2-(4-(dimethylamino)-2-methylphenethyl)-8-methylbenzo[f][1,7]naphthyridin-5-amine as a white solid as a TFA salt. $^1H$ NMR (Acetone-$d_6$) TFA Salt: δ 8.81 (s, 1H), 8.74 (s, 1H), 8.34 (d, 1H), 7.89 (s, 1H), 7.47 (m, 2H), 7.38 (m, 2H), 3.34 (s, 6H), 3.32 (t, 2H), 3.28 (t, 2H), 2.57 (s, 3H), 2.34 (s, 3H). LRMS [M+H]=371.2

Example 193

1-(1-(4-(2-(5-amino-8-methylbenzo[f][1,7]naphthyridin-2-yl)ethyl)phenyl)ethyl)pyrrolidine-3-carboxylic acid

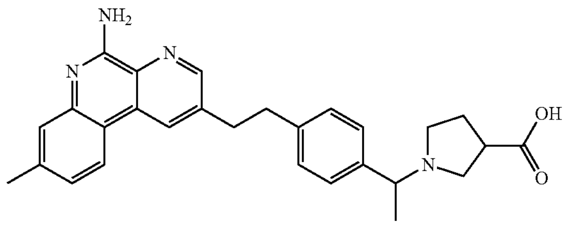 [SMILES: Cc1ccc2c(c1)nc(N)c1ncc(CCc3ccc(C(C)N4CCC(C(=O)O)C4)cc3)cc12]

1-(1-(4-(2-(5-Amino-8-methylbenzo[f][1,7]naphthyridin-2-yl)ethyl)phenyl)ethyl)pyrrolidine-3-carboxylic acid was prepared from 1-(4-(2-(5-amino-8-methylbenzo[f][1,7] naphthyridin-2-yl)ethyl)phenyl)ethanone (from Example 171) and pyrrolidine-3-carboxylic acid (commercially available) following the procedures described for Example 187, except that in this case, acetic acid was used instead of triethylamine (30%). $^1H$ NMR (Acetone-$d_6$) TFA Salt: δ 8.81 (s, 1H), 8.75 (s, 1H), 8.70 (s, 1H), 8.28 (d, 1H), 7.59 (d, 2H), 7.37 (m, 3H), 4.46 (m, 1H), 4.21 (m 1H), 3.45 (m, 2H), 3.32 (m, 2H), 3.21 (m, 2H), 3.17 (m, 2H), 2.27 (m, 2H), 2.07 (s, 3H) 1.77 (d, 3H). LRMS [M+H]=455.2

Example 194

4-(1-(4-(2-(5-amino-8-methylbenzo[f][1,7]naphthyridin-2-yl)ethyl)phenyl)ethylamino)phenol

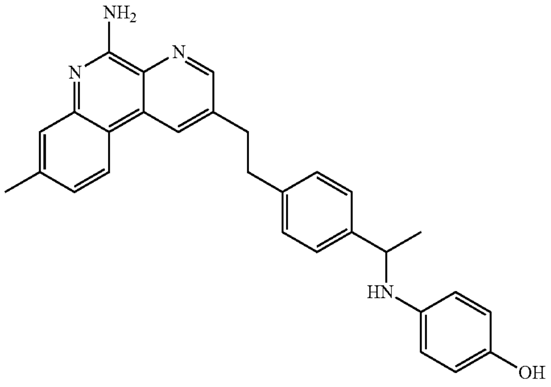 [SMILES: Cc1ccc2c(c1)nc(N)c1ncc(CCc3ccc(C(C)Nc4ccc(O)cc4)cc3)cc12]

4-(1-(4-(2-(5-Amino-8-methylbenzo[f][1,7]naphthyridin-2-yl)ethyl)phenyl)ethylamino)phenol was prepared from 1-(4-(2-(5-amino-8-methylbenzo[f][1,7]naphthyridin-2-yl)ethyl)phenyl)ethanone (from Example 171) and 4-aminophenol following the procedures described for Example 187, except that in this case, acetic acid was used instead of triethylamine (28%). $^1H$ NMR (Acetone-$d_6$) TFA Salt: δ 8.83 (s, 1H), 8.73 (s, 1H), 8.33 (d, 1H), 7.44 (s, 1H), 7.40 (d, 2H), 7.36 (d, 1H), 7.24 (d, 2H), 7.10 (d, 2H), 6.76 (d, 2H), 4.72 (m, 1H) 3.27 (t, 2H), 3.12 (t, 2H), 2.50 (s, 3H), 2.06 (d, 3H). LRMS [M+H]=449.2

Example 195

1-(1-(4-(2-(5-amino-8-methylbenzo[f][1,7]naphthyridin-2 yl)ethyl)phenyl)ethyl)pyrrolidin-3-ol

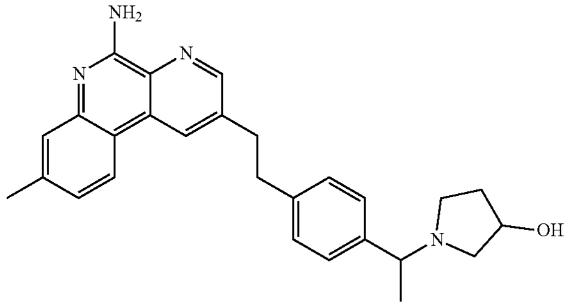 [SMILES: Cc1ccc2c(c1)nc(N)c1ncc(CCc3ccc(C(C)N4CCC(O)C4)cc3)cc12]

1-(1-(4-(2-(5-Amino-8-methylbenzo[f][1,7]naphthyridin-2 yl)ethyl)phenyl)ethyl)pyrrolidin-3-ol was prepared from 1-(4-(2-(5-amino-8-methylbenzo[f][1,7]naphthyridin-2-yl)ethyl)phenyl)ethanone (from Example 171) and pyrrolidin-3-ol following the procedures described for Example 187, except that in this case, acetic acid was used instead of triethylamine (20%). $^1H$ NMR (Acetone-$d_6$) TFA Salt: δ 8.83 (s, 1H), 8.76 (s, 1H), 8.72 (s, 1H), 8.29 (d, 1H), 7.57 (s, 1H), 7.42 (s, 1H), 7.33-7.38 (m, 3H), 4.41 (m, 2H), 3.77 (m, 2H), 3.33 (t, 2H), 3.21 (t, 2H), 3.19 (m, 2H), 3.10 (m, 2H), 2.10 (s, 3H), 1.75 (d, 3H). LRMS [M+H]=427.2

Example 196

2-(4-(2-aminopropan-2-yl)phenethyl)-8-methylbenzo[f][1,7]naphthyridin-5-amine

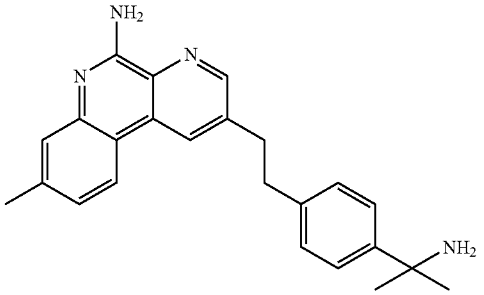 [SMILES: Cc1ccc2c(c1)nc(N)c1ncc(CCc3ccc(C(C)(C)N)cc3)cc12]

To a solution of 4-(2-(5-amino-8-methylbenzo[f][1,7]naphthyridin-2-yl)ethyl)benzonitrile (from Example 64, step 1) (1 eq), dissolved in dry THF (0.029M) was added very slowly methyl magnesium bromide (6 eq) and the reaction mixture was stirred at room temperature for half hour. Then was added to the reaction flask titanium tetra-isopropoxide (3 eq) over ten minutes. The reaction mixture was refluxed for 16 hours. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous $MgSO_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 2-(4-(2-aminopropan-2-yl)phenethyl)-8-methylbenzo[f][1,7]naphthyridin-5-amine as a white solid of TFA salt. $^1H$ NMR (Methanol-$d_4$) TFA Salt: δ 9.01 (s, 2H), 8.92 (s, 1H), 8.42 (s, 1H), 7.65 (d, 2H), 7.56 (s, 1H), 7.39 (m, 2H), 3.19 (m, 4H), 2.54 (s, 3H), 1.82 (6H). LRMS [M+H]=371.2.

Example 197

N-(2-acetamidoethyl)-4-(2-(5-amino-8-methylbenzo[f][1,7]naphthyridin-2-yl)ethyl)-3-methylbenzamide

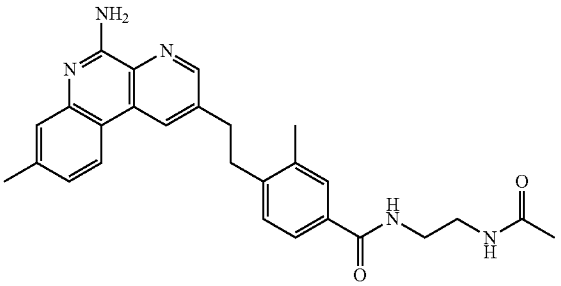 [SMILES: CC(=O)NCCNC(=O)c1ccc(CCc2cnc3c(N)nc4cc(C)ccc4c3c2)c(C)c1]

To a solution of 4-(2-(5-amino-8-methylbenzo[f][1,7]naphthyridin-2-yl)ethyl)-3-methylbenzoyl chloride (Example 116/Step 2) and triethylamine (2.5 eq.) in ether (0.05 M) was added N-(2-aminoethyl)acetamide (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give N-(2-acetamidoethyl)-4-(2-(5-amino-8-methylbenzo[f][1,7]naphthyridin-2-yl)ethyl)-3-methylbenzamide as a white solid. $^1H$ NMR ($CDCl_3$): δ 8.61 (s, 1H), 8.38 (s, 1H), 8.07 (d, 1H), 7.65 (s, 1H), 7.51-7.56 (m, 2H), 7.10-7.16 (m, 2H), 6.25 (br, 2H), 3.50-3.59 (m, 4H), 3.08-3.16 (m, 4H), 2.62 (s, 3H), 2.52 (s, 3H), 2.35 (s, 3H). LRMS [M+H]=455.2.

Other compounds for carrying out the present invention include: 2-methylbenzo[f][1,7]naphthyridin-5-amine; 2-propylbenzo[f][1,7]naphthyridin-5-amine; 2-(3-methoxyphenethyl)benzo[f][1,7]naphthyridin-5-amine; 8-methyl-2-phenethylbenzo[f][1,7]naphthyridin-5-amine; methyl-5-aminobenzo[f][1,7]naphthyridine-3-carboxylate; (5-aminobenzo[f][1,7]naphthyridin-3-yl)methanol; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine, 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-8-(2-cyclopropylvinyl)-2-phenethylbenzo[f][1,7]naphthyridin-5-amine; 8-pentylbenzo[f][1,7]naphthyridin- 5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid, and 8-methyl-2-(4-(1-(phenylamino)ethyl)phenethyl)benzo[f][1,7]naphthyridin-5-amine.

Example 198

The following examples are offered to illustrate, but not to limit, the benzonapthyridine compounds of Formula (VIII) provided herein, and the preparation of such compounds.

Synthesis of Starting Compounds

Preparation of tert-butyl 2-(4,4,5,5-tetramethyl-1,3,2-dioxaborolan-2-yl)phenylcarbamate

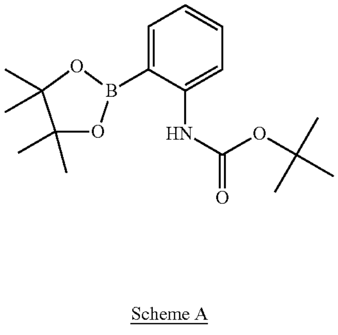

Scheme A

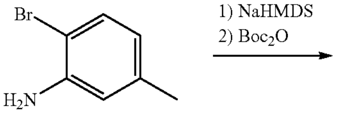

-continued

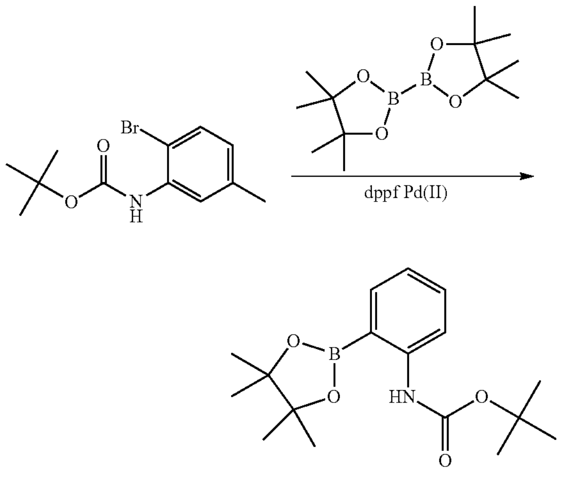

Step 1: tert-butyl 2-bromo-5-methylphenylcarbamate

To a solution of 2-bromo-5-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give tert-butyl 2-bromo-5-methylphenylcarbamate as a light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from previous step) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl)phenylcarbamate.

Preparation of 4-(2-(5-amino-8-methylbenzo[f][1,7]naphthyridin-2-yl)ethyl)-3-methylphenol (4)

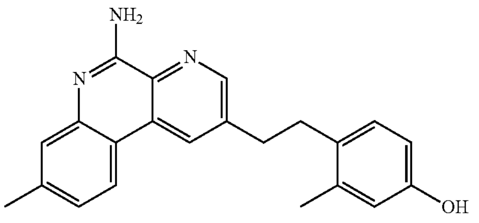 [SMILES: Cc1ccc2c(c1)nc(N)c1ncc(CCc3ccc(O)cc3C)cc12]

denser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-methoxy-2-methylphenyl)ethynyl)picolinonitrile.

Step B-2: 2-((4-methoxy-2-methylphenyl)ethynyl)-8-methylbenzo[f][1,7]naphthyridin-5-amine (2)

To a round bottom flask with refluxing condenser were added 3-chloro-5-((4-methoxy-2-methylphenyl)ethynyl)picolinonitrile (from the previous step) (1 eq.), tert-butyl 2-(4,4,5,5-tetramethyl-1,3,2-dioxaborolan-2-yl)phenylcarbamate (see Scheme A above) (1.25 eq.), $K_3PO_4$ (2 eq.), tris(dibenzylideneacetone)dipalladium(0) (0.05 eq.), and 2-dicyclohexylphosphino-2',6'-dimethoxybiphenyl (Sphos) (0.1 eq.). n-butanol and water (5:2, 0.2 M) were added, and the content was degassed (vacuum followed by nitrogen flush) for three times. The reaction mixture was stirred vigorously under nitrogen at 100° C. overnight in an oil bath. The content was cooled and taken up in 200 mL of water followed by extraction with methylene chloride. Combined organic layers were dried ($Na_2SO_4$) and concentrated. Flash Scheme B

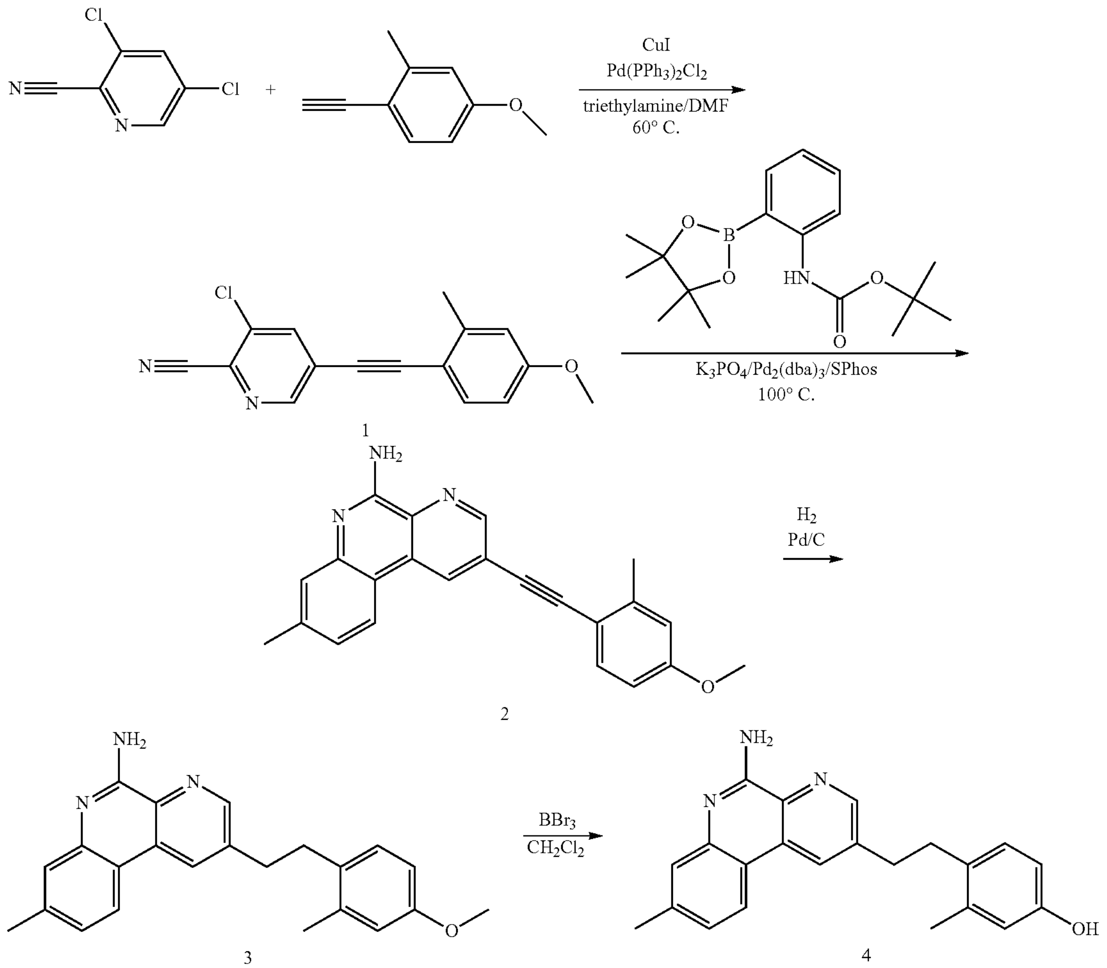

1

2

3

4

Step B-1: 3-chloro-5-((4-methoxy-2-methylphenyl)ethynyl)picolinonitrile (1)

To a round bottom flask capped with septa was added 1-ethynyl-4-methoxy-2-methylbenzene (1.1 eq), 3,5-dichloropicolinonitrile (1 eq.), triethylamine (5 eq.), and anhydrous DMF (0.2 M). The mixture was degassed (vacuum) and nitrogen flushed three times. CuI (0.05 eq.) and bis(triphenylphosphine)dichloro-palladium(II) (0.05 eq) were added and the septum was replaced with a refluxing conchromatography (silica gel, 0-50% EtOAc in $CH_2Cl_2$) afforded the product 2-((4-methoxy-2-methylphenyl)ethynyl)-8-methylbenzo[f][1,7]naphthyridin-5-amine.

Step B-3: 2-(4-methoxy-2-methylphenethyl)-8-methylbenzo[f][1,7]naphthyridin-5-amine (3)

2-(4-methoxy-2-methylphenethyl)-8-methylbenzo[f][1,7]naphthyridin-5-amine was prepared from 2-((4-methoxy-2-methylphenyl)ethynyl)-8-methylbenzo[f][1,7]naphthyridin-5-amine (from the previous step). To a round bottom flask was added 2-((4-methoxy-2-methylphenyl)ethynyl)-8-methylbenzo[f][1,7]naphthyridin-5-amine (1 eq.) with a stirring bar. Ethanol and methylene chloride (1:2, 0.2 M) were added, followed by palladium in carbon (activated powder, wet, 10% on carbon, 0.1 eq.). The content was degassed (vacuum) followed by hydrogen flush (three times). The reaction mixture was stirred vigorously at room temperature overnight, under a hydrogen balloon. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in $CH_2Cl_2$) afforded the product 2-(4-methoxy-2-methylphenethyl)-8-methylbenzo[f][1,7]naphthyridin-5-amine. $^1$H NMR ($CDCl_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

Step B-4: 4-(2-(5-amino-8-methylbenzo[f][1,7]naphthyridin-2-yl)ethyl)-3-methylphenol (4)

To a stirred solution of 2-(4-methoxy-2-methylphenethyl)-8-methylbenzo[f][1,7]naphthyridin-5-amine (from the previous step) in methylene chloride (0.2 M) in an ice-water bath was added 1 N solution of $BBr_3$ (2 eq) in $CH_2Cl_2$ in a drop-wise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-$d_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2.

Compound 6 (See Table 1)

Preparation of 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonic acid (7)

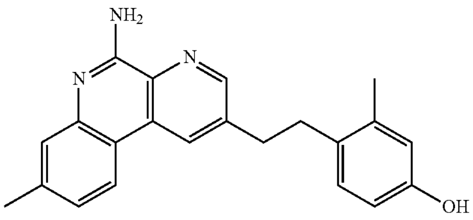

4

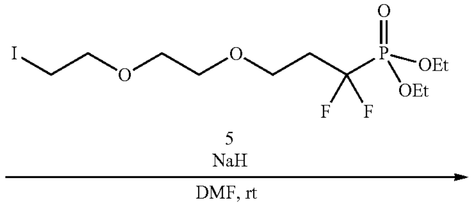

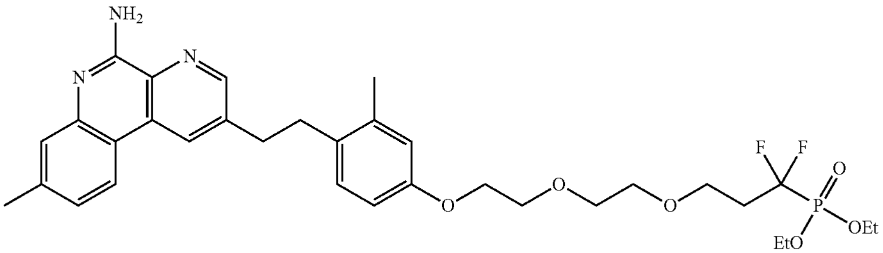

6

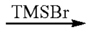

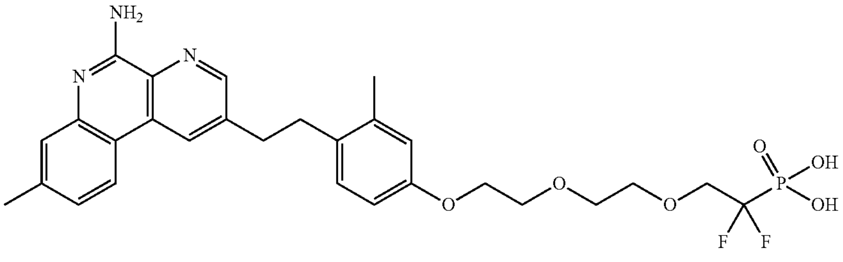

7

Step 1: Synthesis of diethyl 1,1-difluoro-3-(2-(2-iodoethoxy)ethoxy)propylphosphonate (5)

To a solution of diethyl difluoromethylphosphonate (1.0 equiv.) in THF (0.8 M) at −78° C. was slowly added a solution of LDA (2 M, 1.1 equiv.) in heptane/THF/ethylbenzene, and the mixture was vigorously stirred for 30 minutes. In a separate reaction flask, a solution of 1,2-bis(2-iodoethoxy)ethane (1.0 equiv.) in THF (0.8M) was cooled to −78° C. To this solution was transferred, by cannula, the freshly prepared alkyl lithium solution and the reaction mixture was allowed to stir for 1 hour at −78° C. At this point, the cooling bath was removed and the reaction mixture was allowed to warm to room temperature. The reaction mixture was then quenched with a 1 M aqueous solution of HCl. The resulting mixture was transferred to a separatory funnel and washed with $CH_2Cl_2$ three times. The combined organic layers were dried over anhydrous $Na_2SO_4$ and the volatiles were removed in vacuo. The resulting residue was purified by a COMBIFLASH® system (ISCO) using $CH_2Cl_2$ to provide diethyl 1,1-difluoro-3-(2-(2-iodoethoxy)ethoxy)propylphosphonate as a yellow oil. $^1$H NMR ($CDCl_3$): δ 4.23-4.31 (m, 4H), 3.75-3.80 (m, 4H), 3.60-3.67 (m, 4H), 3.26 (t, 2H), 2.33-2.50 (m, 2H), 1.38 (t, 6H).

Step 2: Synthesis of diethyl 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonate (6)

To a solution of 4-(2-(5-amino-8-methylbenzo[f][1,7]naphthyridin-2-yl)ethyl)-3-methylphenol (4) (1.0 equiv.) in dimethylformamide (0.10 M) at 22° C. was added 60% dispersion of sodium hydride in mineral oil (1.5 equiv.) and the resulting mixture was allowed to stir for 30 minutes. At this point, diethyl 1,1-difluoro-3-(2-(2-iodoethoxy)ethoxy)propylphosphonate (1.2 equiv.) was added to this mixture. The reaction mixture was then allowed to stir for 18 hours, after which it was diluted with ethyl acetate and water. The biphasic layers were separated and the organic layer was washed twice with water. The organic layer was dried over anhydrous $Na_2SO_4$ and the volatiles were removed in vacuo. The resulting residue was purified by a COMBIFLASH® system (ISCO) using 0-50% ethyl acetate in hexanes gradient to provide diethyl 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonate as a solid.

Step 3: Synthesis of 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonic acid (7)

To a solution of diethyl 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonate (1.0 equiv.) in $CH_2Cl_2$ (0.10 M) at 0° C. was slowly added trimethylsilyl bromide (10 equiv.). After 1 hour the ice-bath was removed and the reaction mixture was allowed to stir at 22° C. for 18 hours. At this point, the volatiles were removed in vacuo and the resulting residue was purified by Reverse Phase-HPLC using a 20-90% 0.5 mM $NH_4OAc$ (in MeCN) to 10 mM $NH_4OAc$ (in water) gradient to deliver 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonic acid as a solid. $^1$H NMR (Dimethylsulfoxide-d6): δ 8.83 (s, 1H), 8.68 (s, 1H), 8.32 (s, 1H), 7.34 (s, 1H), 7.14 (d, 1H), 7.09 (br, 2H), 7.08 (d, 1H), 6.74 (s, 1H), 6.68 (d, 1H), 4.01 (t, 2H), 3.70 (t, 2H), 3.61 (t, 2H), 3.54-3.59 (m, 2H), 3.48-3.50 (m, 2H), 3.07 (t, 2H), 2.94 (t, 2H), 2.43 (s, 3H), 2.25 (s, 3H), 2.06-2.21 (m, 2H). LRMS [M+H]=590.2

Compound 16 (See Table 1)

Preparation of 3-(5-amino-2-(4-(4,4-difluoro-4-phosphonobutoxy)-2-methylphenethyl)benzo[f][1,7]naphthyridin-8-yl)propanoic acid (23)

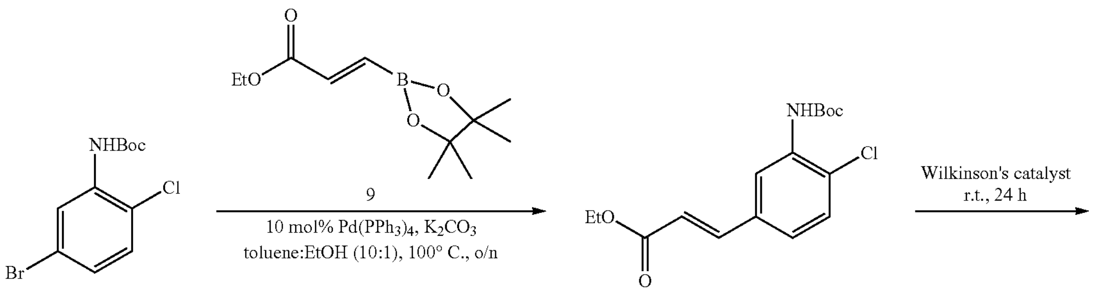

8 10

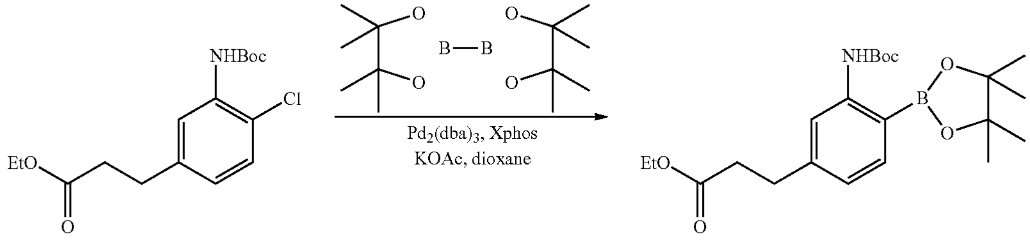

11 12

-continued
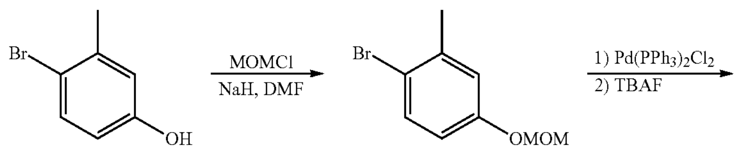
13 14
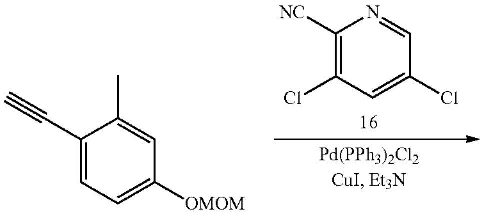
15 16
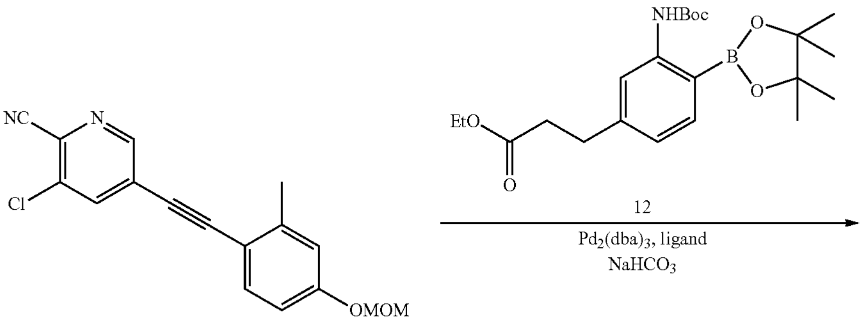
17 12
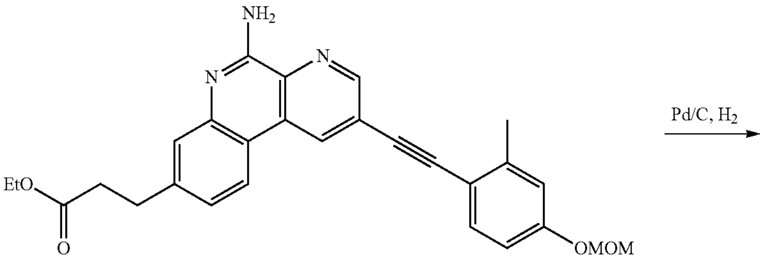
18
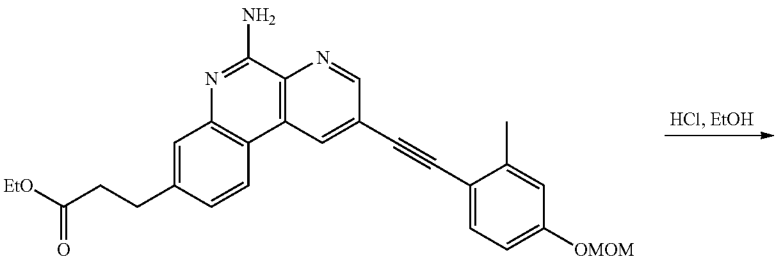
19

-continued

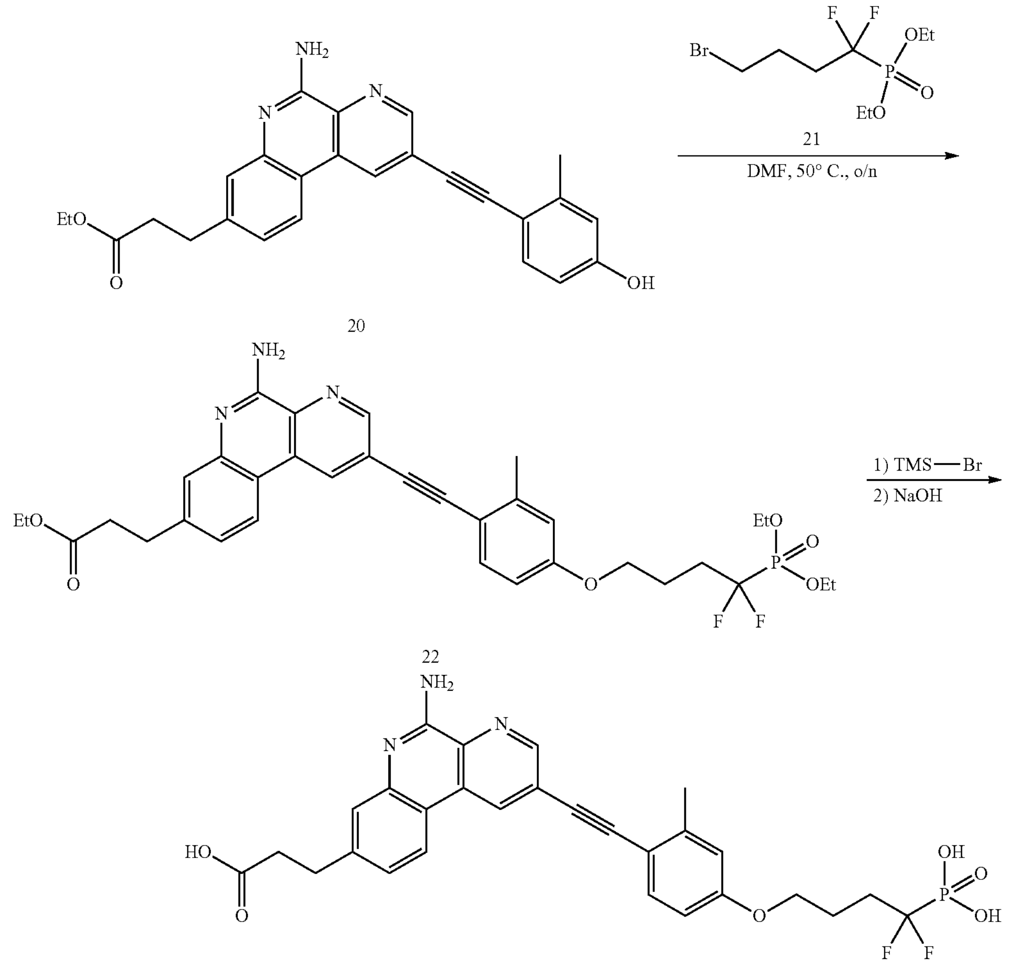

20

22

23

Step 1: (E)-ethyl 3-(3-(tert-butoxycarbonylamino)-4-chlorophenyl)acrylate (10)

A solution of tert-butyl 5-bromo-2-chlorophenylcarbamate (1.0 eq.), (E)-ethyl 3-(4,4,5,5-tetramethyl-1,3,2-dioxaborolan-2-yl)acrylate (1.5 eq.), tetrakis(triphenylphosphine) Palladium(0) (10 mol %), and potassium carbonate (2.0 eq.) in toluene/ethanol (10:1, 0.04 M) was stirred at 100° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give the subtitle compound as a white solid.

Step 2: ethyl 3-(3-(tert-butoxycarbonylamino)-4-chlorophenyl)propanoate (11)

To a solution of (E)-ethyl 3-(3-(tert-butoxycarbonylamino)-4-chlorophenyl)acrylate (Step 1) in ethyl acetate/ethanol (1:1, 0.05 M) was added wilkinson's catalyst (0.1 eq.). Hydrogen gas was introduced via a ballon, and the reaction was stirred for 24 hours. The mixture was filtered through a pad of celite, washed with dichloromethane. The filtrate was concentrated en vaccuo and purified by a COMBIFLASH® system (ISCO) using 0-80% ethyl acetate in hexane to give ethyl 3-(3-(tert-butoxycarbonylamino)-4-chlorophenyl)propanoate as a solid.

Step 3: ethyl 3-(3-(tert-butoxycarbonylamino)-4-(4,4,5,5-tetramethyl-1,3,2-dioxaborolan-2-yl)phenyl)propanoate (12)

A solution of ethyl 3-(3-(tert-butoxycarbonylamino)-4-chlorophenyl)propanoate (1.0 eq.), 4,4,4',4',5,5,5',5'-octamethyl-2,2'-bi(1,3,2-dioxaborolane) (2.0 eq.), tris(dibenzylideneacetone)dipalladium(0) (5 mol %), 2-dicyclohexylphosphino-2',4',6'-triisopropylbiphenyl (20 mol %), and potassium acetate (2.0 eq.) in 1,4-dioxane (0.04 M) was stirred at 100° C. overnight. After cooling to ambient temperature, the reaction content was concentrated en vaccuo. The crude material was purified by flash chromatography on a COMBIFLASH® system (ISCO) using 0-50% ethyl acetate in hexane to give the subtitle compound as an oil.

Step 4: 1-bromo-4-(methoxymethoxy)-2-methylbenzene (14)

A solution of 4-bromo-3-methylphenol (1.0 eq.), and sodium hydride (1.5 eq.), in DMF (0.04 M) was stirred at room temperature for 30 minutes. Then chloro(methoxy) methane (1.5 eq.) was added slowly and stirred for 4 hours. The reaction content was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-50% ethyl acetate in hexane to give the subtitle compound as a white solid.

Step 5: triethyl((4-(methoxymethoxy)-2-methylphenyl)ethynyl)silane

A solution of 1-bromo-4-(methoxymethoxy)-2-methylbenzene (1.0 eq.), triethyl(ethynyl)silane (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction content was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-50% ethyl acetate in hexane to give the subtitle compound as a white solid.

Step 6: 1-ethynyl-4-(methoxymethoxy)-2-methylbenzene (15)

To a stirred solution of triethyl((4-(methoxymethoxy)-2-methylphenyl)ethynyl)silane (1.0 eq.) in THF (0.2 M) was slowly added TBAF (0.2 eq.) at 0° C. Then the reaction mixture was stirred at 0° C. for 1 hour. After warmed to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-50% ethyl acetate in hexane to give the subtitle compound as a white solid.

Step 7: 3-chloro-5-((4-(methoxymethoxy)-2-methylphenyl)ethynyl)picolinonitrile (17)

A solution of 3,5-dichloropicolinonitrile (1.0 eq.), 1-ethynyl-4-(methoxymethoxy)-2-methylbenzene (1.0 eq.), bis (triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction content was diluted with ethyl acetate and water. The two phases were separated. The organic layer was washed twice with water, dried over anhydrous $MgSO_4$, and concentrated en vaccuo. The crude material was purified by flash chromatography on a COMBIFLASH® system (ISCO) using 0-80% ethyl acetate in hexane to give the subtitle compound as a white solid.

Step 8: ethyl 3-(5-amino-2-((4-(methoxymethoxy)-2-methylphenyl)ethynyl)-benzo[f][1,7]naphthyridin-8-yl)propanoate (18)

A solution of 3-chloro-5-((4-(methoxymethoxy)-2-methylphenyl)ethynyl)picolinonitrile (from step 7, 1.0 eq.), ethyl 3-(3-(tert-butoxycarbonylamino)-4-(4,4,5,5-tetramethyl-1,3,2-dioxaborolan-2-yl)phenyl)propanoate (from step 3, 1.5 eq.), Tris(dibenzylideneacetone)dipalladium(0) (10 mol %), dicyclohexyl(2',6'-dimethoxybiphenyl-2-yl)phosphine (20 mol %), and sodium bicarbonate (2.0 eq.) in n-butanol/$H_2O$ (5:1, 0.04 M) was stirred at 100° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give the subtitle compound as a yellow solid.

Step 9: ethyl 3-(5-amino-2-(4-(methoxymethyl)-2-methylphenethyl)benzo[f][1,7]naphthyridin-8-yl) propanoate (19)

To a solution of ethyl 3-(5-amino-2-((4-(methoxymethoxy)-2-methylphenyl)ethynyl)benzo[f][1,7] naphthyridin-8-yl)propanoate (from step 8) in ethyl acetate/ethanol (1:1, 0.05 M) was added 10% wt palladium on carbon (0.2 eq.). Hydrogen gas was introduced via a ballon, and the reaction was stirred for 3 hours. The mixture was filtered through a pad of celite, washed with dichloromethane. The filtrate was concentrated en vaccuo and purified by a COMBIFLASH® system (ISCO) using 0-80% ethyl acetate in hexane to give ethyl 3-(5-amino-2-(4-(methoxymethyl)-2-methylphenethyl)benzo[f][1,7]naphthyridin-8-yl) propanoate as a solid.

Step 10: ethyl 3-(5-amino-2-(4-hydroxy-2-methylphenethyl)benzo[f][1,7]naphthyridin-8-yl)propanoate (20)

A solution of ethyl 3-(5-amino-2-(4-(methoxymethyl)-2-methylphenethyl)benzo[f][1,7]naphthyridin-8-yl)propanoate (1.0 eq.), and hydrogen chloride (1.0 eq.) in ethanol (0.04 M) was stirred at ambient temperature for 4 hours. Then the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give the subtitle compound as a white solid.

Step 11: ethyl 3-(5-amino-2-(4-(4-(diethoxyphosphoryl)-4,4-difluorobutoxy)-2-methylphenethyl) benzo[f][1,7]naphthyridin-8-yl)propanoate (22)

A solution of ethyl 3-(5-amino-2-(4-hydroxy-2-methylphenethyl)benzo[f][1,7]naphthyridin-8-yl)propanoate (1.0 eq.), and potassium carbonate (2.0 eq.) in DMF (0.04 M) was stirred for 30 minutes. Then diethyl 4-bromo-1,1-difluorobutylphosphonate (1.5 eq.) was added slowly and the resulting mixture was stirred at 50° C. overnight. After cooling to ambient temperature, the reaction content was diluted with ethyl acetate and water. The two phases were separated. The organic layer was washed twice with water, dried over anhydrous $MgSO_4$, and concentrated en vaccuo. The crude material was carried on to the next step without further purification.

Step 12: 4-(4-(2-(5-amino-8-(3-ethoxy-3-oxopropyl) benzo[f][1,7]naphthyridin-2-yl)ethyl)-3-methylphenoxy)-1,1-difluorobutylphosphonic acid A solution of ethyl 3-(5-amino-2-(4-(4-(diethoxyphosphoryl)-4,4-difluorobutoxy)-2-methylphenethyl)benzo[f][1,7]naphthyridin-8-yl)propanoate (from step 11, 1.0 eq.), and bromotrimethylsilane (10.0 eq.), in dichloromethane (0.04 M) was stirred at room temperature overnight. The reaction content was concentrated en vaccuo. The crude material was carried on to the next step without further purification.

Step 13: 3-(5-amino-2-(4-(4,4-difluoro-4-phosphonobutoxy)-2-methylphenethyl)benzo[f][1,7]naphthyridin-8-yl)propanoic acid (23)

A solution of 4-(4-(2-(5-amino-8-(3-ethoxy-3-oxopropyl) benzo[f][1,7]naphthyridin-2-yl)ethyl)-3-methylphenoxy)-1,1-difluorobutylphosphonic acid (1.0 eq.) and 1M sodium hydroxide (4 eq.) in ethanol (0.2 M) was stirred at 70° C. for 4 hour. After cooling to ambient temperature, the crude material was purified by reverse phase high performance liquid chromatography (HPLC) to give the subtitle compound as a white solid. $^1$H NMR ($CD_3OD$): δ 8.68 (s, 1H), 8.44 (s, 1H), 8.22 (d, 1H), 7.53 (s, 1H), 7.45 (d, 1H), 6.88 (d, 1H), 6.69 (s, 1H), 6.60 (d, 1H), 3.95 (t, 2H), 3.10-3.20 (m, 4H), 3.01 (t, 2H), 2.72 (t, 2H), 2.22 (s, 3H), 1.99-2.05 (m, 4H). $^{19}$F NMR (MeOD): δ-163.70. LRMS [M+H]=574.2

Additional representative compounds of Formula (VIII), prepared following the procedures described above, are set forth in Table 1.

TABLE 1

| Compound Number | Structure | Physical Data NMR and/or MS (m/z) [M + H] | Human TLR7 EC50 (nM) HEK293 |
|---|---|---|---|
| 1 | 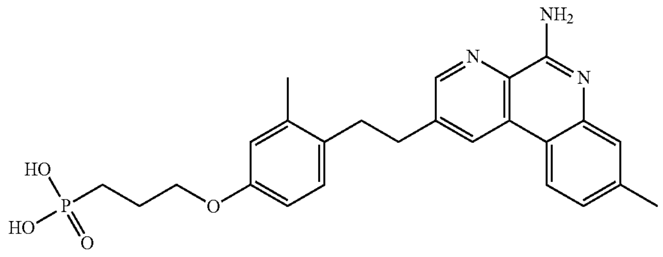 [SMILES: Cc1ccc2c(c1)nc(N)c1ncc(CCc3ccc(OCCCP(=O)(O)O)cc3C)cc12] | 466.2 | 226 |
| 2 | 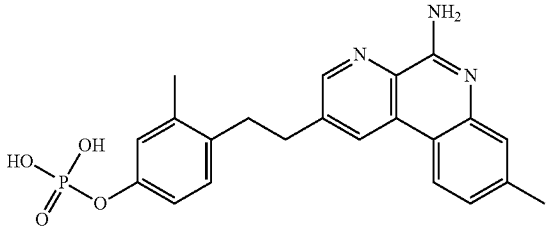 [SMILES: Cc1ccc2c(c1)nc(N)c1ncc(CCc3ccc(OP(=O)(O)O)cc3C)cc12] | 424.0 | 315 |
| 3 | 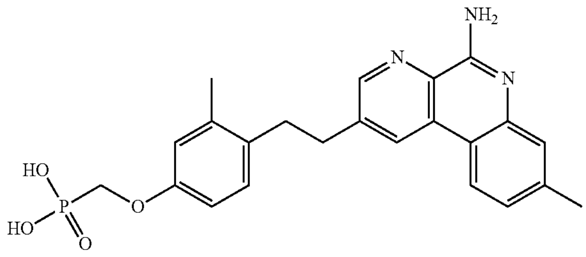 [SMILES: Cc1ccc2c(c1)nc(N)c1ncc(CCc3ccc(OCP(=O)(O)O)cc3C)cc12] | 438.0 | 3170 |
| 4 | 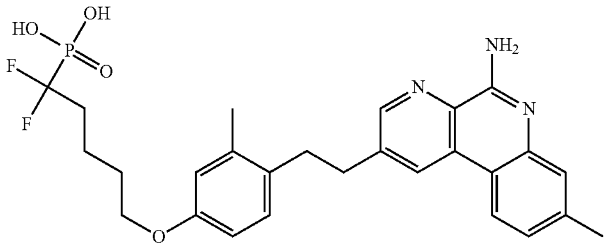 [SMILES: Cc1ccc2c(c1)nc(N)c1ncc(CCc3ccc(OCCCCC(F)(F)P(=O)(O)O)cc3C)cc12] | 530.2 | 559 |

TABLE 1-continued
| Compound Number | Structure | Physical Data NMR and/or MS (m/z) [M + H] | Human TLR7 EC50 (nM) HEK293 |
|---|---|---|---|
| 5 | 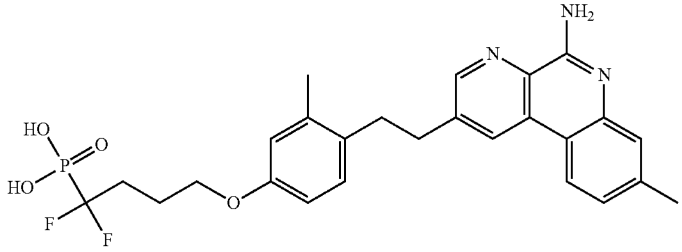 [SMILES: Cc1ccc2c(c1)nc(N)c1ncc(CCc3ccc(OCCCC(F)(F)P(=O)(O)O)cc3C)cc12] | 516.2 | 308 |
| 6 | 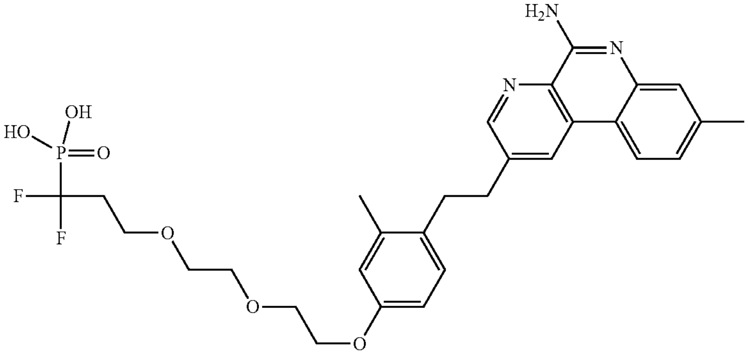 [SMILES: Cc1ccc2c(c1)nc(N)c1ncc(CCc3ccc(OCCOCCOCCC(F)(F)P(=O)(O)O)cc3C)cc12] | 590.2 | 1640 |
| 7 | 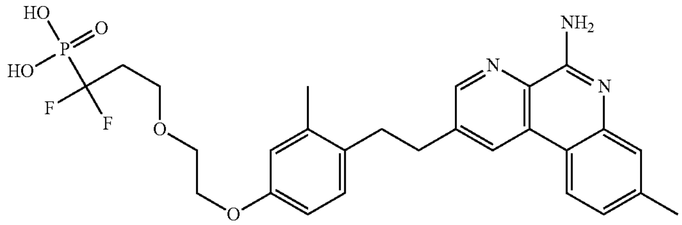 [SMILES: Cc1ccc2c(c1)nc(N)c1ncc(CCc3ccc(OCCOCCC(F)(F)P(=O)(O)O)cc3C)cc12] | 546.3 | 1010 |
| 8 | 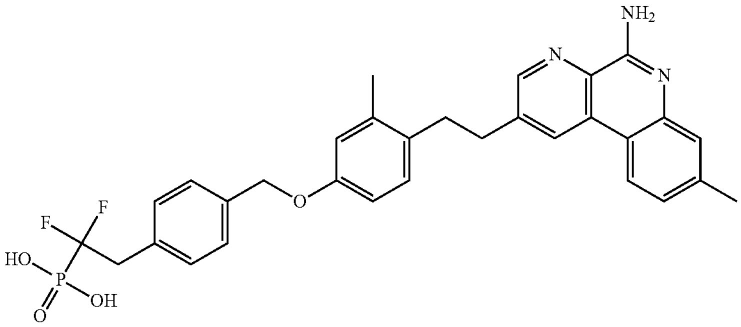 [SMILES: Cc1ccc2c(c1)nc(N)c1ncc(CCc3ccc(OCc4ccc(CC(F)(F)P(=O)(O)O)cc4)cc3C)cc12] | 578.2 | 375 |
| 9 | 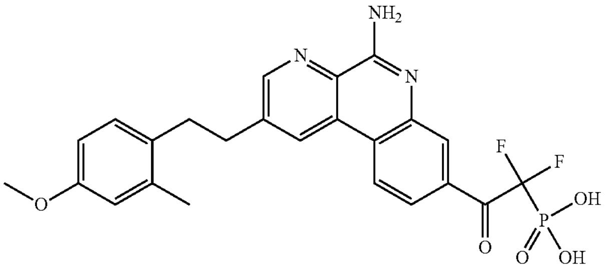 [SMILES: COc1ccc(CCc2cnc3c(N)nc4cc(C(=O)C(F)(F)P(=O)(O)O)ccc4c3c2)c(C)c1] | 502.6 | 390 |

TABLE 1-continued
| Compound Number | Structure | Physical Data NMR and/or MS (m/z) [M + H] | Human TLR7 EC50 (nM) HEK293 |
|---|---|---|---|
| 10 | 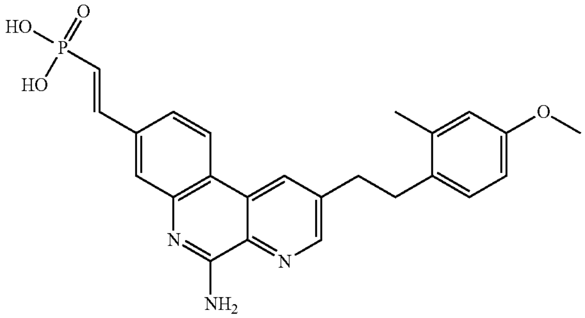 [SMILES: COc1ccc(CCc2cnc3c(N)nc4cc(/C=C/P(=O)(O)O)ccc4c3c2)c(C)c1] | 450.2 | 153 |
| 11 | 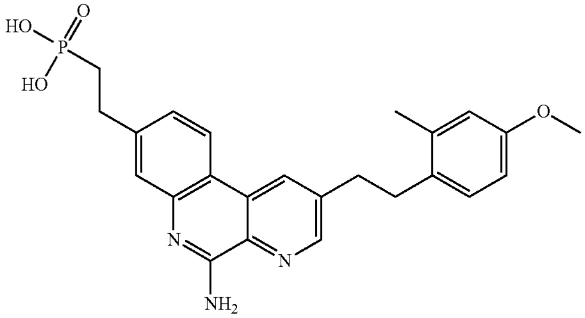 [SMILES: COc1ccc(CCc2cnc3c(N)nc4cc(CCP(=O)(O)O)ccc4c3c2)c(C)c1] | 452.2 | 90 |
| 12 | 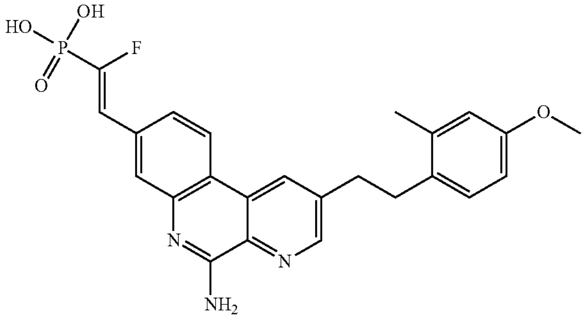 [SMILES: COc1ccc(CCc2cnc3c(N)nc4cc(/C=C(\F)P(=O)(O)O)ccc4c3c2)c(C)c1] | $^1$H NMR TFA salt (dmso-d6): δ 9.81 (s, 1H), 9.41 (s, 1H), 9.05 (d, 1H), 8.87 (d, 1H), 8.65 (s, 1H), 8.08 (s, 1H), 7.76 (dd, 1H), 7.08 (d, 1H), 6.82-6.65 (m, 3H), 3.69 (s, 3H), 3.18-3.11 (m, 2H), 3.02-2.96 (m, 2H), 2.29 (s, 3H); $^{19}$F NMR (dmso-d6, TFA as external standard): δ-176.833 (s); LRMS [M + H] = 468.1 | 201 |
| 13 | 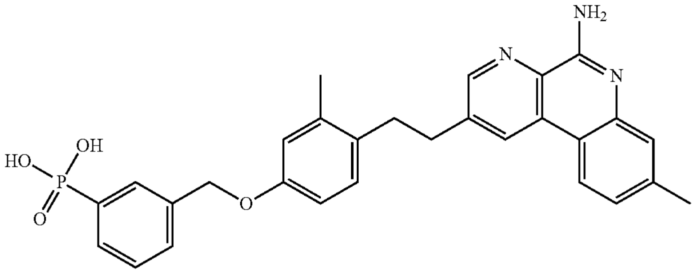 [SMILES: Cc1ccc2c(c1)nc(N)c1ncc(CCc3ccc(OCc4cccc(P(=O)(O)O)c4)cc3C)cc12] | 514.2 | 1051 |
| 14 | 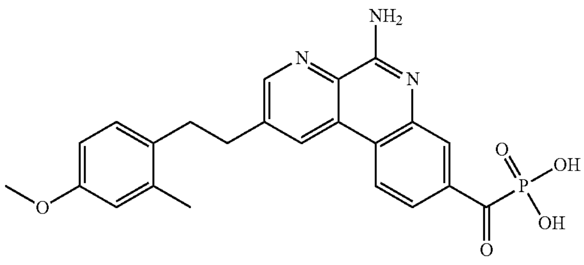 [SMILES: COc1ccc(CCc2cnc3c(N)nc4cc(C(=O)P(=O)(O)O)ccc4c3c2)c(C)c1] | $^1$H NMR TFA salt (dmso-d6): δ 9.84 (s, 1H), 9.09 (d, 1H), 8.88 (d, 1H), 8.76 (d, 1H), 8.60 (d, 1H), 8.18 (dd, 1H), 7.04 (d, 1H), 6.69 (d, 1H), 6.62 (dd, 1H), 3.64 (s, 3H), 3.15-3.08 (m, 2H), 3.98-2.91 (m, 2H), 2.23 (s, 3H); LRMS [M + H] = 452.2 | 885 |

TABLE 1-continued
| Compound Number | Structure | Physical Data NMR and/or MS (m/z) [M + H] | Human TLR7 EC50 (nM) HEK293 |
| --- | --- | --- | --- |
| 15 | 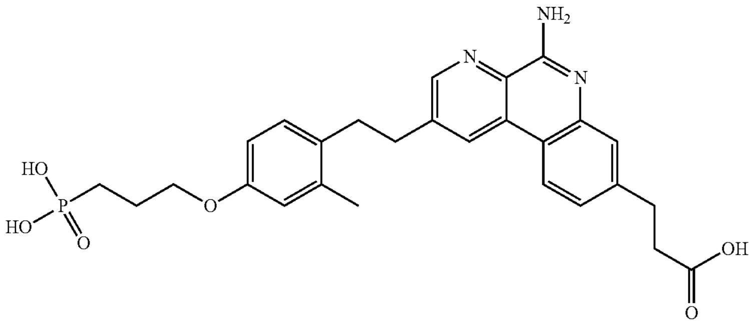 [SMILES: Cc1cc(OCCCP(=O)(O)O)ccc1CCc1cnc2c(N)nc3cc(CCC(=O)O)ccc3c2c1] | 524.2 | 65 |
| 16 | 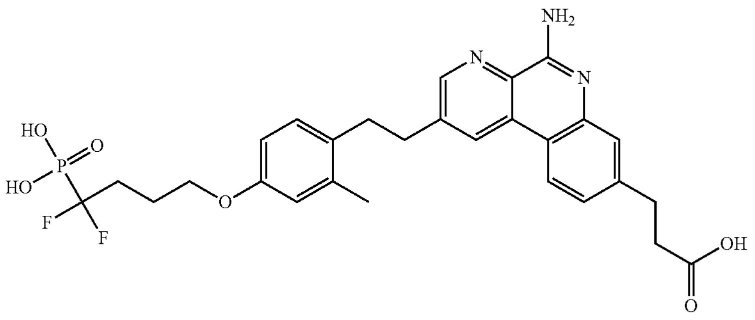 [SMILES: Cc1cc(OCCCC(F)(F)P(=O)(O)O)ccc1CCc1cnc2c(N)nc3cc(CCC(=O)O)ccc3c2c1] | 574.2 | 137 |
| 17 | 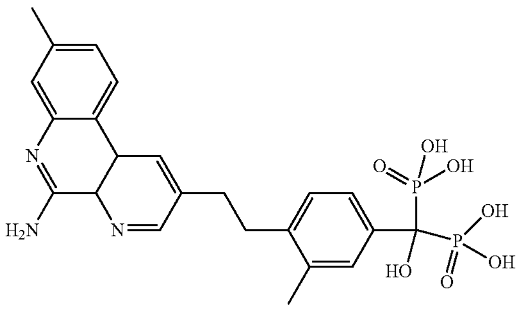 [SMILES: Cc1ccc2c(c1)N=C(N)C1N=CC(CCc3ccc(C(O)(P(=O)(O)O)P(=O)(O)O)cc3C)=CC21] | 518.1 | — |
| 18 | 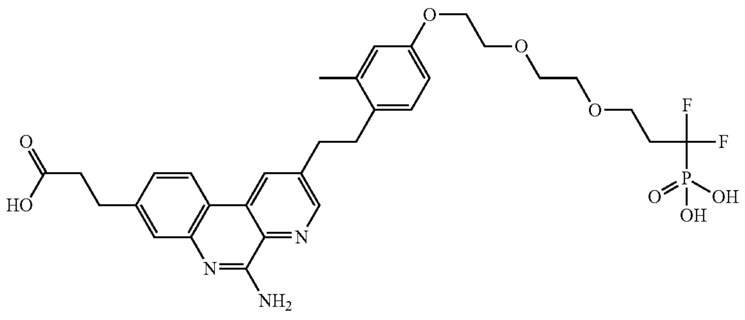 [SMILES: Cc1cc(OCCOCCOCCC(F)(F)P(=O)(O)O)ccc1CCc1cnc2c(N)nc3cc(CCC(=O)O)ccc3c2c1] | 648.2 | 5 |

TABLE 1-continued
| Compound Number | Structure | Physical Data NMR and/or MS (m/z) [M + H] | Human TLR7 EC50 (nM) HEK293 |
|---|---|---|---|
| 19 | 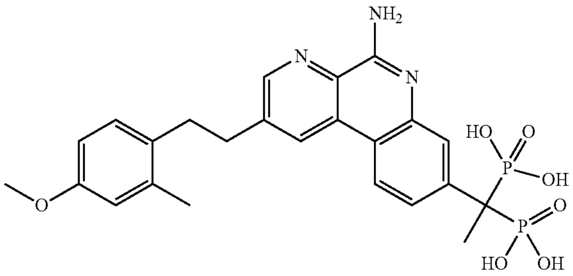 [SMILES: COc1ccc(CCc2cnc3c(N)nc4cc(C(C)(P(=O)(O)O)P(=O)(O)O)ccc4c3c2)c(C)c1] | 534.1 | 23750 |
| 20 | 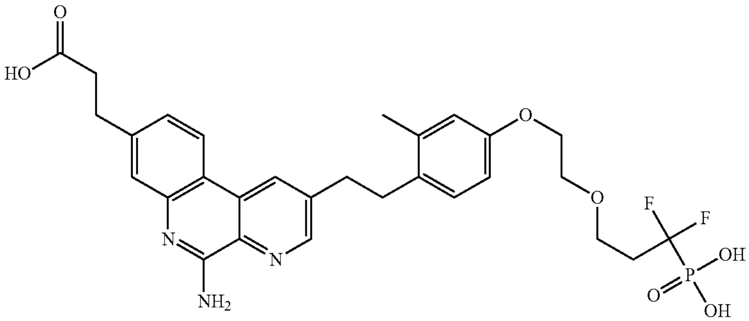 [SMILES: Cc1cc(OCCOCCC(F)(F)P(=O)(O)O)ccc1CCc1cnc2c(N)nc3cc(CCC(=O)O)ccc3c2c1] | 604.2 | 360 |
| 21 | 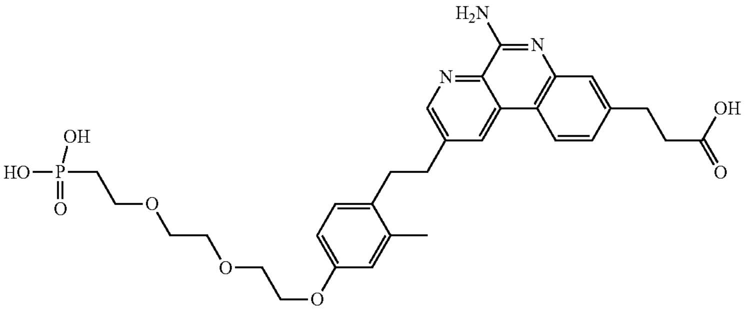 [SMILES: Cc1cc(OCCOCCOCCP(=O)(O)O)ccc1CCc1cnc2c(N)nc3cc(CCC(=O)O)ccc3c2c1] | 598.2 | 384 |
| 22 | 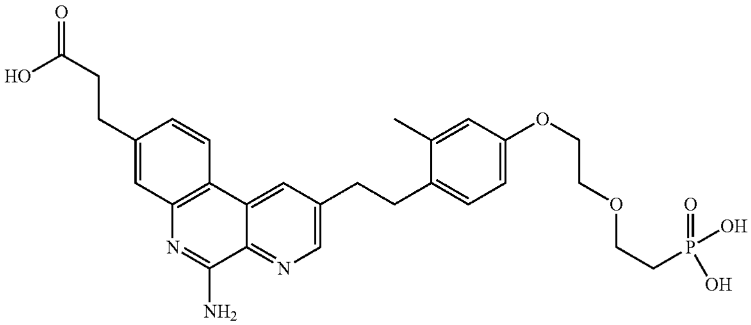 [SMILES: Cc1cc(OCCOCCP(=O)(O)O)ccc1CCc1cnc2c(N)nc3cc(CCC(=O)O)ccc3c2c1] | 554.2 | 204 |
| 23 | 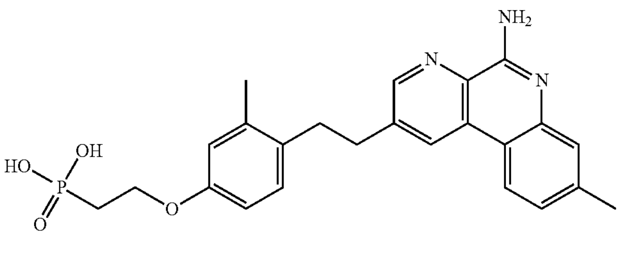 [SMILES: Cc1ccc2c(c1)nc(N)c1ncc(CCc3ccc(OCCP(=O)(O)O)cc3C)cc12] | 452.2 | 1160 |

TABLE 1-continued

| Compound Number | Structure | Physical Data NMR and/or MS (m/z) [M + H] | Human TLR7 EC50 (nM) HEK293 |
|---|---|---|---|
| 24 | 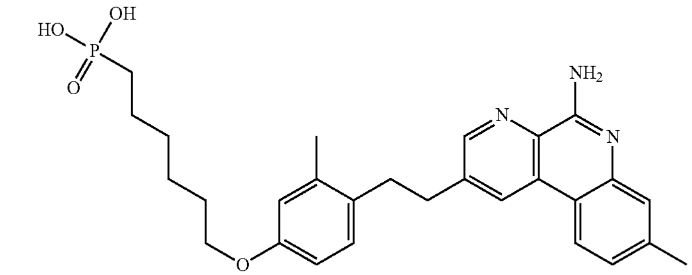 [SMILES: Cc1ccc2c(c1)nc(N)c1ncc(CCc3ccc(OCCCCCCP(=O)(O)O)cc3C)cc12] | 508.2 | 791 |
| 25 | 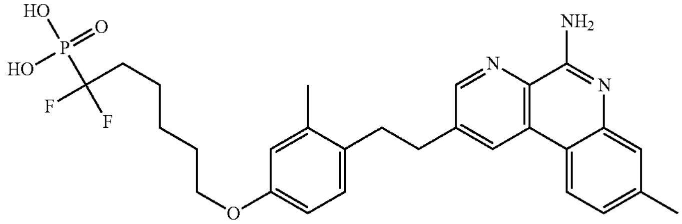 [SMILES: Cc1ccc2c(c1)nc(N)c1ncc(CCc3ccc(OCCCCCC(F)(F)P(=O)(O)O)cc3C)cc12] | 544.2 | 4260 |
| 26 | 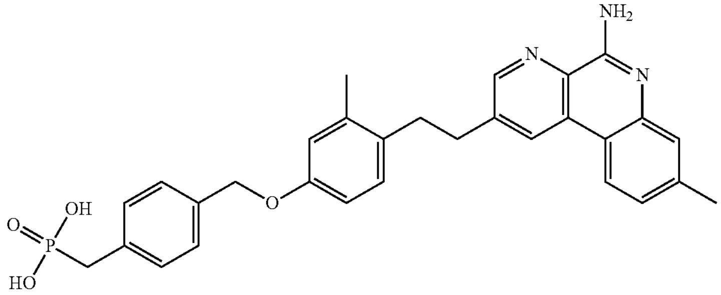 [SMILES: Cc1ccc2c(c1)nc(N)c1ncc(CCc3ccc(OCc4ccc(CP(=O)(O)O)cc4)cc3C)cc12] | 528.2 | 975 |
| 27 | 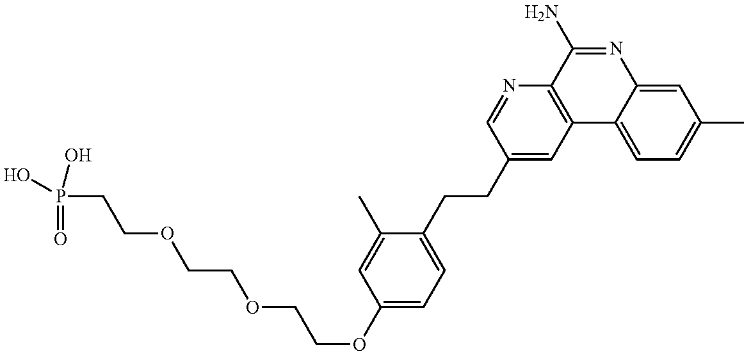 [SMILES: Cc1ccc2c(c1)nc(N)c1ncc(CCc3ccc(OCCOCCOCCP(=O)(O)O)cc3C)cc12] | 540.2 | 2592 |

Assays

Compounds of Formula (VIII) provided herein were assayed to measure their capacity to modulate toll-like receptor 7.

Human Peripheral Blood Mononuclear Cell Assay

The bioactivity of the compounds of Formula (VIII) provided herein were tested in the human peripheral blood assay (human PBMC) using a panel of independent normal human donors according to approved guidelines by the institutional review committee. Human PBMC were isolated from freshly peripheral blood using a Ficoll density gradient (GE healthcare 17-1440-03). 30-35 mLs of peripheral human blood were layered onto 15 mLs of Ficoll in 50 ml conical tubes, followed by centrifugation at 1800 rpm (Eppendorf Centrifuge 5810R with biohazard caps over the tube buckets) at room temperature for 30 minutes with no acceleration and no brake. The buffy layers were then collected and transferred onto new 50 ml conical tubes and washed twice in complete media consisting of RPMI 1640 (11875085 from Invitrogen Corporation, Carlsbad, Calif.) supplemented with 10% heat inactivated fetal bovine serum (Gibco 10099-141), 1% Pen-Strep (Gibco#15140-122), 1 mM non essential amino acids (Gibco#11140-050), 1 mM sodium pyruvate (Gibco#11360-070), 2 mM L-Glutamine (Gibco#25030-081) and 1 mM HEPES (Gibco#15630-080). Viable cells were then counted using trypan blue staining, plated in 96 well flat bottom plates (Becton Dickinson #353070) at $2\times10^5$ cells per well in 200 μl total volume of complete media. Compounds were then added in a 10 point dose response format starting at 100 μM, 3 fold dilution. Negative controls wells received equal concentration of DMSO. Culture supernatants were collected after 18-24 hours incubation at 37° C., 5% $CO_2$, stored at −20° C. until further use.

IL-6 levels in the culture supernatants were measured using a Luminex kit (Biorad). Data analysis is performed using Prism software from GraphPad (San Diego, Calif.). Dose response curves are generated for each compound and $EC_{50}$ values were determined as the concentration that gives 50% of the maximal signal.

Reporter Gene Assay

Human embryonic kidney 293 (HEK 293) cells were stably transfected with human TLR7 and an NF-kB-driven luciferase reporter vector (pNifty-Luciferase). As a control assay, normal Hek293 transfected with pNifty-Luc were used. Cells were cultured in DMEM supplemented with 2 mM L-glutamine, 10% heart inactivated FBS, 1% penicillin and streptomycin, 2 μg/ml puromycin (InvivoGen #ant-pr-5) and 5 μg/ml of blasticidin (Invitrogen #46-1120). Bright-Glo™ Luciferase assay buffer and substrate were supplied by Promega #E263B and #E264B (assay substrate and buffer respectively). 384 well clear-bottom plates were supplied by Greiner bio-one (#789163-G) and were custom bar-coded plates.

Cells were plated at 25,000 cells/well in 384-well plates in a final volume of 50 μl of media. Cells were allowed to adhere to the plates after overnight (18 hours) culture at 37° C. and 5% $CO_2$. Serially diluted experimental and positive control compounds were then dispensed to each well and incubated for 7 hours at 37° C. and 5% $CO_2$. Cells stimulated with DMSO alone also serve as negative controls. After the incubation, 30 μl of the pre-mix assay buffer and substrate buffer were added to each well according to manufacturer's instructions. The luminescence signal was read on a CLIPR machine with an integration time of 20 seconds per plate.

Dose response curves are generated for each compound and $EC_{50}$ values were determined as the concentration that gives 50% of the maximal signal.

Certain Assay Results

Various compounds of Formula (VIII) in free form or in pharmaceutically acceptable salt form, exhibit pharmacological properties, for example, as indicated by the in vitro tests described in this application. The $EC_{50}$ value in those experiments is given as that concentration of the test compound in question that provoke a response halfway between the baseline and maximum responses. In certain examples compounds of Formula (VIII) have $EC_{50}$ values in the range from 1 nM to 100 μM. In other examples, compounds of Formula (VIII) have $EC_{50}$ values in the range from 1 nM to 50 μM. In other examples, compounds of Formula (VIII) have $EC_{50}$ values in the range from 1 nM to 25 μM. In other examples, compounds of Formula (VIII) have $EC_{50}$ values in the range from 1 nM to 20 μM. In other examples, compounds of Formula (VIII) have $EC_{50}$ values in the range from 1 nM to 15 μM. In other examples, compounds of Formula (VIII) have $EC_{50}$ values in the range from 1 nM to 10 μM. In other examples, compounds of Formula (VIII) have $EC_{50}$ values in the range from 1 nM to 5 μM. In other examples, compounds of Formula (VIII) have $EC_{50}$ values in the range from 1 nM to 2 μM. In other examples, compounds of Formula (VIII) have $EC_{50}$ values in the range from 1 nM to 1 μM. In other examples, compounds of Formula (VIII) have $EC_{50}$ values in the range from 1 nM to 500 nM. In other examples, compounds of Formula (VIII) have $EC_{50}$ values in the range from 1 nM to 250 nM. In other examples, compounds of Formula (VIII) have $EC_{50}$ values in the range from 1 nM to 100 nM. In other examples, compounds of Formula (VIII) have $EC_{50}$ values in the range from 1 nM to 50 nM. In other examples, compounds of Formula (VIII) have $EC_{50}$ values in the range from 1 nM to 25 nM. In other examples, compounds of Formula (VIII) have $EC_{50}$ values in the range from 1 nM to 10 nM. Such $EC_{50}$ values are obtained relative to the activity of resiquimod set to 100%.

By way of example only, the $EC_{50}$ for TLR-7 stimulation by certain compounds of Formula (VIII) are listed in Table 1.

Example 199

Benzonapthyridine SMIPs Administered Intraperitoneally Protected Mice in Ebola Challenge Model In Example 199, SMIPs of the invention are referred to as follows:

TABLE 2

SMIPs of the Invention

| SMIP | Name of Benzonapthyridine SMIP or Lipopeptide SMIP | Structure |
|---|---|---|
| 28 | 2-(4-methoxy-2-methylphenethyl)-8-methylbenzo[f][1,7]naphthyridin-5-amine | 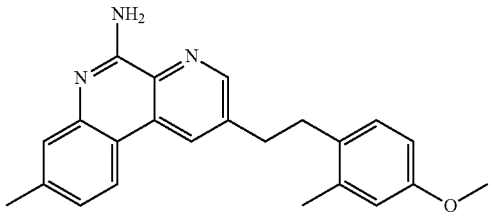 |

TABLE 2-continued

SMIPs of the Invention

| SMIP | Name of Benzonapthyridine SMIP or Lipopeptide SMIP | Structure |
|---|---|---|
| 29 | 2-(2-(4-(2-(5-amino-8-methylbenzo[f][1,7]naphthyridin-2-yl)ethyl)-3-methylphenoxy)ethoxy)ethanol | 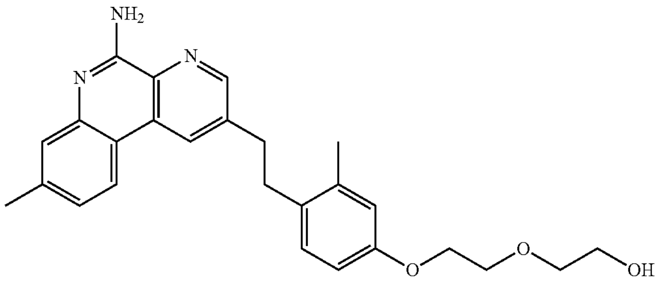 [SMILES: Cc1ccc2c(c1)nc(N)c1ncc(CCc3ccc(OCCOCCO)cc3C)cc12] |
| 30 | 2-(4-(2-(5-amino-8-methylbenzo[f][1,7]naphthyridin-2-yl)ethyl)-3-methylphenyl)propan-2-ol | 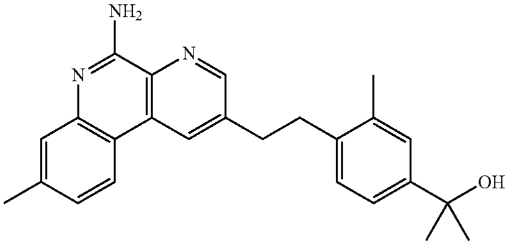 [SMILES: Cc1ccc2c(c1)nc(N)c1ncc(CCc3ccc(C(C)(C)O)cc3C)cc12] |
| 31 | palmitoyl-Cys(2[R], 3-dilauroyloxy-propyl)-Ala-D-Glu-$NH_2$ | 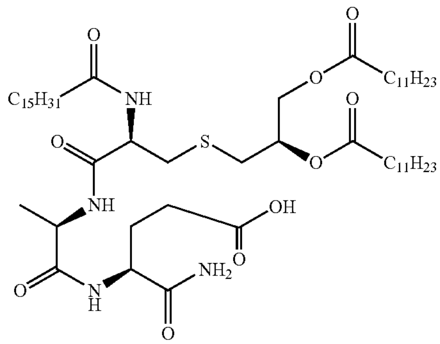 |

Ebola Challenge Model

A mouse-adapted Ebola virus (EBOV) forms the basis for this model. M. Bray et al., *The Journal of Infectious Diseases* 178 (3), 651-61 (September 1998). Injection of EBOV is uniformly fatal, with mice succumbing to infection in about 7 days. However, mice can be protected by injection of Ebola virus-like particles (VLP). In the studies described below the effects of SMIPs as disclosed herein were tested. Mice were given SMIPs by intraperitoneal (IP) injection 2 h prior to IP injection of EBOV. The mice were given 4 additional daily IP injections. To evaluate potency of the SMIPs, groups of 10 mice were given different doses. The negative control group did not receive SMIPs and the positive control group received VLP. Survival of mice was monitored and is reported in the tables below.

SMIPs 28, 29, 30 and 31 were administered by intraperitoneal (IP) injection on days 0 (2 h prior to virus injection), and on days 1, 2, 3 and 4. For SMIPs 28, 29 and 30, the doses administered were 1, 10, and 100 micrograms (μg). For SMIP 31, the doses administered were 10 and 100 μg, each in vehicle. For comparison, R-848 (resiquimod) was administered at doses 1, 10, and 100 μg and Pam3CSK4 (a synthetic triacylated lipopeptide) was administered at doses 10 and 100 μg. On day 0 (zero), 2 hours after the initial infection of SMIP 28, 29, 30, or 31, or R-848 or Pam3CSK4, each test mouse was intraperitoneally infected with 50 μg of mouse-adapted Ebola VLP (EBOV). As positive protective controls, mice were administered either 50 μg of mouse-adapted Ebola VLP (EBOV) on day 1 or 100 μg of polyriboinosinic:polyribocytidylic acid (Poly I:C) on days 0, 1, 2, 3, and 4. Phosphate buffered saline (PBS) was administered as a negative control. All SMIPs were dissolved in PBS. For each dose of compound or dose of control compound tested, ten mice were treated.

Survival of mice was monitored on a daily basis and is summarized in Table 3. FIG. 1 presents some of the data shown in Table 3. As shown in FIG. 1 and Table 3, a dose of 10 μg SMIP 28 protected 100% of mice that were infected or challenged with EBOV. A dose of 10 μg SMIP 29 protected 60% of mice that were infected or challenged with EBOV. A dose of 10 μg SMIP 30 protected 80% of mice that were infected or challenged with EBOV. In contrast, neither 1 μg R-848 nor 10 μg R-848 protected mice that were infected with EBOV. Additionally, none of the doses tested of SMIP 31 or Pam3CSK4 protected mice that had been infected or challenged with EBOV.

TABLE 3

Benzonapthyridine SMIPs 28, 29, and 30 Protected Mice in Ebola Virus Challenge Model.

| Compound | Dose (μg) | % mice alive on indicated day (challenged with EboZ on day 0) 0 | 1 | 2 | 3 | 4 | 5 | 6 | 7 | 8 | 9 | 10 | 11 | 12 | 13 |
|---|---|---|---|---|---|---|---|---|---|---|---|---|---|---|---|
| R-848 | 1 | 100 | 100 | 100 | 100 | 100 | 100 | 100 | 100 | 60 | 40 | 10 | 0 | 0 | 0 |
| | 10 | 100 | 100 | 100 | 100 | 100 | 100 | 100 | 100 | 30 | 20 | 10 | 0 | 0 | 0 |
| | 100 | 100 | 100 | 100 | 100 | 100 | 100 | 100 | 0 | 0 | 0 | 0 | 0 | 0 | 0 |
| SMIP 28 | 1 | 100 | 100 | 100 | 100 | 100 | 100 | 70 | 60 | 0 | 0 | 0 | 0 | 0 | 0 |
| | 10 | 100 | 100 | 100 | 100 | 100 | 100 | 100 | 100 | 100 | 100 | 100 | 100 | 100 | 100 |
| | 100 | 100 | 100 | 100 | 100 | 100 | 90 | 90 | 90 | 50 | 30 | 20 | 10 | 10 | 10 |
| SMIP 29 | 1 | 100 | 100 | 100 | 100 | 90 | 90 | 90 | 90 | 60 | 40 | 40 | 40 | 40 | 40 |
| | 10 | 100 | 100 | 100 | 100 | 100 | 100 | 100 | 100 | 100 | 80 | 60 | 60 | 60 | 60 |
| | 100 | 100 | 100 | 90 | 90 | 90 | 90 | 90 | 90 | 60 | 20 | 0 | 0 | 0 | 0 |
| SMIP 30 | 1 | 100 | 100 | 100 | 100 | 100 | 100 | 100 | 90 | 20 | 0 | 0 | 0 | 0 | 0 |
| | 10 | 100 | 100 | 100 | 100 | 100 | 100 | 100 | 100 | 90 | 90 | 80 | 80 | 80 | 80 |
| | 100 | 100 | 100 | 100 | 90 | 90 | 90 | 90 | 90 | 10 | 0 | 0 | 0 | 0 | 0 |
| SMIP 31 | 10 | 100 | 100 | 100 | 100 | 100 | 100 | 40 | 30 | 10 | 10 | 0 | 0 | 0 | 0 |
| | 100 | 100 | 100 | 100 | 100 | 100 | 80 | 10 | 0 | 0 | 0 | 0 | 0 | 0 | 0 |
| Pam3CSK4 | 10 | 100 | 100 | 100 | 100 | 100 | 30 | 0 | 0 | 0 | 0 | 0 | 0 | 0 | 0 |
| | 100 | 100 | 100 | 100 | 100 | 100 | 30 | 10 | 0 | 0 | 0 | 0 | 0 | 0 | 0 |
| Ebola VLP | 50 | 100 | 100 | 100 | 100 | 100 | 100 | 100 | 100 | 100 | 100 | 100 | 100 | 100 | 100 |
| poly(IC) | 100 | 100 | 100 | 100 | 100 | 100 | 100 | 100 | 100 | 100 | 100 | 100 | 100 | 100 | 100 |
| PBS | none | 100 | 100 | 100 | 100 | 100 | 100 | 100 | 90 | 40 | 20 | 20 | 20 | 20 | 10 |

Figure 2:
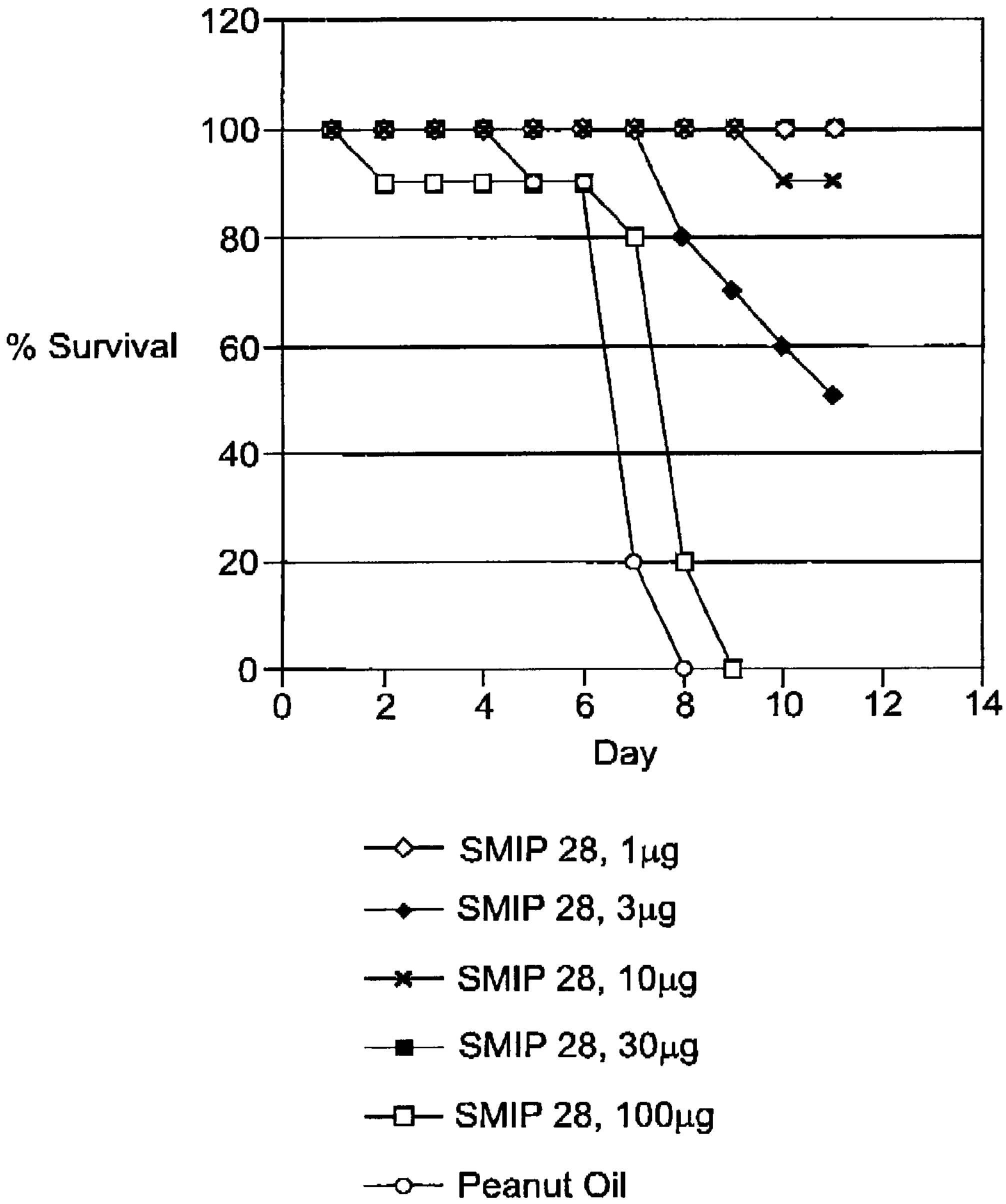
FIG. 2 also shows that compositions comprising benzonapthyridine SMIPs protected mice that had been challenged with a mouse-adapted strain of the Zaire strain of Ebola virus. Mice were administered 1 μg, 3 μg, 10 μg, 30 μg, or 100 μg of 2-(4-methoxy-2-methylphenethyl)-8-methylbenzo[f][1,7]naphthyridin-5-amine or peanut oil-vehicle. Following administration, the animals were monitored for survival.

Additional doses, as indicated in Tables 4 and 5, of benzonapthyridine SMIP 28 and SMIP 29 were tested. The same experimental design was used as in the experiments conducted to generate the date in Table 3 with one exception. Instead of PBS as a negative control, peanut oil was used, and all SMIPs were dissolved in peanut oil. For each dose of compound or dose of control compound tested, ten mice were treated. FIG. 2 presents some of the data shown in Table 4. Consistent with the previous study (Study 3), SMIPs 28 and 29 protected mice that were infected with EBOV. Protection measured on day 8 was observed at doses as low as 1 μg of SMIP 28 or SMIP 29. As observed with the experiments for which data is presented in Table 3, R-848, in the experiments for which data is presented in Tables 4 and 5, did not protect mice infected with EBOV. It should be noted that the failure of the Ebola VLP to protect was considered highly unusual and not reproducible, and probably the result of some unexplained technical failure.

Tables 4 and 5: SIMPs 28 and 29 protected mice in Ebola Virus Challenge model.

TABLE 4

| Compound | Dose (μg) | % mice alive on indicated day (challenged with EboZ on day 0) 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Peanut oil | none | 100 | 100 | 100 | 100 | 100 | 90 | 90 | 20 | 10 | nr | nr | nr | nr | nr | nr |
| R-848 | 1 | 100 | 100 | 100 | 100 | 100 | 100 | 100 | 100 | 40 | nr | nr | nr | nr | nr | nr |
| | 10 | 100 | 100 | 100 | 100 | 100 | 100 | 100 | 80 | 10 | nr | nr | nr | nr | nr | nr |
| | 100 | 100 | 100 | 100 | 100 | 100 | 100 | 100 | 50 | 10 | nr | nr | nr | nr | nr | nr |
| SMIP 28 | 1 | 100 | 100 | 100 | 100 | 100 | 100 | 100 | 100 | 100 | 100 | 100 | 100 | nr | nr | nr |
| | 3 | 100 | 100 | 100 | 100 | 100 | 100 | 100 | 100 | 80 | nr | nr | 50 | nr | nr | nr |
| | 10 | 100 | 100 | 100 | 100 | 100 | 100 | 100 | 100 | 100 | nr | nr | 90 | nr | nr | nr |
| | 30 | 100 | 100 | 100 | 100 | 100 | 100 | 100 | 100 | 100 | 100 | 100 | 100 | nr | nr | nr |
| | 100 | 100 | 100 | 90 | 90 | 90 | 90 | 90 | 80 | 30 | nr | nr | 0 | 0 | 0 | 0 |
| SMIP 29 | 1 | 100 | 100 | 100 | 100 | 100 | 100 | 100 | 100 | 100 | nr | nr | 90 | nr | nr | nr |
| | 3 | 100 | 100 | 100 | 100 | 100 | 100 | 100 | 90 | 80 | nr | nr | 70 | nr | nr | nr |
| | 10 | 100 | 100 | 100 | 100 | 100 | 100 | 90 | 90 | 90 | nr | nr | 50 | nr | nr | nr |
| | 30 | 100 | 100 | 100 | 100 | 100 | 100 | 100 | 100 | 80 | nr | nr | 0 | nr | nr | nr |
| | 100 | 100 | 100 | 100 | 100 | 100 | 100 | 100 | 40 | 40 | nr | nr | 20 | nr | nr | nr |
| Ebola VLP | 50 | 100 | 100 | 100 | 100 | 100 | 100 | 100 | 50 | 0 | 0 | 0 | 0 | 0 | 0 | 0 |

nr: not reported

EboZ: mouse-adapted strain derived from the Zaire strain of Ebola virus

TABLE 5

| Compound | Dose (μg) | % mice alive on indicated day (challenged with EboZ on day 0) 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Peanut oil | none | 100 | 100 | 100 | 100 | 100 | 100 | 70 | 20 | 20 | 10 | 10 | 0 | 0 | 0 | 0 |
| SMIP 28 | 0.3 | 100 | 100 | 100 | 100 | 100 | 100 | 90 | 10 | 10 | 10 | 10 | 0 | 0 | 0 | 0 |
| | 1 | 100 | 100 | 100 | 100 | 100 | 100 | 100 | 70 | 30 | 20 | 20 | 10 | 0 | 0 | 0 |
| | 3 | 100 | 100 | 100 | 100 | 100 | 100 | 100 | 100 | 100 | 100 | 90 | 80 | 80 | 80 | 80 |
| | 10 | 100 | 100 | 100 | 100 | 100 | 100 | 100 | 100 | 100 | 100 | 100 | 100 | 100 | 100 | 100 |

TABLE 5-continued

| | Dose | % mice alive on indicated day (challenged with EboZ on day 0) | | | | | | | | | | | | | | |
|---|---|---|---|---|---|---|---|---|---|---|---|---|---|---|---|---|
| Compound | (μg) | 0 | 1 | 2 | 3 | 4 | 5 | 6 | 7 | 8 | 9 | 10 | 11 | 12 | 13 | 14 |
| | 30 | 100 | 100 | 100 | 100 | 100 | 100 | 100 | 100 | 100 | 100 | 100 | 100 | 100 | 100 | 100 |
| | 100 | 100 | 100 | 100 | 100 | 100 | 100 | 100 | 100 | 80 | 80 | 40 | 30 | 30 | 30 | 30 |
| SMIP 29 | 0.3 | 100 | 100 | 100 | 100 | 100 | 100 | 100 | 90 | 70 | 50 | 50 | 50 | 50 | 50 | 50 |
| | 1 | 100 | 100 | 100 | 100 | 100 | 100 | 100 | 100 | 100 | 100 | 90 | 90 | 90 | 90 | 90 |
| | 3 | 100 | 100 | 100 | 100 | 100 | 100 | 100 | 100 | 90 | 80 | 80 | 70 | 70 | 70 | 70 |
| | 10 | 100 | 100 | 100 | 90 | 90 | 90 | 90 | 90 | 70 | 30 | 20 | 20 | 20 | 20 | 20 |
| | 30 | 100 | 100 | 100 | 100 | 100 | 100 | 100 | 100 | 30 | 10 | 10 | 0 | 0 | 0 | 0 |
| | 100 | 100 | 100 | 100 | 100 | 100 | 100 | 100 | 100 | 30 | 0 | 0 | 0 | 0 | 0 | 0 |

nr: not reported
EboZ: mouse-adapted strain derived from the Zaire strain of Ebola virus

Example 200

Efficacy of Immunomodulatory Compounds In Ebola Challenge Model

Additional testing in an Ebola Challenge Model was conducted with the immunomodulatory agents CpG (ODN-1826), poly I:C, LPS, Pam2CSK4 and Pam3CSK4 (synthetic triacylated lipopeptides), and R-848 (resiquimod). The compounds were administered to eight to twelve-week old C57BL/6 mice by intraperitoneal (IP) or intramuscular (IM) injection. For IP injection, compounds were administered 2 h prior to IP injection of EBOV, and then again on days 2, 4, 6 and 8 following EBOV challenge. For IM injection, compounds were administered 2 hours prior to IP injection of EBOV. Efficacy of the immunomodulatory compounds compared to vehicle-control treatment was assessed on 14-day survival.

Survival of mice was monitored and is reported in the tables below.

TABLE 6

Efficacy of Immunomodulatory Agents Against Ebola Virus in Mice

| | Target Receptor | IP | IM |
|---|---|---|---|
| CpG (ODN-1826) | TLR9 | X | X |
| Poly I:C | TLR3, RIGI, others | ✓ | X |
| LPS | TLR4 | X | X |
| Pam2CSK4 | TLR 2/6 | NT | X |
| Pam3CSK4 | TLR1/2 | X | X |
| R-848 | TLR7/8 | X | X |

X = agent showed no efficacy
✓ = agent showed efficacy
NT = Not tested.

Example 201

Benzonapthyridine SMIPs Administered Intraperitoneally and Intramuscularly in Guinea Pigs Induced an Immune Response Guinea pigs were given SMIPs of the invention by intraperitoneal (IP) or intramuscular (IM) injection 2 hours prior to subcutaneous injection of guinea pig-adapted Ebola virus. On day 0 (zero), 2 hours after the administration of compounds, each guinea pig was administered a subcutaneous injection of 1,000 PFU of guinea pig-adapted Ebola virus. Guinea pigs (6 guinea pigs per group) were administered, vehicle (peanut oil) alone, PolyI:C (100 μg), R-848 (100 μg), or SMIP 28 (100 μg or 10 μg). The guinea pigs were given additional daily IP injections of SMIP, vehicle alone, Poly I:C, or R-848 on days 1, 2, 3, 4, 6, 8, and 10 post-infection with guinea pig-adapted Ebola virus. Survival of guinea pigs was monitored on a daily basis for sixteen days following initial treatment. In addition to survival, weight gain or loss, and individual guinea pigs were given clinical scores based on cage-side observations. The clinical scores were determined according to the criteria provided in Table 7.

TABLE 7

| Clinical Score | Clinical Observations |
|---|---|
| 0 | Healthy; no clinical signs of disease, animal active and responsive |
| 1 | Slightly ruffled fur, reduced mobility |
| 2 | Severely reduced mobility, hunched posture, ruffled fur, reduced responsiveness |
| 3 | Moribund; Unresponsive, non-mobile, labored breathing |
| 4 | Dead |

Figure 3:
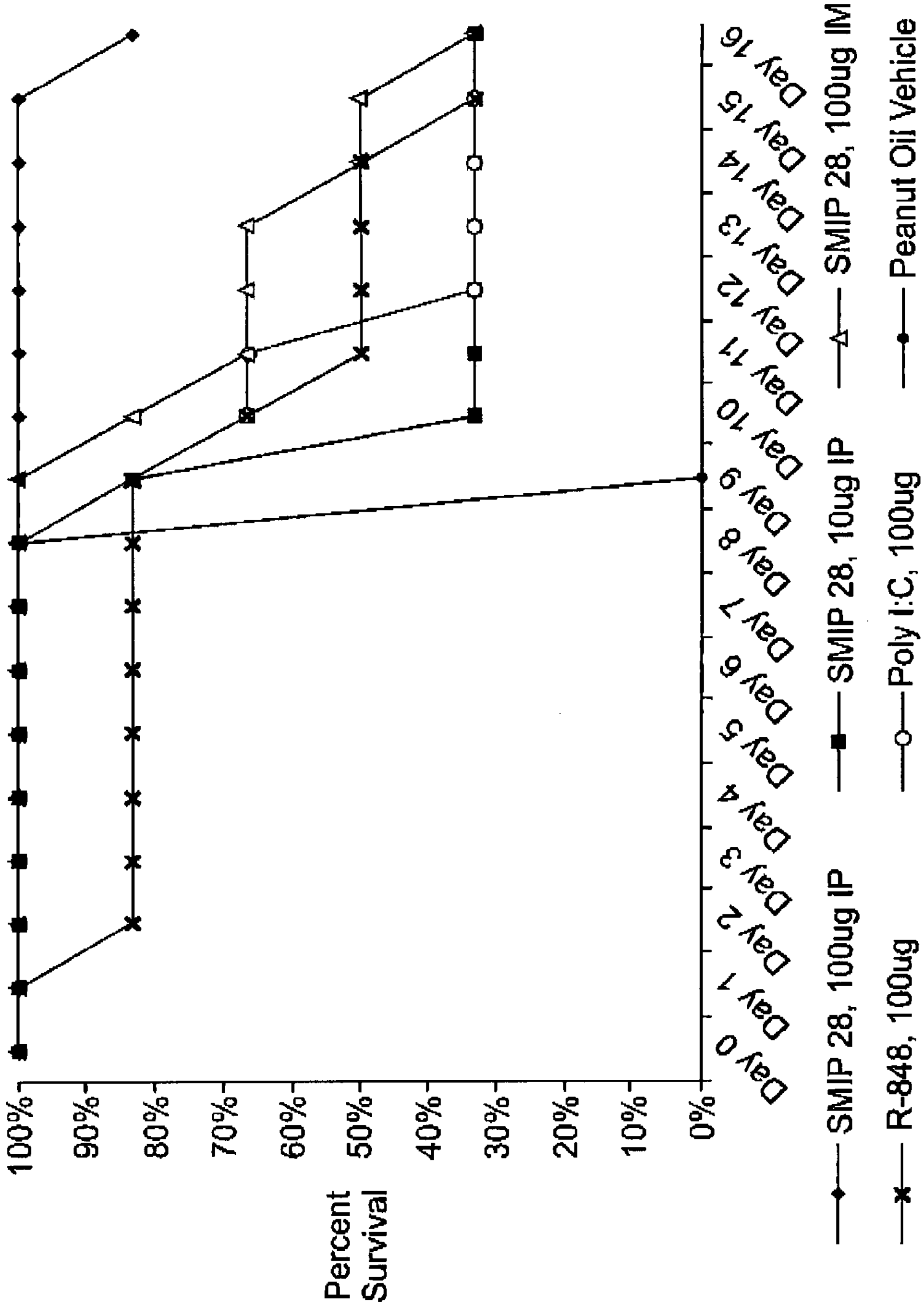
FIG. 3 shows that compositions comprising benzonapthyridine SMIPs protected guinea pigs that had been challenged with a guinea pig-adapted strain of the Zaire strain of Ebola virus. Guinea pigs were administered either 1) intraperitoneally 10 μg or 100 μg of 2-(4-methoxy-2-methylphenethyl)-8-methylbenzo[f][1,7]naphthyridin-5-amine in peanut oil; 2) intramuscularly 100 μg of 2-(4-methoxy-2-methylphenethyl)-8-methylbenzo[f][1,7]naphthyridin-5-amine in peanut oil; 3) 100 μg of R-848 in peanut oil; 4) 100 μg of Poly I:C in peanut oil or 6) peanut oil vehicle. Following administration, the animals were monitored sixteen days for survival.
Figure 4A:
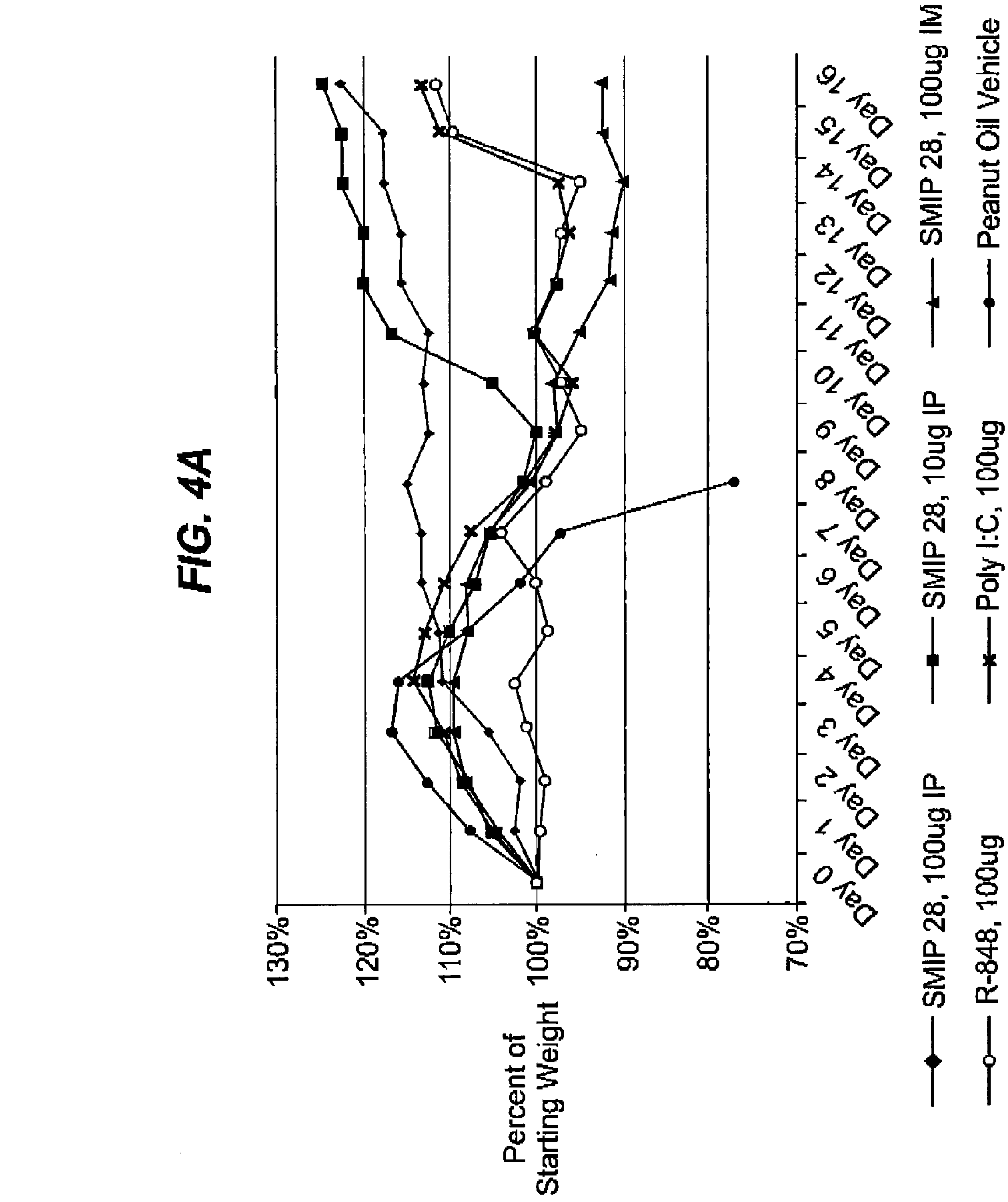
FIG. 4 shows over sixteen days the weight as a percent of the guinea pigs' starting weights (FIG. 4A) after the guinea pigs were administered either 1) intraperitoneally 10 μg or 100 μg of 2-(4-methoxy-2-methylphenethyl)-8-methylbenzo[f][1,7]naphthyridin-5-amine in peanut oil; 2) intramuscularly 100 μg of 2-(4-methoxy-2-methylphenethyl)-8-methylbenzo[f][1,7]naphthyridin-5-amine in peanut oil; 3) 100 μg of R-848 in peanut oil; 4) 100 μg of Poly I:C in peanut oil or 6) peanut oil vehicle.
FIG. 4B shows the clinical scores over the sixteen days assigned to the guinea pigs based upon cage-side observations.
Figure 4B:
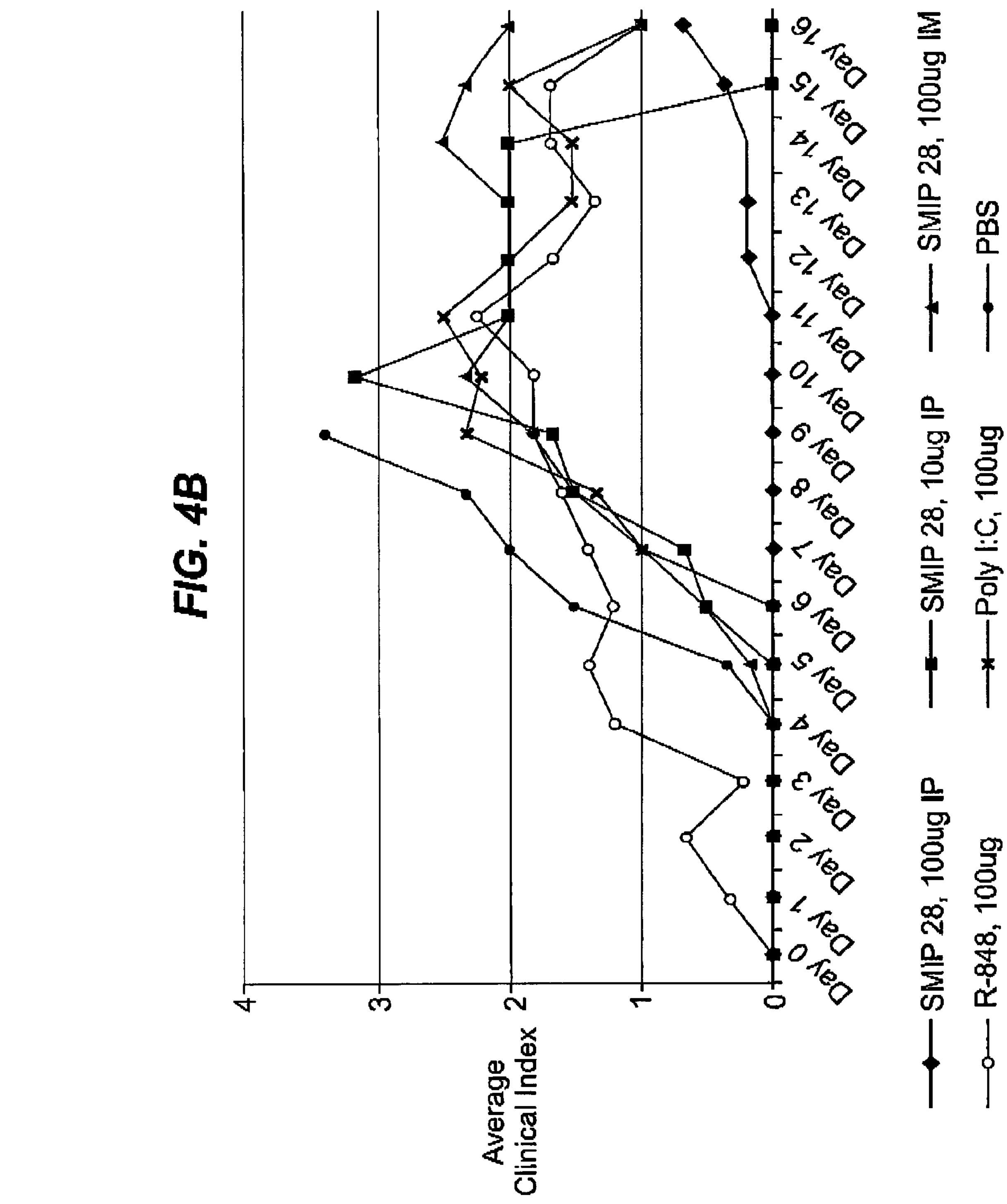

Results of the study are presented in FIGS. 3, 4A, and 4B.

As shown in FIG. 3, IP or IM SMIP 28 prolonged survival and resulted in an overall increase in survival. SMIP 28 at 100 μg delayed mortality and resulted in increased survival in comparison to R-848 and Poly I:C.

FIG. 4A provides the guinea pigs' weights, as a percent of the starting weights, over the course of the experiment. The results show that guinea pigs to which 100 μg of R-848 or Poly I:C was administered intraperitoneally experienced a steady increase in weight. Also, guinea pigs to which 100 μg or 10 μg SMIP 28 was administered intraperitoneally experienced a steady increase in weight. The weight gain in the SMIP 28-treated guinea pigs was greater than those treated with R-848 or Poly I:C. The weight gain results correlate with the delayed mortality and increased survival rate of guinea pigs treated with SMIP 28 at 100 μg compared to those treated with 100 μg R-848 or Poly I:C.

FIG. 4B provides the clinical scores given to the guinea pigs of this experiment. The results show that SMIP 28-treated guinea pigs had less severe symptoms than untreated animals, and that the group that received 100 μg SMIP 28 IP had a marked delay in onset and decrease in severity of symptoms.

The data demonstrate that SMIP 28 administered intraperitoneally and intramuscularly is capable of protecting guinea pigs challenged with guinea pig-adapted Ebola virus. Additionally, the data demonstrate that SMIP 28 outperformed the anti-viral efficacy of R-848 and Poly I:C.

Example 202

Benzonapthyridine SMIPs Administered Intraperitoneally and Intramuscularly in Guinea Pigs Challenged Intraperitoneally and Subcutaneously with Guinea Pig-Adapted Ebola Virus Induced an Immune Response Guinea pigs were given SMIPs of the invention by intraperitoneal (IP) or intramuscular (IM) injection 2 hours prior to IP or subcutaneous injection of guinea pig-adapted Ebola virus. On day 0 (zero), 2 hours after the administration of compounds, each guinea pig was administered an IP or subcutaneous injection of 1,000 PFU of guinea pig-adapted Ebola virus. Guinea pigs were administered, vehicle alone, PolyI:C (100 μg), R-848 (100 μg), or SMIP 28 (100 μg or 10 μg), each in vehicle. The guinea pigs were given additional daily IP injections of SMIP, vehicle alone, Poly I:C, or R-848 on days 1, 2, 3, 4, 6, 8, and 10 post-infection with guinea pig-adapted Ebola virus. Survival of guinea pigs was monitored on a daily basis for sixteen days following initial treatment.

Figure 5A:
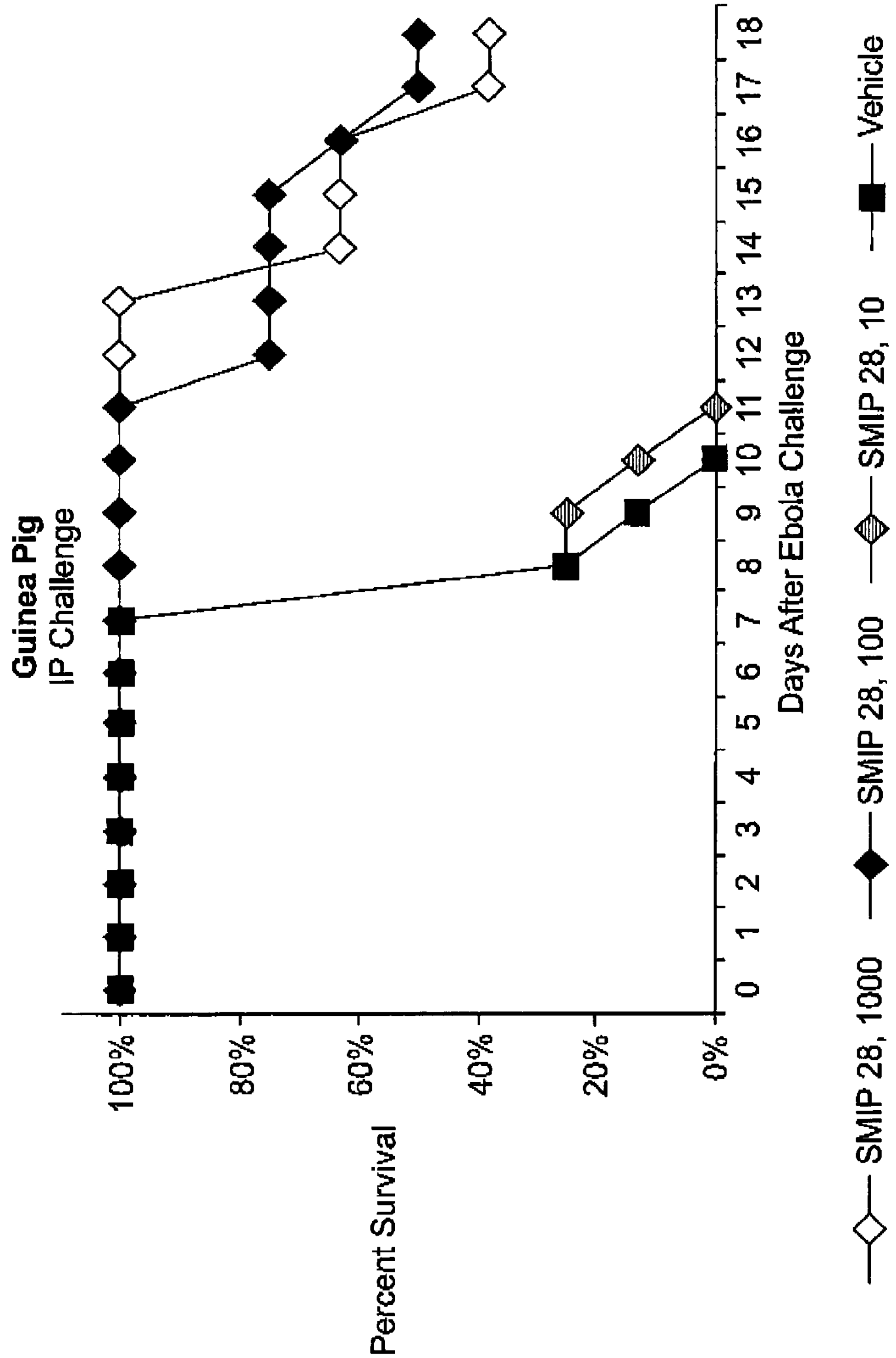
FIG. 5A shows data collected from guinea pigs that were administered either 1) intraperitoneally 10 μg, 100 μg, or 1000 μg of 2-(4-methoxy-2-methylphenethyl)-8-methylbenzo[f][1,7]naphthyridin-5-amine or 2) intraperitoneally vehicle, and then challenged with an intraperitoneal injection of 1,000 PFU of guinea pig-adapted Ebola. Following administration, all animals were monitored until day eighteen for survival.
Figure 5B:
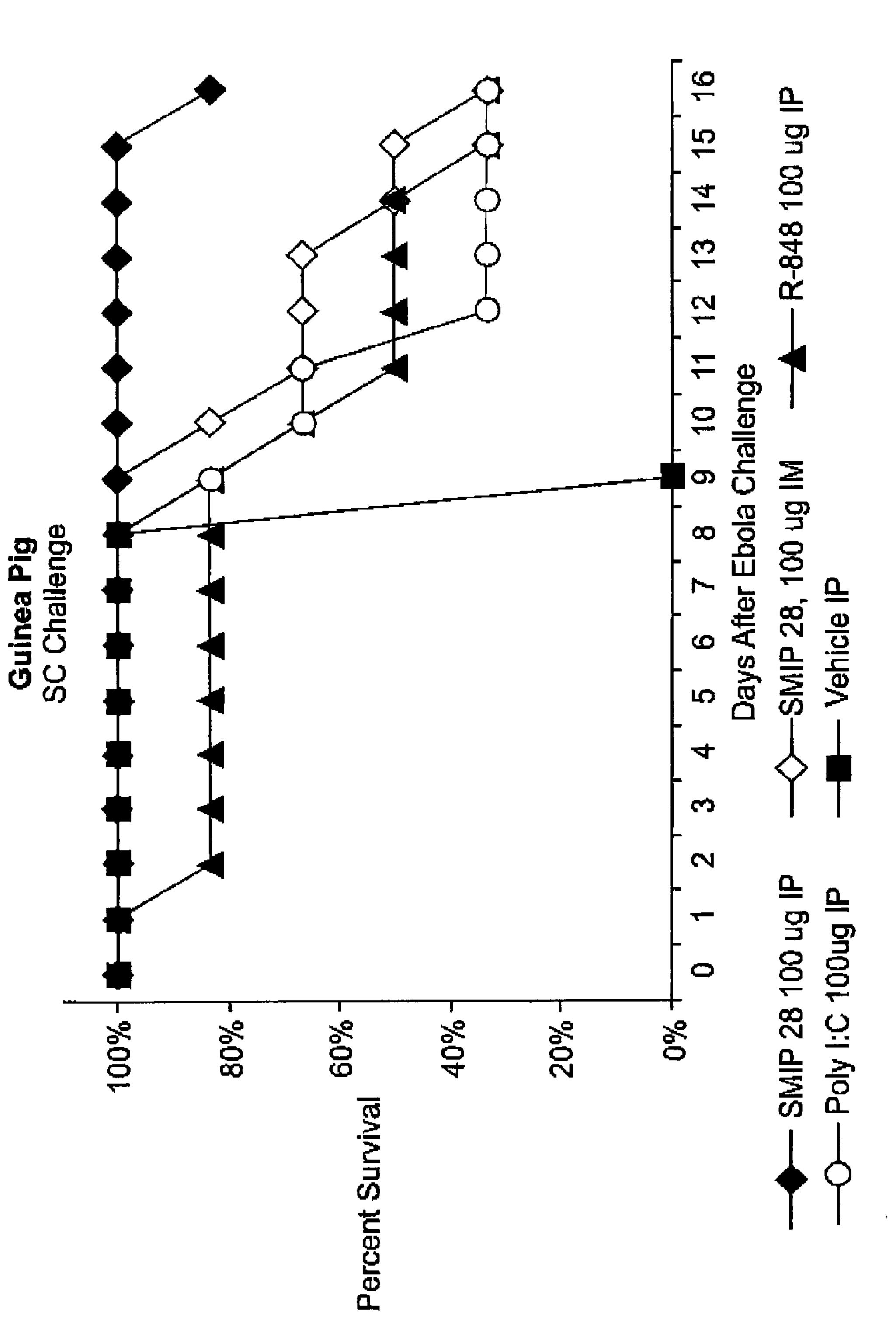
FIG. 5B shows data collected from guinea pigs that were administered 1) intraperitoneally 100 μg of 2-(4-methoxy-2-methylphenethyl)-8-methylbenzo[f][1,7]naphthyridin-5-amine in vehicle; 2) intramuscularly 100 μg of 2-(4-methoxy-2-methylphenethyl)-8-methylbenzo[f][1,7]naphthyridin-5-amine in vehicle; 3) intraperitoneally 100 μg of R-848 in peanut oil; 4) intraperitoneally 100 μg of Poly I:C in vehicle or 6) intraperitoneally vehicle. Following administration, all animals were monitored until day sixteen for survival.

Results of the study are presented in FIGS. 5A and 5B.

As shown in FIG. 5A, a dose of 100 μg IP SMIP 28 protected guinea pigs that were infected intraperitoneally with guinea pig-adapted Ebola virus. SMIP 28 at 100 μg and at 1000 μg delayed mortality and resulted in increased survival in comparison to 10 μg IP SMIP 28 and vehicle.

As shown in FIG. 5B IP or IM SMIP 28 prolonged survival and resulted in an overall increase in survival. IP SMIP 28 at 100 μg delayed mortality and resulted in increased survival in comparison to R-848 and Poly I:C.

The data demonstrate that SMIP 28 administered intraperitoneally and intramuscularly is capable of protecting guinea pigs that have been challenged intraperitoneally and subcutaneously with guinea pig-adapted Ebola virus.

Example 203

Benzonapthyridine SMIPs Administered Intraperitoneally in Mice Induced an Immune Response In the studies described below the effects of SMIPs as disclosed herein were tested. Mice were given SMIPs by intraperitoneal (IP) injection and peak cytokine concentration for particular cytokines was measured over a 24 hour period following SMIP treatment. Cytokine levels were measured for interferon gamma (IFN-γ), interleukin-10 (IL-10), the p40 (40 kDa) subunit of interleukin 12 (IL-12 p40), interleukin 1 beta (IL-1β), interleukin 5 (IL-5), interleukin 6 (IL-6), monocyte chemotactic protein-1 (MCP-1), keratinocyte chemokine (KC), tumor necrosis factor alpha (TNF-α). To measure the ability of SMIPs to induce an immune response, groups of 3 mice were given vehicle (peanut oil) alone, SMIP 28 or R848. Peak cytokine concentration was measured over a 24-hr period.

Figure 6A:
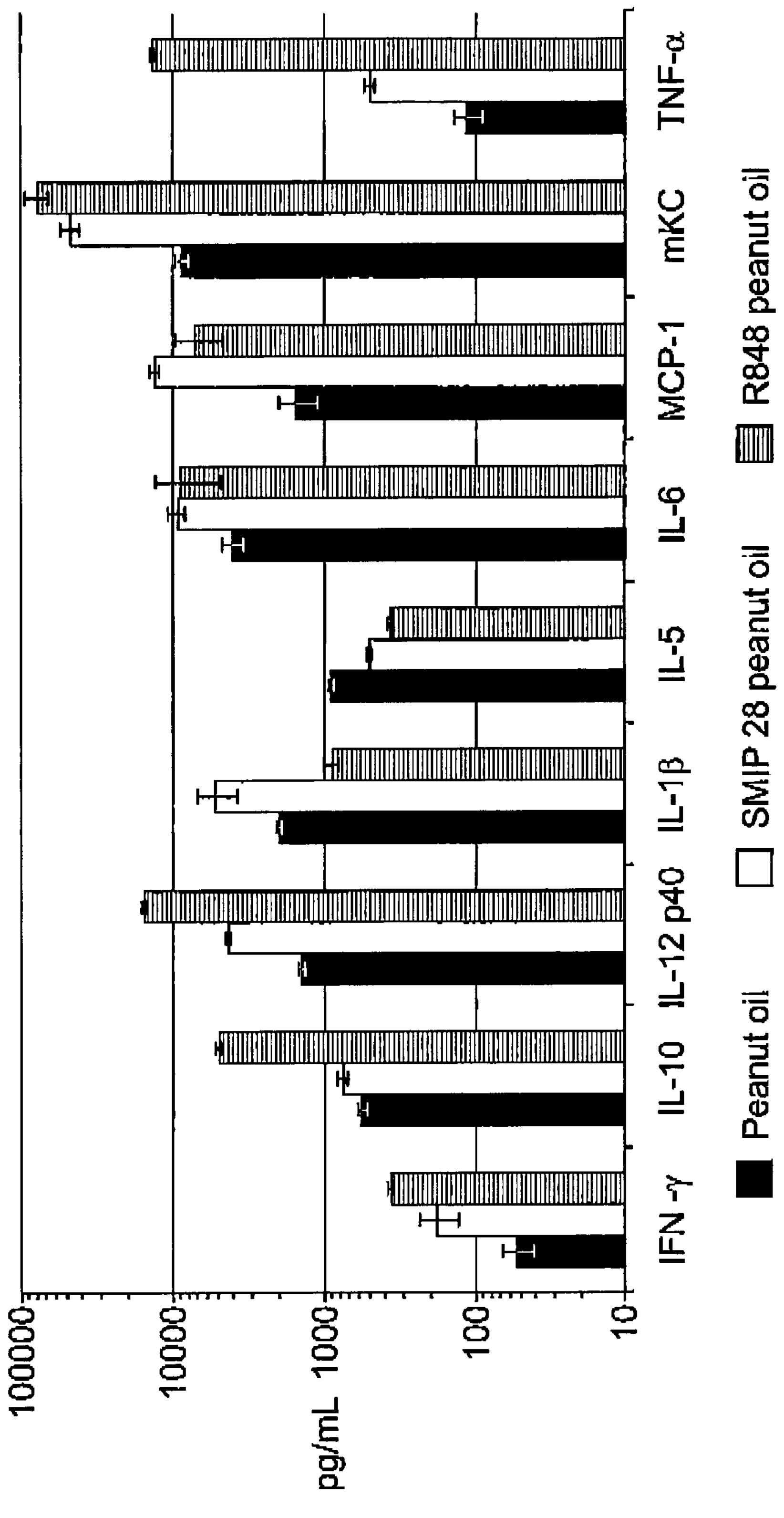
FIG. 6 shows that administration to mice of a composition comprising SMIP 28 induced an immune response. Specifically.
Figure 6B:
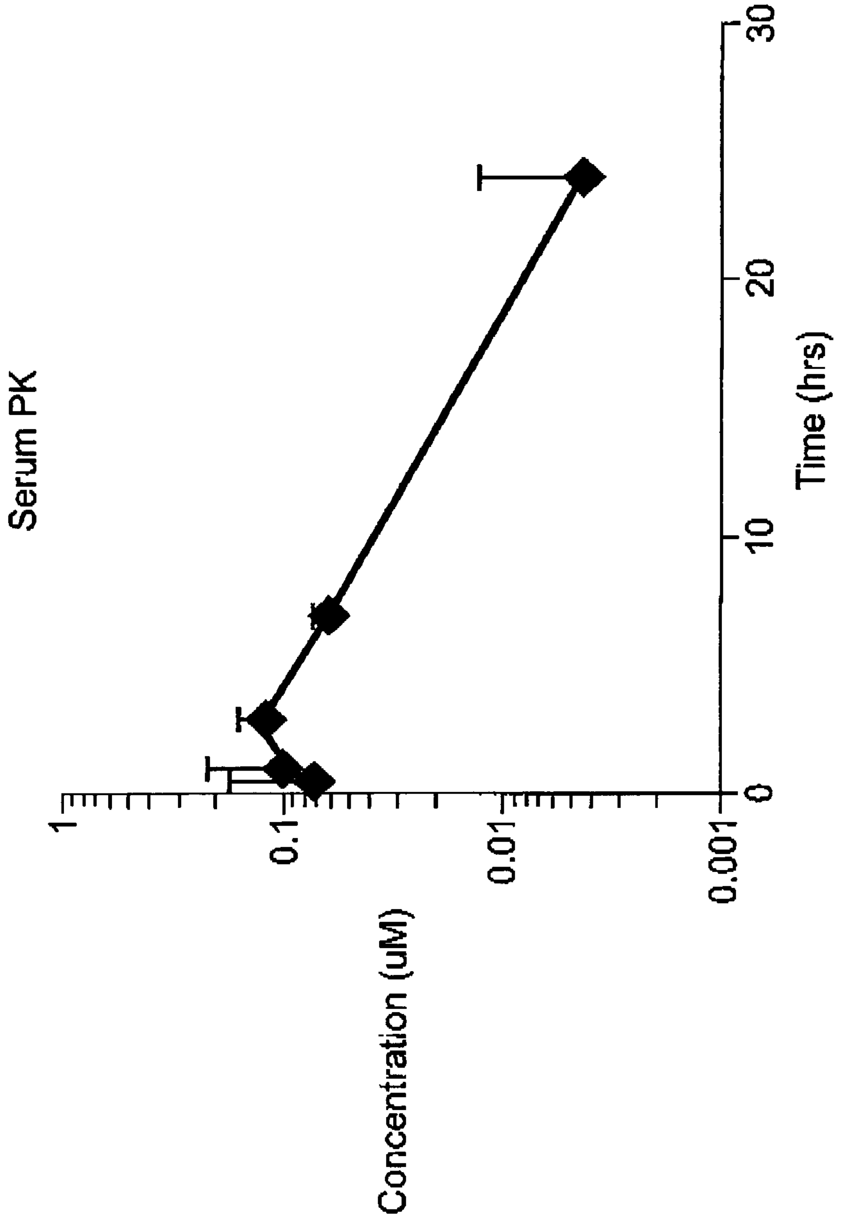

As shown in FIG. 6 SMIP 28, compared to peanut oil-control, induced an immune response consisting of cytokine induction of IFN-γ, IL-12 p40, IL-1β, IL-6, MCP-1, mKC, and TNF-α. R-848 resulted in cytokine induction of IFN-γ, IL-10, IL-12 p40, IL-6, MCP-1, mKC, and TNF-α. Neither administration of SMIP 28 nor R-848, compared to peanut oil-control, resulted in a cytokine induction of IL-5. SMIP 28, compared to R-848, resulted in a significantly greater cytokine induction of IL-1β.

The data demonstrate that SMIP 28 is capable of stimulating cytokine production. SMIP 28 induced an immune response that induced a cytokine profile. comprising induction of IFN-γ, (IL-12 p40), IL-1β, IL-6, MCP-1, mKC, and TNF-α.

It is understood that the examples and aspects described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of potentiating an immune response to a hemorrhagic fever virus, comprising administering to a subject a pharmaceutically effective amount of a composition comprising a benzonapthyridine TLR7 agonist or salt, solvate, or derivative thereof.

2. A method of treating a subject who has been exposed to a hemorrhagic fever virus, comprising administering to said subject a pharmaceutically effective amount of a composition comprising a benzonapthyridine TLR7 agonist or salt, solvate, or derivative thereof.

3. A method for inducing an immune response to a hemorrhagic fever virus, comprising administering to said subject an immunogenic composition comprising: (a) a benzonapthyridine TLR7 agonist or salt, solvate, or derivative thereof, and (b) an antigen derived from a hemorrhagic fever virus.

4. The method of claim 1, wherein the benzonapthyridine TLR7 agonist is a benzonapthyridine compound of Formula (II) having the structure:

Formula (II)

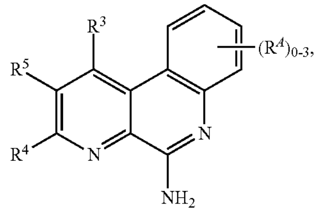

wherein:

$R^3$ is selecyed from H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —C(O)$R^8$, —OC(O)$R^8$, —C(O)O$R^8$, —N($R^9$)$_2$, —C(O)N($R^9$)$_2$, —S(O)$_2R^8$, —S(O)$_2$N($R^9$)$_2$ and —N$R^9$S(O)$_2$ $R^8$;

$R^4$ and $R^5$ are each independently selected from H, halogen, —C(O)O$R^7$, —C(O)$R^7$, —C(O)N($R^{11}R^{12}$), —N($R^{11}R^{12}$), —N($R^9$)$_2$, —NHN($R^9$)$_2$, —S$R^7$, —$(CH_2)_n$O$R^7$, —$(CH_2)_nR^7$, -L$R^8$, -L$R^{10}$, —OL$R^8$, —OL$R^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH{=}CHCO_2R^8$, —$C({=}NH)$—$N(R^9)_2$, and —$(CH_2)_nNHC(O)R^8$; or two adjacent $R^A$ substituents form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6; and t is 1, 2, 3, 4, 5, 6, 7 or 8.

5. The method of claim 4, wherein the benzonapthyridine TLR7 agonist is 2-(4-methoxy-2-methylphenethyl)-8-methylbenzo[f][1,7]naphthyridin-5-amine having the structure of

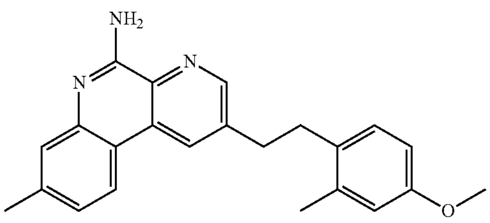

.

6. The method of claim 4, wherein the benzonapthyridine TLR7 agonist is 2-(4-(2-(5-amino-8-methylbenzo[f][1,7]naphthyridin-2-yl)ethyl)-3-methylphenyl)propan-2-ol having the structure of

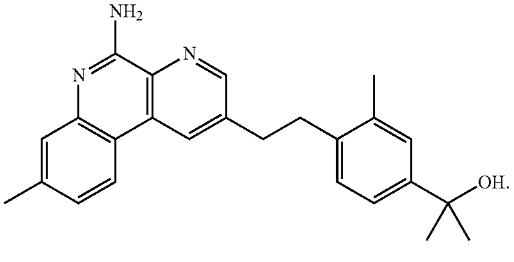 [SMILES: Cc1ccc2c(c1)nc(N)c1ncc(CCc3ccc(C(C)(C)O)cc3C)cc12]

7. The method of claim 4, wherein the benzonapthyridine TLR7 agonist is 2-(2-(4-(2-(5-amino-8-methylbenzo[f][1,7]naphthyridin-2-yl)ethyl)-3-methylphenoxy)ethoxy)ethanol having the structure of

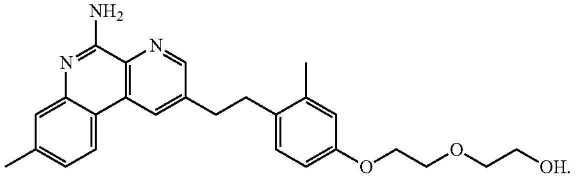 [SMILES: Cc1ccc2c(c1)nc(N)c1ncc(CCc3ccc(OCCOCCO)cc3C)cc12]

8. The method of claim 1, wherein the hemorrhagic fever virus is a Filoviridae virus.

9. The method of claim 8, wherein the Filoviridae virus is selected from the group consisting of Marburg virus and Ebola virus.

10. An immunogenic composition comprising:

(a) benzonapthyridine compound, or salt, solvate, or derivative thereof, and (b) an antigen derived from a hemorrhagic fever virus, wherein the benzonapthyridine compound, or salt, solvent, or derivative thereof, has the structure of:

Formula (II)

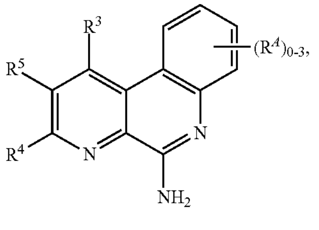

wherein:

$R^3$ is selected H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —C(O)$R^8$, —OC(O)$R^8$, —C(O)$OR^8$, —$N(R^9)_2$, —C(O)$N(R^9)_2$, —$S(O)_2R^8$, —$S(O)_2N(R^9)_2$ and —$NR^9S(O)_2R^8$;

$R^4$ and $R^5$ are each independently selected from H, halogen, —C(O)$OR^7$, —C(O)$R^7$, —C(O)$N(R^{11}R^{12})$, —$N(R^{11}R^{12})$, —$N(R^9)_2$, —NHN$(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$NO_2$, —$R^7$, —$OR^8$, —C(O)$R^8$, —OC(O)$R^8$, —C(O)$OR^8$, —$N(R^9)_2$, —P(O)$(OR^8)_2$, —OP(O)$(OR^8)_2$, —P(O)$(OR^{10})_2$, —OP(O)$(OR^{10})_2$, —C(O)$N(R^9)_2$, —$S(O)_2R^8$, —S(O)$R^8$, —$S(O)_2N(R^9)_2$, and —$NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —P(O)$(OR^8)_2$, —OP(O)$(OR^8)_2$, —P(O)$(OR^{10})_2$, and —OP(O)$(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -LC(O)$R^8$, —OLC(O)$R^8$, -LC(O)$OR^8$, -LC(O)$R^{10}$, -LOC(O)$OR^8$, -LC(O)$NR^9R^{11}$, -LC(O)$NR^9R^8$, -$LN(R^9)_2$, -$LNR^9R^8$, -$LNR^9R^{10}$, -LC(O)$N(R^9)_2$, -$LS(O)_2R^8$, -LS(O)$R^8$, -LC(O)$NR^8$OH, -$LNR^9$C(O)$R^8$, -$LNR^9$C(O)$OR^8$, -$LS(O)_2N(R^9)_2$, —$OLS(O)_2N(R^9)_2$, -$LNR^9S(O)_2R^8$, -LC(O)$NR^9LN(R^9)_2$, -LP(O)$(OR^8)_2$, -LOP(O)$(OR^8)_2$, -LP(O)$(OR^{10})_2$ and —OLP(O)$(OR^{10})_2$;

each $R^8$ is independently selected from H, —CH$(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —C(O)$R^{11}$, —OC(O)$R^{11}$, —C(O)$N(R^9)_2$, —C(O)$OR^{11}$, —$NR^9$C(O)$R^{11}$, —$NR^9R^{10}$, —$NR^{11}R^{12}$, —$N(R^9)_2$, —$OR^9$, —$OR^{10}$, —C(O)$NR^{11}R^{12}$, —C(O)$NR^{11}$OH, —$S(O)_2R^{11}$, —S(O)$R^{11}$, —$S(O)_2NR^{11}R^{12}$, —$NR^{11}S(O)_2R^{11}$, —P(O)$(OR^{11})_2$, and —OP(O)$(OR^{11})_2$;

each $R^9$ is independently selected from H, —C(O)$R^8$, —C(O)O$R^8$, —C(O)$R^{10}$, —C(O)O$R^{10}$, —S(O)$_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$cycloalkyl, or $C_3$-$C_8$heterocycloalkyl groups of $R^9$ are each optionally substituted with 1 to 3 substituents independently selected from —CN, $R^{11}$, —O$R^{11}$, —S$R^{11}$, —C(O)$R^{11}$, —OC(O)$R^{11}$, —C(O)O$R^{11}$, —N$R^{11}R^{12}$, —C(O)N$R^{11}R^{12}$, —C(O)N$R^{11}$OH, —S(O)$_2R^{11}$, —S(O)$R^{11}$, —S(O)$_2$N$R^{11}R^{12}$, —N$R^{11}$S(O)$_2R^{11}$, —P(O)(O$R^{11}$)$_2$, and —OP(O)(O$R^{11}$)$_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —O$R^8$, -L$R^9$, -LO$R^9$, —N($R^9$)$_2$, —N$R^9$C(O)$R^8$, —N$R^9$CO$_2R^8$, —CO$_2R^8$, —C(O)$R^8$ and —C(O)N($R^9$)$_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —O$R^8$, —C(O)$R^8$, —OC(O)$R^8$, —C(O)O$R^8$, —N($R^9$)$_2$, —N$R^8$C(O)$R^8$, —N$R^8$C(O)O$R^8$, —C(O)N($R^9$)$_2$, $C_3$-$C_8$heterocycloalkyl, —S(O)$_2R^8$, —S(O)$_2$N($R^9$)$_2$, —N$R^9$S(O)$_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^A$ is independently selected from halogen, —$R^8$, —$R^7$, —O$R^7$, —O$R^8$, —$R^{10}$, —O$R^{10}$, —S$R^8$, —NO$_2$, —CN, —N($R^9$)$_2$, —N$R^9$C(O)$R^8$, —N$R^9$C(S)$R^8$, —N$R^9$C(O)N($R^9$)$_2$, —N$R^9$C(S)N($R^9$)$_2$, —N$R^9$CO$_2R^8$, —N$R^9$N$R^9$C(O)$R^8$, —N$R^9$N$R^9$C(O)N($R^9$)$_2$, —N$R^9$N$R^9$CO$_2R^8$, —C(O)C(O)$R^8$, —C(O)CH$_2$C(O)$R^8$, —CO$_2R^8$, —(CH$_2$)$_n$CO$_2R^8$, —C(O)$R^8$, —C(S)$R^8$, —C(O)N($R^9$)$_2$, —C(S)N($R^9$)$_2$, —OC(O)N($R^9$)$_2$, —OC(O)$R^8$, —C(O)N(O$R^8$)$R^8$, —C(NO$R^8$)$R^8$, —S(O)$_2R^8$, —S(O)$_3R^8$, —SO$_2$N($R^9$)$_2$, —S(O)$R^8$, —N$R^9$SO$_2$N($R^9$)$_2$, —N$R^9$SO$_2R^8$, —P(O)(O$R^8$)$_2$, —OP(O)(O$R^8$)$_2$, —P(O)(O$R^{10}$)$_2$, —OP(O)(O$R^{10}$)$_2$, —N(O$R^8$)$R^8$, —CH═CHCO$_2R^8$, —C(═NH)—N($R^9$)$_2$, and —(CH$_2$)$_n$NHC(O)$R^8$; or two adjacent $R^A$ substituents form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6; and t is 1, 2, 3, 4, 5, 6, 7 or 8.

11. The immunogenic composition of claim 10, further comprising (c) an adjuvant.

12. The immunogenic composition of claim 10, wherein the benzonapthyridine TLR7 agonist is 2-(4-methoxy-2-methylphenethyl)-8-methylbenzo[f][1,7]naphthyridin-5-amine having the structure of

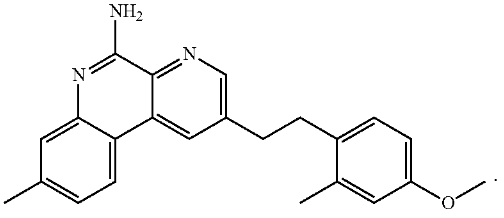

13. The immunogenic composition of claim 10, wherein the benzonapthyridine TLR7 agonist is 2-(4-(2-(5-amino-8-methylbenzo[f][1,7]naphthyridin-2-yl)ethyl)-3-methylphenyl)propan-2-ol having the structure of

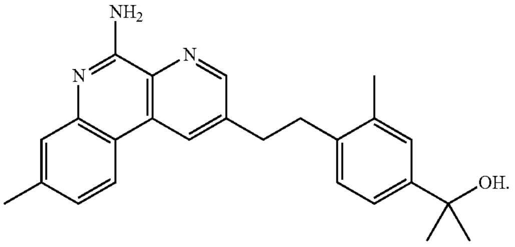 [SMILES: Cc1ccc2c(c1)nc(N)c1ncc(CCc3ccc(C(C)(C)O)cc3C)cc12]

14. The immunogenic composition of claim 10, wherein the benzonapthyridine TLR7 agonist is 2-(2-(4-(2-(5-amino-8-methylbenzo[f][1,7]naphthyridin-2-yl)ethyl)-3-methylphenoxy)ethoxy)ethanol having the structure of

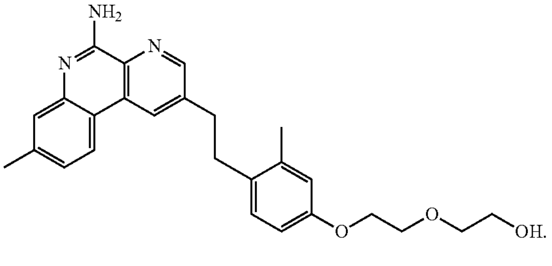 [SMILES: Cc1ccc2c(c1)nc(N)c1ncc(CCc3ccc(OCCOCCO)cc3C)cc12]

15. The method of claim 3, wherein the immune response comprises induction of a cytokine profile.

* * * * *